(12) United States Patent
Fox et al.

(10) Patent No.: US 7,414,122 B2
(45) Date of Patent: Aug. 19, 2008

(54) NUCLEIC ACIDS ENCODING B7-LIKE MOLECULES AND USES THEREOF

(75) Inventors: Gary M. Fox, Newbury Park, CA (US); John K Sullivan, Newbury Park, CA (US); Paige Holst, Camarillo, CA (US); Steven Kiyoshi Yoshinaga, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 314 days.

(21) Appl. No.: 10/998,526

(22) Filed: Nov. 29, 2004

(65) Prior Publication Data

US 2005/0228170 A1 Oct. 13, 2005

Related U.S. Application Data

(63) Continuation of application No. 09/955,866, filed on Sep. 19, 2001, now abandoned.

(60) Provisional application No. 60/233,867, filed on Sep. 20, 2000.

(51) Int. Cl.
*C07H 21/04* (2006.01)
*C12N 15/00* (2006.01)
*C12N 1/21* (2006.01)
*C12N 5/16* (2006.01)
*A61K 31/713* (2006.01)

(52) U.S. Cl. ................ 536/23.5; 435/320.1; 435/252.3; 435/455; 435/69.1; 514/44

(58) Field of Classification Search ........................ None
See application file for complete search history.

(56) References Cited

U.S. PATENT DOCUMENTS

| 6,635,750 B1 * | 10/2003 | Coyle et al. ................ 536/23.5 |
| 6,965,018 B2 * | 11/2005 | Mikesell et al. .......... 530/388.1 |
| 2002/0110836 A1 * | 8/2002 | Freeman et al. .............. 435/7.2 |
| 2003/0208058 A1 * | 11/2003 | Fiscella et al. ............. 536/23.5 |

FOREIGN PATENT DOCUMENTS

| EP | 10 74 617 A2 | 2/2001 |
| WO | WO 00/36107 A2 | 6/2000 |
| WO | WO 00/36107 A3 | 6/2000 |
| WO | WO 00/55375 A1 | 9/2000 |
| WO | WO 00/61612 A2 | 10/2000 |
| WO | WO 00/61612 A3 | 10/2000 |
| WO | WO 01/34659 A | 5/2001 |

OTHER PUBLICATIONS

Attwood T., Science 2000; 290:471-473.*
Skolnick et al., Trends in Biotech. 2000; 18(1)34-39.*
Metzler et al., Nature Structural Biol. 1997; 4:527-531.*
Burgess et al, J Cell Biol. 111:2129-2138, 1990.*
Lazar et al., Mol Cell Biol. 8:1247-1252, 1988.*
Bowie et al. Science, 247:1306-1310, 1990.*
Henry et al., "Structure and evolution of the extended B7 family" *Immunology Today*, vol. 20, No. 6, Jun. 1999, pp. 285-288.
Database EMBL 'Online! Feb. 22, 2000, Isogai T et al.: *Homo sapiens* cDNA FLJ11010 fis, clone PLACE1003145 Database accession No. AK001872, (2000).
Database EMBL 'Online! Jun. 1, 1999, Tseng et al.: "Mus musculus butyrophilin-like protein (btdc) mRNA, complete cds" retrieved from EBI Database accession No. AF142780, (1999).
Database EMBL 'Online Mar. 9, 2001, Latchman et al.: "*Homo sapiens* PD-1-ligand 2 protein (PDL2) m RNA, complete cds", Database accession No. AF344424, (2001).
Database EMBL, Online "*Homo sapiens* butyrophilin precursor B7-DC mRNA, complete cds", Database Accession No. AF329193.1, (2000).
Yoshinaga et al., T-cell co-stimulation through B7RP-1 and ICOS, Nature, 402:827-32 (1999).
Ishida et al.,"Induced expression of PD-1, a novel member of the immunoglobulin gene superfamily, upon programmed cell death", EMBO J. 11:3887-95 (1992).
Dong et al., B7-H1, a third member of the B7 family, co-stimulates T-cell proliferation and interleukin-10 secretion, Nat. Med. 5:1365-69 (1999).
Latchman et al., "PD-L2 is a second ligand for PD-1 and inhibits T cell activation", 2001 Nature Immunology 2:261-68 (2001).
Nishimura et al., "Development of Lupus-like Autoimmune Diseases by Disruption of the PD-1 Gene Encoding an ITIM Motif-Carrying Immunoreceptor", Immunity, 11:141-51 (1999).
Tseng et al., B7-DC, a New Dendritic Cell Molecule with Potent Costimulatory Properties for T Cells, J. Exp. Med. 193:839-45(2001).

* cited by examiner

*Primary Examiner*—Ilia Ouspenski
(74) *Attorney, Agent, or Firm*—McDonnell Boehnen Hulbert & Berghoff LLP

(57) ABSTRACT

The present invention provides B7-Like (B7-L) polypeptides and nucleic acid molecules encoding the same. The invention also provides selective binding agents, vectors, host cells, and methods for producing B7-L polypeptides. The invention further provides pharmaceutical compositions and methods for the diagnosis, treatment, amelioration, and/or prevention of diseases, disorders, and conditions associated with B7-L polypeptides.

12 Claims, 36 Drawing Sheets

FIG. 1A

```
                                                  atg atc ttc ctc ctg cta atg      53
cagaaagaga cctatatgat caaatacaga ac               Met Ile Phe Leu Leu Leu Met
                                                   1               5 ttg agc ctg gaa ttg cag ctt cac cag ata gca gct tta ttc aca gtg     101
Leu Ser Leu Glu Leu Gln Leu His Gln Ile Ala Ala Leu Phe Thr Val
         10                  15                  20 aca gtc cct aag gaa ctg tac ata ata gag cat ggc agc aat gtg acc    149
Thr Val Pro Lys Glu Leu Tyr Ile Ile Glu His Gly Ser Asn Val Thr
     25                  30                  35 ctg gaa tgc aac ttt gac act gga agt cat gtg aac ctt gga gca ata    197
Leu Glu Cys Asn Phe Asp Thr Gly Ser His Val Asn Leu Gly Ala Ile
40                   45                  50                  55 aca gcc agt ttg caa aag gtg gaa aat gat aca tcc cca cac cgt gaa    245
Thr Ala Ser Leu Gln Lys Val Glu Asn Asp Thr Ser Pro His Arg Glu
                 60                  65                  70 aga gcc act ttg ctg gag gag cag ctg ccc cta ggg aag gcc tcg ttc    293
Arg Ala Thr Leu Leu Glu Glu Gln Leu Pro Leu Gly Lys Ala Ser Phe
             75                  80                  85 cac ata cct caa gtc caa gtg agg gac gaa gga cag tac caa tgc ata    341
His Ile Pro Gln Val Gln Val Arg Asp Glu Gly Gln Tyr Gln Cys Ile
         90                  95                 100 atc atc tat ggg gtc gcc tgg gac tac aag tac ctg act ctg aaa gtc    389
Ile Ile Tyr Gly Val Ala Trp Asp Tyr Lys Tyr Leu Thr Leu Lys Val
    105                 110                 115 aaa gct tcc tac agg aaa ata aac act cac atc cta aag gtt cca gaa    437
Lys Ala Ser Tyr Arg Lys Ile Asn Thr His Ile Leu Lys Val Pro Glu
120                 125                 130                 135 aca gat gag gta gag ctc acc tgc cag gct aca ggt tat cct ctg gca    485
Thr Asp Glu Val Glu Leu Thr Cys Gln Ala Thr Gly Tyr Pro Leu Ala
                140                 145                 150 gaa gta tcc tgg cca aac gtc agc gtt cct gcc aac acc agc cac tcc    533
Glu Val Ser Trp Pro Asn Val Ser Val Pro Ala Asn Thr Ser His Ser
            155                 160                 165 agg acc cct gaa ggc ctc tac cag gtc acc agt gtt ctg cgc cta aag    581
Arg Thr Pro Glu Gly Leu Tyr Gln Val Thr Ser Val Leu Arg Leu Lys
        170                 175                 180 cca ccc cct ggc aga aac ttc agc tgt gtg ttc tgg aat act cac gtg    629
Pro Pro Pro Gly Arg Asn Phe Ser Cys Val Phe Trp Asn Thr His Val
185                 190                 195
```

FIG. 1B

```
agg gaa ctt act ttg gcc agc att gac ctt caa agt cag atg gaa ccc    677
Arg Glu Leu Thr Leu Ala Ser Ile Asp Leu Gln Ser Gln Met Glu Pro
200                 205                 210                 215 agg acc cat cca act tgg ctg ctt cac att ttc atc ccc tcc tgc atc    725
Arg Thr His Pro Thr Trp Leu Leu His Ile Phe Ile Pro Ser Cys Ile
                    220                 225                 230 att gct ttc att ttc ata gcc aca gtg ata gcc cta aga aaa caa ctc    773
Ile Ala Phe Ile Phe Ile Ala Thr Val Ile Ala Leu Arg Lys Gln Leu
            235                 240                 245 tgt caa aag ctg tat tct tca aaa gac aca aca aaa aga cct gtc acc    821
Cys Gln Lys Leu Tyr Ser Ser Lys Asp Thr Thr Lys Arg Pro Val Thr
        250                 255                 260 aca aca aag agg gaa gtg aac agt gct atc tga acctgtggtc ttgggagcca 874
Thr Thr Lys Arg Glu Val Asn Ser Ala Ile
    265                 270 gggtgacctg atatgacatc taaagaagct tctggactct gaacaagaat tcggtggcct 934 gcagagcttg ccatttgcac ttttcaaatg cctttggatg acccagcact ttaatctgaa 994 acctgcaaca agactagcca acacctggcc atgaaacttg ccccttcact gatctggact 1054 cacctctgga gcctatggct ttaagcaagc actactgcac tttacagaat taccccactg 1114 gatcctggac ccacagaatt ccttcaggat ccttcttgct gccagactga aagcaaaagg 1174 aattatttcc cctcaagttt tctaagtgat ttcca                            1209
```

```
                         560         *        580         *        600         *        620
Cd80_Human    :
Cd86_Human    :
GA16817596    :
B7-H1_Huma    :
B7rp-1_Hum    :
Pro352_Hum    :
Btf1_Human    :
Btsf2a2_Hu    : FFRL.GSDDSPIFICPALTGASGVMVPEEGLKLHRVGTHQSL                                    : 523
Btf4_Human    :
Btn3a3_Hum    : VFRILTLEPTALTICPIPKEVESSPDDLVPDHSLETPLTPGLANESGEPQAEVTSLLLPAHPGAEVSPSATTNQNHKLQARTEALY : 584
Btn_Human     : FFCLWSSGKKPLTICPIADGPERVTVIANAQDLSKEIPLSPMGEESAPRDADTLHSKLIPTQPSQGAP                  : 526
```

FIG. 3A

```
ataagaagct gaattaaggt gatggcagtg gggtggaaga aaggagagcc accatgcaaa  60
aagtatccag gagggagaat taacaggact aggggatggg ccatatttgc aagatgagaa  120
atgcagaggt ctaagattct agctnnnnnn nnnnnnnnnn nnnnnnnnnn nnnnnnnnnn  180
nnnnnnnnnn nnnnnnnnnn nnnnnnnnnn nnnnnnnnnn nnnnnnnnnn nnnnnnnnnn  240
nnnnnnnnnn nnnnnnnnnn nnnnnnnnnn nnnnnnnnnn nnnnnnnnnn nngcataaac  300
catattttcc ccagaggagg attagtagga aaggaagctg ctggttggaa agtatcttta  360
tagcagtgtc tgttcctcgg tttgctcaag gggacagtgt gccaggaaag tccccgtgga  420
agggcaagga agaaggggaa gttaaagcca gtggcaggtg atccaagaat cttttctgtt  480
gctagagcta tgttacatgc tgtcctttca tgctctaaaa ataagagtgc tggcaagtgc  540
caggcctgtt ggtgcagctt aagatgatac ctttcttgga tatatatgca tctgaataag  600
gaaggctatc ttctggtcaa gctaaggtat gccatgagca tttccctgtg gaaagcactt  660
aattctgttc ccagttgtta cctgctgtaa gatctccctt tctaaaataa aaacaagaat  720
acagctcact gaggacctta catttccctc tagctactga ctcatttctc ttctcctttt  780
tatagcactc ttcttgagag agttgcctat atttgttgcc acatctttac ccattctctt  840
ttgaacctat tcaagctttc atctgtacaa aactcactga tactgtgctt gtcaggatca  900
tccatgacct ccatactgct aaatgcaact ctcaagagta tttggctcta ctgatcactc  960
ctttgtagca ctgtgtttta aaatataggt tttattatta tttaggtatg gtgaggccaa  1020
tatatcagga aatgactgtc gttgaaaaaa gtatgttgta ctcacagatc caagagaag   1080
ggggcacac catgccacaa agggccacat ggggaagcac cagggtcagc caggaggtgg   1140
gtgggggtg cgcaagatct ttattgtggt ttcaacagga agaaatgggt gaagcagggt   1200
gagtggattt aggattagct gatataaata atttcagcag gctctggggc ataggggctg  1260
tccctagtct tctggtactt ggccctgggg tgattaaggc agttgcatag tgttgggaat  1320
gtgaaagccc ccaataaatg aggcagttgt gggtatgggc tctgaaatgg gttggtttgc  1380
atttgaaagg tgtgctcatg ggcaagtggt ttactctctc ttagaggtta gaattggcta  1440
accctgggag cggcagtccc ttcagggtca gcaaggcccc aggtgtcaaa gcatcagaat  1500
acagaaaata aaatgcatgg ataatacaca ctgccatttg cctttgtacc cttcctttca  1560
atcttctctg ctggtgaccg ctcttcacaa agatctataa atgttggaat accccatgtc  1620
```

FIG. 3B

```
tcagtccttg ggcactctct ttcctatctc tctgtaggtg atgtaatgca gatatccatg 1680
actttaaatc tttaacactt ctgcattgat gactcctaaa tttacatctc taccccaact 1740
gcctactaaa cacctccact tggctatcta ataggcattt caaaccaaat ctacaacaaa 1800
cgtaactctt tttcccttc cttaatttgc ttctccccca gccttctcca ttttaataaa 1860
cagcatctcc attgccttag tgactcaagc cccaaactta ggaattttcc cagatttccc 1920
tcttttctc aaactatata tctagcctgt cagcagttcc cttcaggtct tttttcnnnn 1980
nnnnnnnnnn nnnnnnnnnn nnnnnnnnnn nnnnnnnnnn nnnnnnnnnn nnnnnnnnnn 2040
nnnnnnnnnn nnnnnnnnnn nnnnnnnnnn nnnnnnnnnn nnnnnnnnnn nnnnnnnnnn 2100
nnnnnnnnnn nnnnnnnnnn nnnnnnnnnn nnnnnnnnnn nnnnnnnnnn nnnnnnnnnn 2160
nnnnnnnnnn nnnnnnnnnn nnnnnnnnnn nnnnnnnnnn nnnnnnnnnn nnnnnnnnnn 2220
nnnnnnnnnn nnnnnnnnnn nnnnnnnnnn nnnnnnnnnn nnnnnnnnnn nnnnnnnnnn 2280
nnnnnnnnnn nnnnnnnnnn nnnnnnnnnn nnnnnnnnnn nnnnnnnnnn nnnnnnnnnn 2340
nnnnnnnnnn nnnnnnnnnn nnnnnnnnnn nnnnnnnnnn nnnnnnnnnn nnnnnnnnnn 2400
nnnnnnnnnn nnnnnnnnnn nnnnnnnnnn nnnnnnnnnn nnnnnnnnnn nnnnnnnnna 2460
ctaannnnnn nnnnnnnnnn nnnnnnnnnn nnnnnnnnnn nnnnnnnnnn nnnnnnnnnn 2520
nnnnnnnnnn nnnnnnnnnn nnnnnnnnnn nnnnnnnnnn nnnnnnnnnn nnnnnngctc 2580
catttatatt tannnnnnnn nnnnnnnnnn nnnnnnnnnn nnnnnnnnnn nnnnnnnnnn 2640
nnnnnnnnnn nnnnnnnnnn nnnnnnnnnn nnnnnnnnnn nnnnnnnnnn nnnnnnnnnn 2700
nnnnnnnnnn nnnnnnnnnn nnnnnnnnnn nnnnnnnnnn nnnnnnnnnn nnnnnnnnnn 2760
nnnnnnnnnn nnnnnnnnnn nnnnnnnnnn nnnnnnnnnn nnnnnnnnnn nnnnnnnnnn 2820
nnnnnnnnnn nnnnnnnnnn nnnnnnnnnn nnnnnnnnnn nnnnnnnnnn nnnnnnnnnn 2880
nnnnnnnnnn nnnnnnnnnn nnnnnnnnnn nnnnnnnnnn nnnnnnnnnn nnnnnnnnnn 2940
nnnnnnnnnn nnnnnnnnnn nnnnnnnnnn nnnnnnnnnn nnnnnnnnnn nnnnnnnnnn 3000
nnnnnnnnnn nnnnnnnnnn nnnnnnnnnn nnnnnnnnnn nnnnnnnnnn nnnnnnnnnn 3060
nnnnnnnnnn nnnnnnnnnn nnnnnnnnnn nnnnnnnnnn nnnnnnnnnn nnnnnnnnnn 3120
nnnnnnnnnn nnnnnnnnnn nnnnnnnnnn nnnnnnnnnn nnnnnnnnnn nnnnnnnnnn 3180
nnnnnnnnnn nnnnnnnnnn nnnnnnnnnn nnnnnnnnnn nnnnnnnnnn nnnnnnnnnn 3240
```

FIG. 3C

```
nnnnnnnnnn nnnnnnnnnn nnnnnnnnnn nnnnnnnnnn nnnnnnnnnn nnnnnnnnnn 3300
nnnnnnnnnn nnnnnnnnnn nnnnnnnnnn nnnnnnnnnn nnnnnnnnnn nnnnnnnnnn 3360
nnnnnnnnnn nnnnnnnnnn nnnnnnnnnn nnnnnnnnnn nnnnnnnnnn ttgtgtttta 3420
aatatatata cacacttaga cacatataac cctctttcgt atatcaatta tactttaata 3480
aagctgttgn nnnnnnnnnn nnnnnnnnnn nnnnnnnnnn nnnnnnnnnn nnnctcgcca 3540
acagaccact tctcacccct actagcccct ctactctaag ctatcagcat ttctgcaaac 3600
acattcctaa ccgatctcac tgcttgtaat cttgccagca acctctccct ctcagcaata 3660
gtctattgcc tacaccaaag cttagttgtc tcttaatgat gtaaatgagg ttctatcatt 3720
ctcctgaccc aaaccctcca ctgcttttca tcacactcag agcagctctg ctgttgcctg 3780
atttagatgt atggctccaa cagatttccc ctgaagaaat gattccatgg ctgataaaag 3840
ttggaaagcc tcctcagttt cagaccatta tcagattagc tgtgtgctct gtccctttcc 3900
tcaaccataa gaagtccatg gataaagaaa gcttcagagt aaaggagaaa gcatgggagg 3960
tacagcagga ccaaggtggg gcattcgcag cccccaccct catcagagcc agttccctac 4020
tctccctgtc taaacctctt agtaagaggt agttcaagag agggcaaac tcaattccag 4080
cactcaaaag cacttgacta ctttgctcag tcaactagca agtatttatt gagaatgtag 4140
ctctgttcta tggagtctta ttttcaagtg tcagactccc agacatccag tccaggtaaa 4200
gaagatggtg tccattattc atttgacaaa caaagttggg gttcaagggc cagctattga 4260
aaaaagctat ggaaagcttc atgagacgtg caggtaactg ccaatatgtg tggttcacaa 4320
ggactggttc atattcagaa acggccatta gaaaggaag aagaacttct catttggatt 4380
tataaagagt gtcttgttta ctcttaattt atatcttctc ttctccagga aatcaaccta 4440
taacttctcc tcccagctcc actctaccat ggtctgtcac cttccccaaa tgatttgtta 4500
ttcccctgtt ttcaaaagtg aacaaagaac caaagaccca gcaaagtttc acaaggccct 4560
gagactttca attgtctatt tcagatcaaa tacagaac atg atc ttc ctc ctg cta 4616
                                       Met Ile Phe Leu Leu Leu      6
atg ttg agc ctg gaa ttg cag ctt cac cag ata gca ggtaagaaag           4662
Met Leu Ser Leu Glu Leu Gln Leu His Gln Ile Ala                     18
gacaaaggga gaggcttaag aaagaagagc aggtggtggt tcctagccaa agccaaaaat   4722
gagaatgtgg ccctcaggct gagggctttc tttgagagga cgtatgattt ctgggctatt   4782
```

FIG. 3D

```
ccaagcacca caaaaaaaaa aagagtcccc atggtggctt atacatgcca atgtccctat 4842
ctgacagaaa cggtgactga gaatattgct ccatctattc ccactatcca gtgagggtaa 4902
tgacaagaag acaggatcac tcagaccatg taaatctaaa ctgatacaag agggcagggg 4962
ttgagttccc ttaaaggtga gatgccaagc agctgtcccc ttcctttctg gcagggagag 5022
taaggagaca atggccaggg aacaccgtta ctctaaagat aatgtcttga agacattctg 5082
catattatta gttgtttctg tgagtttctt ttttgaaaag caacaatagc agccgttggt 5142
cattcatacc ttaatgtggt ttactgagtc ttcctaaaac ccaaatgaac aatgaacctt 5202
aaggctatcc ctttggactt gaagaaagga cttctattgg aggatgaggg tgagcagaaa 5262
gaaaagcagt ttcacagttg gttgttctcc tggggaaggt agttcagacc attcgagggt 5322
gtagttagaa ccatgagtgc actattttgg atgaacacca ggagctaaga gagtaacata 5382
gaggtgtgga cagaggatta agtcctcaag acaatagccc cagccccatg ggaaatcatc 5442
tttctgctca tgattgagaa ataatggctc ccttggcact tgataacctt tcgaagagct 5502
ttctcctccc tactagctgg ttccagatca ctcttcaccc agtcacattc ctctcactca 5562
cttgagctgc ccagcctggt ctggcactag agacatgcac ttggggccct cctcaaagga 5622
agaccctgag atattctgct tacttctact ctgctcctgc ctgcagggcc agctaaagga 5682
acttttcatg ttttctttgc aaggaaccct gcctggctgg cattttagag acaagcaaaa 5742
ggggcaataa cttccttgct acaaaacagc ttcaagtttc catagagtga taagggaaat 5802
gagggccaaa agacactgtt ccccatcctg tgcaggact ggggcttca ggagaaaact 5862
tggggaatgt gtaacctctg tgggtttgta gcttaaaaac actgagatcc tgggttttct 5922
gtctttgttt tttgccttt ctcttaggaa aggagtgagc tagggtgaca aggggcaaca 5982
tttttttatcc ctcattggct ctttctacag aggaaggatc ttttcttcta agataatcag 6042
cacaagacaa tgaagatagg cactagctcc cagttaggta tactaatggg gcaaaaggaa 6102
gagcatttnn nnnnnnnnnn nnnnnnnnnn nnnnnnnnnn nnnnnnnnnn nnnnnnnnnn 6162
nnnnnnnnnn nnnnnnnnnn nnnnnnnnnn nnatttgca ggtgagggaa ctagaactca 6222
gaaaaggtac ttaatttccc caagattaca tagttattag gtgacaccgg caagatttca 6282
acaaagctaa tgtcctttct actttactgt gctaccatga tgatggtaat caaaaatggc 6342
agacaaccca taaatcttcc aactttggaa taggttttg cactgaagtc tgaatatgga 6402
```

FIG. 3E

```
tacgtattga atgtttattc tggatattca cagaatcaaa aaatatgtgt aatgaattat 6462
gttgctgaat taactgaaag gaaagtaaaa atgtagcgct ttctcatttt cttcacgaat 6522
ttggaattct tttctgcttt ccactatgca gataacatca gttcagacaa atattaaata 6582
cctacctaaa ttagaatgcc ttctcctcat gggattttt taaaatcttg tcatttcatg 6642
tctctttaat taaagagttt tgatttcaga ggagggtacc tgcaaaagaa aacaacaaaa 6702
aaactaaagg atctgagaaa taattagtgt ttacttctgg ggaggggagg aggtctggga 6762
tggggtaaa aaggatagtc ttatctatta tgtatattca ggttttgtt ttttacaaga 6822
agcatgtatt aggnnnnnnn nnnnnnnnnn nnnnnnnnnn nnnnnnnnca agaaatttct 6882
catataaaaa tatgaaagta atcagactgc aacactcagt gcctgagaca gagctacagc 6942
tatcagggtg tccagacaga cagaagatta catttttcttc cttgctcctt gtacagcccc 7002
agacctgcat gcttcattga aaagaaaaga agatacctga attaaatcaa tgtgatgctt 7062
agtaccctat cagtgcacat ttctttttcnn nnnnnnnnnn nnnnnnnnnn cacttnnnnn 7122
nnnnnnnnnn nnnnnnnnnn nnnnnnnnnn nnnnnnnnnn nnnnnnnnnn nnnnnnnnnn 7182
nnnnnnnnnn nnnnnnnnnn nnnnnnnnnn nnnnnnnnnn nnnnnnnnnn nnnnnnnnnn 7242
nnnnnnnnnn nnnnnnnnnn nnnnnnnnnn nnnnnnnnnn nnnnnnnnnn nnnnnnnnnn 7302
nnnnnnnnnn nnnnnnnnnn nnnnnnnnnn nnnnnnnnnn nnnnnnnnnn nnnnnnnnnn 7362
nnnnnnnnnn nnnnnnnnnn nnnnnnnnnn nnnnnnnnnn nnnnnnnnnn nnnnnnnnca 7422
cttatggcgg tattctcagt cattacaaat aaataaaaac aatccatatg ccctggagaa 7482
tttgattcca ggagtaggtc tagaagaact tcaactggag aatggataga gaaatcatgg 7542
tatatttgca gnnnnnnnnn nnnnnnnnnn nnngatagca tgtgaataaa ttaattacaa 7602
aaacatatga ctacatctat tattatatag catgtagata aattacaaaa acatgtaact 7662
acatctatga atcttagagc ataatattga gnnnnnnnnn nnnnnnnnnn nnnnnnggcc 7722
agaagataac acatagcaca atgtccttt cataaataaa tatattgctt aagcatacct 7782
tatatataga agataaagct taaaagtaa agaagag                          7819
```

FIG. 4

```
attatcactt atgagggtgn nnnnnnnnnn nnnnnnnnnn nnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnn nnnnnctgcc 180
ctttattttt tcatgaaaga aattgctgaa gaggactaaa agaagtttta gtaagcattc 240
aataaatgta tgttctttat agtttccaaa tcagcaaata tagacatcct gcatttttaa 300
ggagatttat atatttatt ggacatgctg taatttattt aaccacttcc ctgttggtag 360
acattatttc catttcttc tgctagatta atgcttgaaa aaaatgtgtg cctcctaaag 420
actgtgatga aagttgcctc tgaataaaac tcaaacaaat cattaatcat taactctttc 480
cttacttgta tgctctttgg atgctctact gtgttatcta taaaataaag tttgaagtga 540
aaaattaggg taaaacattt tatatcattt ttaaggata tacatgga tgtacttaca 600
tatgcatgtt taaatttata taccataaca tttatttctt tttttaaaaa             650
```

FIG. 5A

```
tatatttgtt ttttttctta cattttttatt tcaaaatcta aggacatctt ataacccaga 60
aatattttttt ataccttgtc atgtcttaga ggaaagagcc accccagtct tttttcattg 120
atgtttttct tctctcttcg tactccagag gtagatgaaa accagagggc cacaatgacc 180
atggtgatgc ctgaggtcat tctggggcac agacctcagc ctaggttact ccacttcgcc 240
tatctttaga tccaaaacta ccctgctgac tgctgagata aacaaggag aataatcagg 300
ttggggaaag gatttctatg cgaagacatg tctccatgca gtcctcctac actgagcaga 360
gcatgagtca ggtgcttaga gcaggatttt gtcctaaacc aggaacttca gagttttctg 420
aagaatgtgg ctatgtaaag cacccccca ccccaccctt acttctcaag tacattacgt 480
ggcaagtctg aaaaaactta cacttctgtt gttaaatgtg ggggataaaa tataaactta 540
gtttcaagag gaagctatct tgggaggtaa tgcaaataat tcgttgtgtg tttcctgaat 600
aagtgacagg tgctgactac cattgatgct tcattgcaat aaaatgcaaa gctcccccaa 660
gaattttttga aatgcatcaa gctaggtgtt ctaatctagc aaaaggacct gcatacatga 720
attttcatg cttttgccaa gtcttttgcc ctttagttta gttaagggcc ccacatgaat 780
ggaaagcctg tgttgtcagc ttaattttgt agttgtggaa accttccagt tttctccttt 840
gtctaatacc ttcaggagtt caatcctagg ttgaagctta atttaataac catgtggcat 900
gtaaagtaga aaacaaaaca tcttttcctt agcatacagc aaaaaaaaaa aaaaaactca 960
ctcatggatg tagtgtacac atgccagtgg atatatagtc ataactgcag tcattggtag 1020
cacagaaata aatgtgcatt gaagacacag agannnnnnn nnnnnnnnnnn nnnnnnnnnn 1080
nnnnnnnnnn nnnnnnnnnn nnnnnnnnnn nnnnnnnnnn nnnnnnnnnn nnnnnnnnnn 1140
nnnnnnnnnn nnnnnnnnnn nnnnnnnnnn nnnnnnnnnn nnnnnnnnnn nnnnnnnngg 1200
gctagcccag tgtctgactt actgtgttta agaaatatca actattacgc tacttcccag 1260
tgacagtcca aatgcagacc agtgttataa ctctacnnnn nnnnnnnnnn nnnnnnnnnn 1320
nnnnnnnnnn nnnnnnnnnn nnnnnnnnnn nnnnnnnnnn nnnnnnnnnn nnnnnnnnnn 1380
nnnnnnnnnn nnnnnnnnnn nnnnnnnnnn nnnnnnnnnn nnnnnnnnnn aggcaaggtg 1440
gtaaaagacg cttgcacgtg caaatgttac tttgtgtaac tnnnnnnnnn nnnnnnnnnn 1500
nnnnnnnnnn nnnnnnnnnn nnnnnnnnnn nnnnnnnnnn nnnnnnnnnn nnnnnnnnnn 1560
nnnnnnnnnn nnnnnnnnnn nnnnnnnnnn nnnnnnnnnn nnnnnnnnnn nnnnnnnnnn 1620
```

FIG. 5B

```
nnnnnnnnnn nnnnnnnnnn nnnnnnnnnn nnnnnnnnct tagtgaatct aatttgcagc 1680
tgggcttgag aaaaaacctc ttcatagaat tgtttgcatc agtgtcttga ttgcctctgt 1740
aacttacaat aagcaagaat gtttcaggat ttcaaaaatc tattgcattg cctaaacctc 1800
ttattttgta tggagtaatc aagctcaaag tttgcatgtc ttagaaactt tacttggggc 1860
aaaattagac caagtaacaa ttaatcttct aggtattctg agctattcag acatatgatt 1920
catgtttgct aattgctctt ttctcttgta aatattagct gaaaatgtc acctgtctga 1980
caagtagcat attttatgcc tatcactcct ggcacgcatt cttacaaggc agacaggaaa 2040
aataggaaga aaatggactt ttatcaaagg cccaggcagt aaagagggga gttctgctgt 2100
aagctaaggg gagttccaga ggaagttata ggcgttccct ttcttatgac aagaaagcat 2160
agtgcagtaa ataaatttgc taaatagatt caacagtctc tacccaaagt catctattta 2220
attcttgttg ttatgcagac tcagcaacta accttccttg taagccccat tttcttccct 2280
gtttcctgtt tatcaaatgt aattaaacaa gagaagtatt atagaagagt aaaagtagta 2340
ggtaattctt gaacttggca tatgattact acatatttga tgaatagttg aatattattc 2400
ttcaaggaca gattggattt ggtatcaggt ggctctgcat taagttataa gggacttaat 2460
aactcaagta tttaaggacg gcttccatca taaagggatc tgcccttaag agggtcccat 2520
tatggagatt ctgaggtgag agctattcca agtgtgcagt ggattaaaat aaaagaatca 2580
tacaggaaat ctcttttttac atgccttatt ccagggtctt tgcaacctgg cacagcaagt 2640
gcagatatga ttagcattgt tttacacatg tacactcacc ttatagccct gcccctgtgc 2700
ccctcctgca caaagaatg ctgggcacac gtgaactcct ctctgtagaa aggcacatta 2760
atgttctagc catggttaaa acagggatag aggcaagcca aaaatgtcgg tcatttgaaa 2820
taaatctcaa gtttgtgcat atcactatca agtgtgctgt gtggcaatta agaatgccaa 2880
tttgtgtgat cacaggcaag ttgcagtttg atgaaaggaa agcagaggtg aatatataac 2940
cagggtcatc ctttctttct ccctctctct ctttctgtca tttatttgcc aagctcttaa 3000
ctagaacttg ctatgtgcta ggtactggat atatcaaagc aaactcagcc tggtctttgc 3060
cttcaaagat ttgcaggata gtgggaagaa aaacttgaat cagaggacat ctgcagtggg 3120
aatcattcaa gcagcagaaa acccaaaagt tacttatact gtgaaatctg atcagagaat 3180
ggactgtcct ggttagtaaa atatcctgga ggataaagat tggccatgca ttccacatat 3240
```

FIG. 5C

```
gaattaccac tttcccaaga attaaaacat ggtacgaaag aaaggnnnnn nnnnnnnnnn 3300
nnnnnnnnnn nnnnnnnnnn nnnnnnnnnn nnnnnnnnnn nnnnnnnnnn nnnnnnnnnn 3360
nnnnnnnnnn nnnnnnnnnn nnnnnnnnnn nnnnnnnnnn nnnnnnnnnn nnnnnnnnnn 3420
nnnnnnnnnn nnnnnnnnnn nnnnnnnnnn nnnnnnnnnn nnnnnnnnnn nnnnnnnnnn 3480
nnnnnnnnnn nnnnnnnnnn nnnnnnnnnn nnnnnnnnnn nnnnnnnnna aacaacttct 3540
ggaatagcta atgcttagaa gcagctccca aatatttgtn nnnnnnnnnn nnnnnnnnnn 3600
nnnnnnnnnn nnnnnnnnnn gcaagctcta ctgaacataa tttgatctaa tcttctgtga 3660
ttattcagaa actacttcaa gattttccta tacctccatc ataatgaata cccattcatt 3720
aatgatggaa gcagcctaat tttgtcattt ttcacacttt attgatgtaa cactaccttt 3780
actagtttgg ccactcctta tgctttttt atagaactat ttagatcaat tcaacttta 3840
aaaataaag ccacataccc ctgtggtaga tgaaaaacaa gtatcatttg cactggtaaa 3900
tagagaatag gaagaaaaat aaatgcagtg aaaataaagc agtgttatca aatcctaccc 3960
agatactgtt atctacccgg aagcttcctg tttgattaaa aggaaaaata gccagtgtta 4020
gaggtgtgga agtctagttg aaattatatg caattgaagg attaaaatag aattgaaaag 4080
ggaataaatt cctctctgaa taatttaact cccctttaggc tttgattctg cctcatctaa 4140
aatcatctta catacttcta gtggcgtgtc cctcacattt tggtaaactc tgnnnnnnnn 4200
nnnnnnnnnn nnnnnnnnnn nnnnnnnnnn nnnnnnnnnn nnnnnnnnnn nnnnnnnnnn 4260
nnnnnnnnnn nnnnnnnnnn nnnnnnnnnn nnnnnnnnnn nnnnnnnnnn nnnnnnnnnn 4320
nnnnnnnnnn nnnnnnnnnn nnnnnnnnnn nnnnnnnnnn nnnnnnnnnn nnnnnnnnnn 4380
nnnnnnnnnn nnnnnnnnnn nnnnnnnnnn nnnnnnccat ttttcctttc cctttattgt 4440
cagaaaatag aaagcatcta cagtgggctt gtatgatgtg gtggttagaa atacctgatc 4500
tgattnnnnn nnnnnnnnnn nnnnnnnnnn nnnnnnnnnn nnnnnnnnnn nnnnnnnnnn 4560
nnnnnnnnnn nnnnnnnnnn nnnnnnnnnn nnnnnnnnnn nnnnnnnnnn nnnnnnnnnn 4620
nnnnnnnnnn nnnnnnnnnn nnnnnnnnnn nnnnnnnnnn nnnnnnnnnn nnnnnnnnnn 4680
nnaccatcac tggtgagagg aagtgatacc tggcacaaaa atatatggat taatcaatat 4740
ggattgaggg aaacaaacct ggagaatagg atgtgaaggt atttaagtaa catgagctca 4800
gaccttgatg gtagggaagt cgaaaggaag cattttgttc ttatatgaca gatgacctgg 4860
```

FIG. 5D

```
aatgactgca gggcttgggg ggtcagggac tggaggtggg agaggcctct gagagcaagc  4920
agtgctgtcc accagaagct cttgctgggg tgcccagaga ggagcaaagg gcagtcagct  4980
gcacaggagg gaatgtttgg aggagagagc cacctcagat cagcgggtca agaatcccac  5040
tcttgcccag atggatgggg caaaggagaa aaaggattcg ccacgggaat gtccagataa  5100
gacaggtgcc ttttggaaaa tggggtgag atgggtctca ggttacactt cgtaagaact  5160
ggaatgtaaa gtaaaggcag acaatgacaa aatatcttgt tttcttttca gct tta     5216
                                                         Ala Leu    20 ttc aca gtg aca gtc cct aag gaa ctg tac ata ata gag cat ggc agc   5264
Phe Thr Val Thr Val Pro Lys Glu Leu Tyr Ile Ile Glu His Gly Ser    36 aat gtg acc ctg gaa tgc aac ttt gac act gga agt cat gtg aac ctt   5312
Asn Val Thr Leu Glu Cys Asn Phe Asp Thr Gly Ser His Val Asn Leu    52 gga gca ata aca gcc agt ttg caa aag gtg gaa aat gat aca tcc cca   5360
Gly Ala Ile Thr Ala Ser Leu Gln Lys Val Glu Asn Asp Thr Ser Pro    68 cac cgt gaa aga gcc act ttg ctg gag gag cag ctg ccc cta ggg aag   5408
His Arg Glu Arg Ala Thr Leu Leu Glu Glu Gln Leu Pro Leu Gly Lys    84 gcc tcg ttc cac ata cct caa gtc caa gtg agg gac gaa gga cag tac   5456
Ala Ser Phe His Ile Pro Gln Val Gln Val Arg Asp Glu Gly Gln Tyr   100 caa tgc ata atc atc tat ggg gtc gcc tgg gac tac aag tac ctg act   5504
Gln Cys Ile Ile Ile Tyr Gly Val Ala Trp Asp Tyr Lys Tyr Leu Thr   116 ctg aaa gtc aaa ggtgagtggt gtcaaggact agaatccatg gaagctctct       5556
Leu Lys Val Lys                                                   120 ccaacagagg atctgcaagt cacagaaacc cattaaaggt agctcaagca aaacaagca  5616 ggctgctttt aaggagacag ctatttcaga gaaaatgaaa gcatctgctc ggaaataatt  5676
tttgacatct gagtacaaag cagccgaagt acaagtgaaa gggggtagga cctataggaa  5736
taaaatggga ctggaggaag ccaggaaaat tagtccctga aatgtgggag ggtatgaaaa  5796
ataagctttg cctaattcac aattctccca tggaacatcc ctgacttgat tattaagata  5856 ctcttttca atagtttata ccctgaatcc agagttttta aaccatggt ttgccgccca   5916 ttcatggatt aaaatatcaa tttagtgagt agcaaccaga tgcacgtttc ccgcccttta  5976 aaaataatg tatagaagag aatagacaga gtagatcaga cgatatcaca gagtaggact   6036
gagtactgta aaactaattt ctgagggacg tgtgtgtgtg tgtgcgtgtt gggtcatggt  6096
ataaattttt tttttcttac tttggatcat aaaaagttac aagtttggaa aacactgctc  6156
```

FIG. 5E

```
aaatgcaagn nnnnnnnnnn nnnnnnnnnn nnnnnnnnnn nnnnnnnnnn nnnnnnnnnn 6216
nnnnnnnaga gtcccatgaa gtctatagct gtccctattc ctctggattc agggatctct 6276
ccactccagc acaattgaaa atctaaatat aaagagaatc ttcacactct tgtttgttct 6336
agaaaggtg atttgaggaa agacatataa caactataaa aaatagattt tgcttgttca 6396
ttggcttatg gtctccaggc ttgaatgctc tgagataaat gatgccaata tttctctggc 6456
ctcttcccat cccacgcatt ggacctcaga tggtctgtac tgtcttctag agggtttgtg 6516
ggttttggcc ccaaaaaacc attaaccttg gcagaaagtg tgtgacttta tgatctggta 6576
caaagaagga caaactagag ggactggaca tgaggatgaa tattgtgttc gcccttatnn 6636
nnnnnnnnnn nnnnnnnnnn nnnnnnnnnn nnnnnnnnnn nnnnnnnnnn nnnnnnnnnn 6696
nnnnnnnnnn nnnnnnnnnn nnnnnnnnnn nnnnnnnnnn nnnnnnnnnn nnnnnnnnnn 6756
nnnnnnnnnn nnnnnnnnnn nnnnnnnnnn nnnnnnnnnn nnnnnnnaaa gaccctcagt 6816
tgttacaggg gcagtgacct cctcacacct caaccatcaa tgagtcacca ggaaagccat 6876
tagcctagat gtaactgttt tctatcttta ttgcatttcc tacatccagg cagcagctgg 6936
gaggaactct agaacactga agtttgtctg agttcccta atgtaaggct gtacattctc 6996
aggatgcctt gatgtactcg aatatctgca accctaaatc accacctctg tttttattga 7056
tctctatctg aatgctgtat taatgggcca ggccttctgc ccattctctc aaactgagaa 7116
ctgtctctca ttcctgggga ggcaccctgc ctactcctta cctagatcag ggatttctca 7176
gttgtggaga gatttgttcc ttatagtgtt ggtcatcaaa ctgggatatt tggggattac 7236
aaagactttt caagggatgt atgggcacag gcagttttag gaagtgagtt cctagatcct 7296
catcttcccc aaatactcgt tcccaaaatt gacgagcctg acaatgtgca tgccaggcaa 7356
ggctcttggg gttcccctaa aacacttcct cttttaagcc taccactcac tcatcatgaa 7416
tatagtccat tgtcccaggg tgtaaaaccc tctatagtgt taaataaaag aatgattggg 7476
aacattgaca cctgatggaa ctgttatgac taaaaaccct tttgcaaata atgtggtatc 7536
taattttctg ctttcaacaa aattgaagga ggcccttata aagttaataa ctgataatca 7596
aaaatgagta attttttgcca tgtaaatcag gtcaaagaat gaaatggcat tgctgtaacg 7656
aaactgcttc cattcccatt gatttactca tacgaacaag attccttagc ctttataagc 7716
tacaaaaaaa tgaaaaatag aaatagaatt gaggctgaat tctattatat aaaatcattc 7776
```

FIG. 5F

```
caaccatgtc atatggttct tcggattcat gaataatttg gaaaagagag ccatatccat 7836
cttattaagg gacacattcc caataaattt tcatctttca tgtttaataa ttatcaatat 7896
tcataacatt ttacattttg atcaaatatg tgttaataat aatagaaatn nnnnnnnnnn 7956
nnnnnnnnnn nnnnnnnnnn nnnnnnnnnn nnnnnnnnnn nnnnnnnnnn nnnnnnnnnn 8016
nnnnnnnnnn nnnnnnnnnn nnnnnnnnnn nnnnnnnnnn nnnnnnnnnn nnnnnnnnnn 8076
nnnnnnnnnn nnnnnnnnnn nnnnnnnnnn nnnnnnnnnn nnnnnnnnnn nnnnnnnnnn 8136
nnnnnnnnnn nnnnnnnnnn nnnnnnnnnn nnnnnnnnnn nnnnnnnnnn nnnnnnnnnn 8196
nnnnnnnnnn nnnnnnnnnn nnnnnnnnnn nnnnnnnnnn nnnnnnnnnn nnnnnnnnnn 8256
nnnnnnnnnn nnnnnnnnnn nnnnnnnnnn nnnnnnnnnn nnnnnnnnnn nnnnnnnnnn 8316
nnnnnnnnnn nnnnnnnnnn nnnnnnnnnn nnnnnattag atcttaatgc agaacaccct 8376
gaacatttaa agcttcatag tcacaagaga aaagttttca tttcaatagc tataaatatt 8436
ttgttgttgt aaagacatat aacgataatc aatacaaaat ctgtcaaaca aaaatatgtt 8496
acattaagat aaaattctgt agggaaggtg aaattggaag tgagtttcaa tgaatgaaaa 8556
gaaacaattt agacagagaa gnnnnnnnnn nnnnnnnnnn nnnnnnnnnn nnncttagaa 8616
ggaattgaat agattaggtt ccttacccaa aaagcctctg ttatttgtct tatttattta 8676
ttctcttttt tccacattct ccagtctcat tcccctttt taacacagga aattattcca 8736
gcatgtttca tacatattct tttgtttgta agagcttatt taaaatatgt aatattgttt 8796
tagatgcata tatttttttt cttgtggaaa ctatattgta ctatatatat atattttaga 8856
aatggacaca ttannnnnnn nnnnnnnnnn nnnnnnnnnn nnnnnnnnnn nnnnnnnnnn 8916
nnnnnnnnnn nnnnnnnnnn nnnnnnnnnn nnnnnnnnnn nnnnnnnnnn nnnnnnnnnn 8976
nnnnnnnnnn nnnnnnnnnn nnnnnnnnnn nnnnnnnnnn nnnnnnnnnn nnnnnnnnnn 9036
nnnnnnnnnn nnnnnnnnnn nnnnnnnnnn nnnnnnnnnn nnnnnnnnnn nnnnnnnnnn 9096
nnnnnnnnnn nnnnnnnnnn nnnnnnnnnn nnnnnnnnnn nnnnnnnnnn nnnnnnnnnn 9156
nnnnnnnnnn nnnnnnnnnn nnt                                         9179
```

FIG. 6A

```
tagatctcag ctttcttgag gcagggagcc atatctgttt aattcactca gcatatactg    60
caaagaagca gnnnnnnnnn nnnnnnnnnn nnnnnnnnnn nnnnnnnnnn nnnnnnnnta   120
gggagaagtg cagaataaat atacccaact ctttactatg tatagacatt atctaggtct   180 ttatttttt  tctcttctta atctcaaaga aaacagagga aaggaggaag taaaaagtaa   240
atttttgcct gaagatgttt ggaaaaaata ccaaataaag tgagatagtg ggtaatctag   300
tgatttttat ttttccgtcc tctttctggc ctccaattgt gaaataattt atagcactgt   360
aagaaagaag ccacaaattg tggtagcttg gaccactgtt gaggnnnnnn nnnnnnnnnn   420
nnnnnnnnnn nnnnnnnnnn nnnnnnnnnn nnnnnnnnnn nnnnnnnnnn nnnnnnnnnn   480
nnnnnnnnnn nnnnnnnnnn nnnnnnnnnn nnnnnnnnnn nnnnnnnnnn nnnnnnnnnn   540
nnnnnnnnnn nnnnnnnnnn nnnnnnnnnn nnnnnnnnnn nnnnnnnnnn nnnnnnnnnn   600
nnnnnnnnnn nnnnnnnnnn nnnnnnnnnn acttaatatt gatagtgata attttattca   660
tttcacatgg catgaagtac caagctctat aggaatcaga aaataaagtc ttatttcttt   720
ttcttctcta ttgtcca gct tcc tac agg aaa ata aac act cac atc cta        770
                    Ala Ser Tyr Arg Lys Ile Asn Thr His Ile Leu       131 aag gtt cca gaa aca gat gag gta gag ctc acc tgc cag gct aca ggt       818
Lys Val Pro Glu Thr Asp Glu Val Glu Leu Thr Cys Gln Ala Thr Gly       147 tat cct ctg gca gaa gta tcc tgg cca aac gtc agc gtt cct gcc aac       866
Tyr Pro Leu Ala Glu Val Ser Trp Pro Asn Val Ser Val Pro Ala Asn       163 acc agc cac tcc agg acc cct gaa ggc ctc tac cag gtc acc agt gtt       914
Thr Ser His Ser Arg Thr Pro Glu Gly Leu Tyr Gln Val Thr Ser Val       179 ctg cgc cta aag cca ccc cct ggc aga aac ttc agc tgt gtg ttc tgg       962
Leu Arg Leu Lys Pro Pro Pro Gly Arg Asn Phe Ser Cys Val Phe Trp       195 aat act cac gtg agg gaa ctt act ttg gcc agc att gac ctt caa agt      1010
Asn Thr His Val Arg Glu Leu Thr Leu Ala Ser Ile Asp Leu Gln Ser       211 aagagctgcc cccacttcct aggtctatca gttagggttc agacaagaaa cagatggcat   1070
actcgagtga tttgaggaga gtgtaataaa gggactgttt acaaaggtgt gatcaccatt   1130
tggagaaact acaaggata  gtgcagaaca ctggggcttc aatgttggga gggcaattac   1190
cactgttgga gaagttactg gaatcagaag ggagctgtag ggaaagcccc acttcccagg   1250
agctgtagcc acagaatagg gaagctgcca catgcagcga ctccaaaggg tggaaactgg   1310
atgaatgaat accccaactc attctcctcc caccctccaa tctcctgcta gcacctccca   1370
```

FIG. 6B

```
ttggctgaac ccagctagaa gtcagagaat acaagggtcc actgttgtat tccataaaag 1430
tcaacttctc agggctcaga gcaatattga catgtacaga atagatctgg agaggaaaca 1490
gaaaatatct agtacaatag ctaatcactg tgattcatgc acagtgtcat gagccagcag 1550
gatgaatatt cctttgctgt acttgctgcc agtcagctgg ttatgggttt ttccaagaaa 1610
tttggtctct aacaaaattc ttcagagcct ttactgacta tgctggatat ttttggaagg 1670
gatcccatac ttttgaactt catacagcag aatttcaaac aatcttggga aaataacaac 1730
ttttatctgc ccagtaagga caactaacac ctagtatcat aatcatttcg taagagacag 1790
gtaatttcat caccgagtgc atat                                      1814
```

FIG. 7A

```
ctactgagaa gggatatact ctcagactaa aggacagtcc ctagtactga ttcaatctgg 60
ctttatagaa aattcactat attgtcattg tatttcacag tttgcccttt gtcttagctg 120
gtaagacaga gcctatgata aggacttgtg tggcatgcag gtatttaatt ggcaacccca 180
gagggcagaa gcaagagatt taggagttta agagagggta atataagagt atattatcaa 240
agttgtagtg tggacaacag aaactcaaat attcaaggac cagcatgtag acagcctcct 300
aagatgtcta ctcagacaaa gaatttcagg tggaaggact tgttcatctg cttcacgccc 360
attggttgac aggaatatga actccattct gctgctgggc tagacatgca tgtgggctga 420
gtgagctttc cccagtatcc gtagcatcag aaaagtcgca gggcagaaag aaaagtatcc 480
aatttgaggt gaattactga ccttgaagtg agtgtaagcc taactagaat tctaccccag 540
ctggctgaag tgaaggtga ggctgagagg aaataaggca ggactgcaca gtccccaatt 600
gtactgttca aatccactca tgcccttcat taagtcagct ctgccactga gccttccagc 660
tgggaggcag ccacaatctc tgcagaagat ttaatataca ccagtttgtg gaacaagctg 720
tnnnnnnnnn nnnnnnnnnn nnnnnnnnnn nnnnnnnnnn nnnnnnnnnn nnnnnnnnnn 780
nnnnnnnnnn nnnnnnnnnn nnnnnnnnnn nnnnnnnnnn nnnnnnnnnn nnnnnnnnnn 840
nnnnnnnnnn nnnnnnnnnn nnnnnnnnnn nnnnnnnnnn nnnnnnnnnn nnnnnnnnnn 900
nnnnnnnnnn nnnnnnnnnn nnnnnnnnnn nnnnnnnnnn nnnnnnnnnn nnnnnnnnnn 960
nnnnnnnnnn nnnnnnnnnn nnnnnnnnnn nnnnnnnnnn nnnnnnnnnn nnnnnnnnnn 1020
nnnnnnnnnn nnnnnnnnnn nnnnnnnnnn nnnnnnnnnn nnnnnnnnnn nnnnnnnnnn 1080
nnnnnnnnnn nnnnnnnnnn nnnnnnnnnn nnnnnnnnnn nnnnnnnnnn nnnnnnnnnn 1140
nnnnnnnnnn nnnnnnnnnn nnnnnnnnnn nnnnnnnnnn nnnnnnnnnn nnnnnnnnnn 1200
nnnnnnnnnn nnnnnnnnnn nnnnnnnnnn nnnnnnnnnn nnnnnnnnnn nnnnnnnnnn 1260
nnnnnnnnnn nnnnnnnacc tgcagcactg ggatagccct ggtacagacg tagaacatgc 1320
ttgaggaggt tgtcaggagg aaatgagtta gaccttgcac agaactacca ccatcaagta 1380
cagttggggt gaggcagaca tggtatgagt tgaggcatca gagatatctg atgctttatg 1440
ccaaattaaa attaattttt tcatggagtg acactgatcc acagaccaga ctccaagaac 1500
tttgcagtga ctaaataccc atctcatcat aacttcctg gtattttctt ctggaaaaaa 1560
ttcttccctg atacagtttt cagaggcagc tagatgcact gtcatctctc ccctttccc 1620
```

FIG. 7B

```
acttccctac ctatccacaa tttactaccc aatgccaaca ctaaagttag cccaacttcc 1680
ttctaactaa attattagtt tagaaggaaa gagaggagtc atgctaagga tcttaactgn 1740
nnnnnnnnnn nnnnnnnnnn nnnnnnnnnn nnnnnnnnnn nnnnnnnnnn nnnnnnnnnn 1800
nnnnnnnnnn nnnnnnnnnn nnnnnnnnnn nnnnnnnnnn nnnnnnnnnn nnnnnnnnnn 1860
nnnnnnnnnn nnnnnnnnnn nnnnnnnnnn nnnnnnnnnn nnnnnnnnnn nnnnnnnnnn 1920
nnnngggag aggaggggag aggaggtagg gagggaaag aaagaaacta gaaatccatc 1980
aattttagga ccaacttcag gtaaaaaaat gaattaggca agttggtctt tcaacattct 2040
ctacctctct ttatatcatg gttgagacca cagacttctc acctcatgaa agatgaactc 2100
taactaattc atactaaagc taaagcctct aaagaggatt aaatatgagc aatcccacga 2160
gaactttttt ccctggaat tgtttattca actgtcgttc gttatatgga atttcctgcc 2220
tggttaagtg taggccagta ctttggatga attgtagttt tctagaaaga cgcttcttat 2280
ataagaacct ctccagggaa acagggcct gtatgagatg aattgagaaa taactttaca 2340
ccactgatta tgtcagtgtt ctattctgca tggtagagat gtgaaagggc agactgacca 2400
ttgctctgga agcctttacg ctgtgagaag ttaacagtgg agtaaaatgg ccactccact 2460
ctcttcatgg aagccaacat ggcttactaa atagtcaaca accatgggag agacctgtgg 2520
ggtcttcatc agagctcagg atctcctagg gtatcactca taaatacagc catcagggag 2580
atggagaaat ctttgtgcag ccagaaattc tcaacctggt tttacccatc cttcccaact 2640
ttgtattcgt cctactgttt actgacatgg atcctctgct tcattaacca tcccttcctc 2700
accacatgct ctctgaactt ggctgcacct tttctacctc catgccttct ttgctcaggt 2760
ttttccacat aaatatcatt atttccctct ctactagctc caagcccacc ctctctctgg 2820
ggcagctcag tcactccagg gcacaagggg gtctttccct catcccacat tttgagacct 2880
actacctgga ccatttgttt gccttgtaac tatgcttgcc tttttaattg ctattttatt 2940
ttccatgtat tttcattgtt cacacaagtc ttctttattc cacactaagg caaaagcaga 3000
gtcctgtgtt cataataagt gctcaacaaa tgttgggttg attgggttgg agattccatc 3060
ttagataatc gcagtcccat catgccagct accagactgt gtggacagcc aggtcagagc 3120
agccaaatga tattctagct tgtggcacaa ataccagcaa caaaataacc aaagtcacac 3180
atctgcctct gagttcctgg cttctatttc tcaagggcat ttttaagttg tcttatgact 3240
```

FIG. 7C

```
gttcccttto tactcattct cataaattga gctgtggact gctgtgaccc acaagcttct 3300
ccggaagtca atgtataaaa caaacacgga aacgaagagt atggtgggtg gagggtactc 3360
cactgactct agaatggatg actgaacatt ccaaatttca agcacaagtt agggagcaac 3420
agatcatttt ccttttgaaa tagggtttct tctgctcagc cagttgttgt attttcatta 3480
ggaaatggaa tgggactaca gcacaaaaaa taaatataaa aggacccttg tagggctggc 3540
agaaaagaga atccttccta ggagacctgg aggtgattcc aggcnnnnnn nnnnnnnnnn 3600
nnnnnnnnnn nnnnnnnnnn nnnnnnnnnn nnnnnnnnnn nnnnnnnnnn nnnnnnnnnn 3660
nnnnnnnnnn nnnnnnnnnn nnnnnnnnnn nnnnnnnnnn nnnnnnnnnn nnnnnnnnnn 3720
nnnnnnnnnn nnnnnnnnnn nnnnnnnnnn nnnnnnnnnn nnnnnnnnnn nnnnnnnnnn 3780
nnntcagaaa gtgtgcaaac agtaaaaaaa aatggtatat ctagcaagtt gcatgcctta 3840
cttgtgagtt catgaagttg tggcaaggat aagacaaata tttttgcca ttgcatcatt 3900
atatcattgc taagagtatg ccattattnn nnnnnnnnnn nnnnnnnnnn nnnnnnnnnn 3960
nnnnnnnnnn nnnnnnnnnn nnnnnnnnnn nnnnnnnnnn nnnnnnnnnn nnnnnnnnnn 4020
nnnnnnnnnn nnnnnnnnnn nnnnnnnnnn nnnnnnnnnn nnnnnnnnnn nnnnnnnnnn 4080
nnnnnnnnnn nnnnnnnnnn nnnnnnnnnn nnnnnnnnnn nnnnnnnnnn nnnnnnnnnn 4140
nnnnnnnnnn nnnnnnnnnn nnnnnnnnnn nnnnnnnnnn nnnnnnnnnn nnnnnnnnnn 4200
nnnnnnnnnn nnnnnnnnnn nnnnttaatt aattaaatta agaaacgac aaaagagtat 4260
gcaagaattt taaaacaact tagaggaata tgtatgagga tacaggctaa gctaccataa 4320
tgaagagacc tcgaaataca gtgagaagcg agacagaagt atctttcgtt ccatgtaaca 4380
ctcaggtggt tcagagcagc taagcagcta tgttccatag agtcattcag tgatccagat 4440
tattttcatc tgttgctctg ccattctcca ggatgttgtc cctataaaat tgtcaaagct 4500
cagtcagtgc caaacccatg tttcaacctt cagaaagtaa acgagtggtg gaaaacacat 4560
tcaatgtttt aaggccaaga ccttgaaaac tcactctctt agcctgaact tagattacat 4620
ggctgggccc acttaactat aggggaggct tggaaacata gtctctgaga agccatgtgt 4680
ccagctaatt ccctaatact aaagttgaaa gaaagaatgg attaaccagc agtataccac 4740
aagtaacaa atgactagga ggatcaggct aggtggacta gaaaagagac agtcaattca 4800
gtgcaacaat tccatattga cacttttcat gtagctgttg cttggctcta tctagagagg 4860
```

FIG. 7D

```
actcagaggt agtttagata aggcctttgc cctccaaata cagtctaagc agactgattt 4920
cctactggat gttcaacttt ggagtcttca gggatgagta gggcttctgt acgtggaaga 4980
gactatgagg gaacctgcac aggacaaggg tttgcataaa gacactgagg tagggacctc 5040
tcctgttgtg gggacagtga gaggcccagg tctccttgac tcacaaagtg cttactaagc 5100
acttactaga aattaagaag cagattataa tcaatatggg ttatccaatg tttggatgag 5160
caaggctcct tatctttct tcgttaatgt taatcacact cttttggatg gagacaaata 5220
tctgtggggg ctnnnnnnnn nnnnnnnnnn nnnnnnnnnn nnnnnnnnnn nnnnnnnnnn 5280
nnnnnnnnnn nnnnnnnnnn nnnnnnnnnn nnnnnnnnnn nnnnnnnnnn nnnnnnnnnn 5340
nnnnnnnnnn nnggctcaga ctaaataatg tctaatctct tctccagtaa aacaatccgt 5400
ggttctcaga tagcactgtg ctggaggtag tggggtttga gggctgggaa gttgggagga 5460
ctgagccctt cccgctgagc agtttcgtcc agtttttcct gtaccagcct gtcatgttta 5520
ttccatgtga atgactccag aggcaaaatt caagcttttg aatagggcac aaattaactt 5580
gagtacccct tcatttccct gtaggtgaac actcctctag ccctgccttt tgtcagtctg 5640
gagcccttgt tctaatctgt acacaccaga ggactttaca aggctttccc cagcctccag 5700
aattattctt ctgatccacc ctctactaaa ctcacccttt cctcagtgct aggacgttga 5760
aaaaccgaaa caaggcaaag ggccaattgt aataattcac actaaggcat gagtgactag 5820
gtttagtata ttaacactac ctaggatatt ctatttcttc caaaaggatc ctgttaatcc 5880
ttgaaattta acaactaatg gtatagattc taagcactgt gagtacttgt cagtggggga 5940
aagacatttt tgggctgaga gactttgcca ctgnnnnnnn nnnnnnnnnn nnnnnnnnnn 6000
nnnnnnnnnn nnnnnnnnnn nnnnnnnnnn aagaaagatg attagatnnn nnnnnnnnnn 6060
nnnnnnnnnn nnnaaaaaat aacatgagag nnnnnnnnnn nnnnnnnnnn nnnnnnnnnn 6120
nnnnnnnnnn nnnnnnnnnn nnnnnnnnnn nnnnnnnnnn nnnnnnnnnn nnnnnnnnnn 6180
nnnnnnnnnn nnnnnnnnnn nnnnnnnnnn nnnnnnnnnn nnnnnnnnnn nnnnnnnnnn 6240
nnnnnnnnnn nnnnnnnnnn nnnnnnnnnn nnnnnnnnnn nnnnnnnnnn nnnnnnnnnn 6300
nnnnnncaca gagctagccg tgttggctgt cacccactca tgtggccagc ctgttggtct 6360
acctcttagt tgccatgtaa caggattctg gtgcttttcc tttgcccagg t cag atg 6417
                                                         Gln Met 213
```

FIG. 7E

```
gaa ccc agg acc cat cca act tgg ctg ctt cac att ttc atc ccc tcc    6465
Glu Pro Arg Thr His Pro Thr Trp Leu Leu His Ile Phe Ile Pro Ser     229 tgc atc att gct ttc att ttc ata gcc aca gtg ata gcc cta aga aaa    6513
Cys Ile Ile Ala Phe Ile Phe Ile Ala Thr Val Ile Ala Leu Arg Lys     245 caa ctc tgt caa aag ctg tat tct tca aaa ggtaagtgag ttttattcat      6563
Gln Leu Cys Gln Lys Leu Tyr Ser Ser Lys                             255 ggtaacccaa tgcactgggt gtctgcagca tgagccactg ctttgcactg caggcctatg   6623
gcttgctgct ttcatgctaa acccactcag agcttatgaa ccactttgag cttgtcttga   6683
tgattatttt tccccagaag aaaatggctc tcatcgtcag tgagctgaac ttcttacact   6743
gagttttta aagggaatgt tttgttctta tgtctgaaag agtttgtctt attctttgag    6803
ccaagagctt tcatcagcct catgagagtg atgttatttt ggcaatgcag agagctacgt   6863
gctccgattt tgctggtggg aggttgccag gatcctttct gaggattcct tccattttca   6923
cccctctttt ccccagtctg gatatgacct gggttaaacc caccccctct cccaggaatc   6983
tcaacctcac ggttgggtaa ggaaaggaga aaggtttgtg aggccatttg gggataagga   7043
aacagctggt tggtggtgca ttaacgtctt tcagcagctc ccttcgagtt tctccttagc   7103
ctgttgtatt cttaccaaca cactcctgtt ctgttgtacc agctgggaca gagcatgctg   7163
aagcctttca gccctgattt cattgcttca ttgttcatgt gtctgtcttt ggtttcctgg   7223
gtggagcctg cccacaaaac ccccagaatg tatgcaggcc tagctggtgc tttcctaaac   7283
ggctcccttg tctgcactca atgaacttct ccaaagatct atacatggcc tcatctatag   7343
aaagagaaat gacatgtgga ataattcag taggagtttg cagcagcact atctgaggac    7403
tagggggaatt ttaagtggtt gttatcttac atttatactc ataacttcta tattttcatc   7463
tgccataaaa tattgtcatg ttctatttgt ccattgccct atgtgtgtat gtattcactt    7523
gggtgctgac cacaatattt ctaactgtag aatgcaagga attgttgcca aannnnnnnn   7583
nnnnnnnnnn nnnnnnnnnn nnnnnnnnnn nnnnnnnnnn nnnnnnnnnn nnnnnnnnnn   7643
nnnnnnnnnn nnnnnnnnnn nnnnnnnnnn nnnnnnnnnn nnnnncttca tggtaaagga   7703
ggaggtatgt ccaacagaac ttcgactttt aaatagaacc acttcagaga gttgtgtcag   7763
gtgcacctca gttgtcttat cttctgccat tcttctttta cctctcacac ccatacctca   7823
gggttcaagg cctggggcct gaggactcct taataacttc agaaatgagc agctgagtgt   7883
```

FIG. 7F

```
tccgttccag ctgtctttgg gagaatggaa tggagtcaca ctcaaagata gagtggaaat 7943
aaatcctctc ctcatccttc accccaatct taagagtgag tgaggatatc agtagctccg 8003
agctgggagg taaagctcaa gttctaactg tgattaggag acctttctta caaataagaa 8063
ttaagtgaat aaatgtgcaa acaatttctt ttatattttt aatgaaccag agagaaatca 8123
tggttgccta tataacccct gtctccaact cacttgcatt cagatctgct ttcttacatg 8183
tgtctgccat gcacacaaac ttgtgtgcca tggaaaaggg ttgagaactg ctggtgatgc 8243
agacagagct ttaaannnnn nnnnnnnnnn nnnnnnnnnn nnnnnnnnnn nnnnnnnnnn 8303
nnnnnnnnnn nnnnnnnnnn nnnnnnnnnn nnnnnnnnnn nnnnnnnnnn nnnnnnnnnn 8363
nnnnngcagc aagagaagga acattttaca gcttattggc cgaacttcac tgccgctagt 8423
gtggttcaac ttggactaca gagaaatctt cctaactggt ttccctgtat tcactcctgc 8483
tacctccaac ttggtctgtt ctcactttt gctataatag gcttttaaaa atcataaatc 8543
taccatgtgt cctctgtcca gaccttctcc atggcttctt attgctcact ggatgaagtt 8603
ccaacgagcc caggatggtt tgactcatgt ctccagcttt aactgcatca ccatcacctt 8663
cattgtctaa agctctaacc acacaggatt ttctagtcct cagaggcatg gcagtctttc 8723
aattccgagt tttctcatac aatattgtct cttcttaaaa tattttttct tgttgtccac 8783
ctgagttgga gtcatctttt aaatctcagc taagcttata cttcatcaag tctttcctaa 8843
ttctacctcc acgcaccaca cccattacat taaatcccct tattatatgt ttccatagca 8903
cctactttct tcttttcagt atactcagca cacaatcaca tgtctaggat ctgttttaat 8963
agcttggact accaattaaa ttgcatccct tttaattgtc cattgattcc tcaagtaccc 9023
acatgcccat cttagcaaga agttcagtgt ctccctctta tagcatgtac ttctccacct 9083
cccacaaact gccagaaagc ttacttagcc cacagggcca gtgctaggca gctaggttag 9143
tcctccagag ggccctggtt tgagcagtt gctgtctact ccggccatgc agaatctctg 9203
gtccttccag atgtctccat ccactgtgca aaggtaacct tgctggttcc gatccccaca 9263
cagaccacag tgctacaaga ttacagttct tatggttccc caacacatgc tctgtcattg 9323
gtcccaaagc aggacccccta tgggttgatg aggtaggagg aggtccctgc cttagccaca 9383
gctgcacaca gccagcctct tcccttctag gccctcatgt tgagcctggg acgccagtcc 9443
taacttcctt ctcttcagtt cctcttaggg ccattggtat cctgaatttc ttagtccatt 9503
```

FIG. 7G

```
gcaaagttaa gtaaagaagc agcaggcttg gtcccttttcc ttccagatgg cttcttagct 9563
cctgaacaga tttacccacc tatacctcag tgactagctc tgtgtactaa agtgtattgg 9623
gagggcagcc attattggtc cataaaaggt cctgcttacc attttcccct aagaggaacc 9683
attcaacagt ttggggctcg agggtgacct gctgggctct agagaagaag ctggcaactt 9743
ctgttgcaaa ataatgttaa attctgcttc atctgcttgt cttnnnnnnn nnnnnnnnnn 9803
nnnnnnnnnn nnnnnnnnnn nnnnnnnnnn nnnnnnnnnn nnnnnnnnnn nnnnnnnnnn 9863
nnnnnnnnnn nnnnnnnnnn nntaaacatt gaacctacta tatgcaggtg agtatgctag 9923
atnnnnnnnn nnnnnnnnnn nnnnnnnnnn nnnnnnnnnn nnnnnnnnnn nnnnnnnnnn 9983
nnnnnnnnnn nnnnnnnnnn nnnnnnnnnn nnnnnnnnnn nnnnnnnnnn nnnnnnnnnn 10043
nnnnnnnnnn nnnnnnnnnn nnnnnnnnnn nnnnnnnnnn nnnnnnnnnn nnnnnnnnnn 10103
nnnnnnntgn nnnnnnnnnn nnnnnnnnnn nnnnnnnnnn nnnnnnnnnn nnnnnnnnnn 10163
nnnnnnnnnn nnnnnnnnnn nnnnnnnnnn nnnnnnnnnn nnnnnnnnnn nnnnnnnnnn 10223
nnnnnnnnnn nnnnnnnnga tttgaataca ggtctgtttg actccaaaac ttgtggccta 10283
tttgttgcaa aagtgcttaa tacaaattgg ttcagtcaat attattatct ttgaacaatg 10343
gaaggagaaa gtaagtttca atccaaaata attgagtgac ttatacattg acttgctgag 10403
ccaatggcaa agtcaagtta gaatccagca gaagtcacca gctacagaat ctagatcttt 10463
agaacatgtc ttcagatctt cagaacagtg tttcttaaac tctcttgtga aggaacagtt 10523
atcatcatag gctggtaaca gttcacctac cagcaccagc ccatgaacca gactctaagt 10583
ggcacagccc tagaagattg agccagaatt ttacagaggt ttaaagacca aatatgctgg 10643
tttatggtta cctgtggccc acagagaatg gcagcactaa cctcaggcat aaatgaggta 10703
cccactgaag ccaacattca agagcaattc ctatgggtta accattgggc tcctttcaaa 10763
tgcaaaccct catgaaagag actacagtgc tgaatagaga cctccaaatt ccaggccaag 10823
ctcaggatag tcatgaggga attactaaaa acctggtata tagggcaaaa gcagaattag 10883
gaatggactg atttcaggaa cccaggcaat ggcaggagtt gggcattaaa tcctaaaaga 10943
gaatcagagt gggagggaat atgtgaaatc agaggttaag aaaaaagtga aaacctnnnn 11003
nnnnnnnnnn nnnnnnnnnn nnnnnnnnnn nnnnnnnnnn nnnnnnnnnn nnnnnnnnnn 11063
nnnnnnnnnn nnnnnnnnnn nnnnnnnnnn nnnnnnnnnn nnnnnnnnnn nnnnnnnnnn 11123
```

FIG. 7H

```
nnnnnnnnnn nnnnnnnnnn nnnnnnnnnn nnnnnnnnnn nnnnnnnnnn nnnnnnnnnn 11183
nnnnnnnnnn nnnnnnnnnn nnnnnnnnnn nnnnnnnnnn nnnnnnnnnn nnnnnnnnnn 11243
nnnnnnnnnn nnnnnnnnnn nnnnnnnnnn nnnnnnnnnn nnnnnnnnnn nnnnnnnnnn 11303
nnnnnnnnnn nnnnnnnnnn nnnnnnnnnn nnnnnnnnnn nnnnnnnnnn nnnnnnnnnn 11363
nnnnnnnnnn nnnnnnnnnn nnnnnnnnnn nnnnnnnnnn nnnnnnnnnn nnnnnnnnnn 11423
nnnnnnnnnn nnnnnaaaaa attaaaagaa agatgtgaaa tcaaggaaac ttactggtga 11483
gcagcatccc attatgtgaa cttgtgcttc tgaaccagta acttgagtta ctttgagcca 11543
gtatcagtca cttataccct agtgcaaaat taattgatca gacattctga cctggaccag 11603
ggaaggcagg cagaagtagc agtcaagact aaagcagaaa agggagagct aattctgcag 11663
ccagacattt cctggattga atacccaaat tagtccctca gcctttaagt gcctgagggc 11723
caggagtaga cagaggaatg gaaagtgtga gacttctttg ttcacactct ttgcctaggg 11783
gccagatttt gctttatgca ttaccatccg aagtcccagg ccacagtgaa catttgggct 11843
tcgctatgtg gatttattta gatttacttt ttgtcctgcc atattttaat ctataagcca 11903
aacagttttc tcattaatct tattccattt ctggaatttt tccttttca gac aca aca 11961
                                                       Asp Thr Thr  258 aaa aga cct gtc acc aca aca aag agg gaa gtg aac agt gct          12003
Lys Arg Pro Val Thr Thr Thr Lys Arg Glu Val Asn Ser Ala          272 gtgagtaagc atgattttta cttttctttc ttactttctt ttctctctca gcttgaattt 12063
taaagtaacc actgttctat taattcatgg aaggcaactg aatagttcca gcttatagaa 12123
tcttcctgtt tggtagcatt tcagcgaagc ctcgttctta gccccagaac aatcatgcca 12183
tcttttgctc ggtctatatt cctaagcact cctagatgat actgcactgg acctctggtc 12243
tcacatagtt agaaacagag ttaaaatcga acagcaaaga gaagatattc aactgcgatg 12303
caattgacaa tggatgtttt tgcaacaaac aatgattaag aagtacattg ttgtgggctc 12363
tgagtcaaga gtaatatggg aaaaacacaa gtctcttcat gaggttgaca ggtttggagc 12423
tggaatctgt ggaggaggaa ggatatgatc tagggggtcag aagaagtggg ttactaaaat 12483
cattaagcct ggttggatga aaagcttaga ctcaggggaa gcagnnnnnn nnnnnnnnnn 12543
nnnnnnnnnn nnnnnnnnnn nnnnnnnnnn nnnnnnnnnn nnnnnnnnnn nnnnnnnnnn 12603
nnnnnnnnnn nnnnnnnnnn nnnnnnnnnn nnnnnnnnnn nnnnnnnnnn nnnnnnnnnn 12663
```

FIG. 7I

```
nnnnnnnnnn nnnnnnnnnn nnnnnnnnnn nnnnnnnnnn nnnnnnnnnn nnnnnnnnnn 12723
nnnnnnnnnn nnnnnnnnnn nnnnnnnnnn nnnnnnnnnn nnnnnnnnnn nnnnnnnnnn 12783
nnnnnnnnnn nnnnnnnnnn nnnnnnnnnn nnnnnnnnnn nnnnnnnnnn nnnnnnnnnn 12843
nggcaccaag agatgagggg ggcagtcttg gccatatatt tggctgaagt aagtcaattt 12903
gtcattcctg catgagcctt tataaacaga agtaagtaac caactactat ttggtcattg 12963
gagttgtcca agaggccagg gttctgtcta atacctgttc atgcatgaac atgccaacct 13023
agattgcatg cagactacca gttttgggtt tttgtttagt tcagcaggat ttttctcagc 13083
tcactgcctc tcaaactttc agcaacaaaa ggacatctgt gatatcagaa tctaccactc 13143
taagtatttg gatgcaatag caatgaatat ctgagtaaat ctaggtgggg agtgggggca 13203
ccctgtagcc aaaatgattt aacaaaatca aaccaaaatt ttggaaatga tgccttggta 13263
caatgaagag actacttgag gtaggtttga cttatctaat atcttatttt ctttaccaat 13323
acctaatgag gaatttaaat atttctagat agctttggaa aggtcccttta aagaggcacc 13383
agcataccac tgccagatct aatccccca aacactgttt tcatcatcat catgtcatct 13443
cttgtctcta tagatcatat caaatccttc ccagagtttt tcaggccttt tgacaactag 13503
ccacatttca ctaagccaac tcatctacca ctcttcaaca aaacttttcc tcaagttgag 13563
ctgctccacc aacaccactg ccatgagctc attcccactt ctgtggcttt gctcatgttg 13623
gttatttttt tggagtgtcc tccctattcc ttcttacttg tcccaatccc aactttggc 13683
atggtctact ttaagataca gtaatgagta actttannnn nnnnnnnnnn nnnnnnnnnn 13743
nnnnnnnnnn nnnnnnnnnn nnnnnnnnnn nnnnnnnnnn nnnnnnnnnn nnnnnnnnnn 13803
nnnnnnnnnn nnnnnnnnnn nnnnnnnnnn nnnnnnnnnn nnnnnnnnnn nnnnnnnnnn 13863
nnnnnnnnnn nnnnnnnnnn nnnnnnnnnn nnnnnnnnnn nnnnnnnnnn nnnnnnnnnn 13923
nnnnnnnnnn nnnnnnnnnn nnnnnnnnnn nnnnnnnnnn ttttttaaaat ttaattcaan 13983
nnnnnnnnnn nnnnnnnnnn nnnnnnnnnn nnnnnnnnnn nnnnnnnnnn nnnnnnnnnn 14043
nnnnnnnnnn nnnnnnnnnn nnnnnnnnnn nnnnnnnnnn nnnnnnnnnn nnnnnnnnnn 14103
nnnnnnnnnn nnnnnnnnnn nnnnnnnnnn nnnnnnnnnn nnnnnnnnnn nnnnnnnnnn 14163
nnnnnnnnnn nnnnnnnnnn nnnnnnnnnn nnnnnnnnnn nnnnnnnnnn nnnnnnnnnn 14223
nnnnnnnnnn nnnnnnnnnn nnnnnnnnnn nnnnnnnnnn nnnnnnnnnn nntacataca 14283
```

FIG. 7J

```
caacactctc ttgcttaatc tgtaagactc tctcccccac tcatacctttt ttatttttcc 14343
tctgcattgt acacacaatc tataccactc ttaagcacat gattacagcg ttattttctg 14403
gctgcttcta tgtgtctata ttttaggtcc acctggtcaa tataataaag tgggatatta 14463
gtgttaatgc aactatatgg tatttgatat ttgtctttct gtccgtttat caatgtttct 14523
tatagnnnnn nnnnnnnnnn nnnnnnnngg tgtctgattt tgaccaaatt tgactaaata 14583
cnnnnnnnnn nnnnnnnnnn nnnnnnnnnn nnnnnnnngt tgagtctatc aactcaaaaa 14643
agaataacct acaacaataa caagtttcag aacattttt aaattactga ttttatgagn 14703
nnnnnnnnnn nnnnnnnnnn nnnnnnnnnn nnnnnnnnnn nnnnnngaat ccattgccta 14763
gaaattgcca tggttaagat tttaatattg ctcaggccca gacagctcag ggctttgaca 14823
ttcccacacc cattctctgc catcccagtt ctatctcatc ccaaaaccat ccattatgag 14883
gagagtgtac agctctaggc tgcccgggag ccatcccgca ctctcatttt gtgactcggc 14943
atcttgggag atggagtctt gggacttagc ctggacatgt cccttgcatg tacttcttac 15003
aagactttta ttcagatgaa tattttccct tccaacttaa gaagcacagg gcttgctggt 15063
tttgcttcac taaccagcaa ctgaagcaag acctgacttg tgaaaatgcc taatagagtt 15123
cagtattagc gctgtttcac catttcctgg atctcttgcc tttgtgcaca tgatagaatt 15183
gcacttctct gtgattaatt tgtagttaag tgtggtcatg taactcgctt tggtcaatta 15243
aatgtaagca taagtgatgc gtgttatttc tgggtagaag atgtaagagt tggcatatgc 15303
tttgccatat tttctttatc catctggcat ggtaaccagt aacattctag gtagtaattg 15363
ctccatcagt ctcagtctct gagtgactaa aattgacaga gtccctgct gaccctcaat 15423
gtacatggaa catgaacaag aataagcttt tgtttttat attgagattt tggagttgtt 15483
tgttcctaca gcattaccta gtttactcta atacaacatg gaaaaactg gaacctataa 15543
taaatagacc ctacgttgcc atttaaactt ctagttctga ggaataataa tgtggggaaa 15603
tactttctat ataataaaaa aatagaaaat tgcaaaataa aaatatactt atgtatcatt 15663
catgtcctat taaaaatgtt atttatagac tcaccatatt cccttcctcc agaaaaatag 15723
aagtaaaaat atgaaaatgc ctgtaatcat gtttttggat tatggaatca agtattgctt 15783
tttactttta tgttttctga attttttgttg tacttcacta cattttttgag tgccctgatg 15843
tattactttc aaaaagaaga agaatacttt ctgaagccat ttcaaccatc cccactcacc 15903
```

FIG. 7K

```
tctctagatc ccagtaacca aatacattat ataggactct tcatcagtcc ttatcaagtt 15963
taggaagggc gatgctatac cttctttaaa ggacacctac caatgtctta gttgcctttc 16023
aaagactcct agcacagcta aatgtgatgg atatgctcta aggatataag agctgaagtg 16083
acttgcataa ggtcatatca taacttactg ttagaaatgg agctagaact cagacccact 16143
gagtccttgt ctgtgacaca ctgcccttc catttgtgga agttgttctt gtatctaact 16203
ttatctgtgc tactatttgg gcctagccat tctccctctt atgcagacaa gcagataaac 16263
agtaaaactt taggagtgga ttatgatacc atagatatat atcatctatc ctttacaaaa 16323
tagttattac agtcatcaag ccttggttag agtttacaga ccatgtatcc tagctannnn 16383
nnnnnnnnnn nnnnnnnnnn nnnnnnnnnn nnnnnnnnnn nnnnnnnnnn nnntgaaaca 16443
gtagcagacc aaaagaagtc atgattccca gcatagtgct nnnnnnnnnn nnnnnnnnnn 16503
nnnnnnnnnn nnnnaaacct gtattaagtt tctgttattt gcaagaccct gtcagttagg 16563
ccatgtggga actagaagga tgaatttatc agtcatccaa gattcttaca attaagtatt 16623
accgataagg tactcaagaa acagttctca ttcacataat ttgggttaaa acaaaaagaa 16683
gccagctttc tatatacttt tggtccagtc tttacgtttt ttgttttgtt ttgtttgttt 16743
tcatgagtat cccgacttcc ttctaagaac ttccacctga gaactgacca cagcgtcagc 16803
attccacatg ggtgtgtttc cttccccctt tccatttca gtggtttcca atttcttttt 16863
cttttggcac tataaacctt tcgcaaagga aatattagac agaactccta catgtcaagc 16923
aaattaaaat agtggtgaaa ttagagtgga ggacataatc accctatcat ataggctatt 16983
tgtccatatc atatttgtcc ctacaaaggc tctaaggnn nnnnnnnnnn nnnnnnnnnn 17043
nnnnnnnnnn nnnnnnnnnn nnnnnnnnnn nnnnnnnnnn nnnnnnnnnn nnnnnnnnnn 17103
nnnnnnnnnn nnnnnnnnnn nnnnnnnnnn nnnnnnnnnn nnnnnnnnnn nnnnnnnnnn 17163
nnnnnnnnnn nnnnnnnnnn nnnnnnnnnn nnnnnnnnnn nnnnnnnnnn nnnnnnnnnn 17223
nnnnnnnnnn nnnnnnnnnn nnnnnnnnnn nnnnnnnnnn nnnnnnnnnn nnnnnnnnnn 17283
nnnnnnnnnn nnnnnnnnnn nnnnnnnnnn nnnnnnnnnn nnnnnnnnnn nnnnnnnnnn 17343
nnnnnnnnnn nnnnnnnnnn nnnctctaag ataccttgtg cttcttggaa catatttgga 17403
aaatcatgta gctctcaaat tatccctatg tcctgaagcc caccttacca tcaatcctca 17463
gaaatacccca acccatgtca ggcaacttca cactttcttt cttcaggcag cacagttgtc 17523
```

FIG. 7L

```
tcagggaggg aggagagtgc tattagcaag aggagtcact aacagcttca ctcacctgtg 17583
cccatgaatt tttaatggtg tgaaaagtct gtgtattttt tatggttctc tatggctcat 17643
ataagaggga caaacaatac atgaaagttc agagatgggg acaaatatca ctttaagctg 17703
gggataatca gggaagaaga aagttttcat ggagaaggtg acttttgaat caggaagaaa 17763
tggaaacagc aaactcttct agatagagga gacactaaca ggaaaggcag agaggcagga 17823
aggtgtggga aagtgcacgt gacccgttc agagagaaag ccaggtgtga gataagggg 17883
aaagactgtt agggcatgta ttgtaaacca ctaattccag gcaaaagtta gattttactt 17943
actaagcaag agtgcttcag ttagatccta gcaggaaatg gagggtatgc ttagaagagg 18003
taactgaggc aagtttaatt tataaaggtg tgtgcagcat taagggaaac cagcaaggga 18063
tactgagcat gccaggatgc aagagcaggc agggaaggtg actattccta ggtctgaagg 18123
agaaagggga gggagcagtt cccagaaccc tagtaaaaat ggcaatgaga aagtccatc 18183
tggcaggacc tatggtcttt aacagaggga caaagtcaac ccacaacttg tctgggaggt 18243
tgctgaggaa tagataccc aacctctctc tcaacccact gcaacactct ttttccccta 18303
gactgagccc agtcaaagac agagggagga gcccagtgat gcagtctgca atgtcatcat 18363
cctggagcat gaatagagtg cagcagggtg aataatgagt ctgcaggaat taatagaaat 18423
atctgacaca atagggaact ataagaggtt ttgaatagga gaggccctg aaatgtgctc 18483
caatattact gaactatgtg tggcccaaag aatggaagag gaacagctct tgcaataggt 18543
ctgaggagag aagctgaaga cttggactag ggcaatggta aaaactgtgg aaagaagttt 18603
taaatgaaaa gttttaaacc atgcggcttc cagctagatg aactttttta aaaaaattag 18663
ttcctcactc aaattttggg gaggttatat attttctaat cataaaaaat gatttttctt 18723
atttgtgggc ttttctcccc ag atc tga acctgtggtc ttgggagcca gggtgacctg 18781
                         Ile                                    273
atatgacatc taaagaagct tctggactct gaacaagaat tcggtggcct gcagagcttg 18841
ccatttgcac ttttcaaatg cctttggatg acccagcact ttaatctgaa acctgcaaca 18901
agactagcca acacctggcc atgaaacttg ccccttcact gatctggact cacctctgga 18961
gcctatggct ttaagcaagc actactgcac tttacagaat taccccactg gatcctggac 19021
ccacagaatt ccttcaggat ccttcttgct gccagactga aagcaaaagg aattatttcc 19081
```

FIG. 7M

```
cctcaagttt tctaagtgat ttccaaaagc agaggtgtgt ggaaatttcc agtaacagaa  19141
acagatgggt tgccaataga gttatttttt atctatagct tcctctgggt actagaagag  19201
gctattgaga ctatga                                                   19217
```

US 7,414,122 B2

NUCLEIC ACIDS ENCODING B7-LIKE MOLECULES AND USES THEREOF

This application is a continuation of U.S. application Ser. No. 09/955,866, filed on Sep. 19, 2001, which claims the benefit of priority of U.S. Provisional Application No. 60/233,867, filed on Sep. 20, 2000, the disclosure of each of which is explicitly incorporated by reference herein.

FIELD OF THE INVENTION

The present invention relates to B7-Like (B7-L) polypeptides and nucleic acid molecules encoding the same. The invention also relates to selective binding agents, vectors, host cells, and methods for producing B7-L polypeptides. The invention further relates to pharmaceutical compositions and methods for the diagnosis, treatment, amelioration, and/or prevention of diseases, disorders, and conditions associated with B7-L polypeptides.

BACKGROUND OF THE INVENTION

Technical advances in the identification, cloning, expression, and manipulation of nucleic acid molecules and the deciphering of the human genome have greatly accelerated the discovery of novel therapeutics. Rapid nucleic acid sequencing techniques can now generate sequence information at unprecedented rates and, coupled with computational analyses, allow the assembly of overlapping sequences into partial and entire genomes and the identification of polypeptide-encoding regions. A comparison of a predicted amino acid sequence against a database compilation of known amino acid sequences allows one to determine the extent of homology to previously identified sequences and/or structural landmarks. The cloning and expression of a polypeptide-encoding region of a nucleic acid molecule provides a polypeptide product for structural and functional analyses. The manipulation of nucleic acid molecules and encoded polypeptides may confer advantageous properties on a product for use as a therapeutic.

In spite of the significant technical advances in genome research over the past decade, the potential for the development of novel therapeutics based on the human genome is still largely unrealized. Many genes encoding potentially beneficial polypeptide therapeutics or those encoding polypeptides, which may act as "targets" for therapeutic molecules, have still not been identified. Accordingly, it is an object of the invention to identify novel polypeptides, and nucleic acid molecules encoding the same, which have diagnostic or therapeutic benefit.

SUMMARY OF THE INVENTION

A novel polypeptide, which is related to proteins in the T-cell costimulatory pathway, has been identified. This polypeptide, termed B7-like polypeptide (B7-L), represents a B7-related polypeptide having a structure similar to and sharing homology with CD80, CD86, B7RP-1, and B7-H1. Human B7-L polypeptide shares a greater amino acid identity with human B7-H1 (35%) than with other members of the B7 family (B7rp-1, 20%; B7-1, 12%). In addition, the mouse and human orthologs of B7-L polypeptide and B7-H1 share a greater degree of amino acid similarity (approximately 70%) than the mouse and human orthologs of B7-1, B7-2, or B7rp-1 (approximately 40%). Furthermore, both B7-H1 and B7-L bind to the same receptor, PD-1.

The present invention relates to novel B7-L nucleic acid molecules and encoded polypeptides.

The invention provides for an isolated nucleic acid molecule comprising a nucleotide sequence selected from the group consisting of:

(a) the nucleotide sequence as set forth in SEQ ID NO: 1;
(b) the nucleotide sequence of the DNA insert in ATCC Deposit No. PTA 2481;
(c) a nucleotide sequence encoding the polypeptide as set forth in SEQ ID NO: 2;
(d) a nucleotide sequence that hybridizes under at least moderately stringent conditions to the complement of the nucleotide sequence of any of (a)-(c); and
(e) a nucleotide sequence complementary to the nucleotide sequence of any of (a)-(c).

The invention also provides for an isolated nucleic acid molecule comprising a nucleotide sequence selected from the group consisting of:

(a) a nucleotide sequence encoding a polypeptide that is at least about 70 percent identical to the polypeptide as set forth in SEQ ID NO: 2 or the nucleotide sequence of the DNA insert in ATCC Deposit No. PTA 2481, wherein the encoded polypeptide has an activity of the polypeptide set forth in SEQ ID NO: 2;
(b) a nucleotide sequence encoding an allelic variant or splice variant of the nucleotide sequence as set forth in SEQ ID NO: 1, the nucleotide sequence of the DNA insert in ATCC Deposit No. PTA 2481, or the nucleotide sequence of (a);
(c) a region of the nucleotide sequence of SEQ ID NO: 1, the nucleotide sequence of the DNA insert in ATCC Deposit No. PTA 2481, or the nucleotide sequence of (a) or (b) encoding a polypeptide fragment of at least about 25 amino acid residues, wherein the polypeptide fragment has an activity of the polypeptide set forth in SEQ ID NO: 2, or is antigenic;
(d) a region of the nucleotide sequence of SEQ ID NO: 1, the nucleotide sequence of the DNA insert in ATCC Deposit No. PTA 2481, or the nucleotide sequence of either (c) or (d) comprising a fragment of at least about 16 nucleotides;
(e) a nucleotide sequence that hybridizes under at least moderately stringent conditions to the complement of the nucleotide sequence of any of (a)-(d); and
(f) a nucleotide sequence complementary to the nucleotide sequence of any of (a)-(d).

The invention further provides for an isolated nucleic acid molecule comprising a nucleotide sequence selected from the group consisting of:

(a) a nucleotide sequence encoding a polypeptide as set forth in SEQ ID NO: 2 with at least one conservative amino acid substitution, wherein the encoded polypeptide has an activity of the polypeptide set forth in SEQ ID NO: 2;
(b) a nucleotide sequence encoding a polypeptide as set forth in SEQ ID NO: 2 with at least one amino acid insertion, wherein the encoded polypeptide has an activity of the polypeptide set forth in SEQ ID NO: 2;
(c) a nucleotide sequence encoding a polypeptide as set forth in SEQ ID NO: 2 with at least one amino acid deletion, wherein the encoded polypeptide has an activity of the polypeptide set forth in SEQ ID NO: 2;
(d) a nucleotide sequence encoding a polypeptide as set forth in SEQ ID NO: 2 that has a C- and/or N-terminal truncation, wherein the encoded polypeptide has an activity of the polypeptide set forth in SEQ ID NO: 2;
(e) a nucleotide sequence encoding a polypeptide as set forth in SEQ ID NO: 2 with at least one modification selected from the group consisting of amino acid substitutions, amino acid insertions, amino acid deletions, C-terminal truncation, and N-terminal truncation, wherein the encoded polypeptide has an activity of the polypeptide set forth in SEQ ID NO: 2;

(f) a nucleotide sequence of any of (a)-(e) comprising a fragment of at least about 16 nucleotides;

(g) a nucleotide sequence that hybridizes under at least moderately stringent conditions to the complement of the nucleotide sequence of any of (a)-(f); and (h) a nucleotide sequence complementary to the nucleotide sequence of any of (a)-(e).

The present invention provides for an isolated polypeptide comprising an amino acid sequence selected from the group consisting of:

(a) the amino acid sequence as set forth in SEQ ID NO: 2; and (b) the amino acid sequence encoded by the DNA insert of ATCC Deposit No. PTA 2481.

The invention also provides for an isolated polypeptide comprising an amino acid sequence selected from the group consisting of:

(a) the amino acid sequence as set forth in SEQ ID NO: 3, optionally further comprising an amino-terminal methionine;

(b) an amino acid sequence for an ortholog of SEQ ID NO: 2;

(c) an amino acid sequence that is at least about 70 percent identical to the amino acid sequence of SEQ ID NO: 2 or the amino acid sequence encoded by the DNA insert of ATCC Deposit No. PTA 2481, wherein the polypeptide has an activity of the polypeptide set forth in SEQ ID NO: 2;

(d) a fragment of the amino acid sequence set forth in SEQ ID NO: 2 or the amino acid sequence encoded by the DNA insert of ATCC Deposit No. PTA 2481 comprising at least about 25 amino acid residues, wherein the fragment has an activity of the polypeptide set forth in SEQ ID NO: 2, or is antigenic; and (e) an amino acid sequence for an allelic variant or splice variant of the amino acid sequence as set forth in SEQ ID NO: 2, the amino acid sequence encoded by the DNA insert of ATCC Deposit No. PTA 2481, or the amino acid sequence of any of (a)-(c).

The invention further provides for an isolated polypeptide comprising an amino acid sequence selected from the group consisting of:

(a) the amino acid sequence as set forth in SEQ ID NO: 2 with at least one conservative amino acid substitution, wherein the polypeptide has an activity of the polypeptide set forth in SEQ ID NO: 2;

(b) the amino acid sequence as set forth in SEQ ID NO: 2 with at least one amino acid insertion, wherein the polypeptide has an activity of the polypeptide set forth in SEQ ID NO: 2;

(c) the amino acid sequence as set forth in SEQ ID NO: 2 with at least one amino acid deletion, wherein the polypeptide has an activity of the polypeptide set forth in SEQ ID NO: 2;

(d) the amino acid sequence as set forth in SEQ ID NO: 2 that has a C- and/or N-terminal truncation, wherein the polypeptide has an activity of the polypeptide set forth in SEQ ID NO: 2; and (e) the amino acid sequence as set forth in SEQ ID NO: 2 with at least one modification selected from the group consisting of amino acid substitutions, amino acid insertions, amino acid deletions, C-terminal truncation, and N-terminal truncation, wherein the polypeptide has an activity of the polypeptide set forth in SEQ ID NO: 2.

The invention still further provides for an isolated polypeptide comprising the amino acid sequence as set forth in SEQ ID NO: 2 with at least one conservative amino acid substitution selected from the group consisting of: valine at position 4; isoleucine or valine at position 6; leucine or valine at position 7; methionine or valine at position 8; isoleucine at position 10; leucine or valine at position 17; glycine at position 19; serine at position 22; leucine at position 23; aspartic acid at position 28; leucine or valine at position 31; valine at position 32; isoleucine at position 40; leucine at position 50; valine at position 52; valine, leucine, or methionine at position 55; arginine at position 61; methionine at position 62; lysine at position 70; serine at position 74; isoleucine or methionine at position 75; valine at position 76; aspartic acid at position 78; methionine or isoleucine at position 80; arginine at position 84; leucine at position 89; asparagine at position 91; isoleucine or leucine at position 92; isoleucine or leucine at position 94; glutamic acid at position 96; aspartic acid at position 97; phenylalanine at position 100; valine at position 104; leucine at position 105; arginine at position 107; tyrosine at position 110; glutamic acid at position 111; valine or isoleucine at position 115; serine at position 116; valine at position 117; glycine at position 121; valine or methionine at position 126; valine or isoleucine at position 131; isoleucine or leucine at position 139; isoleucine at position 141; serine at position 146; phenylalanine at position 148; isoleucine, methionine, or leucine at position 153; isoleucine at position 160; threonine at position 165; aspartic acid at position 171; phenylalanine at position 174; serine at position 177; threonine at position 178; valine at position 180; methionine, valine, or isoleucine at position 182; arginine at position 183; lysine at position 188; isoleucine or leucine at position 193; lysine at position 200; valine at position 202; isoleucine at position 204; valine or methionine at position 209; isoleucine at position 213; isoleucine or valine at position 222; valine at position 223; leucine at position 225; valine or leucine at position 227; leucine or valine at position 231; leucine at position 232; valine or leucine at position 235; methionine or isoleucine at position 240; arginine at position 250; arginine at position 255; glutamic acid at position 256; serine at position 264; arginine at position 266; and leucine at position 268; wherein the polypeptide has an activity of the polypeptide as set forth in SEQ ID NO: 2.

Also provided are fusion polypeptides comprising B7-L amino acid sequences.

The present invention also provides for an expression vector comprising the isolated nucleic acid molecules as set forth herein, recombinant host cells comprising the recombinant nucleic acid molecules as set forth herein, and a method of producing a B7-L polypeptide comprising culturing the host cells and optionally isolating the polypeptide so produced.

A transgenic non-human animal comprising a nucleic acid molecule encoding a B7-L polypeptide is also encompassed by the invention. The B7-L nucleic acid molecules are introduced into the animal in a manner that allows expression and increased levels of a B7-L polypeptide, which may include increased circulating levels. Alternatively, the B7-L nucleic acid molecules are introduced into the animal in a manner that prevents expression of endogenous B7-L polypeptide (i.e., generates a transgenic animal possessing a B7-L polypeptide gene knockout). The transgenic non-human animal is preferably a mammal, and more preferably a rodent, such as a rat or a mouse.

Also provided are derivatives of the B7-L polypeptides of the present invention.

Additionally provided are selective binding agents such as antibodies and peptides capable of specifically binding the B7-L polypeptides of the invention. Such antibodies and peptides may be agonistic or antagonistic.

Pharmaceutical compositions comprising the nucleotides, polypeptides, or selective binding agents of the invention and one or more pharmaceutically acceptable formulation agents are also encompassed by the invention. The pharmaceutical compositions are used to provide therapeutically effective amounts of the nucleotides or polypeptides of the present invention. The invention is also directed to methods of using the polypeptides, nucleic acid molecules, and selective binding agents.

The B7-L polypeptides and nucleic acid molecules of the present invention may be used to treat, prevent, ameliorate, and/or detect diseases and disorders, including those recited herein.

The present invention also provides a method of assaying test molecules to identify a test molecule that binds to a B7-L polypeptide. The method comprises contacting a B7-L polypeptide with a test molecule to determine the extent of binding of the test molecule to the polypeptide. The method further comprises determining whether such test molecules are agonists or antagonists of a B7-L polypeptide. The present invention further provides a method of testing the impact of molecules on the expression of B7-L polypeptide or on the activity of B7-L polypeptide.

Methods of regulating expression and modulating (i.e., increasing or decreasing) levels of a B7-L polypeptide are also encompassed by the invention. One method comprises administering to an animal a nucleic acid molecule encoding a B7-L polypeptide. In another method, a nucleic acid molecule comprising elements that regulate or modulate the expression of a B7-L polypeptide may be administered. Examples of these methods include gene therapy, cell therapy, and anti-sense therapy as further described herein.

In another aspect of the present invention, the B7-L polypeptides may be used for identifying receptors thereof ("B7-L polypeptide receptors"). Various forms of "expression cloning" have been extensively used to clone receptors for protein ligands. See, e.g., Simonsen and Lodish, 1994, *Trends Pharmacol. Sci.* 15:437-41 and Tartaglia et al., 1995, *Cell* 83:1263-71. The isolation of a B7-L polypeptide receptor is useful for identifying or developing novel agonists and antagonists of the B7-L polypeptide signaling pathway. Such agonists and antagonists include soluble B7-L polypeptide receptors, anti-B7-L polypeptide receptor-selective binding agents (such as antibodies and derivatives thereof), small molecules, and antisense oligonucleotides, any of which can be used for treating one or more disease or disorder, including those disclosed herein.

BRIEF DESCRIPTION OF THE FIGURES

FIGS. 1A-1B illustrate the nucleotide sequence of the human B7-L gene (SEQ ID NO: 1) and the deduced amino acid sequence of human B7-L polypeptide (SEQ ID NO: 2). The predicted signal peptide (underline) and transmembrane domain (doubleunderline) are indicated;

FIGS. 2A-2C illustrate an amino acid sequence alignment of human B7-L polypeptide (GA16817596; SEQ ID NO: 2), human CD80 or B7-1 (Cd80_Human; SEQ ID NO: 4; GenBank accession no. P33681), human CD86 or B7-2 (Cd86_Human; SEQ ID NO: 5; GenBank accession no. U04343), human B7-H1 (B7-H1_Human; SEQ ID NO: 6; GenBank accession no. AF177937), human B7rp-1 (B7rp-1_Human; SEQ ID NO: 7; GenBank accession no. AF199028), human PRO352 (Pro352_Human; SEQ ID NO: 8; GenBank accession no. Y41705), human butyrophilin BTF1 (Btf1_Human; SEQ ID NO: 9; GenBank accession no. U90543), human butyrophilin BTF2 (Btsf2a2_Hu; SEQ ID NO: 10; GenBank accession no. U90550), human butyrophilin BTF4 (Btf4_Human; SEQ ID NO: 11; GenBank accession no. U90546), human butyrophilin BTF3 (Btn3a3_Human; SEQ ID NO: 12; GenBank accession no. U90548), and butyrophilin (Btn_Human; SEQ ID NO: 13; GenBank accession no. U39576);

FIGS. 3A-3E illustrate a portion of the genomic nucleotide sequence for human B7-L polypeptide (SEQ ID NO: 14). The location of the deduced amino acid sequence of exon 1 (SEQ ID NO: 19) is indicated.

FIG. 4 illustrates a portion of the genomic nucleotide sequence for human B7-L polypeptide (SEQ ID NO: 15).

FIGS. 5A-5F illustrate a portion of the genomic nucleotide sequence for human B7-L polypeptide (SEQ ID NO: 16). The location of the deduced amino acid sequence of exon 2 (SEQ ID NO: 20) is indicated.

FIGS. 6A-6B illustrate a portion of the genomic nucleotide sequence for human B7-L polypeptide (SEQ ID NO: 17). The location of the deduced amino acid sequence of exon 3 (SEQ ID NO: 21) is indicated.

FIGS. 7A-7M illustrate a portion of the genomic nucleotide sequence for human B7-L polypeptide (SEQ ID NO: 18). The locations of the deduced amino acid sequence of exons 4 (SEQ ID NO: 22), 5 (SEQ ID NO: 23), and 6 are indicated.

DETAILED DESCRIPTION OF THE INVENTION

Figure 8:
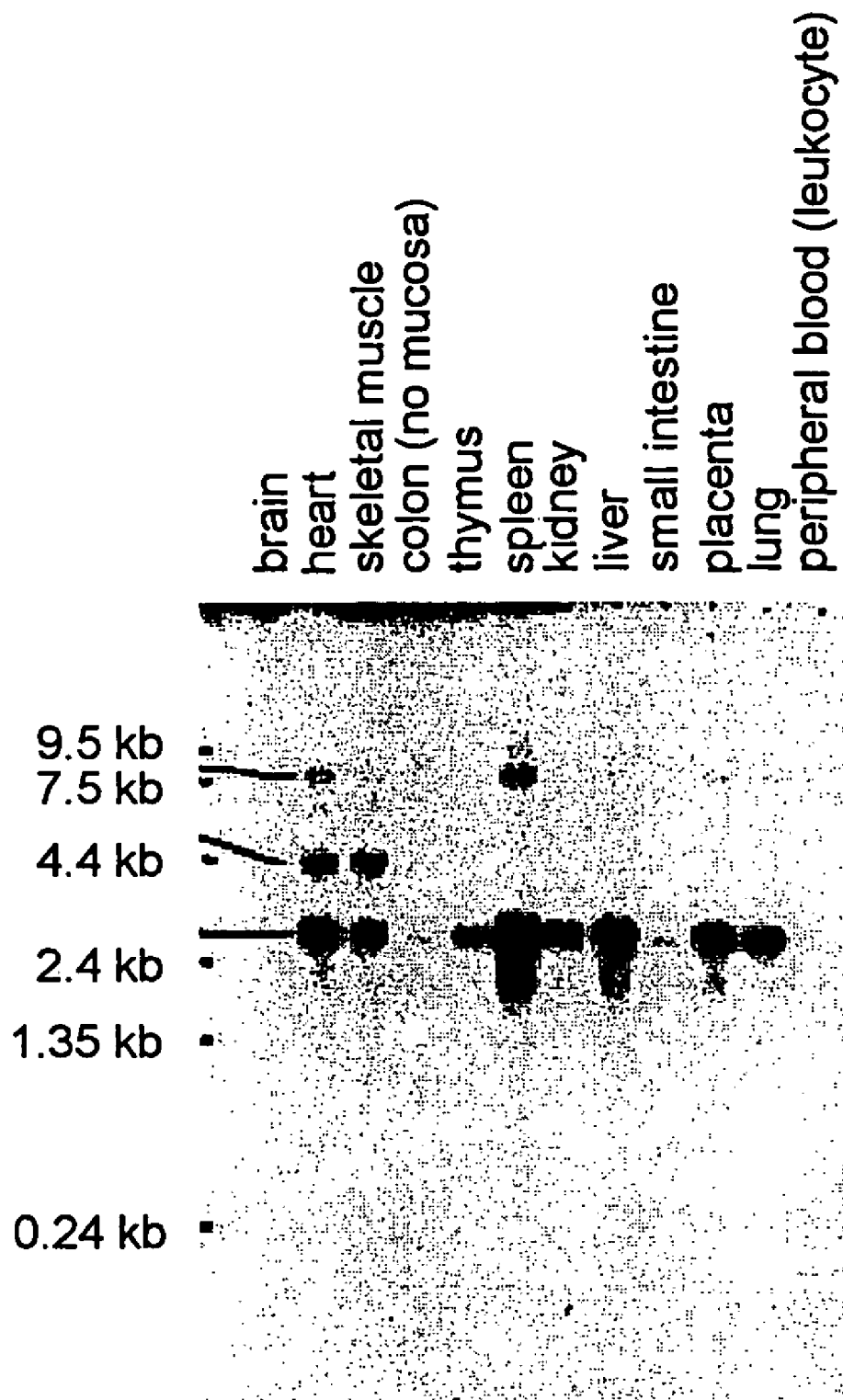
FIG. 8 shows the results for Northern blot analysis of human B7-L mRNA expression.

The section headings used herein are for organizational purposes only and are not to be construed as limiting the subject matter described. All references cited in this application are expressly incorporated by reference herein.

Definitions

The terms "B7-L gene" or "B7-L nucleic acid molecule" or "B7-L polynucleotide" refer to a nucleic acid molecule comprising or consisting of a nucleotide sequence as set forth in SEQ ID NO: 1, a nucleotide sequence encoding the polypeptide as set forth in SEQ ID NO: 2, a nucleotide sequence of the DNA insert in ATCC Deposit No. PTA 2481, and nucleic acid molecules as defined herein.

The term "B7-L polypeptide allelic variant" refers to one of several possible naturally occurring alternate forms of a gene occupying a given locus on a chromosome of an organism or a population of organisms.

The term "B7-L polypeptide splice variant" refers to a nucleic acid molecule, usually RNA, which is generated by alternative processing of intron sequences in an RNA transcript of B7-L polypeptide amino acid sequence as set forth in SEQ ID NO: 2.

The term "isolated nucleic acid molecule" refers to a nucleic acid molecule of the invention that (1) has been separated from at least about 50 percent of proteins, lipids, carbohydrates, or other materials with which it is naturally found when total nucleic acid is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Preferably, the isolated nucleic acid molecule of the present invention is substantially free from any other contaminating nucleic acid molecule(s) or other contaminants that are found in its natural environment that would interfere with its use in polypeptide production or its therapeutic, diagnostic, prophylactic or research use.

The term "nucleic acid sequence" or "nucleic acid molecule" refers to a DNA or RNA sequence. The term encompasses molecules formed from any of the known base analogs of DNA and RNA such as, but not limited to 4-acetylcytosine, 8-hydroxy-N-6-methyladenosine, aziridinyl-cytosine, pseudoisocytosine, S-(carboxyhydroxylmethyl) uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N-6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "vector" is used to refer to any molecule (e.g. nucleic acid, plasmid, or virus) used to transfer coding information to a host cell.

The term "expression vector" refers to a vector that is suitable for transformation of a host cell and contains nucleic acid sequences that direct and/or control the expression of inserted heterologous nucleic acid sequences. Expression includes, but is nbt limited to, processes such as transcription, translation, and RNA splicing, if introns are present.

The term "operably linked" is used herein to refer to an arrangement of flanking sequences wherein the flanking sequences so described are configured or assembled so as to perform their usual function. Thus, a flanking sequence operably linked to a coding sequence may be capable of effecting the replication, transcription and/or translation of the coding sequence. For example, a coding sequence is operably linked to a promoter when the promoter is capable of directing transcription of that coding sequence. A flanking sequence need not be contiguous with the coding sequence, so long as it functions correctly. Thus, for example, intervening untranslated yet transcribed sequences can be present between a promoter sequence and the coding sequence and the promoter sequence can still be considered "operably linked" to the coding sequence.

The term "host cell" is used to refer to a cell which has been transformed, or is capable of being transformed with a nucleic acid sequence and then of expressing a selected gene of interest. The term includes the progeny of the parent cell, whether or not the progeny is identical in morphology or in genetic make-up to the original parent, so long as the selected gene is present.

The term "B7-L polypeptide" refers to a polypeptide comprising the amino acid sequence of SEQ ID NO: 2 and related polypeptides. Related polypeptides include B7-L polypeptide fragments, B7-L polypeptide orthologs, B7-L polypeptide variants, and B7-L polypeptide derivatives, which possess at least one activity of the polypeptide as set forth in SEQ ID NO: 2. B7-L polypeptides may be mature polypeptides, as defined herein, and may or may not have an amino-terminal methionine residue, depending on the method by which they are prepared.

The term "B7-L polypeptide fragment" refers to a polypeptide that comprises a truncation at the amino-terminus (with or without a leader sequence) and/or a truncation at the carboxyl-terminus of the polypeptide as set forth in SEQ ID NO: 2. The term "B7-L polypeptide fragment" also refers to amino-terminal and/or carboxyl-terminal truncations of B7-L polypeptide orthologs, B7-L polypeptide derivatives, or B7-L polypeptide variants, or to amino-terminal and/or carboxyl-terminal truncations of the polypeptides encoded by B7-L polypeptide allelic variants or B7-L polypeptide splice variants. B7-L polypeptide fragments may result from alternative RNA splicing or from in vivo protease activity. Membrane-bound forms of a B7-L polypeptide are also contemplated by the present invention. In preferred embodiments, truncations and/or deletions comprise about 10 amino acids, or about 20 amino acids, or about 50 amino acids, or about 75 amino acids, or about 100 amino acids, or more than about 100 amino acids. The polypeptide fragments so produced will comprise about 25 contiguous amino acids, or about 50 amino acids, or about 75 amino acids, or about 100 amino acids, or about 150 amino acids, or about 200 amino acids. Such B7-L polypeptide fragments may optionally comprise an amino-terminal methionine residue. It will be appreciated that such fragments can be used, for example, to generate antibodies to B7-L polypeptides.

The term "B7-L polypeptide ortholog" refers to a polypeptide from another species that corresponds to B7-L polypeptide amino acid sequence as set forth in SEQ ID NO: 2. For example, mouse and human B7-L polypeptides are considered orthologs of each other.

The term "B7-L polypeptide variants" refers to B7-L polypeptides comprising amino acid sequences having one or more amino acid sequence substitutions, deletions (such as internal deletions and/or B7-L polypeptide fragments), and/or additions (such as internal additions and/or B7-L fusion polypeptides) as compared to the B7-L polypeptide amino acid sequence set forth in SEQ ID NO: 2 (with or without a leader sequence). Variants may be naturally occurring (e.g., B7-L polypeptide allelic variants, B7-L polypeptide orthologs, and B7-L polypeptide splice variants) or artificially constructed. Such B7-L polypeptide variants may be prepared from the corresponding nucleic acid molecules having a DNA sequence that varies accordingly from the DNA sequence as set forth in SEQ ID NO: 1. In preferred embodiments, the variants have from 1 to 3, or from 1 to 5, or from 1 to 10, or from 1 to 15, or from 1 to 20, or from 1 to 25, or from 1 to 50, or from 1 to 75, or from 1 to 100, or more than 100 amino acid substitutions, insertions, additions and/or deletions, wherein the substitutions may be conservative, or non-conservative, or any combination thereof.

The term "B7-L polypeptide derivatives" refers to the polypeptide as set forth in SEQ ID NO: 2, B7-L polypeptide fragments, B7-L polypeptide orthologs, or B7-L polypeptide variants, as defined herein, that have been chemically modified. The term "B7-L polypeptide derivatives" also refers to the polypeptides encoded by B7-L polypeptide allelic variants or B7-L polypeptide splice variants, as defined herein, that have been chemically modified.

The term "mature B7-L polypeptide" refers to a B7-L polypeptide lacking a leader sequence. A mature B7-L polypeptide may also include other modifications such as proteolytic processing of the amino-terminus (with or without a leader sequence) and/or the carboxyl-terminus, cleavage of a smaller polypeptide from a larger precursor, N-linked and/or O-linked glycosylation, and the like. An exemplary mature B7-L polypeptide is depicted by the amino acid sequence of SEQ ID NO: 3.

The term "B7-L fusion polypeptide" refers to a fusion of one or more amino acids (such as a heterologous protein or peptide) at the amino- or carboxyl-terminus of the polypeptide as set forth in SEQ ID NO: 2, B7-L polypeptide fragments, B7-L polypeptide orthologs, B7-L polypeptide variants, or B7-L derivatives, as defined herein. The term "B7-L fusion polypeptide" also refers to a fusion of one or more amino acids at the amino- or carboxyl-terminus of the polypeptide encoded by B7-L polypeptide allelic variants or B7-L polypeptide splice variants, as defined herein.

The term "biologically active B7-L polypeptides" refers to B7-L polypeptides having at least one activity characteristic of the polypeptide comprising the amino acid sequence of SEQ ID NO: 2. In addition, a B7-L polypeptide may be active as an immunogen; that is, the B7-L polypeptide contains at least one epitope to which antibodies may be raised.

The term "isolated polypeptide" refers to a polypeptide of the present invention that (1) has been separated from at least about 50 percent of polynucleotides, lipids, carbohydrates, or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. Preferably, the isolated polypeptide is substantially free from any other contaminating polypeptides or other contaminants that are found in its natural environment that would interfere with its therapeutic, diagnostic, prophylactic or research use.

The term "identity," as known in the art, refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms").

The term "similarity" is a related concept, but in contrast to "identity," "similarity" refers to a measure of relatedness that includes both identical matches and conservative substitution matches. If two polypeptide sequences have, for example, 10/20 identical amino acids, and the remainder are all non-conservative substitutions, then the percent identity and similarity would both be 50%. If in the same example, there are five more positions where there are conservative substitutions, then the percent identity remains 50%, but the percent similarity would be 75% (15/20). Therefore, in cases where there are conservative substitutions, the percent similarity between two polypeptides will be higher than the percent identity between those two polypeptides.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" as used herein refers to a material that is not found in nature or that has been structurally modified or synthesized by man.

The terms "effective amount" and "therapeutically effective amount" each refer to the amount of a B7-L polypeptide or B7-L nucleic acid molecule used to support an observable level of one or more biological activities of the B7-L polypeptides as set forth herein.

The term "pharmaceutically acceptable carrier" or "physiologically acceptable carrier" as used herein refers to one or more formulation materials suitable for accomplishing or enhancing the delivery of the B7-L polypeptide, B7-L nucleic acid molecule, or B7-L selective binding agent as a pharmaceutical composition.

The term "antigen" refers to a molecule or a portion of a molecule capable of being bound by a selective binding agent, such as an antibody, and additionally capable of being used in an animal to produce antibodies capable of binding to an epitope of that antigen. An antigen may have one or more epitopes.

The term "selective binding agent" refers to a molecule or molecules having specificity for a B7-L polypeptide. As used herein, the terms, "specific" and "specificity" refer to the ability of the selective binding agents to bind to human B7-L polypeptides and not to bind to human non-B7-L polypeptides. It will be appreciated, however, that the selective binding agents may also bind orthologs of the polypeptide as set forth in SEQ ID NO: 2, that is, interspecies versions thereof, such as mouse and rat B7-L polypeptides.

The term "transduction" is used to refer to the transfer of genes from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52:456; Sambrook et al., *Molecular Cloning, A Laboratory Manual* (Cold Spring Harbor Laboratories, 1989); Davis et al., *Basic Methods in Molecular Biology* (Elsevier, 1986); and Chu et al., 1981, *Gene* 13:197. Such techniques can be used to introduce one or more exogenous DNA moieties into suitable host cells.

The term "tansformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is considered to have been stably transformed when the DNA is replicated with the division of the cell.

Relatedness of Nucleic Acid Molecules and/or Polypeptides

It is understood that related nucleic acid molecules include allelic or splice variants of the nucleic acid molecule of SEQ ID NO: 1, and include sequences which are complementary to any of the above nucleotide sequences. Related nucleic acid molecules also include a nucleotide sequence encoding a polypeptide comprising or consisting essentially of a substitution, modification, addition and/or deletion of one or more amino acid residues compared to the polypeptide as set forth in SEQ ID NO: 2. Such related B7-L polypeptides may comprise, for example, an addition and/or a deletion of one or more N-linked or O-linked glycosylation sites or an addition and/or a deletion of one or more cysteine residues.

Related nucleic acid molecules also include fragments of B7-L nucleic acid molecules which encode a polypeptide of at least about 25 contiguous amino acids, or about 50 amino acids, or about 75 amino acids, or about 100 amino acids, or about 150 amino acids, or about 200 amino acids, or more than 200 amino acid residues of the B7-L polypeptide of SEQ ID NO: 2.

In addition, related B7-L nucleic acid molecules also include those molecules which comprise nucleotide sequences which hybridize under moderately or highly stringent conditions as defined herein with the fully complementary sequence of the B7-L nucleic acid molecule of SEQ ID NO: 1, or of a molecule encoding a polypeptide, which polypeptide comprises the amino acid sequence as shown in SEQ ID NO: 2, or of a nucleic acid fragment as defined herein, or of a nucleic acid fragment encoding a polypeptide as defined herein. Hybridization probes may be prepared using the B7-L sequences provided herein to screen cDNA, genomic or synthetic DNA libraries for related sequences. Regions of the DNA and/or amino acid sequence of B7-L polypeptide that exhibit significant identity to known sequences are readily determined using sequence alignment algorithms as described herein and those regions may be used to design probes for screening.

The term "highly stringent conditions" refers to those conditions that are designed to permit hybridization of DNA strands whose sequences are highly complementary, and to exclude hybridization of significantly mismatched DNAs. Hybridization stringency is principally determined by temperature, ionic strength, and the concentration of denaturing agents such as formamide. Examples of "highly stringent conditions" for hybridization and washing are 0.015 M sodium chloride, 0.0015 M sodium citrate at 65-68° C. or 0.015 M sodium chloride, 0.0015 M sodium citrate, and 50% formamide at 42° C. See Sambrook, Fritsch & Maniatis, *Molecular Cloning: A Laboratory Manual* (2nd ed., Cold Spring Harbor Laboratory, 1989); Anderson et al., *Nucleic Acid Hybridisation: A Practical Approach* Ch. 4 (IRL Press Limited).

More stringent conditions (such as higher temperature, lower ionic strength, higher formamide, or other denaturing agent) may also be used—however, the rate of hybridization will be affected. Other agents may be included in the hybridization and washing buffers for the purpose of reducing non-specific and/or background hybridization. Examples are 0.1% bovine serum albumin, 0.1% polyvinyl-pyrrolidone, 0.1% sodium pyrophosphate, 0.1% sodium dodecylsulfate, NaDodSO$_4$, (SDS), ficoll, Denhardt's solution, sonicated salmon sperm DNA (or another non-complementary DNA), and dextran sulfate, although other suitable agents can also be used. The concentration and types of these additives can be changed without substantially affecting the stringency of the hybridization conditions. Hybridization experiments are usually carried out at pH 6.8-7.4; however, at typical ionic strength conditions, the rate of hybridization is nearly independent of pH. See Anderson et al., *Nucleic Acid Hybridisation: A Practical Approach* Ch. 4 (IRL Press Limited).

Factors affecting the stability of DNA duplex include base composition, length, and degree of base pair mismatch. Hybridization conditions can be adjusted by one skilled in the art in order to accommodate these variables and allow DNAs of different sequence relatedness to form hybrids. The melting temperature of a perfectly matched DNA duplex can be estimated by the following equation:

$$T_m(° C.) = 81.5 + 16.6(\log[Na+]) + 0.41(\% G+C) - 600/N - 0.72(\% \text{formamide})$$

where N is the length of the duplex formed, [Na+] is the molar concentration of the sodium ion in the hybridization or washing solution, % G+C is the percentage of (guanine+cytosine) bases in the hybrid. For imperfectly matched hybrids, the melting temperature is reduced by approximately 1° C. for each 1% mismatch.

The term "moderately stringent conditions" refers to conditions under which a DNA duplex with a greater degree of base pair mismatching than could occur under "highly stringent conditions" is able to form. Examples of typical "moderately stringent conditions" are 0.015 M sodium chloride, 0.0015 M sodium citrate at 50-65° C. or 0.015 M sodium chloride, 0.0015 M sodium citrate, and 20% formamide at 37-50° C. By way of example, "moderately stringent conditions" of 50° C. in 0.015 M sodium ion will allow about a 21% mismatch.

It will be appreciated by those skilled in the art that there is no absolute distinction between "highly stringent conditions" and "moderately stringent conditions." For example, at 0.015 M sodium ion (no formamide), the melting temperature of perfectly matched long DNA is about 71° C. With a wash at 65° C. (at the same ionic strength), this would allow for approximately a 6% mismatch. To capture more distantly related sequences, one skilled in the art can simply lower the temperature or raise the ionic strength.

A good estimate of the melting temperature in 1M NaCl* for oligonucleotide probes up to about 20 nt is given by:

$$Tm = 2° C. \text{ per } A\text{-}T \text{ base pair} + 4° C. \text{ per } G\text{-}C \text{ base pair}$$

*The sodium ion concentration in 6× salt sodium citrate (SSC) is 1M. See Suggs et al., *Developmental Biology Using Purified Genes* 683 (Brown and Fox, eds., 1981).

High stringency washing conditions for oligonucleotides are usually at a temperature of 0-5° C. below the Tm of the oligonucleotide in 6× SSC, 0.1% SDS.

In another embodiment, related nucleic acid molecules comprise or consist of a nucleotide sequence that is at least about 70 percent identical to the nucleotide sequence as shown in SEQ ID NO: 1. In preferred embodiments, the nucleotide sequences are about 75 percent, or about 80 percent, or about 85 percent, or about 90 percent, or about 95, 96, 97, 98, or 99 percent identical to the nucleotide sequence as shown in SEQ ID NO: 1. Related nucleic acid molecules encode polypeptides possessing at least one activity of the polypeptide set forth in SEQ ID NO: 2.

Differences in the nucleic acid sequence may result in conservative and/or non-conservative modifications of the amino acid sequence relative to the amino acid sequence of SEQ ID NO: 2.

Conservative modifications to the amino acid sequence of SEQ ID NO: 2 (and the corresponding modifications to the encoding nucleotides) will produce a polypeptide having functional and chemical characteristics similar to those of B7-L polypeptides. In contrast, substantial modifications in the functional and/or chemical characteristics of B7-L polypeptides may be accomplished by selecting substitutions in the amino acid sequence of SEQ ID NO: 2 that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution" may involve a substitution of a native amino acid residue with a normative residue such that there is little or no effect on the polarity or charge of the amino acid residue at that position. Furthermore, any native residue in the polypeptide may also be substituted with alanine, as has been previously described for "alanine scanning mutagenesis."

Conservative amino acid substitutions also encompass non-naturally occurring amino acid residues that are typically incorporated by chemical peptide synthesis rather than by synthesis in biological systems. These include peptidomimetics, and other reversed or inverted forms of amino acid moieties.

Naturally occurring residues may be divided into classes based on common side chain properties:
1) hydrophobic: norleucine, Met, Ala, Val, Leu, Ile;
2) neutral hydrophilic: Cys, Ser, Thr;
3) acidic: Asp, Glu;
4) basic: Asn, Gln, His, Lys, Arg;
5) residues that influence chain orientation: Gly, Pro; and
6) aromatic: Trp, Tyr, Phe.

For example, non-conservative substitutions may involve the exchange of a member of one of these classes for a member from another class. Such substituted residues may be introduced into regions of the human B7-L polypeptide that are homologous with non-human B7-L polypeptides, or into the non-homologous regions of the molecule.

In making such changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte et al., 1982, *J. Mol. Biol.* 157:105-31). It is known that certain amino acids may be substituted for other amino acids having a simiar hydropathic index or score and still retain a similar biological activity. In making changes based upon the hydropathic index, the substitution of amino acids whose hydropathic indices are within ±2 is preferred, those that are within ±1 are particularly preferred, and those within ±0.5 are even more particularly preferred.

It is also understood in the art that the substitution of like amino acids can be made effectively on the basis of hydrophilicity, particularly where the biologically functionally equivalent protein or peptide thereby created is intended for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within ±2 is preferred, those that are within ±1 are particularly preferred, and those within ±0.5 are even more particularly preferred. One may also identify epitopes from primary amino acid sequences on the basis of hydrophilicity. These regions are also referred to as "epitopic core regions."

Desired amino acid substitutions (whether conservative or non-conservative) can be determined by those skilled in the art at the time such substitutions are desired. For example, amino acid substitutions can be used to identify important residues of the B7-L polypeptide, or to increase or decrease the affinity of the B7-L polypeptides described herein. Exemplary amino acid substitutions are set forth in Table I.

TABLE I

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan will be able to determine suitable variants of the polypeptide as set forth in SEQ ID NO: 2 using well-known techniques. For identifying suitable areas of the molecule that may be changed without destroying biological activity, one skilled in the art may target areas not believed to be important for activity. For example, when similar polypeptides with similar activities from the same species or from other species are known, one skilled in the art may compare the amino acid sequence of a B7-L polypeptide to such similar polypeptides. With such a comparison, one can identify residues and portions of the molecules that are conserved among similar polypeptides. It will be appreciated that changes in areas of the B7-L molecule that are not conserved relative to such similar polypeptides would be less likely to adversely affect the biological activity and/or structure of a B7-L polypeptide. One skilled in the art would also know that, even in relatively conserved regions, one may substitute chemically similar amino acids for the naturally occurring residues while retaining activity (conservative amino acid residue substitutions). Therefore, even areas that may be important for biological activity or for structure may be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a B7-L polypeptide that correspond to amino acid residues that are important for activity or structure in similar polypeptides. One skilled in the art may opt for chemically similar amino acid substitutions for such predicted important amino acid residues of B7-L polypeptides.

One skilled in the art can also analyze the three-dimensional structure and amino acid sequence in relation to that structure in similar polypeptides. In view of such information, one skilled in the art may predict the alignment of amino acid residues of B7-L polypeptide with respect to its three dimensional structure. One skilled in the art may choose not to make radical changes to amino acid residues predicted to be on the surface of the protein, since such residues may be involved in important interactions with other molecules. Moreover, one skilled in the art may generate test variants containing a single amino acid substitution at each amino acid residue. The variants could be screened using activity assays known to those with skill in the art. Such variants could be used to gather information about suitable variants. For example, if one discovered that a change to a particular amino acid residue resulted in destroyed, undesirably reduced, or unsuitable activity, variants with such a change would be avoided. In other words, based on information gathered from such routine experiments, one skilled in the art can readily determine the amino acids where further substitutions should be avoided either alone or in combination with other mutations.

A number of scientific publications have been devoted to the prediction of secondary structure. See Moult, 1996, *Curr. Opin. Biotechnol.* 7:422-27; Chou et al., 1974, *Biochemistry* 13:222-45; Chou et al., 1974, *Biochemistry* 113:211-22; Chou et al., 1978, *Adv. Enzymol Relat. Areas Mol. Biol.* 47:45-48; Chou et al., 1978, *Ann. Rev. Biochem.* 47:251-276; and Chou et al., 1979, *Biophys. J.* 26:367-84. Moreover, computer programs are currently available to assist with predicting secondary structure. One method of predicting secondary structure is based upon homology modeling. For example, two polypeptides or proteins that have a sequence identity of greater than 30%, or similarity greater than 40%, often have similar structural topologies. The recent growth of the protein structural database (PDB) has provided enhanced predictability of secondary structure, including the potential number of folds within the structure of a polypeptide or protein. See Holm et al., 1999, *Nucleic Acids Res.* 27:244-47. It has been suggested that there are a limited number of folds in a given polypeptide or protein and that once a critical number of structures have been resolved, structural prediction will become dramatically more accurate (Brenner et al., 1997, *Curr. Opin. Struct. Biol.* 7:369-76).

Additional methods of predicting secondary structure include "threading" (Jones, 1997, *Curr. Opin. Struct. Biol.* 7:377-87; Sippl et al., 1996, *Structure* 4:15-19), "profile analysis" (Bowie et al., 1991, *Science*, 253:164-70; Gribskov et al., 1990, *Methods Enzymol.* 183:146-59; Gribskov et al., 1987, *Proc. Nat. Acad. Sci. U.S.A.* 84:4355-58), and "evolutionary linkage" (See Holm et al., supra, and Brenner et al., supra).

Preferred B7-L polypeptide variants include glycosylation variants wherein the number and/or type of glycosylation sites have been altered compared to the amino acid sequence set forth in SEQ ID NO: 2. In one embodiment, B7-L polypeptide variants comprise a greater or a lesser number of N-linked glycosylation sites than the amino acid sequence set forth in SEQ ID NO: 2. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions that eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional preferred B7-L variants include cysteine variants, wherein one or more cysteine residues are deleted or substituted with another amino acid (e.g., serine) as compared to the amino acid sequence set forth in SEQ ID NO: 2. Cysteine variants are useful when B7-L polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

In other embodiments, B7-L polypeptide variants comprise an amino acid sequence as set forth in SEQ ID NO: 2 with at least one amino acid insertion and wherein the polypeptide has an activity of the polypeptide set forth in SEQ ID NO: 2, or an amino acid sequence as set forth in SEQ ID NO: 2 with at least one amino acid deletion and wherein the polypeptide has an activity of the polypeptide set forth in SEQ ID NO: 2. B7-L polypeptide variants also comprise an amino acid sequence as set forth in SEQ ID NO: 2 wherein the polypeptide has a carboxyl- and/or amino-terminal truncation and further wherein the polypeptide has an activity of the polypeptide set forth in SEQ ID NO: 2. B7-L polypeptide variants further comprise an amino acid sequence as set forth in SEQ ID NO: 2 with at least one modification selected from the group consisting of amino acid substitutions, amino acid insertions, amino acid deletions, carboxyl-terminal truncations, and amino-terminal truncations and wherein the polypeptide has an activity of the polypeptide set forth in SEQ ID NO: 2.

In further embodiments, B7-L polypeptide variants comprise an amino acid sequence that is at least about 70 percent identical to the amino acid sequence as set forth in SEQ ID NO: 2. In preferred embodiments, B7-L polypeptide variants comprise an amino acid sequence that is about 75 percent, or about 80 percent, or about 85 percent, or about 90 percent, or about 95, 96, 97, 98, or 99 percent identical to the amino acid sequence as set forth in SEQ ID NO: 2. B7-L polypeptide variants possess at least one activity of the polypeptide set forth in SEQ ID NO: 2.

In addition, the polypeptide comprising the amino acid sequence of SEQ ID NO: 2, or other B7-L polypeptide, may be fused to a homologous polypeptide to form a homodimer or to a heterologous polypeptide to form a heterodimer. Heterologous peptides and polypeptides include, but are not limited to: an epitope to allow for the detection and/or isolation of a B7-L fusion polypeptide; a transmembrane receptor protein or a portion thereof, such as an extracellular domain or a transmembrane and intracellular domain; a ligand or a portion thereof which binds to a transmembrane receptor protein; an enzyme or portion thereof which is catalytically active; a polypeptide or peptide which promotes oligomerization, such as a leucine zipper domain; a polypeptide or peptide which increases stability, such as an immunoglobulin constant region; and a polypeptide which has a therapeutic activity different from the polypeptide comprising the amino acid sequence as set forth in SEQ ID NO: 2, or other B7-L polypeptide.

Fusions can be made either at the amino-terminus or at the carboxyl-terminus of the polypeptide comprising the amino acid sequence set forth in SEQ ID NO: 2, or other B7-L polypeptide. Fusions may be direct with no linker or adapter molecule or may be through a linker or adapter molecule. A linker or adapter molecule may be one or more amino acid residues, typically from about 20 to about 50 amino acid residues. A linker or adapter molecule may also be designed with a cleavage site for a DNA restriction endonuclease or for a protease to allow for the separation of the fused moieties. It will be appreciated that once constructed, the fusion polypeptides can be derivatized according to the methods described herein.

In a further embodiment of the invention, the polypeptide comprising the amino acid sequence of SEQ ID NO: 2, or other B7-L polypeptide, is fused to one or more domains of an Fc region of human IgG. Antibodies comprise two functionally independent parts, a variable domain known as "Fab," that binds an antigen, and a constant domain known as "Fc," that is involved in effector functions such as complement activation and attack by phagocytic cells. An Fc has a long serum half-life, whereas an Fab is short-lived. Capon et al., 1989, *Nature* 337:525-31. When constructed together with a therapeutic protein, an Fc domain can provide longer half-life or incorporate such functions as Fc receptor binding, protein A binding, complement fixation, and perhaps even placental transfer. Id. Table II summarizes the use of certain Fc fusions known in the art.

fusion to an Fc region allows for dimerization/multimerization of the fusion polypeptide. The Fc region may be a naturally occurring Fc region, or may be altered to improve certain qualities, such as therapeutic qualities, circulation time, or reduced aggregation.

Identity and similarity of related nucleic acid molecules and polypeptides are readily calculated by known methods. Such methods include, but are not limited to those described in *Computational Molecular Biology* (A. M. Lesk, ed., Oxford University Press 1988); *Biocomputing: Informatics and Genome Projects* (D. W. Smith, ed., Academic Press 1993); *Computer Analysis of Sequence Data* (Part 1, A. M. Griffin and H. G. Griffin, eds., Humana Press 1994); G. von Heinle, *Sequence Analysis in Molecular Biology* (Academic Press 1987); *Sequence Analysis Primer* (M. Gribskov and J. Devereux, eds., M. Stockton Press 1991); and Carillo et al., 1988, *SIAM Applied Math.*, 48:1073.

Preferred methods to determine identity and/or similarity are designed to give the largest match between the sequences tested. Methods to determine identity and similarity are described in publicly available computer programs. Preferred computer program methods to determine identity and similarity between two sequences include, but are not limited to, the GCG program package, including GAP (Devereux et al., 1984, *Nucleic Acids Res.* 12:387; Genetics Computer Group, University of Wisconsin, Madison, Wis.), BLASTP, BLASTN, and FASTA (Altschul et al., 1990, *J. Mol. Biol.* 215:403-10). The BLASTX program is publicly available

TABLE II

Fc Fusion with Therapeutic Proteins

| Form of Fc | Fusion partner | Therapeutic implications | Reference |
|---|---|---|---|
| IgG1 | N-terminus of CD30-L | Hodgkin's disease; anaplastic lymphoma; T-cell leukemia | U.S. Pat. No. 5,480,981 |
| Murine Fcγ2a | IL-10 | anti-inflammatory; transplant rejection | Zheng et al., 1995, J. Immunol. 154: 5590-600 |
| IgG1 | TNF receptor | septic shock | Fisher et al., 1996, N. Engl. J. Med. 334: 1697-1702; Van Zee et al., 1996, J. Immunol. 156: 2221-30 |
| IgG, IgA, IgM, or IgE (excluding the first domain) | TNF receptor | inflammation, autoimmune disorders | U.S. Pat. No. 5,808,029 |
| IgG1 | CD4 receptor | AIDS | Capon et al., 1989, Nature 337: 525-31 |
| IgG1, IgG3 | N-terminus of IL-2 | anti-cancer, antiviral | Harvill et al., 1995, Immunotech. 1: 95-105 |
| IgG1 | C-terminus of OPG | osteoarthritis; bone density | WO 97/23614 |
| IgG1 | N-terminus of leptin | anti-obesity | PCT/US 97/23183, filed December 11, 1997 |
| Human Ig Cγ1 | CTLA-4 | autoimmune disorders | Linsley, 1991, J. Exp. Med., 174: 561-69 |

In one example, a human IgG hinge, CH2, and CH3 region may be fused at either the amino-terminus or carboxyl-terminus of the B7-L polypeptides using methods known to the skilled artisan. In another example, a human IgG hinge, CH2, and CH3 region may be fused at either the amino-terminus or carboxyl-terminus of a B7-L polypeptide fragment (e.g., the predicted extracellular portion of B7-L polypeptide).

The resulting B7-L fusion polypeptide may be purified by use of a Protein A affinity column. Peptides and proteins fused to an Fc region have been found to exhibit a substantially greater half-life in vivo than the unfused counterpart. Also, a from the National Center for Biotechnology Information (NCBI) and other sources (Altschul et al., *BLAST Manual* (NCB NLM NIH, Bethesda, Md.); Altschul et al., 1990, supra). The well-known Smith Waterman algorithm may also be used to determine identity.

Certain alignment schemes for aligning two amino acid sequences may result in the matching of only a short region of the two sequences, and this small aligned region may have very high sequence identity even though there is no significant relationship between the two full-length sequences. Accordingly, in a preferred embodiment, the selected alignment method (GAP program) will result in an alignment that spans at least 50 contiguous amino acids of the claimed polypeptide.

For example, using the computer algorithm GAP (Genetics Computer Group, University of Wisconsin, Madison, Wis.), two polypeptides for which the percent sequence identity is to be determined are aligned for optimal matching of their respective amino acids (the "matched span," as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 0.1× the gap opening penalty), as well as a comparison matrix such as PAM 250 or BLOSUM 62 are used in conjunction with the algorithm. A standard comparison matrix is also used by the algorithm (see Dayhoff et al., 5 *Atlas of Protein Sequence and Structure* (Supp. 3 1978)(PAM250 comparison matrix); Henikoff et al., 1992, *Proc. Natl. Acad. Sci USA* 89:10915-19 (BLOSUM 62 comparison matrix)).

Preferred parameters for polypeptide sequence comparison include the following:
  Algorithm: Needleman and Wunsch, 1970, *J. Mol. Biol.* 48:443-53;
  Comparison matrix: BLOSUM 62 (Henikoff et al., supra);
  Gap Penalty: 12
  Gap Length Penalty: 4
  Threshold of Similarity: 0

The GAP program is useful with the above parameters. The aforementioned parameters are the default parameters for polypeptide comparisons (along with no penalty for end gaps) using the GAP algorithm.

Preferred parameters for nucleic acid molecule sequence comparison include the following:
  Algorithm: Needleman and Wunsch, supra;
  Comparison matrix: matches =+10, mismatch=0
  Gap Penalty: 50
  Gap Length Penalty: 3

The GAP program is also useful with the above parameters. The aforementioned parameters are the default parameters for nucleic acid molecule comparisons.

Other exemplary algorithms, gap opening penalties, gap extension penalties, comparison matrices, and thresholds of similarity may be used, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are generally preferred) or between one sequence and a large database of sequences (in which case FASTA or BLASTA are preferred).

Nucleic Acid Molecules

The nucleic acid molecules encoding a polypeptide comprising the amino acid sequence of a B7-L polypeptide can readily be obtained in a variety of ways including, without limitation, chemical synthesis, cDNA or genomic library screening, expression library screening, and/or PCR amplification of cDNA.

Recombinant DNA methods used herein are generally those set forth in Sambrook et al., *Molecular Cloning: A Laboratory Manual* (Cold Spring Harbor Laboratory Press, 1989) and/or *Current Protocols in Molecular Biology* (Ausubel et al., eds., Green Publishers Inc. and Wiley and Sons 1994). The invention provides for nucleic acid molecules as described herein and methods for obtaining such molecules.

Where a gene encoding the amino acid sequence of a B7-L polypeptide has been identified from one species, all or a portion of that gene may be used as a probe to identify orthologs or related genes from the same species. The probes or primers may be used to screen cDNA libraries from various tissue sources believed to express the B7-L polypeptide. In addition, part or all of a nucleic acid molecule having the sequence as set forth in SEQ ID NO: 1 may be used to screen a genomic library to identify and isolate a gene encoding the amino acid sequence of a B7-L polypeptide. Typically, conditions of moderate or high stringency will be employed for screening to minimize the number of false positives obtained from the screening.

Nucleic acid molecules encoding the amino acid sequence of B7-L polypeptides may also be identified by expression cloning which employs the detection of positive clones based upon a property of the expressed protein. Typically, nucleic acid libraries are screened by the binding an antibody or other binding partner (e.g., receptor or ligand) to cloned proteins that are expressed and displayed on a host cell surface. The antibody or binding partner is modified with a detectable label to identify those cells expressing the desired clone.

Recombinant expression techniques conducted in accordance with the descriptions set forth below may be followed to produce these polynucleotides and to express the encoded polypeptides. For example, by inserting a nucleic acid sequence that encodes the amino acid sequence of a B7-L polypeptide into an appropriate vector, one skilled in the art can readily produce large quantities of the desired nucleotide sequence. The sequences can then be used to generate detection probes or amplification primers. Alternatively, a polynucleotide encoding the amino acid sequence of a B7-L polypeptide can be inserted into an expression vector. By introducing the expression vector into an appropriate host, the encoded B7-L polypeptide may be produced in large amounts.

Another method for obtaining a suitable nucleic acid sequence is the polymerase chain reaction (PCR). In this method, cDNA is prepared from poly(A)+ RNA or total RNA using the enzyme reverse transcriptase. Two primers, typically complementary to two separate regions of cDNA encoding the amino acid sequence of a B7-L polypeptide, are then added to the cDNA along with a polymerase such as Taq polymerase, and the polymerase amplifies the cDNA region between the two primers.

Another means of preparing a nucleic acid molecule encoding the amino acid sequence of a B7-L polypeptide is chemical synthesis using methods well known to the skilled artisan such as those described by Engels et al., 1989, *Angew. Chem. Intl. Ed.* 28:716-34. These methods include, inter alia, the phosphotriester, phosphoramidite, and H-phosphonate methods for nucleic acid synthesis. A preferred method for such chemical synthesis is polymer-supported synthesis using standard phosphoramidite chemistry. Typically, the DNA encoding the amino acid sequence of a B7-L polypeptide will be several hundred nucleotides in length. Nucleic acids larger than about 100 nucleotides can be synthesized as several fragments using these methods. The fragments can then be ligated together to form the full-length nucleotide sequence of a B7-L gene. Usually, the DNA fragment encoding the amino-terminus of the polypeptide will have an ATG, which encodes a methionine residue. This methionine may or may not be present on the mature form of the B7-L polypeptide, depending on whether the polypeptide produced in the host cell is designed to be secreted from that cell. Other methods known to the skilled artisan may be used as well.

In certain embodiments, nucleic acid variants contain codons which have been altered for optimal expression of a B7-L polypeptide in a given host cell. Particular codon alterations will depend upon the B7-L polypeptide and host cell selected for expression. Such "codon optimization" can be carried out by a variety of methods, for example, by selecting codons which are preferred for use in highly expressed genes in a given host cell. Computer algorithms which incorporate codon frequency tables such as "Eco_high.Cod" for codon preference of highly expressed bacterial genes may be used and are provided by the University of Wisconsin Package Version 9.0 (Genetics Computer Group, Madison, Wis.). Other useful codon frequency tables include "Celegans_high.cod," "Celegans_low.cod," "*Drosophila*_high.cod," "Human_high.cod," "Maize_high.cod," and "Yeast_high.cod."

In some cases, it may be desirable to prepare nucleic acid molecules encoding B7-L polypeptide variants. Nucleic acid molecules encoding variants may be produced using site directed mutagenesis, PCR amplification, or other appropriate methods, where the primer(s) have the desired point mutations (see Sambrook et al., supra, and Ausubel et al., supra, for descriptions of mutagenesis techniques). Chemical synthesis using methods described by Engels et al., supra, may also be used to prepare such variants. Other methods known to the skilled artisan may be used as well.

Vectors and Host Cells

A nucleic acid molecule encoding the amino acid sequence of a B7-L polypeptide is inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding the amino acid sequence of a B7-L polypeptide may be amplified/expressed in prokaryotic, yeast, insect (baculovirus systems) and/or eukaryotic host cells. Selection of the host cell will depend in part on whether a B7-L polypeptide is to be post-translationally modified (e.g., glycosylated and/or phosphorylated). If so, yeast, insect, or mammalian host cells are preferable. For a review of expression vectors, see *Meth. Enz.*, vol. 185 (D. V. Goeddel, ed., Academic Press 1990).

Typically, expression vectors used in any of the host cells will contain sequences for plasmid maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation sequence, a polylinker region for inserting the nucleic acid encoding the polypeptide to be expressed, and a selectable marker element. Each of these sequences is discussed below.

Optionally, the vector may contain a "tag"-encoding sequence, i.e., an oligonucleotide molecule located at the 5' or 3' end of the B7-L polypeptide coding sequence; the oligonucleotide sequence encodes polyHis (such as hexaHis), or another "tag" such as FLAG, HA (hemaglutinin influenza virus), or myc for which commercially available antibodies exist. This tag is typically fused to the polypeptide upon expression of the polypeptide, and can serve as a means for affinity purification of the B7-L polypeptide from the host cell. Affinity purification can be accomplished, for example, by column chromatography using antibodies against the tag as an affinity matrix. Optionally, the tag can subsequently be removed from the purified B7-L polypeptide by various means such as using certain peptidases for cleavage.

Flanking sequences may be homologous (i.e., from the same species and/or strain as the host cell), heterologous (i.e., from a species other than the host cell species or strain), hybrid (i.e., a combination of flanking sequences from more than one source), or synthetic, or the flanking sequences may be native sequences that normally function to regulate B7-L polypeptide expression. As such, the source of a flanking sequence may be any prokaryotic or eukaryotic organism, any vertebrate or invertebrate organism, or any plant, provided that the flanking sequence is functional in, and can be activated by, the host cell machinery.

Flanking sequences useful in the vectors of this invention may be obtained by any of several methods well known in the art. Typically, flanking sequences useful herein—other than the B7-L gene flanking sequences—will have been previously identified by mapping and/or by restriction endonuclease digestion and can thus be isolated from the proper tissue source using the appropriate restriction endonucleases. In some cases, the full nucleotide sequence of a flanking sequence may be known. Here, the flanking sequence may be synthesized using the methods described herein for nucleic acid synthesis or cloning.

Where all or only a portion of the flanking sequence is known, it may be obtained using PCR and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose will be readily apparent to one of ordinary skill in the art.

An origin of replication is typically a part of those prokaryotic expression vectors purchased commercially, and the origin aids in the amplification of the vector in a host cell. Amplification of the vector to a certain copy number can, in some cases, be important for the optimal expression of a B7-L polypeptide. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria and various origins (e.g., SV40, polyoma, adenovirus, vesicular stomatitus virus (VSV), or papillomaviruses such as HPV or BPV) are useful for cloning vectors in mammalian cells. Generally, the origin of replication component is not needed for mammalian expression vectors (for example, the SV40 origin is often used only because it contains the early promoter).

A transcription termination sequence is typically located 3' of the end of a polypeptide coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein.

A selectable marker gene element encodes a protein necessary for the survival and growth of a host cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Preferred selectable markers are the kanamycin resistance gene, the ampicillin resistance gene, and the tetracycline resistance gene. A neomycin resistance gene may also be used for selection in prokaryotic and eukaryotic host cells.

Other selection genes may be used to amplify the gene that will be expressed. Amplification is the process wherein genes that are in greater demand for the production of a protein critical for growth are reiterated in tandem within the chromosomes of successive generations of recombinant cells. Examples of suitable selectable markers for mammalian cells include dihydrofolate reductase (DHFR) and thymidine kinase. The mammalian cell transformants are placed under selection pressure wherein only the transformants are uniquely adapted to survive by virtue of the selection gene present in the vector. Selection pressure is imposed by culturing the transformed cells under conditions in which the concentration of selection agent in the medium is successively changed, thereby leading to the amplification of both the selection gene and the DNA that encodes a B7-L polypeptide. As a result, increased quantities of B7-L polypeptide are synthesized from the amplified DNA.

A ribosome binding site is usually necessary for translation initiation of mRNA and is characterized by a Shine-Dalgarno sequence (prokaryotes) or a Kozak sequence (eukaryotes). The element is typically located 3' to the promoter and 5' to the coding sequence of a B7-L polypeptide to be expressed. The Shine-Dalgarno sequence is varied but is typically a polypurine (i.e., having a high A-G content). Many Shine-Dalgarno sequences have been identified, each of which can be readily synthesized using methods set forth herein and used in a prokaryotic vector.

A leader, or signal, sequence may be used to direct a B7-L polypeptide out of the host cell. Typically, a nucleotide sequence encoding the signal sequence is positioned in the coding region of a B7-L nucleic acid molecule, or directly at the 5' end of a B7-L polypeptide coding region. Many signal sequences have been identified, and any of those that are functional in the selected host cell may be used in conjunction with a B7-L nucleic acid molecule. Therefore, a signal sequence may be homologous (naturally occurring) or heterologous to the B7-L nucleic acid molecule. Additionally, a signal sequence may be chemically synthesized using methods described herein. In most cases, the secretion of a B7-L polypeptide from the host cell via the presence of a signal peptide will result in the removal of the signal peptide from the secreted B7-L polypeptide. The signal sequence may be a component of the vector, or it may be a part of a B7-L nucleic acid molecule that is inserted into the vector.

Included within the scope of this invention is the use of either a nucleotide sequence encoding a native B7-L polypeptide signal sequence joined to a B7-L polypeptide coding region or a nucleotide sequence encoding a heterologous signal sequence joined to a B7-L polypeptide coding region. The heterologous signal sequence selected should be one that is recognized and processed, i.e., cleaved by a signal peptidase, by the host cell. For prokaryotic host cells that do not recognize and process the native B7-L polypeptide signal sequence, the signal sequence is substituted by a prokaryotic signal sequence selected, for example, from the group of the alkaline phosphatase, penicillinase, or heat-stable enterotoxin II leaders. For yeast secretion, the native B7-L polypeptide signal sequence may be substituted by the yeast invertase, alpha factor, or acid phosphatase leaders. In mammalian cell expression the native signal sequence is satisfactory, although other mammalian signal sequences may be suitable.

In some cases, such as where glycosylation is desired in a eukaryotic host cell expression system, one may manipulate the various presequences to improve glycosylation or yield. For example, one may alter the peptidase cleavage site of a particular signal peptide, or add pro-sequences, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated form of the desired B7-L polypeptide, if the enzyme cuts at such area within the mature polypeptide.

In many cases, transcription of a nucleic acid molecule is increased by the presence of one or more introns in the vector; this is particularly true where a polypeptide is produced in eukaryotic host cells, especially mammalian host cells. The introns used may be naturally occurring within the B7-L gene especially where the gene used is a full-length genomic sequence or a fragment thereof. Where the intron is not naturally occurring within the gene (as for most cDNAs), the intron may be obtained from another source. The position of the intron with respect to flanking sequences and the B7-L gene is generally important, as the intron must be transcribed to be effective. Thus, when a B7-L cDNA molecule is being transcribed, the preferred position for the intron is 3' to the transcription start site and 5' to the poly-A transcription termination sequence. Preferably, the intron or introns will be located on one side or the other (i.e., 5' or 3') of the cDNA such that it does not interrupt the coding sequence. Any intron from any source, including viral, prokaryotic and eukaryotic (plant or animal) organisms, may be used to practice this invention, provided that it is compatible with the host cell into which it is inserted. Also included herein are synthetic introns. Optionally, more than one intron may be used in the vector.

The expression and cloning vectors of the present invention will typically contain a promoter that is recognized by the host organism and operably linked to the molecule encoding the B7-L polypeptide. Promoters are untranscribed sequences located upstream (i.e., 5') to the start codon of a structural gene (generally within about 100 to 1000 bp) that control the transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no control over gene expression. A large number of promoters, recognized by a variety of potential host cells, are well known. A suitable promoter is operably linked to the DNA encoding B7-L polypeptide by removing the promoter from the source DNA by restriction enzyme digestion and inserting the desired promoter sequence into the vector. The native B7-L promoter sequence may be used to direct amplification and/or expression of a B7-L nucleic acid molecule. A heterologous promoter is preferred, however, if it permits greater transcription and higher yields of the expressed protein as compared to the native promoter, and if it is compatible with the host cell system that has been selected for use.

Promoters suitable for use with prokaryotic hosts include the beta-lactamase and lactose promoter systems; alkaline phosphatase; a tryptophan (trp) promoter system; and hybrid promoters such as the tac promoter. Other known bacterial promoters are also suitable. Their sequences have been published, thereby enabling one skilled in the art to ligate them to the desired DNA sequence, using linkers or adapters as needed to supply any useful restriction sites.

Suitable promoters for use with yeast hosts are also well known in the art. Yeast enhancers are advantageously used with yeast promoters. Suitable promoters for use with mammalian host cells are well known and include, but are not limited to, those obtained from the genomes of viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Additional promoters which may be of interest in controlling B7-L gene expression include, but are not limited to: the SV40 early promoter region (Bernoist and Chambon, 1981, *Nature* 290:304-10); the CMV promoter; the promoter contained in the 3' long terminal repeat of Rous sarcoma virus (Yamamoto, et al., 1980, *Cell* 22:787-97); the herpes thymidine kinase promoter (Wagner et al., 1981, *Proc. Natl. Acad. Sci. U.S.A.* 78:1444-45); the regulatory sequences of the metallothionine gene (Brinster et al., 1982, *Nature* 296:39-42); prokaryotic expression vectors such as the beta-lactamase promoter (Villa-Kamaroff et al., 1978, *Proc. Natl. Acad. Sci. U.S.A.*, 75:3727-31); or the tac promoter (DeBoer et al., 1983, *Proc. Natl. Acad. Sci. U.S.A.*, 80:21-25). Also of interest are the following animal transcriptional control regions, which exhibit tissue specificity and have been utilized in transgenic animals: the elastase I gene control region which is active in pancreatic acinar cells (Swift et al., 1984, *Cell* 38:639-46; Ornitz et al., 1986, *Cold Spring Harbor Symp. Quant. Biol.* 50:399-409 (1986); MacDonald, 1987, *Hepatology* 7:425-515); the insulin gene control region which is active in pancreatic beta cells (Hanahan, 1985, *Nature* 315:115-22); the immunoglobulin gene control region which is active in lymphoid cells (Grosschedl et al., 1984, *Cell* 38:647-58; Adames et al., 1985, *Nature* 318:533-38; Alexander et al., 1987, *Mol. Cell. Biol.*, 7:1436-44); the mouse mammary tumor virus control region which is active in testicular, breast, lymphoid and mast cells (Leder et al., 1986, *Cell* 45:485-95); the albumin gene control region which is active in liver (Pinkert et al., 1987, *Genes and Devel.* 1:268-76); the alpha-feto-protein gene control region which is active in liver (Krumlauf et al., 1985, *Mol. Cell. Biol.*, 5:1639-48; Hammer et al., 1987, *Science* 235:53-58); the alpha 1-antitrypsin gene control region which is active in the liver (Kelsey et al., 1987, *Genes and Devel.* 1:161-71); the beta-globin gene control region which is active in myeloid cells (Mogram et al., 1985, *Nature* 315:338-40; Kollias et al., 1986, *Cell* 46:89-94); the myelin basic protein gene control region which is active in oligodendrocyte cells in the brain (Readhead et al., 1987, *Cell* 48:703-12); the myosin light chain-2 gene control region which is active in skeletal muscle (Sani, 1985, *Nature* 314:283-86); and the gonadotropic releasing hormone gene control region which is active in the hypothalamus (Mason et al., 1986, *Science* 234: 1372-78).

An enhancer sequence may be inserted into the vector to increase the transcription of a DNA encoding a B7-L polypeptide of the present invention by higher eukaryotes. Enhancers are cis-acting elements of DNA, usually about 10-300 bp in length, that act on the promoter to increase transcription. Enhancers are relatively orientation and position independent. They have been found 5' and 3' to the transcription unit. Several enhancer sequences available from mammalian genes are known (e.g., globin, elastase, albumin, alpha-feto-protein and insulin). Typically, however, an enhancer from a virus will be used. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a B7-L nucleic acid molecule, it is typically located at a site 5' from the promoter.

Expression vectors of the invention may be constructed from a starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

Preferred vectors for practicing this invention are those that are compatible with bacterial, insect, and mammalian host cells. Such vectors include, inter alia, pCRII, pCR3, and pcDNA3.1 (Invitrogen, San Diego, Calif.), pBSII (Stratagene, La Jolla, Calif.), pET15 (Novagen, Madison, Wis.), pGEX (Pharmacia Biotech, Piscataway, N.J.), pEGFP-N2 (Clontech, Palo Alto, Calif.), pETL (BlueBacII, Invitrogen), pDSR-alpha (International Pub. No. WO 90/14363) and pFastBacDual (Gibco-BRL, Grand Island, N.Y.).

Additional suitable vectors include, but are not limited to, cosmids, plasmids, or modified viruses, but it will be appreciated that the vector system must be compatible with the selected host cell. Such vectors include, but are not limited to plasmids such as Bluescript® plasmid derivatives (a high copy number ColE1-based phagemid; Stratagene Cloning Systems, La Jolla Calif.), PCR cloning plasmids designed for cloning Taq-amplified PCR products (e.g., TOPO™ TA Cloning® Kit and PCR2.1® plasmid derivatives; Invitrogen), and mammalian, yeast or virus vectors such as a baculovirus expression system (pBacPAK plasmid derivatives; Clontech).

After the vector has been constructed and a nucleic acid molecule encoding a B7-L polypeptide has been inserted into the proper site of the vector, the completed vector may be inserted into a suitable host cell for amplification and/or polypeptide expression. The transformation of an expression vector for a B7-L polypeptide into a selected host cell may be accomplished by well known methods including methods such as transfection, infection, calcium chloride, electroporation, microinjection, lipofection, DEAE-dextran method, or other known techniques. The method selected will in part be a function of the type of host cell to be used. These methods and other suitable methods are well known to the skilled artisan, and are set forth, for example, in Sambrook et al., supra.

Host cells may be prokaryotic host cells (such as *E. coli*) or eukaryotic host cells (such as a yeast, insect, or vertebrate cell). The host cell, when cultured under appropriate conditions, synthesizes a B7-L polypeptide that can subsequently be collected from the culture medium (if the host cell secretes it into the medium) or directly from the host cell producing it (if it is not secreted). The selection of an appropriate host cell will depend upon various factors, such as desired expression levels, polypeptide modifications that are desirable or necessary for activity (such as glycosylation or phosphorylation) and ease of folding into a biologically active molecule.

A number of suitable host cells are known in the art and many are available from the American Type Culture Collection (ATCC), Manassas, Va. Examples include, but are not limited to, mammalian cells, such as Chinese hamster ovary cells (CHO), CHO DHFR(−) cells (Urlaub et al., 1980, *Proc. Natl. Acad. Sci. U.S.A.* 97:4216-20), human embryonic kidney (HEK) 293 or 293T cells, or 3T3 cells. The selection of suitable mammalian host cells and methods for transformation, culture, amplification, screening, product production, and purification are known in the art. Other suitable mammalian cell lines, are the monkey COS-1 and COS-7 cell lines, and the CV-1 cell line. Further exemplary mammalian host cells include primate cell lines and rodent cell lines, including transformed cell lines. Normal diploid cells, cell strains derived from in vitro culture of primary tissue, as well as primary, explants, are also suitable. Candidate cells may be genotypically deficient in the selection gene, or may contain a dominantly acting selection gene. Other suitable mammalian cell lines include but are not limited to, mouse neuroblastoma N2A cells, HeLa, mouse L-929 cells, 3T3 lines derived from Swiss, Balb-c or NIH mice, BHK or HaK hamster cell lines. Each of these cell lines is known by and available to those skilled in the art of protein expression.

Similarly useful as host cells suitable for the present invention are bacterial cells. For example, the various strains of *E. coli* (e.g., HB101, DH5α, DH10, and MC1061) are well-known as host cells in the field of biotechnology. Various strains of *B. subtilis*, *Pseudomonas* spp., other *Bacillus* spp., *Streptomyces* spp., and the like may also be employed in this method.

Many strains of yeast cells known to those skilled in the art are also available as host cells for the expression of the polypeptides of the present invention. Preferred yeast cells include, for example, *Saccharomyces cerivisae* and *Pichia pastoris*.

Additionally, where desired, insect cell systems may be utilized in the methods of the present invention. Such systems are described, for example, in Kitts et al., 1993, *Biotechniques*, 14:810-17; Lucklow, 1993, *Curr. Opin. Biotechnol.* 4:564-72; and Lucklow et al., 1993, *J. Virol.*, 67:4566-79. Preferred insect cells are Sf-9 and Hi5 (Invitrogen).

One may also use transgenic animals to express glycosylated B7-L polypeptides. For example, one may use a transgenic milk-producing animal (a cow or goat, for example) and obtain the present glycosylated polypeptide in the animal milk. One may also use plants to produce B7-L polypeptides, however, in general, the glycosylation occurring in plants is different from that produced in mammalian cells, and may result in a glycosylated product which is not suitable for human therapeutic use.

Polypeptide Production

Host cells comprising a B7-L polypeptide expression vector may be cultured using standard media well known to the skilled artisan. The media will usually contain all nutrients necessary for the growth and survival of the cells. Suitable media for culturing *E. coli* cells include, for example, Luria Broth (LB) and/or Terrific Broth (TB). Suitable media for culturing eukaryotic cells include Roswell Park Memorial Institute medium 1640 (RPMI 1640), Minimal Essential Medium (MEM) and/or Dulbecco's Modified Eagle Medium (DMEM), all of which may be supplemented with serum and/or growth factors as necessary for the particular cell line being cultured. A suitable medium for insect cultures is Grace's medium supplemented with yeastolate, lactalbumin hydrolysate, and/or fetal calf serum as necessary.

Typically, an antibiotic or other compound useful for selective growth of transfected or transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline, and neomycin.

The amount of a B7-L polypeptide produced by a host cell can be evaluated using standard methods known in the art. Such methods include, without limitation, Western blot analysis, SDS-polyacrylamide gel electrophoresis, non-denaturing gel electrophoresis, High Performance Liquid Chromatography (HPLC) separation, immunoprecipitation, and/or activity assays such as DNA binding gel shift assays.

If a B7-L polypeptide has been designed to be secreted from the host cells, the majority of polypeptide may be found in the cell culture medium. If however, the B7-L polypeptide is not secreted from the host cells, it will be present in the cytoplasm and/or the nucleus (for eukaryotic host cells) or in the cytosol (for gram-negative bacteria host cells).

For a B7-L polypeptide situated in the host cell cytoplasm and/or nucleus (for eukaryotic host cells) or in the cytosol (for bacterial host cells), the intracellular material (including inclusion bodies for gram-negative bacteria) can be extracted from the host cell using any standard technique known to the skilled artisan. For example, the host cells can be lysed to release the contents of the periplasm/cytoplasm by French press, homogenization, and/or sonication followed by centrifugation.

If a B7-L polypeptide has formed inclusion bodies in the cytosol, the inclusion bodies can often bind to the inner and/or outer cellular membranes and thus will be found primarily in the pellet material after centrifugation. The pellet material can then be treated at pH extremes or with a chaotropic agent such as a detergent, guanidine, guanidine derivatives, urea, or urea derivatives in the presence of a reducing agent such as dithiothreitol at alkaline pH or tris carboxyethyl phosphine at acid pH to release, break apart, and solubilize the inclusion bodies. The solubilized B7-L polypeptide can then be analyzed using gel electrophoresis, immunoprecipitation, or the like. If it is desired to isolate the B7-L polypeptide, isolation may be accomplished using standard methods such as those described herein and in Marston et al., 1990, *Meth. Enz.*, 182:264-75.

In some cases, a B7-L polypeptide may not be biologically active upon isolation. Various methods for "refolding" or converting the polypeptide to its tertiary structure and generating disulfide linkages can be used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In most cases the refolding/oxidation solution will also contain a reducing agent or the reducing agent plus its oxidized form in a specific ratio to generate a particular redox potential allowing for disulfide shuffling to occur in the formation of the protein's cysteine bridges. Some of the commonly used redox couples include cysteine/cystamine, glutathione (GSH)/dithiobis GSH, cupric chloride, dithiothreitol(DTT)/dithiane DTT, and 2-2- mercaptoethanol(bME)/dithio-b(ME). In many instances, a cosolvent may be used or may be needed to increase the efficiency of the refolding, and the more common reagents used for this purpose include glycerol, polyethylene glycol of various molecular weights, arginine and the like.

If inclusion bodies are not formed to a significant degree upon expression of a B7-L polypeptide, then the polypeptide will be found primarily in the supernatant after centrifugation of the cell homogenate. The polypeptide may be further isolated from the supernatant using methods such as those described herein.

The purification of a B7-L polypeptide from solution can be accomplished using a variety of techniques. If the polypeptide has been synthesized such that it contains a tag such as Hexahistidine (B7-L polypeptide/hexaHis) or other small peptide such as FLAG (Eastman Kodak Co., New Haven, Conn.) or myc (Invitrogen) at either its carboxyl- or amino-terminus, it may be purified in a one-step process by passing the solution through an affinity column where the column matrix has a high affinity for the tag.

For example, polyhistidine binds with great affinity and specificity to nickel. Thus, an affinity column of nickel (such as the Qiagen® nickel columns) can be used for purification of B7-L polypeptide/polyHis. See, e.g., *Current Protocols in Molecular Biology* § 10.11.8 (Ausubel et al., eds., Green Publishers Inc. and Wiley and Sons 1993).

Additionally, B7-L polypeptides may be purified through the use of a monoclonal antibody that is capable of specifically recognizing and binding to a B7-L polypeptide.

Other suitable procedures for purification include, without limitation, affinity chromatography, immunoaffinity chromatography, ion exchange chromatography, molecular sieve chromatography, HPLC, electrophoresis (including native gel electrophoresis) followed by gel elution, and preparative isoelectric focusing ("Isoprime" machine/technique, Hoefer Scientific, San Francisco, Calif.). In some cases, two or more purification techniques may be combined to achieve increased purity.

B7-L polypeptides may also be prepared by chemical synthesis methods (such as solid phase peptide synthesis) using techniques known in the art such as those set forth by Merrifield et al., 1963, *J. Am. Chem. Soc.* 85:2149; Houghten et al., 1985, *Proc Natl Acad. Sci. USA* 82:5132; and Stewart and Young, *Solid Phase Peptide Synthesis* (Pierce Chemical Co. 1984). Such polypeptides may be synthesized with or without a methionine on the amino-terminus. Chemically synthesized B7-L polypeptides may be oxidized using methods set forth in these references to form disulfide bridges. Chemically synthesized B7-L polypeptides are expected to have comparable biological activity to the corresponding B7-L polypeptides produced recombinantly or purified from natural sources, and thus may be used interchangeably with a recombinant or natural B7-L polypeptide.

Another means of obtaining B7-L polypeptide is via purification from biological samples such as source tissues and/or fluids in which the B7-L polypeptide is naturally found. Such purification can be conducted using methods for protein purification as described herein. The presence of the B7-L polypeptide during purification may be monitored, for example, using an antibody prepared against recombinantly produced B7-L polypeptide or peptide fragments thereof.

A number of additional methods for producing nucleic acids and polypeptides are known in the art, and the methods can be used to produce polypeptides having specificity for B7-L polypeptide. See, e.g., Roberts et al., 1997, *Proc. Natl. Acad. Sci. U.S.A.* 94:12297-303, which describes the production of fusion proteins between an mRNA and its encoded peptide. See also, Roberts, 1999, *Curr. Opin. Chem. Biol.* 3:268-73. Additionally, U.S. Pat. No. 5,824,469 describes methods for obtaining oligonucleotides capable of carrying out a specific biological function. The procedure involves generating a heterogeneous pool of oligonucleotides, each having a 5' randomized sequence, a central preselected sequence, and a 3' randomized sequence. The resulting heterogeneous pool is introduced into a population of cells that do not exhibit the desired biological function. Subpopulations of the cells are then screened for those that exhibit a predetermined biological function. From that subpopulation, oligonucleotides capable of carrying out the desired biological function are isolated.

U.S. Pat. Nos. 5,763,192; 5,814,476; 5,723,323; and 5,817,483 describe processes for producing peptides or polypeptides. This is done by producing stochastic genes or fragments thereof, and then introducing these genes into host cells which produce one or more proteins encoded by the stochastic genes. The host cells are then screened to identify those clones producing peptides or polypeptides having the desired activity.

Another method for producing peptides or polypeptides is described in International Pub. No. WO99/15650, filed by Athersys, Inc. Known as "Random Activation of Gene Expression for Gene Discovery" (RAGE-GD), the process involves the activation of endogenous gene expression or over-expression of a gene by in situ recombination methods. For example, expression of an endogenous gene is activated or increased by integrating a regulatory sequence into the target cell that is capable of activating expression of the gene by non-homologous or illegitimate recombination. The target DNA is first subjected to radiation, and a genetic promoter inserted. The promoter eventually locates a break at the front of a gene, initiating transcription of the gene. This results in expression of the desired peptide or polypeptide.

It will be appreciated that these methods can also be used to create comprehensive B7-L polypeptide expression libraries, which can subsequently be used for high throughput phenotypic screening in a variety of assays, such as biochemical assays, cellular assays, and whole organism assays (e.g., plant, mouse, etc.).

Synthesis

It will be appreciated by those skilled in the art that the nucleic acid and polypeptide molecules described herein may be produced by recombinant and other means.

Selective Binding Agents

The term "selective binding agent" refers to a molecule that has specificity for one or more B7-L polypeptides. Suitable selective binding agents include, but are not limited to, antibodies and derivatives thereof, polypeptides, and small molecules. Suitable selective binding agents may be prepared using methods known in the art. An exemplary B7-L polypeptide selective binding agent of the present invention is capable of binding a certain portion of the B7-L polypeptide thereby inhibiting the binding of the polypeptide to a B7-L polypeptide receptor.

Selective binding agents such as antibodies and antibody fragments that bind B7-L polypeptides are within the scope of the present invention. The antibodies may be polyclonal including monospecific polyclonal; monoclonal (MAbs); recombinant; chimeric; humanized, such as complementarity-determining region (CDR)-grafted; human; single chain; and/or bispecific; as well as fragments; variants; or derivatives thereof. Antibody fragments include those portions of the antibody that bind to an epitope on the B7-L polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward a B7-L polypeptide generally are produced in animals (e.g., rabbits or mice) by means of multiple subcutaneous or intraperitoneal injections of B7-L polypeptide and an adjuvant. It may be useful to conjugate a B7-L polypeptide to a carrier protein that is immunogenic in the species to be immunized, such as keyhole limpet hemocyanin, serum, albumin, bovine thyroglobulin, or soybean trypsin inhibitor. Also, aggregating agents such as alum are used to enhance the immune response. After immunization, the animals are bled and the serum is assayed for anti-B7-L antibody titer.

Monoclonal antibodies directed toward B7-L polypeptides are produced using any method that provides for the production of antibody molecules by continuous cell lines in culture. Examples of suitable methods for preparing monoclonal antibodies include the hybridoma methods of Kohler et al., 1975, *Nature* 256:495-97 and the human B-cell hybridoma method (Kozbor, 1984, *J. Immunol.* 133:3001; Brodeur et al., *Monoclonal Antibody Production Techniques and Applications* 51-63 (Marcel Dekker, Inc., 1987). Also provided by the invention are hybridoma cell lines that produce monoclonal antibodies reactive with B7-L polypeptides.

Monoclonal antibodies of the invention may be modified for use as therapeutics. One embodiment is a "chimeric" antibody in which a portion of the heavy (H) and/or light (L) chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Also included are fragments of such antibodies, so long as they exhibit the desired biological activity. See U.S. Pat. No. 4,816,567; Morrison et al., 1985, *Proc. Natl. Acad. Sci.* 81:6851-55.

In another embodiment, a monoclonal antibody of the invention is a "humanized" antibody. Methods for humanizing non-human antibodies are well known in the art. See U.S. Pat. Nos. 5,585,089 and 5,693,762. Generally, a humanized antibody has one or more amino acid residues introduced into it from a source that is non-human. Humanization can be performed, for example, using methods described in the art (Jones et al., 1986, *Nature* 321:522-25; Riechmann et al., 1998, *Nature* 332:323-27; Verhoeyen et al., 1988, *Science* 239:1534-36), by substituting at least a portion of a rodent complementarity-determining region for the corresponding regions of a human antibody.

Also encompassed by the invention are human antibodies that bind B7-L polypeptides. Using transgenic animals (e.g., mice) that are capable of producing a repertoire of human antibodies in the absence of endogenous immunoglobulin production such antibodies are produced by immunization with a B7-L polypeptide antigen (i.e., having at least 6 contiguous amino acids), optionally conjugated to a carrier. See, e.g., Jakobovits et al., 1993, *Proc. Natl. Acad. Sci.* 90:2551-55; Jakobovits et al., 1993, *Nature* 362:255-58; Bruggermann et al., 1993, *Year in Immuno.* 7:33. In one method, such transgenic animals are produced by incapacitating the endogenous loci encoding the heavy and light immunoglobulin chains therein, and inserting loci encoding human heavy and light chain proteins into the genome thereof. Partially modified animals (i.e., those having less than the full complement of modifications) are then cross-bred to obtain an animal having all of the desired immune system modifications. When administered an immunogen, these transgenic animals produce antibodies with human (rather than, e.g., murine) amino acid sequences, including variable regions that are immunospecific for these antigens. See International App. Nos. PCT/US96/05928 and PCT/US93/06926. Additional methods are described in U.S. Pat. No. 5,545,807, International App. Nos. PCT/US91/245 and PCT/GB89/01207, and in European Patent Nos. 546073B1 and 546073A1. Human antibodies can also be produced by the expression of recombinant DNA in host cells or by expression in hybridoma cells as described herein.

In an alternative embodiment, human antibodies can also be produced from phage-display libraries (Hoogenboom et al., 1991, *J. Mol. Biol.* 227:381; Marks et al., 1991, *J. Mol. Biol.* 222:581). These processes mimic immune selection through the display of antibody repertoires on the surface of filamentous bacteriophage, and subsequent selection of phage by their binding to an antigen of choice. One such technique is described in International App. No. PCT/US98/17364, which describes the isolation of high affinity and functional agonistic antibodies for MPL- and msk-receptors using such an approach.

Chimeric, CDR grafted, and humanized antibodies are typically produced by recombinant methods. Nucleic acids encoding the antibodies are introduced into host cells and expressed using materials and procedures described herein. In a preferred embodiment, the antibodies are produced in mammalian host cells, such as CHO cells. Monoclonal (e.g., human) antibodies may be produced by the expression of recombinant DNA in host cells or by expression in hybridoma cells as described herein.

The anti-B7-L antibodies of the invention may be employed in any known assay method, such as competitive binding assays, direct and indirect sandwich assays, and immunoprecipitation assays (Sola, *Monoclonal Antibodies: A Manual of Techniques* 147-158 (CRC Press, Inc., 1987)) for the detection and quantitation of B7-L polypeptides. The antibodies will bind B7-L polypeptides with an affinity that is appropriate for the assay method being employed.

For diagnostic applications, in certain embodiments, anti-B7-L antibodies may be labeled with a detectable moiety. The detectable moiety can be any one that is capable of producing, either directly or indirectly, a detectable signal. For example, the detectable moiety may be a radioisotope, such as $^3$H, $^{14}$C, $^{32}$P, $^{35}$S, $^{125}$I, $^{99}$Tc, $^{111}$In, or $^{67}$Ga; a fluorescent or chemiluminescent compound, such as fluorescein isothiocyanate, rhodamine, or luciferin; or an enzyme, such as alkaline phosphatase, β-galactosidase, or horseradish peroxidase (Bayer, et al., 1990, *Meth. Enz.* 184:138-63).

Competitive binding assays rely on the ability of a labeled standard (e.g., a B7-L polypeptide, or an immunologically reactive portion thereof) to compete with the test sample analyte (an B7-L polypeptide) for binding with a limited amount of anti-B7-L antibody. The amount of a B7-L polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies may conveniently be separated from the standard and analyte that remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody that is immobilized on a solid support, and thereafter a second antibody binds to the analyte, thus forming an insoluble three-part complex. See, e.g. U.S. Pat. No. 4,376,110. The second antibody may itself be labeled with a detectable moiety (direct sandwich assays) or may be measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

The selective binding agents, including anti-B7-L antibodies, are also useful for in vivo imaging. An antibody labeled with a detectable moiety may be administered to an animal, preferably into the bloodstream, and the presence and location of the labeled antibody in the host assayed. The antibody may be labeled with any moiety that is detectable in an animal, whether by nuclear magnetic resonance, radiology, or other detection means known in the art.

Selective binding agents of the invention, including antibodies, may be used as therapeutics. These therapeutic agents are generally agonists or antagonists, in that they either enhance or reduce, respectively, at least one of the biological activities of a B7-L polypeptide. In one embodiment, antagonist antibodies of the invention are antibodies or binding fragments thereof which are capable of specifically binding to a B7-L polypeptide and which are capable of inhibiting or eliminating the functional activity of a B7-L polypeptide in vivo or in vitro. In preferred embodiments, the selective binding agent, e.g., an antagonist antibody, will inhibit the functional activity of a B7-L polypeptide by at least about 50%, and preferably by at least about 80%. In another embodiment, the selective binding agent may be an anti-B7-L polypeptide antibody that is capable of interacting with a B7-L polypeptide binding partner (a ligand or receptor) thereby inhibiting or eliminating B7-L polypeptide activity in vitro or in vivo. Selective binding agents, including agonist and antagonist anti-B7-L polypeptide antibodies, are identified by screening assays that are well known in the art.

The invention also relates to a kit comprising B7-L selective binding agents (such as antibodies) and other reagents useful for detecting B7-L polypeptide levels in biological samples. Such reagents may include a detectable label, blocking serum, positive and negative control samples, and detection reagents.

Microarrays

It will be appreciated that DNA microarray technology can be utilized in accordance with the present invention. DNA microarrays are miniature, high-density arrays of nucleic acids positioned on a solid support, such as glass. Each cell or element within the array contains numerous copies of a single nucleic acid species that acts as a target for hybridization with a complementary nucleic acid sequence (e.g., mRNA). In expression profiling using DNA microarray technology, mRNA is first extracted from a cell or tissue sample and then converted enzymatically to fluorescently labeled cDNA. This material is hybridized to the microarray and unbound cDNA is removed by washing. The expression of discrete genes represented on the array is then visualized by quantitating the amount of labeled cDNA that is specifically bound to each target nucleic acid molecule. In this way, the expression of thousands of genes can be quantitated in a high throughput, parallel manner from a single sample of biological material.

This high throughput expression profiling has a broad range of applications with respect to the B7-L molecules of the invention, including, but not limited to: the identification and validation of B7-L disease-related genes as targets for therapeutics; molecular toxicology of related B7-L molecules and inhibitors thereof; stratification of populations and generation of surrogate markers for clinical trials; and enhancing related B7-L polypeptide small molecule drug discovery by aiding in the identification of selective compounds in high throughput screens.

Chemical Derivatives

Chemically modified derivatives of B7-L polypeptides may be prepared by one skilled in the art, given the disclosures described herein. B7-L polypeptide derivatives are modified in a manner that is different—either in the type or location of the molecules naturally attached to the polypeptide. Derivatives may include molecules formed by the deletion of one or more naturally-attached chemical groups. The polypeptide comprising the amino acid sequence of SEQ ID NO: 2, or other B7-L polypeptide, may be modified by the covalent attachment of one or more polymers. For example, the polymer selected is typically water-soluble so that the protein to which it is attached does not precipitate in an aqueous environment, such as a physiological environment. Included within the scope of suitable polymers is a mixture of polymers. Preferably, for therapeutic use of the end-product preparation, the polymer will be pharmaceutically acceptable.

The polymers each may be of any molecular weight and may be branched or unbranched. The polymers each typically have an average molecular weight of between about 2 kDa to about 100 kDa (the term "about" indicating that in preparations of a water-soluble polymer, some molecules will weigh more, some less, than the stated molecular weight). The average molecular weight of each polymer is preferably between about 5 kDa and about 50 kDa, more preferably between about 12 kDa and about 40 kDa and most preferably between about 20 kDa and about 35 kDa.

Suitable water-soluble polymers or mixtures thereof include, but are not limited to, N-linked or O-linked carbohydrates, sugars, phosphates, polyethylene glycol (PEG) (including the forms of PEG that have been used to derivatize proteins, including mono-($C_1$-$C_{10}$), alkoxy-, or aryloxy-polyethylene glycol), monomethoxy-polyethylene glycol, dextran (such as low molecular weight dextran of, for example, about 6 kD), cellulose, or other carbohydrate based polymers, poly-(N-vinyl pyrrolidone) polyethylene glycol, propylene glycol homopolymers, polypropylene oxide/ethylene oxide co-polymers, polyoxyethylated polyols (e.g., glycerol), and polyvinyl alcohol. Also encompassed by the present invention are bifunctional crosslinking molecules that may be used to prepare covalently attached B7-L polypeptide multimers.

In general, chemical derivatization may be performed under any suitable condition used to react a protein with an activated polymer molecule. Methods for preparing chemical derivatives of polypeptides will generally comprise the steps of: (a) reacting the polypeptide with the activated polymer molecule (such as a reactive ester or aldehyde derivative of the polymer molecule) under conditions whereby the polypeptide comprising the amino acid sequence of SEQ ID NO: 2, or other B7-L polypeptide, becomes attached to one or more polymer molecules, and (b) obtaining the reaction products. The optimal reaction conditions will be determined based on known parameters and the desired result. For example, the larger the ratio of polymer molecules to protein, the greater the percentage of attached polymer molecule. In one embodiment, the B7-L polypeptide derivative may have a single polymer molecule moiety at the amino-terminus. See, e.g., U.S. Pat. No. 5,234,784.

The pegylation of a polypeptide may be specifically carried out using any of the pegylation reactions known in the art. Such reactions are described, for example, in the following references: Francis et al., 1992, *Focus on Growth Factors* 3:4-10; European Patent Nos. 0154316 and 0401384; and U.S. Pat. No. 4,179,337. For example, pegylation may be carried out via an acylation reaction or an alkylation reaction with a reactive polyethylene glycol molecule (or an analogous reactive water-soluble polymer) as described herein. For the acylation reactions, a selected polymer should have a single reactive ester group. For reductive alkylation, a selected polymer should have a single reactive aldehyde group. A reactive aldehyde is, for example, polyethylene glycol propionaldehyde, which is water stable, or mono $C_1$-$C_{10}$ alkoxy or aryloxy derivatives thereof (see U.S. Pat. No. 5,252,714).

In another embodiment, B7-L polypeptides may be chemically coupled to biotin. The biotin/B7-L polypeptide molecules are then allowed to bind to avidin, resulting in tetravalent avidin/biotin/B7-L polypeptide molecules. B7-L polypeptides may also be covalently coupled to dinitrophenol (DNP) or trinitrophenol (TNP) and the resulting conjugates precipitated with anti-DNP or anti-TNP-IgM to form decameric conjugates with a valency of 10.

Generally, conditions that may be alleviated or modulated by the administration of the present B7-L polypeptide derivatives include those described herein for B7-L polypeptides. However, the B7-L polypeptide derivatives disclosed herein may have additional activities, enhanced or reduced biological activity, or other characteristics, such as increased or decreased half-life, as compared to the non-derivatized molecules.

Genetically Engineered Non-Human Animals

Additionally included within the scope of the present invention are non-human animals such as mice, rats, or other rodents; rabbits, goats, sheep, or other farm animals, in which the genes encoding native B7-L polypeptide have been disrupted (i.e., "knocked out") such that the level of expression of B7-L polypeptide is significantly decreased or completely abolished. Such animals may be prepared using techniques and methods such as those described in U.S. Pat. No. 5,557,032.

The present invention further includes non-human animals such as mice, rats, or other rodents; rabbits, goats, sheep, or other farm animals, in which either the native form of a B7-L gene for that animal or a heterologous B7-L gene is over-expressed by the animal, thereby creating a "transgenic" animal. Such transgenic animals may be prepared using well known methods such as those described in U.S. Pat. No. 5,489,743 and International Pub. No. WO 94/28122.

The present invention further includes non-human animals in which the promoter for one or more of the B7-L polypeptides of the present invention is either activated or inactivated (e.g., by using homologous recombination methods) to alter the level of expression of one or more of the native B7-L polypeptides.

These non-human animals may be used for drug candidate screening. In such screening, the impact of a drug candidate on the animal may be measured. For example, drug candidates may decrease or increase the expression of the B7-L gene. In certain embodiments, the amount of B7-L polypeptide that is produced may be measured after the exposure of the animal to the drug candidate. Additionally, in certain embodiments, one may detect the actual impact of the drug candidate on the animal. For example, over-expression of a particular gene may result in, or be associated with, a disease or pathological condition. In such cases, one may test a drug candidate's ability to decrease expression of the gene or its ability to prevent or inhibit a pathological condition. In other examples, the production of a particular metabolic product such as a fragment of a polypeptide, may result in, or be associated with, a disease or pathological condition. In such cases, one may test a drug candidate's ability to decrease the production of such a metabolic product or its ability to prevent or inhibit a pathological condition.

Assaying for Other Modulators of B7-L Polypeptide Activity

In some situations, it may be desirable to identify molecules that are modulators, i.e., agonists or antagonists, of the activity of B7-L polypeptide. Natural or synthetic molecules that modulate B7-L polypeptide may be identified using one or more screening assays, such as those described herein. Such molecules may be administered either in an ex vivo manner or in an in vivo manner by injection, or by oral delivery, implantation device, or the like.

"Test molecule" refers to a molecule that is under evaluation for the ability to modulate (i.e., increase or decrease) the activity of a B7-L polypeptide. Most commonly, a test molecule will interact directly with a B7-L polypeptide. However, it is also contemplated that a test molecule may also modulate B7-L polypeptide activity indirectly, such as by affecting B7-L gene expression, or by binding to a B7-L polypeptide binding partner (e.g., receptor or ligand). In one embodiment, a test molecule will bind to a B7-L polypeptide with an affinity constant of at least about $10^{-6}$ M, preferably about $10^{-8}$ M, more preferably about $10^{-9}$ M, and even more preferably about $10^{-10}$ M.

Methods for identifying compounds that interact with B7-L polypeptides are encompassed by the present invention. In certain embodiments, a B7-L polypeptide is incubated with a test molecule under conditions that permit the interaction of the test molecule with a B7-L polypeptide, and the extent of the interaction is measured. The test molecule can be screened in a substantially purified form or in a crude mixture.

In certain embodiments, a B7-L polypeptide agonist or antagonist may be a protein, peptide, carbohydrate, lipid, or small molecular weight molecule that interacts with B7-L polypeptide to regulate its activity. Molecules which regulate B7-L polypeptide expression include nucleic acids which are complementary to nucleic acids encoding a B7-L polypeptide, or are complementary to nucleic acids sequences which direct or control the expression of B7-L polypeptide, and which act as anti-sense regulators of expression.

Once a test molecule has been identified as interacting with a B7-L polypeptide, the molecule may be further evaluated for its ability to increase or decrease B7-L polypeptide activity. The measurement of the interaction of a test molecule with B7-L polypeptide may be carried out in several formats, including cell-based binding assays, membrane binding assays, solution-phase assays, and immunoassays. In general, a test molecule is incubated with a B7-L polypeptide for a specified period of time, and B7-L polypeptide activity is determined by one or more assays for measuring biological activity.

The interaction of test molecules with B7-L polypeptides may also be assayed directly using polyclonal or monoclonal antibodies in an immunoassay. Alternatively, modified forms of B7-L polypeptides containing epitope tags as described herein may be used in solution and immunoassays.

In the event that B7-L polypeptides display biological activity through an interaction with a binding partner (e.g., a receptor or a ligand), a variety of in vitro assays may be used to measure the binding of a B7-L polypeptide to the corresponding binding partner (such as a selective binding agent, receptor, or ligand). These assays may be used to screen test molecules for their ability to increase or decrease the rate and/or the extent of binding of a B7-L polypeptide to its binding partner. In one assay, a B7-L polypeptide is immobilized in the wells of a microtiter plate. Radiolabeled B7-L polypeptide binding partner (for example, iodinated B7-L polypeptide binding partner) and a test molecule can then be added either one at a time (in either order) or simultaneously to the wells. After incubation, the wells can be washed and counted for radioactivity, using a scintillation counter, to determine the extent to which the binding partner bound to the B7-L polypeptide. Typically, a molecule will be tested over a range of concentrations, and a series of control wells lacking one or more elements of the test assays can be used for accuracy in the evaluation of the results. An alternative to this method involves reversing the "positions" of the proteins, i.e., immobilizing B7-L polypeptide binding partner to the microtiter plate wells, incubating with the test molecule and radiolabeled B7-L polypeptide, and determining the extent of B7-L polypeptide binding. See, e.g., *Current Protocols in Molecular Biology*, chap. 18 (Ausubel et al., eds., Green Publishers Inc. and Wiley and Sons 1995).

As an alternative to radiolabeling, a B7-L polypeptide or its binding partner may be conjugated to biotin, and the presence of biotinylated protein can then be detected using streptavidin linked to an enzyme, such as horse radish peroxidase (HRP) or alkaline phosphatase (AP), which can be detected colorometrically, or by fluorescent tagging of streptavidin. An antibody directed to a B7-L polypeptide or to a B7-L polypeptide binding partner, and which is conjugated to biotin, may also be used for purposes of detection following incubation of the complex with enzyme-linked streptavidin linked to AP or HRP.

A B7-L polypeptide or a B7-L polypeptide binding partner can also be immobilized by attachment to agarose beads, acrylic beads, or other types of such inert solid phase substrates. The substrate-protein complex can be placed in a solution containing the complementary protein and the test compound. After incubation, the beads can be precipitated by centrifugation, and the amount of binding between a B7-L polypeptide and its binding partner can be assessed using the methods described herein. Alternatively, the substrate-protein complex can be immobilized in a column with the test molecule and complementary protein passing through the column. The formation of a complex between a B7-L polypeptide and its binding partner can then be assessed using any of the techniques described herein (e.g., radiolabelling or antibody binding).

Another in vitro assay that is useful for identifying a test molecule that increases or decreases the formation of a complex between a B7-L polypeptide binding protein and a B7-L polypeptide binding partner is a surface plasmon resonance detector system such as the BIAcore assay system (Pharmacia, Piscataway, N.J.). The BIAcore system is utilized as specified by the manufacturer. This assay essentially involves the covalent binding of either B7-L polypeptide or a B7-L polypeptide binding partner to a dextran-coated sensor chip that is located in a detector. The test compound and the other complementary protein can then be injected, either simultaneously or sequentially, into the chamber containing the sensor chip. The amount of complementary protein that binds can be assessed based on the change in molecular mass that is physically associated with the dextran-coated side of the sensor chip, with the change in molecular mass being measured by the detector system.

In some cases, it may be desirable to evaluate two or more test compounds together for their ability to increase or decrease the formation of a complex between a B7-L polypeptide and a B7-L polypeptide binding partner. In these cases, the assays set forth herein can be readily modified by adding such additional test compound(s) either simultaneously with, or subsequent to, the first test compound. The remainder of the steps in the assay are as set forth herein.

In vitro assays such as those described herein may be used advantageously to screen large numbers of compounds for an effect on the formation of a complex between a B7-L polypeptide and B7-L polypeptide binding partner. The assays may be automated to screen compounds generated in phage display, synthetic peptide, and chemical synthesis libraries.

Compounds which increase or decrease the formation of a complex between a B7-L polypeptide and a B7-L polypeptide binding partner may also be screened in cell culture using cells and cell lines expressing either B7-L polypeptide or B7-L polypeptide binding partner. Cells and cell lines may be obtained from any mammal, but preferably will be from human or other primate, canine, or rodent sources. The binding of a B7-L polypeptide to cells expressing B7-L polypeptide binding partner at the surface is evaluated in the presence or absence of test molecules, and the extent of binding may be determined by, for example, flow cytometry using a biotinylated antibody to a B7-L polypeptide binding partner. Cell culture assays can be used advantageously to further evaluate compounds that score positive in protein binding assays described herein.

Cell cultures can also be used to screen the impact of a drug candidate. For example, drug candidates may decrease or increase the expression of the B7-L gene. In certain embodiments, the amount of B7-L polypeptide or a B7-L polypeptide fragment that is produced may be measured after exposure of the cell culture to the drug candidate. In certain embodiments, one may detect the actual impact of the drug candidate on the cell culture. For example, the over-expression of a particular gene may have a particular impact on the cell culture. In such cases, one may test a drug candidate's ability to increase or decrease the expression of the gene or its ability to prevent or inhibit a particular impact on the cell culture. In other examples, the production of a particular metabolic product such as a fragment of a polypeptide, may result in, or be associated with, a disease or pathological condition. In such cases, one may test a drug candidate's ability to decrease the production of such a metabolic product in a cell culture.

Internalizing Proteins

The tat protein sequence (from HIV) can be used to internalize proteins into a cell. See, e.g., Falwell et al., 1994, *Proc. Natl. Acad. Sci. U.S.A.* 91:664-68. For example, an 11 amino acid sequence (Y-G-R-K-K-R-R-Q-R-R-R; SEQ ID NO: 24) of the HIV tat protein (termed the "protein transduction domain," or TAT PDT) has been described as mediating delivery across the cytoplasmic membrane and the nuclear membrane of a cell. See Schwarze et al., 1999, *Science* 285:1569-72; and Nagahara et al., 1998, *Nat. Med.* 4:1449-52. In these procedures, FITC-constructs (FITC-labeled G-G-G-G-Y-G-R-K-K-R-R-Q-R-R-R; SEQ ID NO: 25), which penetrate tissues following intraperitoneal administration, are prepared, and the binding of such constructs to cells is detected by fluorescence-activated cell sorting (FACS) analysis. Cells treated with a tat-β-gal fusion protein will demonstrate β-gal activity. Following injection, expression of such a construct can be detected in a number of tissues, including liver, kidney, lung, heart, and brain tissue. It is believed that such constructs undergo some degree of unfolding in order to enter the cell, and as such, may require a refolding following entry into the cell.

It will thus be appreciated that the tat protein sequence may be used to internalize a desired polypeptide into a cell. For example, using the tat protein sequence, a B7-L antagonist (such as an anti-B7-L selective binding agent, small molecule, soluble receptor, or antisense oligonucleotide) can be administered intracellularly to inhibit the activity of a B7-L molecule. As used herein, the term "B7-L molecule" refers to both B7-L nucleic acid molecules and B7-L polypeptides as defined herein. Where desired, the B7-L protein itself may also be internally administered to a cell using these procedures. See also, Straus, 1999, *Science* 285:1466-67.

Cell Source Identification Using B7-L Polypeptide

In accordance with certain embodiments of the invention, it may be useful to be able to determine the source of a certain cell type associated with a B7-L polypeptide. For example, it may be useful to determine the origin of a disease or pathological condition as an aid in selecting an appropriate therapy. In certain embodiments, nucleic acids encoding a B7-L polypeptide can be used as a probe to identify cells described herein by screening the nucleic acids of the cells with such a probe. In other embodiments, one may use anti-B7-L polypeptide antibodies to test for the presence of B7-L polypeptide in cells, and thus, determine if such cells are of the types described herein.

B7-L Polypeptide Compositions and Administration

Therapeutic compositions are within the scope of the present invention. Such B7-L polypeptide pharmaceutical compositions may comprise a therapeutically effective amount of a B7-L polypeptide or a B7-L nucleic acid molecule in admixture with a pharmaceutically or physiologically acceptable formulation agent selected for suitability with the mode of administration. Pharmaceutical compositions may comprise a therapeutically effective amount of one or more B7-L polypeptide selective binding agents in admixture with a pharmaceutically or physiologically acceptable formulation agent selected for suitability with the mode of administration.

Acceptable formulation materials preferably are nontoxic to recipients at the dosages and concentrations employed.

The pharmaceutical composition may contain formulation materials for modifying, maintaining, or preserving, for example, the pH, osmolarity, viscosity, clarity, color, isotonicity, odor, sterility, stability, rate of dissolution or release, adsorption, or penetration of the composition. Suitable formulation materials include, but are not limited to, amino acids (such as glycine, glutamine, asparagine, arginine, or lysine), antimicrobials, antioxidants (such as ascorbic acid, sodium sulfite, or sodium hydrogen-sulfite), buffers (such as borate, bicarbonate, Tris-HCl, citrates, phosphates, or other organic acids), bulking agents (such as mannitol or glycine), chelating agents (such as ethylenediamine tetraacetic acid (EDTA)), complexing agents (such as caffeine, polyvinylpyrrolidone, beta-cyclodextrin, or hydroxypropyl-beta-cyclodextrin), fillers, monosaccharides, disaccharides, and other carbohydrates (such as glucose, mannose, or dextrins), proteins (such as serum albumin, gelatin, or immunoglobulins), coloring, flavoring and diluting agents, emulsifying agents, hydrophilic polymers (such as polyvinylpyrrolidone), low molecular weight polypeptides, salt-forming counterions (such as sodium), preservatives (such as benzalkonium chloride, benzoic acid, salicylic acid, thimerosal, phenethyl alcohol, methylparaben, propylparaben, chlorhexidine, sorbic acid, or hydrogen peroxide), solvents (such as glycerin, propylene glycol, or polyethylene glycol), sugar alcohols (such as mannitol or sorbitol), suspending agents, surfactants or wetting agents (such as pluronics; PEG; sorbitan esters; polysorbates such as polysorbate 20 or polysorbate 80; triton; tromethamine; lecithin; cholesterol or tyloxapal), stability enhancing agents (such as sucrose or sorbitol), tonicity enhancing agents (such as alkali metal halides—preferably sodium or potassium chloride—or mannitol sorbitol), delivery vehicles, diluents, excipients and/or pharmaceutical adjuvants. See *Remington's Pharmaceutical Sciences* (18th Ed., A. R. Gennaro, ed., Mack Publishing Company 1990.

The optimal pharmaceutical composition will be determined by a skilled artisan depending upon, for example, the intended-route of administration, delivery format, and desired dosage. See, e.g., *Remington's Pharmaceutical Sciences*, supra. Such compositions may influence the physical state, stability, rate of in vivo release, and rate of in vivo clearance of the B7-L molecule.

The primary vehicle or carrier in a pharmaceutical composition may be either aqueous or non-aqueous in nature. For example, a suitable vehicle or carrier for injection may be water, physiological saline solution, or artificial cerebrospinal fluid, possibly supplemented with other materials common in compositions for parenteral administration. Neutral buffered saline or saline mixed with serum albumin are further exemplary vehicles. Other exemplary pharmaceutical compositions comprise Tris buffer of about pH 7.0-8.5, or acetate buffer of about pH 4.0-5.5, which may further include sorbitol or a suitable substitute. In one embodiment of the present invention, B7-L polypeptide compositions may be prepared for storage by mixing the selected composition having the desired degree of purity with optional formulation agents (*Remington's Pharmaceutical Sciences*, supra) in the form of a lyophilized cake or an aqueous solution. Further, the B7-L polypeptide product may be formulated as a lyophilizate using appropriate excipients such as sucrose.

The B7-L polypeptide pharmaceutical compositions can be selected for parenteral delivery. Alternatively, the compositions may be selected for inhalation or for delivery through the digestive tract, such as orally. The preparation of such pharmaceutically acceptable compositions is within the skill of the art.

The formulation components are present in concentrations that are acceptable to the site of administration. For example, buffers are used to maintain the composition at physiological pH or at a slightly lower pH, typically within a pH range of from about 5 to about 8.

When parenteral administration is contemplated, the therapeutic compositions for use in this invention may be in the form of a pyrogen-free, parenterally acceptable, aqueous solution comprising the desired B7-L molecule in a pharmaceutically acceptable vehicle. A particularly suitable vehicle for parenteral injection is sterile distilled water in which a B7-L molecule is formulated as a sterile, isotonic solution, properly preserved. Yet another preparation can involve the formulation of the desired molecule with an agent, such as injectable microspheres, bio-erodible particles, polymeric compounds (such as polylactic acid or polyglycolic acid), beads, or liposomes, that provides for the controlled or sustained release of the product which may then be delivered via a depot injection. Hyaluronic acid may also be used, and this may have the effect of promoting sustained duration in the circulation. Other suitable means for the introduction of the desired molecule include implantable drug delivery devices.

In one embodiment, a pharmaceutical composition may be formulated for inhalation. For example, B7-L polypeptide may be formulated as a dry powder for inhalation. B7-L polypeptide or nucleic acid molecule inhalation solutions may also be formulated with a propellant for aerosol delivery. In yet another embodiment, solutions may be nebulized. Pulmonary administration is further described in International Pub. No. WO 94/20069, which describes the pulmonary delivery of chemically modified proteins.

It is also contemplated that certain formulations may be administered orally. In one embodiment of the present invention, B7-L polypeptides that are administered in this fashion can be formulated with or without those carriers customarily used in the compounding of solid dosage forms such as tablets and capsules. For example, a capsule may be designed to release the active portion of the formulation at the point in the gastrointestinal tract when bioavailability is maximized and pre-systemic degradation is minimized. Additional agents can be included to facilitate absorption of the B7-L polypeptide. Diluents, flavorings, low melting point waxes, vegetable oils, lubricants, suspending agents, tablet disintegrating agents, and binders may also be employed.

Another pharmaceutical composition may involve an effective quantity of B7-L polypeptides in a mixture with non-toxic excipients that are suitable for the manufacture of tablets. By dissolving the tablets in sterile water, or another appropriate vehicle, solutions can be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional B7-L polypeptide pharmaceutical compositions will be evident to those skilled in the art, including formulations involving B7-L polypeptides in sustained- or controlled-delivery formulations. Techniques for formulating a variety of other sustained- or controlled-delivery means, such as liposome carriers, bio-erodible microparticles or porous beads and depot injections, are also known to those skilled in the art. See, e.g., International App. No. PCT/US93/00829, which describes the controlled release of porous polymeric microparticles for the delivery of pharmaceutical compositions.

Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919 and European Patent No. 058481), copolymers of L-glutamic acid and gamma ethyl-L-glutamate (Sidman et al., 1983, *Biopolymers* 22:547-56), poly(2-hydroxyethyl-methacrylate) (Langer et al., 1981, *J. Biomed. Mater. Res.* 15:167-277 and Langer, 1982, *Chem. Tech.* 12:98-105), ethylene vinyl acetate (Langer et al., supra) or poly-D(-)-3-hydroxybutyric acid (European Patent No. 133988). Sustained-release compositions may also include liposomes, which can be prepared by any of several methods known in the art. See, e.g., Eppstein et al., 1985, *Proc. Natl. Acad. Sci. USA* 82:3688-92; and European Patent Nos. 036676, 088046, and 143949.

The B7-L pharmaceutical composition to be used for in vivo administration typically must be sterile. This may be accomplished by filtration through sterile filtration membranes. Where the composition is lyophilized, sterilization using this method may be conducted either prior to, or following, lyophilization and reconstitution. The composition for parenteral administration may be stored in lyophilized form or in a solution. In addition, parenteral compositions generally are placed into a container having a sterile access port, for example, an intravenous solution bag or vial having a stopper pierceable by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) requiring reconstitution prior to administration.

In a specific embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

The effective amount of a B7-L pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the B7-L molecule is being used, the route of administration, and the size (body weight, body surface, or organ size) and condition (the age and general health) of the patient. Accordingly, the clinician may titer the dosage and modify the route of administration to obtain the optimal therapeutic effect. A typical dosage may range from about 0.1 µg/kg to up to about 100 mg/kg or more, depending on the factors mentioned above. In other embodiments, the dosage may range from 0.1 µg/kg up to about 100 mg/kg; or 1 µg/kg up to about 100 mg/kg; or 5 µg/kg up to about 100 mg/kg.

The frequency of dosing will depend upon the pharmacokinetic parameters of the B7-L molecule in the formulation being used. Typically, a clinician will administer the composition until a dosage is reached that achieves the desired effect. The composition may therefore be administered as a single dose, as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

The route of administration of the pharmaceutical composition is in accord with known methods, e.g., orally; through injection by intravenous, intraperitoneal, intracerebral (intraparenchymal), intracerebroventricular, intramuscular, intraocular, intraarterial, intraportal, or intralesional routes; by sustained release systems; or by implantation devices. Where desired, the compositions may be administered by bolus injection or continuously by infusion, or by implantation device.

Alternatively or additionally, the composition may be administered locally via implantation of a membrane, sponge, or other appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

In some cases, it may be desirable to use B7-L polypeptide pharmaceutical compositions in an ex vivo manner. In such instances, cells, tissues, or organs that have been removed from the patient are exposed to B7-L polypeptide pharmaceutical compositions after which the cells, tissues, or organs are subsequently implanted back into the patient.

In other cases, a B7-L polypeptide can be delivered by implanting certain cells that have been genetically engineered, using methods such as those described herein, to express and secrete the B7-L polypeptide. Such cells may be animal or human cells, and may be autologous, heterologous, or xenogeneic. Optionally, the cells may be immortalized. In order to decrease the chance of an immunological response, the cells may be encapsulated to avoid infiltration of surrounding tissues. The encapsulation materials are typically biocompatible, semi-permeable polymeric enclosures or membranes that allow the release of the protein product(s) but prevent the destruction of the cells by the patient's immune system or by other detrimental factors from the surrounding tissues.

As discussed herein, it may be desirable to treat isolated cell populations (such as stem cells, lymphocytes, red blood cells, chondrocytes, neurons, and the like) with one or more B7-L polypeptides. This can be accomplished by exposing the isolated cells to the polypeptide directly, where it is in a form that is permeable to the cell membrane.

Additional embodiments of the present invention relate to cells and methods (e.g., homologous recombination and/or other recombinant production methods) for both the in vitro production of therapeutic polypeptides and for the production and delivery of therapeutic polypeptides by gene therapy or cell therapy. Homologous and other recombination methods may be used to modify a cell that contains a normally transcriptionally-silent B7-L gene, or an under-expressed gene, and thereby produce a cell which expresses therapeutically efficacious amounts of B7-L polypeptides.

Homologous recombination is a technique originally developed for targeting genes to induce or correct mutations in transcriptionally active genes. Kucherlapati, 1989, *Prog. in Nucl. Acid Res. & Mol. Biol.* 36:301. The basic technique was developed as a method for introducing specific mutations into specific regions of the mammalian genome (Thomas et al., 1986, *Cell* 44:419-28; Thomas and Capecchi, 1987, *Cell* 51:503-12; Doetschman et al., 1988, *Proc. Natl. Acad. Sci. USA.* 85:8583-87) or to correct specific mutations within defective genes (Doetschman et al., 1987, *Nature* 330:576-78). Exemplary homologous recombination techniques are described in U.S. Pat. No. 5,272,071; European Patent Nos. 9193051 and 505500; International App. No. PCT/US90/07642, and International Pub No. WO 91/09955).

Through homologous recombination, the DNA sequence to be inserted into the genome can be directed to a specific region of the gene of interest by attaching it to targeting DNA. The targeting DNA is a nucleotide sequence that is complementary (homologous) to a region of the genomic DNA. Small pieces of targeting DNA that are complementary to a specific region of the genome are put in contact with the parental strand during the DNA replication process. It is a general property of DNA that has been inserted into a cell to hybridize, and therefore, recombine with other pieces of endogenous DNA through shared homologous regions. If this complementary strand is attached to an oligonucleotide that contains a mutation or a different sequence or an additional nucleotide, it too is incorporated into the newly synthesized strand as a result of the recombination. As a result of the proofreading function, it is possible for the new sequence of DNA to serve as the template. Thus, the transferred DNA is incorporated into the genome.

Attached to these pieces of targeting DNA are regions of DNA that may interact with or control the expression of a B7-L polypeptide, e.g., flanking sequences. For example, a promoter/enhancer element, a suppressor, or an exogenous transcription modulatory element is inserted in the genome of the intended host cell in proximity and orientation sufficient to influence the transcription of DNA encoding the desired B7-L polypeptide. The control element controls a portion of the DNA present in the host cell genome. Thus, the expression of the desired B7-L polypeptide may be achieved not by transfection of DNA that encodes the B7-L gene itself, but rather by the use of targeting DNA (containing regions of homology with the endogenous gene of interest) coupled with DNA regulatory segments that provide the endogenous gene sequence with recognizable signals for transcription of a B7-L gene.

In an exemplary method, the expression of a desired targeted gene in a cell (i.e., a desired endogenous cellular gene) is altered via homologous recombination into the cellular genome at a preselected site, by the introduction of DNA that includes at least a regulatory sequence, an exon, and a splice donor site. These components are introduced into the chromosomal (genomic) DNA in such a manner that this, in effect, results in the production of a new transcription unit (in which the regulatory sequence, the exon, and the splice donor site present in the DNA construct are operatively linked to the endogenous gene). As a result of the introduction of these components into the chromosomal DNA, the expression of the desired endogenous gene is altered.

Altered gene expression, as described herein, encompasses activating (or causing to be expressed) a gene which is normally silent (unexpressed) in the cell as obtained, as well as increasing the expression of a gene which is not expressed at physiologically significant levels in the cell as obtained. The embodiments further encompass changing the pattern of regulation or induction such that it is different from the pattern of regulation or induction that occurs in the cell as obtained, and reducing (including eliminating) the expression of a gene which is expressed in the cell as obtained.

One method by which homologous recombination can be used to increase, or cause, B7-L polypeptide production from a cell's endogenous B7-L gene involves first using homologous recombination to place a recombination sequence from a site-specific recombination system (e.g., Cre/loxP, FLP/FRT) (Sauer, 1994, *Curr. Opin. Biotechnol.*, 5:521-27; Sauer, 1993, *Methods Enzymol.*, 225:890-900) upstream of (i.e., 5' to) the cell's endogenous genomic B7-L polypeptide coding region. A plasmid containing a recombination site homologous to the site that was placed just upstream of the genomic B7-L polypeptide coding region is introduced into the modified cell line along with the appropriate recombinase enzyme. This recombinase causes the plasmid to integrate, via the plasmid's recombination site, into the recombination site located just upstream of the genomic B7-L polypeptide coding region in the cell line (Baubonis and Sauer, 1993, *Nucleic Acids Res.* 21:2025-29; O'Gorman et al., 1991, *Science* 251: 1351-55). Any flanking sequences known to increase transcription (e.g., enhancer/promoter, intron, translational enhancer), if properly positioned in this plasmid, would integrate in such a manner as to create a new or modified transcriptional unit resulting in de novo or increased B7-L polypeptide production from the cell's endogenous B7-L gene.

A further method to use the cell line in which the site specific recombination sequence had been placed just upstream of the cell's endogenous genomic B7-L polypeptide coding region is to use homologous recombination to introduce a second recombination site elsewhere in the cell line's genome. The appropriate recombinase enzyme is then introduced into the two-recombination-site cell line, causing a recombination event (deletion, inversion, and translocation) (Sauer, 1994, *Curr. Opin. Biotechnol.*, 5:521-27; Sauer, 1993, *Methods Enzymol.*, 225:890-900) that would create a new or modified transcriptional unit resulting in de novo or increased B7-L polypeptide production from the cell's endogenous B7-L gene.

An additional approach for increasing, or causing, the expression of B7-L polypeptide from a cell's endogenous B7-L gene involves increasing, or causing, the expression of a gene or genes (e.g., transcription factors) and/or decreasing the expression of a gene or genes (e.g., transcriptional repressors) in a manner which results in de novo or increased B7-L polypeptide production from the cell's endogenous B7-L gene. This method includes the introduction of a non-naturally occurring polypeptide (e.g., a polypeptide comprising a site specific DNA binding domain fused to a transcriptional factor domain) into the cell such that de novo or increased B7-L polypeptide production from the cell's endogenous B7-L gene results.

The present invention further relates to DNA constructs useful in the method of altering expression of a target gene. In certain embodiments, the exemplary DNA constructs comprise: (a) one or more targeting sequences, (b) a regulatory sequence, (c) an exon, and (d) an unpaired splice-donor site. The targeting sequence in the DNA construct directs the integration of elements (a)-(d) into a target gene in a cell such that the elements (b)-(d) are operatively linked to sequences of the endogenous target gene. In another embodiment, the DNA constructs comprise: (a) one or more targeting sequences, (b) a regulatory sequence, (c) an exon, (d) a splice-donor site, (e) an intron, and (f) a splice-acceptor site, wherein the targeting sequence directs the integration of elements (a)-(f) such that the elements of (b)-(f) are operatively linked to the endogenous gene. The targeting sequence is homologous to the preselected site in the cellular chromosomal DNA with which homologous recombination is to occur. In the construct, the exon is generally 3' of the regulatory sequence and the splice-donor site is 3' of the exon.

If the sequence of a particular gene is known, such as the nucleic acid sequence of B7-L polypeptide presented herein, a piece of DNA that is complementary to a selected region of the gene can be synthesized or otherwise obtained, such as by appropriate restriction of the native DNA at specific recognition sites bounding the region of interest. This piece serves as a targeting sequence upon insertion into the cell and will hybridize to its homologous region within the genome. If this hybridization occurs during DNA replication, this piece of DNA, and any additional sequence attached thereto, will act as an Okazaki fragment and will be incorporated into the newly synthesized daughter strand of DNA. The present invention, therefore, includes nucleotides encoding a B7-L polypeptide, which nucleotides may be used as targeting sequences.

B7-L polypeptide cell therapy, e.g., the implantation of cells producing B7-L polypeptides, is also contemplated. This embodiment involves implanting cells capable of synthesizing and secreting a biologically active form of B7-L polypeptide. Such B7-L polypeptide-producing cells can be cells that are natural producers of B7-L polypeptides or may be recombinant cells whose ability to produce B7-L polypeptides has been augmented by transformation with a gene encoding the desired B7-L polypeptide or with a gene augmenting the expression of B7-L polypeptide. Such a modification may be accomplished by means of a vector suitable for delivering the gene as well as promoting its expression and secretion. In order to minimize a potential immunological reaction in patients being administered a B7-L polypeptide, as may occur with the administration of a polypeptide of a foreign species, it is preferred that the natural cells producing B7-L polypeptide be of human origin and produce human B7-L polypeptide. Likewise, it is preferred that the recombinant cells producing B7-L polypeptide be transformed with an expression vector containing a gene encoding a human B7-L polypeptide.

Implanted cells may be encapsulated to avoid the infiltration of surrounding tissue. Human or non-human animal cells may be implanted in patients in biocompatible, semipermeable polymeric enclosures or membranes that allow the release of B7-L polypeptide, but that prevent the destruction of the cells by the patient's immune system or by other detrimental factors from the surrounding tissue. Alternatively, the patient's own cells, transformed to produce B7-L polypeptides ex vivo, may be implanted directly into the patient without such encapsulation.

Techniques for the encapsulation of living cells are known in the art, and the preparation of the encapsulated cells and their implantation in patients may be routinely accomplished. For example, Baetge et al. (International Pub. No. WO 95/05452 and International App. No. PCT/US94/09299) describe membrane capsules containing genetically engineered cells for the effective delivery of biologically active molecules. The capsules are biocompatible and are easily retrievable. The capsules encapsulate cells transfected with recombinant DNA molecules comprising DNA sequences coding for biologically active molecules operatively linked to promoters that are not subject to down-regulation in vivo upon implantation into a mammalian host. The devices provide for the delivery of the molecules from living cells to specific sites within a recipient. In addition, see U.S. Pat. Nos. 4,892,538; 5,011,472; and 5,106,627. A system for encapsulating living cells is described in International Pub. No. WO 91/10425 (Aebischer et al.). See also, International Pub. No. WO 91/10470 (Aebischer et al.); Winn et al., 1991, *Exper. Neurol.* 113:322-29; Aebischer et al., 1991, *Exper. Neurol.* 111:269-75; and Tresco et al., 1992, *ASAIO* 38:17-23.

In vivo and in vitro gene therapy delivery of B7-L polypeptides is also envisioned. One example of a gene therapy technique is to use the B7-L gene (either genomic DNA, cDNA, and/or synthetic DNA) encoding a B7-L polypeptide that may be operably linked to a constitutive or inducible promoter to form a "gene therapy DNA construct." The promoter may be homologous or heterologous to the endogenous B7-L gene, provided that it is active in the cell or tissue type into which the construct will be inserted. Other components of the gene therapy DNA construct may optionally include DNA molecules designed for site-specific integration (e.g., endogenous sequences useful for homologous recombination), tissue-specific promoters, enhancers or silencers, DNA molecules capable of providing a selective advantage over the parent cell, DNA molecules useful as labels to identify transformed cells, negative selection systems, cell specific binding agents (as, for example, for cell targeting), cell-specific internalization factors, transcription factors enhancing expression from a vector, and factors enabling vector production.

A gene therapy DNA construct can then be introduced into cells (either ex vivo or in vivo) using viral or non-viral vectors. One means for introducing the gene therapy DNA construct is by means of viral vectors as described herein. Certain vectors, such as retroviral vectors, will deliver the DNA construct to the chromosomal DNA of the cells, and the gene can integrate into the chromosomal DNA. Other vectors will function as episomes, and the gene therapy DNA construct will remain in the cytoplasm.

In yet other embodiments, regulatory elements can be included for the controlled expression of the B7-L gene in the target cell. Such elements are turned on in response to an appropriate effector. In this way, a therapeutic polypeptide can be expressed when desired. One conventional control means involves the use of small molecule dimerizers or rapalogs to dimerize chimeric proteins which contain a small molecule-binding domain and a domain capable of initiating a biological process, such as a DNA-binding protein or transcriptional activation protein (see International Pub. Nos. WO 96/41865, WO 97/31898, and WO 97/31899). The dimerization of the proteins can be used to initiate transcription of the transgene.

An alternative regulation technology uses a method of storing proteins expressed from the gene of interest inside the cell as an aggregate or cluster. The gene of interest is expressed as a fusion protein that includes a conditional aggregation domain that results in the retention of the aggregated protein in the endoplasmic reticulum. The stored proteins are stable and inactive inside the cell. The proteins can be released, however, by administering a drug (e.g., small molecule ligand) that removes the conditional aggregation domain and thereby specifically breaks apart the aggregates or clusters so that the proteins may be secreted from the cell. See Aridor et al., 2000, *Science* 287:816-17 and Rivera et al., 2000, *Science* 287:826-30.

Other suitable control means or gene switches include, but are not limited to, the systems described herein. Mifepristone (RU486) is used as a progesterone antagonist. The binding of a modified progesterone receptor ligand-binding domain to the progesterone antagonist activates transcription by forming a dimer of two transcription factors that then pass into the nucleus to bind DNA. The ligand-binding domain is modified to eliminate the ability of the receptor to bind to the natural ligand. The modified steroid hormone receptor system is further described in U.S. Pat. No. 5,364,791 and International Pub. Nos. WO 96/40911 and WO 97/10337.

Yet another control system uses ecdysone (a fruit fly steroid hormone), which binds to and activates an ecdysone receptor (cytoplasmic receptor). The receptor then translocates to the nucleus to bind a specific DNA response element (promoter from ecdysone-responsive gene). The ecdysone receptor includes a transactivation domain, DNA-binding domain, and ligand-binding domain to initiate transcription. The ecdysone system is further described in U.S. Pat. No. 5,514,578 and International Pub. Nos. WO 97/38117, WO 96/37609, and WO 93/03162.

Another control means uses a positive tetracycline-controllable transactivator. This system involves a mutated tet repressor protein DNA-binding domain (mutated tet R-4 amino acid changes which resulted in a reverse tetracycline-regulated transactivator protein, i.e., it binds to a tet operator in the presence of tetracycline) linked to a polypeptide which activates transcription. Such systems are described in U.S. Pat. Nos. 5,464,758, 5,650,298, and 5,654,168.

Additional expression control systems and nucleic acid constructs are described in U.S. Pat. Nos. 5,741,679 and 5,834,186, to Innovir Laboratories Inc.

In vivo gene therapy may be accomplished by introducing the gene encoding B7-L polypeptide into cells via local injection of a B7-L nucleic acid molecule or by other appropriate viral or non-viral delivery vectors. Heffi 1994, *Neurobiology* 25:1418-35. For example, a nucleic acid molecule encoding a B7-L polypeptide may be contained in an adeno-associated virus (AAV) vector for delivery to the targeted cells (see, e.g., Johnson, International Pub. No. WO 95/34670; International App. No. PCT/US95/07178). The recombinant AAV genome typically contains AAV inverted terminal repeats flanking a DNA sequence encoding a B7-L polypeptide operably linked to functional promoter and polyadenylation sequences.

Alternative suitable viral vectors include, but are not limited to, retrovirus, adenovirus, herpes simplex virus, lentivirus, hepatitis virus, parvovirus, papovavirus, poxvirus, alphavirus, coronavirus, rhabdovirus, paramyxovirus, and papilloma virus vectors. U.S. Pat. No. 5,672,344 describes an in vivo viral-mediated gene transfer system involving a recombinant neurotrophic HSV-1 vector. U.S. Pat. No. 5,399,346 provides examples of a process for providing a patient with a therapeutic protein by the delivery of human cells that have been treated in vitro to insert a DNA segment encoding a therapeutic protein. Additional methods and materials for the practice of gene therapy techniques are described in U.S. Pat. No. 5,631,236 (involving adenoviral vectors), U.S. Pat. No. 5,672,510 (involving retroviral vectors), U.S. Pat. No. 5,635,399 (involving retroviral vectors expressing cytokines).

Nonviral delivery methods include, but are not limited to, liposome-mediated transfer, naked DNA delivery (direct injection), receptor-mediated transfer (ligand-DNA complex), electroporation, calcium phosphate precipitation, and microparticle bombardment (e.g., gene gun). Gene therapy materials and methods may also include inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture. Such additional methods and materials for the practice of gene therapy techniques are described in U.S. Pat. No. 4,970,154 (involving electroporation techniques), U.S. Pat. No. 5,679,559 (describing a lipoprotein-containing system for gene delivery), U.S. Pat. No. 5,676,954 (involving liposome carriers), U.S. Pat. No. 5,593,875 (describing methods for calcium phosphate transfection), and U.S. Pat. No. 4,945,050 (describing a process wherein biologically active particles are propelled at cells at a speed whereby the particles penetrate the surface of the cells and become incorporated into the interior of the cells), and International Pub. No. WO 96/40958 (involving nuclear ligands).

It is also contemplated that B7-L gene therapy or cell therapy can further include the delivery of one or more additional polypeptide(s) in the same or a different cell(s). Such cells may be separately introduced into the patient, or the cells may be contained in a single implantable device, such as the encapsulating membrane described above, or the cells may be separately modified by means of viral vectors.

A means to increase endogenous B7-L polypeptide expression in a cell via gene therapy is to insert one or more enhancer elements into the B7-L polypeptide promoter, where the enhancer elements can serve to increase transcriptional activity of the B7-L gene. The enhancer elements used will be selected based on the tissue in which one desires to activate the gene—enhancer elements known to confer promoter activation in that tissue will be selected. For example, if a gene encoding a B7-L polypeptide is to be "turned on" in T-cells, the ick promoter enhancer element may be used. Here, the functional portion of the transcriptional element to be added may be inserted into a fragment of DNA containing the B7-L polypeptide promoter (and optionally, inserted into a vector and/or 5' and/or 3' flanking sequences) using standard cloning techniques. This construct, known as a "homologous recombination construct," can then be introduced into the desired cells either ex vivo or in vivo.

Gene therapy also can be used to decrease B7-L polypeptide expression by modifying the nucleotide sequence of the endogenous promoter. Such modification is typically accomplished via homologous recombination methods. For example, a DNA molecule containing all or a portion of the promoter of the B7-L gene selected for inactivation can be engineered to remove and/or replace pieces of the promoter that regulate transcription. For example, the TATA box and/or the binding site of a transcriptional activator of the promoter may be deleted using standard molecular biology techniques; such deletion can inhibit promoter activity thereby repressing the transcription of the corresponding B7-L gene. The deletion of the TATA box or the transcription activator binding site in the promoter may be accomplished by generating a DNA construct comprising all or the relevant portion of the B7-L polypeptide promoter (from the same or a related species as the B7-L gene to be regulated) in which one or more of the TATA box and/or transcriptional activator binding site nucleotides are mutated via substitution, deletion and/or insertion of one or more nucleotides. As a result, the TATA box and/or activator binding site has decreased activity or is rendered completely inactive. This construct, which also will typically contain at least about 500 bases of DNA that correspond to the native (endogenous) 5' and 3' DNA sequences adjacent to the promoter segment that has been modified, may be introduced into the appropriate cells (either ex vivo or in vivo) either directly or via a viral vector as described herein. Typically, the integration of the construct into the genomic DNA of the cells will be via homologous recombination, where the 5' and 3' DNA sequences in the promoter construct can serve to help integrate the modified promoter region via hybridization to the endogenous chromosomal DNA.

Therapeutic Uses

B7-L nucleic acid molecules, polypeptides, and agonists and antagonists thereof can be used to treat, diagnose, ameliorate, or prevent a number of diseases, disorders, or conditions, including those recited herein.

B7-L polypeptide agonists and antagonists include those molecules which regulate B7-L polypeptide activity and either increase or decrease at least one activity of the mature form of the B7-L polypeptide. Agonists or antagonists may be co-factors, such as a protein, peptide, carbohydrate, lipid, or small molecular weight molecule, which interact with B7-L polypeptide and thereby regulate its activity. Potential polypeptide agonists or antagonists include antibodies that react with either soluble or membrane-bound forms of B7-L polypeptides that comprise part or all of the extracellular domains of the said proteins. Molecules that regulate B7-L polypeptide expression typically include nucleic acids encoding B7-L polypeptide that can act as anti-sense regulators of expression.

Since transgenic mice expressing a related member of the B7 family showed seminal vesicle hyperplasia (co-pending U.S. patent application Ser. No. 09/729,264, filed Nov. 28, 2000), B7-L polypeptide agonists and antagonists may be useful in the treatment of reproductive disorders and proliferative disorders.

The overexpression of B7-L polypeptide may play a role in the growth and maintenance of cancer cells by causing seminal vesicle hyperplasia. Accordingly, agonists or antagonists to B7-L polypeptide may be useful for the diagnosis or treatment of cancer. Examples of such cancers include, but are not limited to, seminal vesicle cancer, lung cancer, brain cancer, breast cancer, cancers of the hematopoietic system, prostate cancer, ovarian cancer, and testicular cancer. Other cancers are encompassed within the scope of the invention.

The overexpression of B7-L polypeptide may play a role in the inappropriate proliferation of cells by causing seminal vesicle hyperplasia. B7-L polypeptide may play a role in the inappropriate proliferation of cells based on overexpression causing seminal vesicle hyperplasia. Accordingly, agonists or antagonists to B7-L polypeptide may be useful for the diagnosis or treatment of diseases associated with abnormal cell proliferation. Examples of such diseases include, but are not limited to, arteriosclerosis and vascular restenosis. Other diseases influenced by the inappropriate proliferation of cells are encompassed within the scope of the invention.

The overexpression of B7-L polypeptide may play a role in the reproductive system by causing seminal vesicle hyperplasia. Accordingly, agonists or antagonists to B7-L polypeptide may be useful for the diagnosis or treatment of diseases associated with the reproductive system. Examples of such diseases include, but are not limited to, infertility, miscarriage, pre-term labor and delivery, and endometriosis. Other diseases of the reproductive system are encompassed within the scope of the invention.

Preferably, the B7-L nucleic acid molecules, polypeptides, and agonists and antagonists of the present invention are used to treat, diagnose, ameliorate, or prevent diseases associated with T-cell function (e.g., functioning as a T-cell receptor decoy). For example, antibodies, soluble proteins comprising extracellular domains, or other regulators of B7-L polypeptide that result in prolonged or enhanced T-cell activation can be used to increased the immune response to tumors.

The B7-L nucleic acid molecules, polypeptides, and agonists and antagonists of the present invention may be used in the treatment of autoimmune disease, graft survival, immune cell activation for inhibiting tumor cell growth, T-cell dependent B-cell mediated diseases, and cancer gene immunotherapy. In one embodiment, agonists of B7-L polypeptide function, soluble B7-L polypeptides, or B7-L polypeptide derivatives may be beneficial to alleviate symptoms in diseases with chronic immune cell dysfunction. Autoimmune diseases, such as systemic lupus erythematosis, rheumatoid arthritis, osteoarthritis, immune thrombocytopenic purpura (ITP), and psoriasis, may be treated with agonists of B7-L polypeptide function, soluble B7-L polypeptides, or B7-L polypeptide derivatives. In addition, chronic inflammatory diseases, such as inflammatory bowel disease (Crohn's disease and ulcerative colitis), Grave's disease, Hashimoto's thyroiditis, and diabetes mellitis, may also be treated with agonists of B7-L polypeptide function, soluble B7-L polypeptides, or B7-L polypeptide derivatives.

Agonists of B7-L polypeptide function, soluble B7-L polypeptides, or B7-L polypeptide derivatives may be used as immunosuppressive agents for bone marrow and organ transplantation and may be used to prolong graft survival. Such agonists of B7-L polypeptide function, soluble B7-L polypeptides, or B7-L polypeptide derivatives may provide significant advantages over existing treatments. Bone marrow and organ transplantation therapy must contend with T-cell mediated rejection of the foreign cells or tissue by the host. Present therapeutic regimens for inhibiting T-cell mediated rejection involve treatment with the drugs cyclosporine or FK506. While drugs are effective, patients suffer from serious side effects, including hepatotoxicity, nephrotoxicity, and neurotoxicity. The target for the cyclosporin/FK506 class of therapeutics is calcineurin, a phosphatase with ubiquitous expression. Agonists of B7-L polypeptide function, soluble B7-L polypeptides, or B7-L polypeptide derivatives may lack the severe side effects observed with the use of the present immunotherapeutic agents. Agonists of B7-L polypeptide function, soluble B7-L polypeptides, or B7-L polypeptide derivatives may be used as immunosuppressive agents for autoimmune disorders, such as rheumatoid arthritis, osteoarthritis psoriasis, multiple sclerosis, diabetes, and systemic lupus erythematosus. Agonists of B7-L polypeptide function, soluble B7-L polypeptides, or B7-L polypeptide derivatives may also be used to alleviate toxic shock syndrome, inflammatory bowel disease, allosensitization due to blood transfusions, T-cell dependent B-cell mediated diseases, and the treatment of graft versus host disease.

For instance, many vaccines act by eliciting an effective and specific antibody response. Some vaccines, especially those against intestinal microorganisms (e.g., Hepatitis A virus and *Salmonella*), elicit a short-lived antibody response. It is desirable to potentiate and prolong this response in order to increase the effectiveness of the vaccine. Therefore, soluble B7-L polypeptides may serve as vaccine adjuvants.

Conversely, since B7-L may have negative immune regulatory functions, inhibition of B7-L activity using antibodies, small molecules, peptibodies, or other antagonists of B7-L function may result in immune enhancement and anti-tumor activity.

Anti-viral responses may also be enhanced by activators or agonists of the B7-L polypeptide pathway. The enhancement of cellular immune functions by B7-L polypeptide antagonists may also be beneficial in eliminating virus-infected cells. In a complementary fashion, B7-L polypeptide antagonists may also have effects on humoral immune functions that may enhance antibody mediated responses and that may function to help clear free virus from the body.

Conversely, there are a number of clinical conditions that would be ameliorated by the inhibition of antibody production. Hypersensitivity is a normally beneficial immune response that is exaggerated or inappropriate, and leads to inflammatory reactions and tissue damage. Hypersensitivity reactions that are antibody-mediated may be particularly susceptible to antagonism by agonists of B7-L polypeptide function, soluble B7-L polypeptides, or B7-L polypeptide derivatives. Allergies, hay fever, asthma, and acute edema cause type I hypersensitivity reactions, and these reactions may be suppressed by agonists of B7-L polypeptide function, soluble B7-L polypeptides, or B7-L polypeptide derivatives.

Diseases that cause antibody-mediated hypersensitivity reactions, including systemic lupus erythematosis, arthritis (rheumatoid arthritis, reactive arthritis, and psoriatic arthritis), nephropathies (glomerulo-nephritis, membranous, mesangiocapillary, focal segmental, focal necrotizing, crescentic, and proliferative tubulopathies), skin disorders (pemphigus, pemphigoid, and erythema nodosum), endocrinopathies (thyroiditis, Grave's, Hashimoto's, insulin-dependent diabetes mellitus), various pneumopathies (especially extrinsic alveolitis), various vasculopathies, coeliac disease, with aberrant production of IgA, many anemias and thrombocytopenias, Guillain-Barre Syndrome, and myasthenia gravis, may be treated with agonists of B7-L polypeptide function, soluble B7-L polypeptides, or B7-L polypeptide derivatives.

In addition, lymphoproliferative disorders, such as multiple myeloma, Waldenstrom's macroglobulinemia, and crioglobulinemias, may be inhibited by agonists of B7-L polypeptide function, soluble B7-L polypeptides, or B7-L polypeptide derivatives. Finally, graft versus host disease, an "artificial" immune disorder, may benefit from the inhibition of antibody production by agonists of B7-L polypeptide function, soluble B7-L polypeptides, or B7-L polypeptide derivatives.

Agonists or antagonists of B7-L polypeptide function may be used (simultaneously or sequentially) in combination with one or more cytokines, growth factors, antibiotics, anti-inflammatories, and/or chemotherapeutic agents as is appropriate for the condition being treated.

Other diseases caused by or mediated by undesirable levels of B7-L polypeptides are encompassed within the scope of the invention. Undesirable levels include excessive levels of B7-L polypeptides and sub-normal levels of B7-L polypeptides.

B7-L polypeptide is a ligand for a negative regulator of immune responses, PD-1 (Nishimura et al., 1999, *Immunity* 11:141-51). Therefore, agonists of this B7-L polypeptide pathway are likely to inhibit immune responses and antagonists of the pathway may enhance immune responses. However, agonists or antagonists of B7-L polypeptide function may produce unexpected outcomes due to unknown biological factors.

Uses of B7-L Nucleic Acids and Polypeptides

Nucleic acid molecules of the invention (including those that do not themselves encode biologically active polypeptides) may be used to map the locations of the B7-L gene and related genes on chromosomes. Mapping may be done by techniques known in the art, such as PCR amplification and in situ hybridization.

B7-L nucleic acid molecules (including those that do not themselves encode biologically active polypeptides), may be useful as hybridization probes in diagnostic assays to test, either qualitatively or quantitatively, for the presence of a B7-L nucleic acid molecule in mammalian tissue or bodily fluid samples.

Other methods may also be employed where it is desirable to inhibit the activity of one or more B7-L polypeptides. Such inhibition may be effected by nucleic acid molecules that are complementary to and hybridize to expression control sequences (triple helix formation) or to B7-L mRNA. For example, antisense DNA or RNA molecules, which have a sequence that is complementary to at least a portion of a B7-L gene can be introduced into the cell. Anti-sense probes may be designed by available techniques using the sequence of the B7-L gene disclosed herein. Typically, each such antisense molecule will be complementary to the start site (5' end) of each selected B7-L gene. When the antisense molecule then hybridizes to the corresponding B7-L mRNA, translation of this mRNA is prevented or reduced. Anti-sense inhibitors provide information relating to the decrease or absence of a B7-L polypeptide in a cell or organism.

Alternatively, gene therapy may be employed to create a dominant-negative inhibitor of one or more B7-L polypeptides. In this situation, the DNA encoding a mutant polypeptide of each selected B7-L polypeptide can be prepared and introduced into the cells of a patient using either viral or non-viral methods as described herein. Each such mutant is typically designed to compete with endogenous polypeptide in its biological role.

In addition, a B7-L polypeptide, whether biologically active or not, may be used as an immunogen, that is, the polypeptide contains at least one epitope to which antibodies may be raised. Selective binding agents that bind to a B7-L polypeptide (as described herein) may be used for in vivo and in vitro diagnostic purposes, including, but not limited to, use in labeled form to detect the presence of B7-L polypeptide in a body fluid or cell sample. The antibodies may also be used to prevent, treat, or diagnose a number of diseases and disorders, including those recited herein. The antibodies may bind to a B7-L polypeptide so as to diminish or block at least one activity characteristic of a B7-L polypeptide, or may bind to a polypeptide to increase at least one activity characteristic of a B7-L polypeptide (including by increasing the pharmacokinetics of the B7-L polypeptide).

B7-L polypeptides can be used to clone B7-L ligands using an "expression cloning" strategy. Radiolabeled ($^{125}$Iodine) B7-L polypeptide or "affinity/activity-tagged" B7-L polypeptide (such as an Fc fusion or an alkaline phosphatase fusion) can be used in binding assays to identify a cell type, cell line, or tissue that expresses a B7-L ligand. RNA isolated from such cells or tissues can then be converted to cDNA, cloned into a mammalian expression vector, and transfected into mammalian cells (e.g. COS or 293) to create an expression library. Radiolabeled or tagged B7-L polypeptide can then be used as an affinity reagent to identify and isolate the subset of cells in this library expressing a B7-L ligand. DNA is then isolated from these cells and transfected into mammalian cells to create a secondary expression library in which the fraction of cells expressing the B7-L ligand would be many-fold higher than in the original library. This enrichment process can be repeated iteratively until a single recombinant clone containing the B7-L ligand is isolated. Isolation of B7-L ligands is useful for identifying or developing novel agonists and antagonists of the B7-L signaling pathway. Such agonists and antagonists include B7-L ligands, anti-B7-L ligand antibodies, small molecules or antisense oligonucleotides.

Deposits of cDNA encoding human B7-L polypeptide, subcloned into pGEM-T-Easy (Promega, Madison, Wis.), and having Accession No. PTA 2481, were made with the American Type Culture Collection, 10801 University Boulevard, Manassas, Va. 20110-2209 on Sep. 19, 2000.

The human B7-L nucleic acids of the present invention are also useful tools for isolating the corresponding chromosomal B7-L polypeptide genes. The human B7-L genomic DNA can be used to identify heritable tissue-degenerating diseases.

The following examples are intended for illustration purposes only, and should not be construed as limiting the scope of the invention in any way.

EXAMPLE 1

Cloning of the Human B7-L Polypeptide Genes

Generally, materials and methods as described in Sambrook et al. supra were used to clone and analyze the genes encoding human and murine B7-L polypeptides.

A search of the Genebank-EMBL database was performed using the TBLASTX program and B7-H1 as the query sequence. A human genomic clone (Celera Genomics, Rockville, Md. GA__16817596) was identified as containing nucleic acid sequence encoding a putative new member of the B7 family. The predicted cDNA sequence for this putative new member of the B7 family was assembled using a clone containing a partial B7-L nucleic acid sequence (GenBank accession no. AK001872).

Plasmid DNA from various cDNA libraries and Marathon cDNA libraries (Clontech, Palo Alto, Calif.) was used as a template in PCR amplifications performed with the primers 2515-27 (5'-C-A-T-A-A-T-A-G-A-G-C-A-T-G-G-C-A-G-C-A-A-T-G-T-G-A-C-3'; SEQ ID NO: 26) and 2524-63 (5'-G-G-G-T-C-C-T-G-G-A-G-T-G-G-C-T-G-G-T-G-T-T-G-3'; SEQ ID NO: 27). The PCR primers were designed to correspond to sequences within a putative exon in the cDNA sequence identified above. PCR amplifications were performed using standard techniques.

The expected 400 bp PCR fragment was obtained from cDNA libraries generated from human fetal stomach, thymus, scalp, calvaria, femur, mesentery, spleen, spinal column, trachea, and placenta. In addition, the expected fragment was obtained in human adult T-cells, pons/medula, and midbrain LVN. Furthermore, the expected fragment was obtained in a lymphoma cell line and in colon, breast, ovary, and lung tumors. Marathon cDNA libraries for human fetal adrenal gland, brain, kidney, liver, lung, spleen, and thymus, and adult bone marrow, heart, kidney, liver, lung, pancreas, placenta, retina, skeletal muscle, small intestine, spleen, testis and thymus also yielded the expected fragment. The 400 bp fragment was also obtained from a sub-pool (E4) of human mixed-tissue cDNA (the sub-pool containing approximately 15,000 clones). The sub-pool was derived from a custom synthesized library (LTI-FL, Life Technologies Inc., Rockville, Md.) optimized for full-length cDNA clones.

The 400 bp fragment obtained in PCR amplifications of human mixed-tissue cDNA was isolated and cloned into the pGEM-T-Easy® vector (Promega, Madison, Wis.). The DNA sequence of a selected clone was determined to confirm that the sequence of the clone was identical to that of the originally identified genomic sequence. The 400 bp fragment was then excised from the vector and labeled by incorporation of $^{32}$P-dCTP. The labeled fragment was used to screen 150,000 bacterial colonies derived from the 15,000-clone sub-pool of the LTI-FL cDNA library that tested positive in the prior PCR amplification experiment. Colonies were transferred from LB/ampicillin plates to nitrocellulose filters, pre-hybridized in 6× SSC, 0.5% SDS, 1× Denhardt's solution and 100 µg/ml denatured salmon sperm DNA for 3 hours at 60° C. Following the addition of 1×10$^6$ cpm/ml of the $^{32}$P-labeled probe, hybridization was performed overnight under the same conditions. Filters were washed twice for 30 minutes at room temperature in 2× SSC and 0.1% SDS and then twice for 30 minutes at 65° C. in 0.1× SSC and 0.1% SDS. Filters were then exposed to X-ray film for 6 hours at −80° C. with intensifying screens.

Several positive colonies were identified in this manner and plasmid DNA from these clones was prepared by standard methods. The cDNA inserts from these colonies were all approximately 2.2 kb in length. DNA sequence analysis confirmed that the clones contained the putative coding region of a new member of the B7 family, B7-L, and that the nucleic acid sequence identified in the clones was identical to that identified in the genomic clone GA__16817596.

Sequence analysis of the full-length cDNA for human B7-L polypeptide indicated that the gene comprises a 819 bp open reading frame encoding a protein of 273 amino acids (FIG. 1). Using an HP G100 Protein Sequencer, the amino-terminal end of the mature B7-L polypeptide was sequenced and found to comprise the amino acid sequence L-F-T-V-T-V-P-K-E-L-Y-I-I-E (SEQ ID NO: 28), thus establishing that B7-L polypeptide possesses a signal peptide of 19 amino acids in length at its amino-terminus (see FIG. 1; predicted signal peptide indicated by underline).

The nucleic acid sequence identified in the clones, while containing the entire open reading frame, did not contain the full 5' untranslated region of the B7-L transcript. This sequence is determined using successive rounds of 5' RACE using the primers 2515-24 (5'-G-T-G-G-C-T-C-T-T-T-C-A-C-G-G-T-G-T-G-G-G-A-T-G-3'; SEQ ID NO: 29) and 2538-68 (5'-C-C-A-G-T-G-T-C-A-A-A-G-T-T-G-C-A-T-T-C-C-A-G-G-G-T-3'; SEQ ID NO: 30) and the following templates: Marathon cDNA libraries derived from fetal liver, spleen, and thymus, and adult bone marrow, lung, and spleen; cDNA libraries from a lymphoma cell line and ovary tumor; and cDNA libraries from fetal spleen, placenta, and adult T-cells and spinal column. Standard RACE protocols were employed. Clear bands were obtained for RACE amplification of the lymphoma cell line, fetal spleen, placenta, and adult T-cells. These products were ligated into the pGEM-T-Easy® vector. The sequence of the 5' untranslated region of the B7-L transcript is determined by sequencing selected clones from these transformation reactions.

Figure 2B:
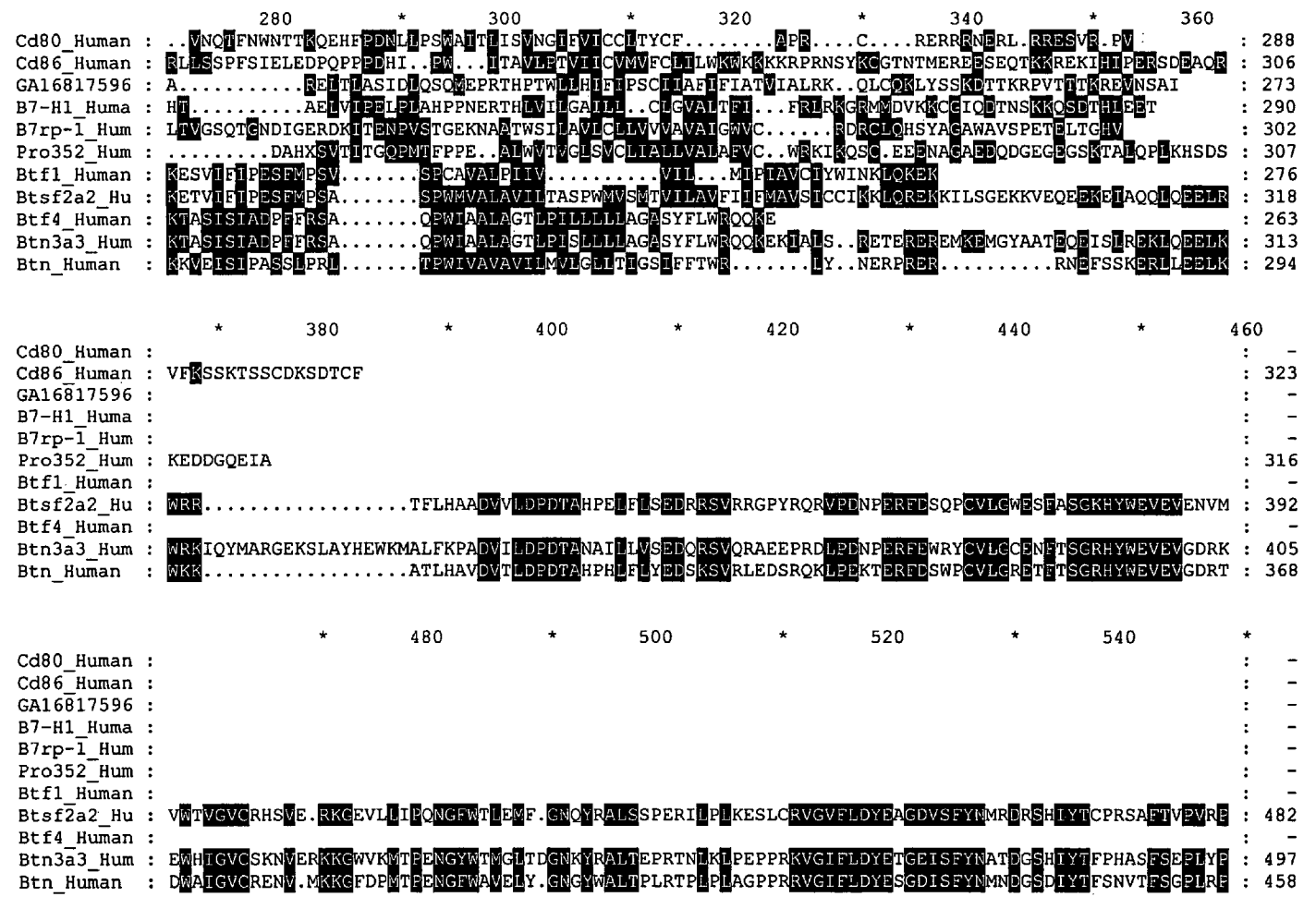

The predicted protein product of the B7-L gene is related to the B7 family of proteins. These proteins are members of the immunoglobulin superfamily and function as regulators of the T-cell mediated immune response. Members of the B7 family of proteins are Type-1 membrane proteins with a small cytoplasmic domain and extracellular regions that contain immunoglobulin V (variable) and C (constant) domains. The known members of the B7 family include CD80 (B7-1), CD86 (B7-2), B7-rp1, and B7-H1. B7-1 and B7-2 interact with CD28 and CTLA-4 and are mediators of the T cell costimulatory pathway. B7-rp1 binds to a distinct receptor (ICOS; inducible co-stimulator) and is also a stimulator of T-cell proliferation. B7-H1 also co-stimulates T cell proliferation, but does not bind CD28, CTLA-4, or ICOS. The protein sequences of this family are poorly conserved and consequently, are difficult to distinguish from other related molecules using computational methods, especially when only a portion of the full-length coding region sequence is compared. Other proteins exhibiting sequence homology to the B7 family include the butyrophilins and PRO352. Still more distantly related are the myelin oligodendrocyte proteins (MOGs). FIGS. 2A-2C illustrate an amino acid sequence alignment of the human proteins B7-L polypeptide (GA16817596), CD80 (B7-1), CD86 (B7-2), B7-H1, B7rp-1, PRO352, butyrophilin BTF1, butyrophilin BTF2, butyrophilin BTF4, butyrophilin BTF3, and butyrophilin.

The full length sequence of the mouse B7-L ortholog was deposited with GenBank on Jun. 1, 1999 (accession no. AF142780). The mouse B7-L ortholog was accurately placed into the B7/butyrophilin family at the time of deposit. A partial human B7-L cDNA sequence, encoding for 173 amino acids from the C-terminal portion of B7-L polypeptide) was deposited with GenBank on Feb. 23, 2000 (accession no. AK001872). The partial polypeptide encoded by this clone was not assigned to a particular family of proteins at the time of deposit.

A partial intron-exon structure for the B7-L gene was derived from the genomic clones GA_43440610, GA_43068628, GA_43068627, and GA_43440600 (Celera Genomics). FIGS. 3A-3E illustrate a portion of the genomic nucleotide sequence for human B7-L polypeptide (SEQ ID NO: 14). The location of the deduced amino acid sequence of exon 1 (SEQ ID NO: 19) is shown in FIG. 3C. The sequence shown in FIGS. 3A-3E is separated by a gap of unknown size from the portion of the genomic nucleotide sequence shown in FIG. 4 (SEQ ID NO: 15). The sequence shown in FIG. 4 is separated by a masked sequence of approximately 2400 bases from the genomic nucleotide sequence shown in FIGS. 5A-5F (SEQ ID NO: 16). The location of the deduced amino acid sequence of exon 2 (SEQ ID NO: 20) is shown in FIG. 5D. The sequence shown in FIGS. 5A-5F is separated by a gap of approximately 9600 bases from the genomic nucleotide sequence shown in FIGS. 6A-6B (SEQ ID NO: 17). The location of the deduced amino acid sequence of exon 3 (SEQ ID NO: 21) is shown in 6A. The sequence shown in FIGS. 6A-6B is separated by a masked sequence of approximately 720 bases from the genomic nucleotide sequence shown in FIGS. 7A-7M (SEQ ID NO: 18). The locations of the deduced amino acid sequence of exons 4 (SEQ ID NO: 22), 5 (SEQ ID NO: 23), and 6 are shown in 7D-7E, 7H, and 7L, respectively.

EXAMPLE 2

B7-L mRNA Expression

A multiple human tissue Northern blot (Clontech) was hybridized to an 874 bp probe corresponding to nucleotides 33-906 of the human B7-L cDNA sequence. The probe was radioactively labeled using a Prime-It RmT Random Primer Labeling kit (Stratagene) according to the manufacturer's instructions. Northern blots were hybridized and washed according to the manufacturer's instructions, and then exposed to autoradiography. FIG. 8 illustrates the results of the Northern blot analysis.

The expression of B7-L mRNA is localized by in situ hybridization. A panel of normal embryonic and adult mouse tissues is fixed in 4% paraformaldehyde, embedded in paraffin, and sectioned at 5 μm. Sectioned tissues are permeabilized in 0.2 M HCl, digested with Proteinase K, and acetylated with triethanolamine and acetic anhydride. Sections are prehybridized for 1 hour at 60° C. in hybridization solution (300 mM NaCl, 20 mM Tris-HCl, pH 8.0, 5 mM EDTA, 1× Denhardt's solution, 0.2% SDS, 10 mM DTT, 0.25 mg/ml tRNA, 25 μg/ml polyA, 25 μg/ml polyC and 50% formamide) and then hybridized overnight at 60° C. in the same solution containing 10% dextran and $2\times10^4$ cpm/μl of a $^{33}$P-labeled antisense riboprobe complementary to the human B7-L gene. The riboprobe is obtained by in vitro transcription of a clone containing human B7-L cDNA sequences using standard techniques.

Following hybridization, sections are rinsed in hybridization solution, treated with RNaseA to digest unhybridized probe, and then washed in 0.1× SSC at 55° C. for 30 minutes. Sections are then immersed in NTB-2 emulsion (Kodak, Rochester, N.Y.), exposed for 3 weeks at 4° C., developed, and counterstained with hematoxylin and eosin. Tissue morphology and hybridization signal are simultaneously analyzed by darkfield and standard illumination for brain (one sagittal and two coronal sections), gastrointestinal tract (esophagus, stomach, duodenum, jejunum, ileum, proximal colon, and distal colon), pituitary, liver, lung, heart, spleen, thymus, lymph nodes, kidney, adrenal, bladder, pancreas, salivary gland, male and female reproductive organs (ovary, oviduct, and uterus in the female; and testis, epididymus, prostate, seminal vesicle, and vas deferens in the male), BAT and WAT (subcutaneous, peri-renal), bone (femur), skin, breast, and skeletal muscle.

EXAMPLE 3

Production of B7-L Polypeptides

A. Expression of B7-L Polypeptides in Bacteria

PCR is used to amplify template DNA sequences encoding a B7-L polypeptide using primers corresponding to the 5' and 3' ends of the sequence. The amplified DNA products may be modified to contain restriction enzyme sites to allow for insertion into expression vectors. PCR products are gel purified and inserted into expression vectors using standard recombinant DNA methodology. An exemplary vector, such as pAMG21 (ATCC no. 98113) containing the lux promoter and a gene encoding kanamycin resistance is digested with Bam HI and Nde I for directional cloning of inserted DNA. The ligated mixture is transformed into an *E. coli* host strain by electroporation and transformants are selected for kanamycin resistance. Plasmid DNA from selected colonies is isolated and subjected to DNA sequencing to confirm the presence of the insert.

Transformed host cells are incubated in 2×YT medium containing 30 μg/mL kanamycin at 30° C. prior to induction. Gene expression is induced by the addition of N-(3-oxohexanoyl)-dl-homoserine lactone to a final concentration of 30 ng/mL followed by incubation at either 30° C. or 37° C. for six hours. The expression of B7-L polypeptide is evaluated by centrifugation of the culture, resuspension and lysis of the bacterial pellets, and analysis of host cell proteins by SDS-polyacrylamide gel electrophoresis.

Inclusion bodies containing B7-L polypeptide are purified as follows. Bacterial cells are pelleted by centrifugation and resuspended in water. The cell suspension is lysed by sonication and pelleted by centrifugation at 195,000×g for 5 to 10 minutes. The supernatant is discarded, and the pellet is washed and transferred to a homogenizer. The pellet is homogenized in 5 mL of a Percoll solution (75% liquid Percoll and 0.15 M NaCl) until uniformly suspended and then diluted and centrifuged at 21,600×g for 30 minutes. Gradient fractions containing the inclusion bodies are recovered and pooled. The isolated inclusion bodies are analyzed by SDS-PAGE.

A single band on an SDS polyacrylamide gel corresponding to E. coli-produced B7-L polypeptide is excised from the gel, and the N-terminal amino acid sequence is determined essentially as described by Matsudaira et al., 1987, *J. Biol. Chem.* 262:10-35.

B. Expression of B7-L Polypeptide in Mammalian Cells

PCR is used to amplify template DNA sequences encoding a B7-L polypeptide using primers corresponding to the 5' and 3' ends of the sequence. The amplified DNA products may be modified to contain restriction enzyme sites to allow for insertion into expression vectors. PCR products are gel purified and inserted into expression vectors using standard recombinant DNA methodology. An exemplary expression vector, pCEP4 (Invitrogen, Carlsbad, Calif.), that contains an Epstein-Barr virus origin of replication, may be used for the expression of B7-L polypeptides in 293-EBNA-1 cells. Amplified and gel purified PCR products are ligated into pCEP4 vector and introduced into 293-EBNA cells by lipofection. The transfected cells are selected in 100 μg/mL hygromycin and the resulting drug-resistant cultures are grown to confluence. The cells are then cultured in serum-free media for 72 hours. The conditioned media is removed and B7-L polypeptide expression is analyzed by SDS-PAGE.

B7-L polypeptide expression may be detected by silver staining. Alternatively, B7-L polypeptide is produced as a fusion protein with an epitope tag, such as an IgG constant domain or a FLAG epitope, which may be detected by Western blot analysis using antibodies to the peptide tag.

B7-L polypeptides may be excised from an SDS-polyacrylamide gel, or B7-L fusion proteins are purified by affinity chromatography to the epitope tag, and subjected to N-terminal amino acid sequence analysis as described herein.

C. Expression of B7-L Polypeptide/Fc Fusion Protein in Mammalian Cells

A 660 bp fragment of B7-L cDNA, encoding 220 amino acids at the amino-terminal end of B7-L polypeptide, and which includes the signal peptide and extracellular domain of B7-L polypeptide, was amplified by PCR using suitable primers and standard techniques. Plasmid DNA isolated from the custom synthesized library described in Example 1 was used as a template in the PCR amplifications.

The 660 bp fragment was then cloned into the expression vector, pCEP4/Fc, which contains nucleic acid sequence encoding the carboxyl-terminal 235 amino acids of human Fc (IgG-1). Colonies were selected following transformation of bacterial cells, and pCEP4-B7-L/Fc plasmid DNA was isolated using standard techniques.

Isolated plasmid DNA was used to transfect 293-EBNA-1 cells using FuGENE 6 Transfection Reagent (Roche Molecular Biochemicals, Indianapolis, Ind.) according to the manufacturer's instructions. Following transfection, the cells were cultured at 37° C. in DMEM medium, supplemented with 10% fetal bovine serum, for 24 hours, and then transferred to DMEM serum-free medium and grown at 37° C. for 5 days. The B7-L polypeptide/Fc fusion protein was purified from the conditioned media on a HiTrap Protein A Column (Amersham Pharmacia Biotech, Piscataway, N.J.) according to the manufacturer's instructions, and the fusion protein was then dialyzed in PBS. The concentration of the purified protein was measured using Coomassie® Plus Protein Assay Reagent (Pierce, Rockford, Ill.) and BSA as a standard, according to the manufacturer's instructions.

EXAMPLE 4

Identification of B7-L Polypeptide as a Novel PD-1 Ligand

To determine whether B7-L polypeptide functions in one of the known B7-mediated co-stimulatory pathways, FACS analysis was performed on CHO D-cells expressing CD28, CRP-1/ICOS, or PD-1 following treatment with a B7-L polypeptide/Fc fusion protein.

The full-length nucleic acid sequence encoding murine PD-1 (mPD-1; Ishida et al., 1992, *EMBO J.* 11:3887-95), and including the native PD-1 signal peptide, was obtained by PCR amplification of a murine activated spleen lymphocyte cDNA library using primers incorporating Hind III and Sal I restriction endonuclease sites. The resulting PCR product was digested with Hind III and Sal I and then ligated into the pDSRa-19 vector. Following transformation into bacterial cells, clones were selected and sequenced. A clone containing the full-length mPD-1 cDNA sequence (clone 1.5) was linearized using the restriction endonuclease Pvu I, and the linearized plasmid was used to transfect CHO D-cells by the calcium phosphate method. Transfected CHO D-cells were cultured, and individual colonies isolated via ring cloning several weeks later. A high expressing transfectant (clone 3.36) was identified for its ability to specifically bind the B7-H1/Fc fusion protein (Dong et al., 1999, *Nat. Med.* 5:1365-69).

CHO D-cells expressing vector alone, mPD-1 (clone 3.36), human CD28, or mCRP1/ICOS (clone 1.41; Yoshinaga et al., 1999, *Nature* 402:827-32) were cultured in T175 flasks in DMEM supplemented with 5% dFBS, 1× PSG, and 1× NEAA. Cells were released from the culture flasks using Cell Dissociation Solution (Sigma, St. Louis, Mo.), diluted in wash buffer (PBS containing 0.5% BSA), and then counted.

Approximately $3.0 \times 10^5$ cells in 0.1 ml of media were reacted for 1 hour on ice with 1 μg of purified murine CRP1/Fc, human B7-L polypeptide/Fc, murine B7rp-1/Fc, or murine B7-2/Fc. CHO D-cells were also incubated with murine B7-H1/Fc as described above, except that the cells were exposed to 10 μg of fusion protein in 1 ml of serum-free conditioned media harvested from CHO D-cells expressing mB7-H1/Fc. Following incubation, cells were diluted with 5 ml of wash buffer, centrifuged, and then washed twice in 5 ml of wash buffer. The cells were then resuspended in 100 μl of wash buffer containing 10 μg/ml of a goat anti-human IgG Fc-specific FITC-conjugated detection antibody (Chemicon, Temecula Calif.). The cells were allowed to react for 30 minutes on ice, and then were washed as described above.

Following washing, cells were resuspended in a final volume of 1 ml wash buffer and then were analyzed using a FACS Star (Beckman Dickinson, Franklin Lakes, N.J.).

Figure 9:
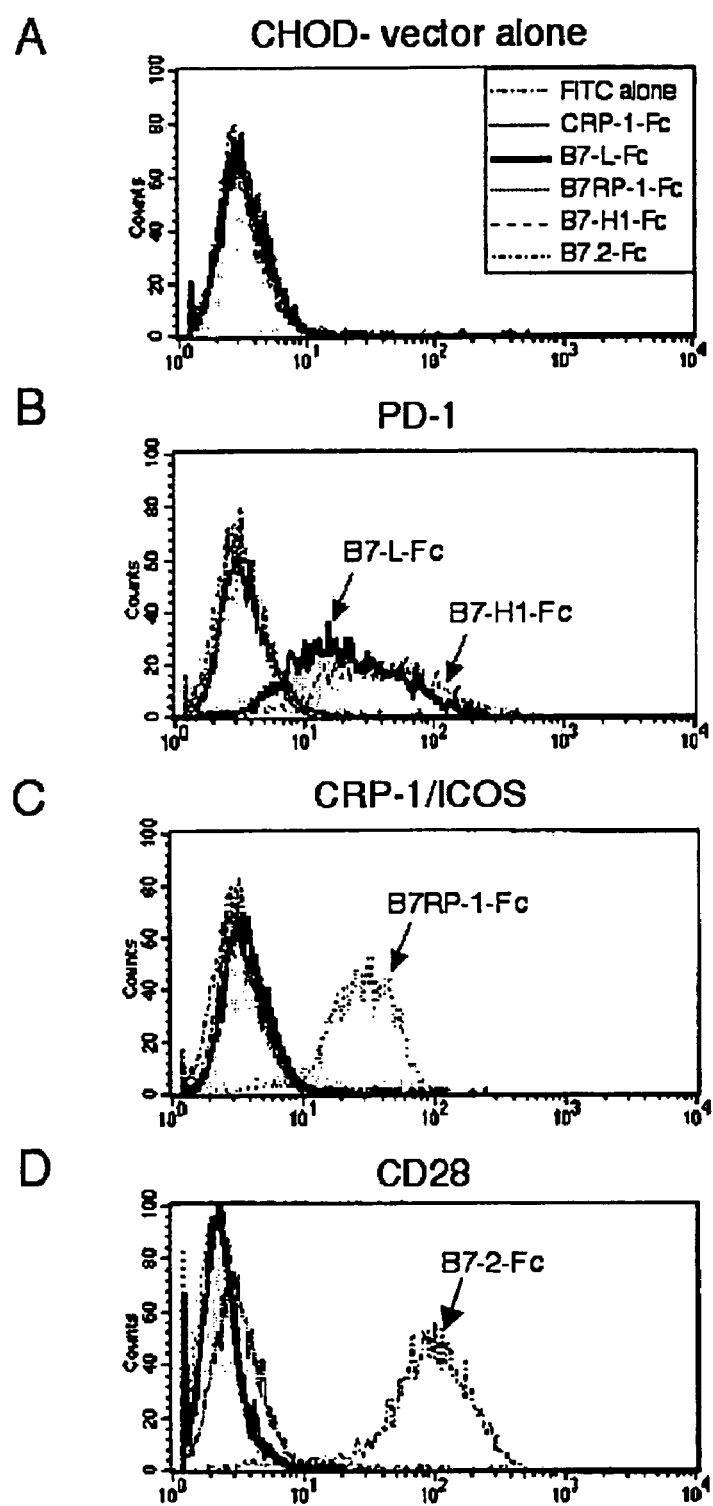
FIG. 9 shows the results for fluorescence-activated cell sorter (FACS) analysis of CHO D-cells transfected with vector alone (A), or with vectors encoding PD-1 (B), CRP-1/ICOS(C) or CD28 (D), and incubated with either FITC alone, or with the following fusion proteins: CRP-1/Fc, B7-L polypeptide/Fc, B7rp-1/Fc, B7-H1/Fc, or B7-2/Fc.

As shown in FIG. 9, B7-L polypeptide specifically binds to the PD-1 receptor, but not the CD28 or CRP-1/ICOS receptors. The fusion proteins B7-2/Fc and B7rp-1/Fc bound to the CD28 and CRP-1/ICOS receptors, as expected. As B7-H1 was also shown to specifically bind the PD-1 receptor (FIG. 9B), FACS analysis indicates that both B7-L polypeptide and B7-H1 are ligands for the PD-1 receptor. Since PD-1 is a negative regulator of T-cell proliferation (Nishimura et al., 1999, *Immunity* 11:141-51), activation of this pathway via soluble B7-L polypeptide may result in a reduced immune response. Conversely, antagonistic antibodies to B7-L polypeptide may increase immune functions.

EXAMPLE 5

Inhibition of T-cell Proliferation by B7-L Polypeptide

To determine whether B7-L polypeptide plays a role in T-cell proliferation, human T-cell proliferation assays were performed using B7-L polypeptide/Fc fusion proteins. Highly purified human T-cells (>98% CD3+) were isolated by negative selection of fresh or thawed, adherence-depleted, peripheral blood mononuclear cells (PBMCs) using the Pan T-cell Isolation kit (Miltenyi Biotec, Auburn, Calif.). Round bottom, 96-well, cell culture plates were precoated overnight at 4° C. with 0.5 or 1.5 µg/ml of anti-CD3 antibody (PharMigen, San Diego, Calif.), 10 µg/ml anti-human IgG Fc (Sigma), and PBS, in a volume of 0.1 ml. The precoating solution was removed, the plates were washed once with PBS, and 0.1 ml of the B7-L polypeptide/Fc, B7-2/Fc or B7rp-1/Fc fusion proteins diluted to 20 µg/ml in RPMI 1640 supplemented with 10% FCS media, or media alone, was added to the wells. The plates were then incubated for 4 hours at 37° C. Following incubation, the media was removed and 0.2 ml of the purified T-cells (containing $10 \times 10^5$ cells) was added to each precoated well. The plates were then incubated for 48 hours at 37° C. Following incubation, 1 µCi/well of [$^3$H]thymidine was added to each well and the cultures were incubated for an additional 18 hrs at 37° C. The cells were then harvested and the counts per minute (CPM) measured.

Figure 10:
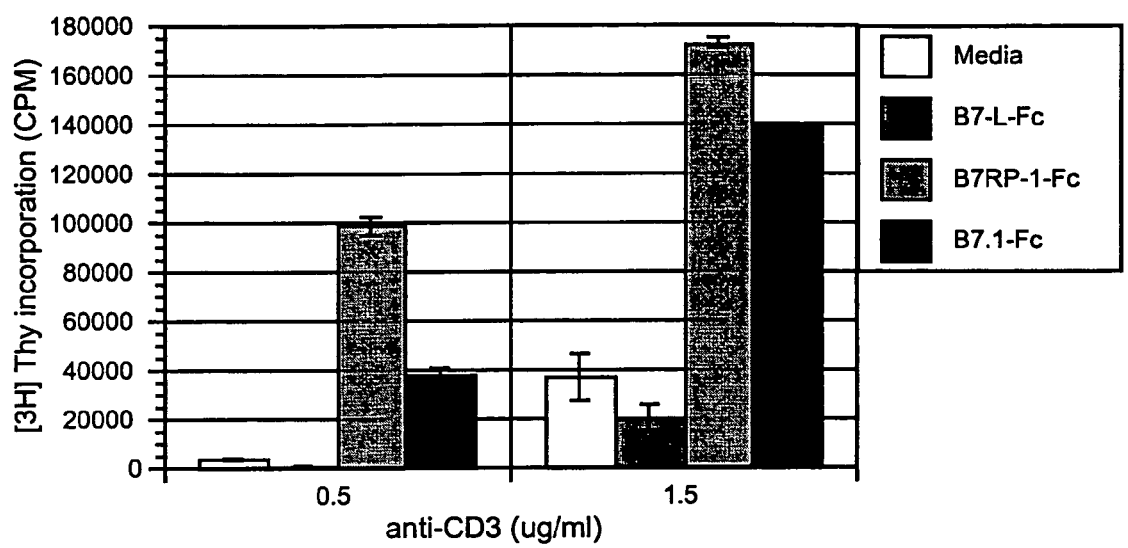
FIG. 10 shows the results obtained in anti-CD3 mediated T-cell proliferation assays using B7-L polypeptide/Fc, B7RP-1/Fc, or B7-1/Fc.

As shown in FIG. 10, the B7-L polypeptide/Fc fusion protein was capable of inhibiting anti-CD3 mediated T-cell proliferation at either concentration of anti-CD3 antibody. Conversely, the B7rp-1/Fc and B7-1/Fc fusion proteins were shown to co-stimulate T-cell proliferation under the same conditions. These results indicate that B7-L polypeptide is a negative regulator of T-cell proliferation. Furthermore, these results suggest that the B7-L polypeptide/Fc fusion protein, or other soluble B7-L polypeptide derivatives, may be used to inhibit immune function, thereby providing favorable therapeutic outcomes. In vitro assays, such as the assay described herein could also be used to screen for antibodies, soluble proteins, or small molecule inhibitors of B7-L polypeptide activity.

EXAMPLE 6

B7-L Polypeptide Receptors are Expressed on Human Peripheral Blood Mononuclear Cells FACS analysis was used to identify B7-L polypeptide receptors on T- and B-cells in human PBMC. Using Ficoll-Paque (Amersham Pharmacia Biotech) gradient centrifugation, PBMC were purified from blood obtained from healthy human volunteers, and the cells stimulated by incubation in 10 µg/ml lipopolysaccharide (LPS) for 3 days. Following LPS treatment, $5 \times 10^5$ cells in a volume of 0.2 ml were blocked with 100 µg/ml human IgG Fc for 10 minutes on ice. The cells were then incubated with 10 µg/ml of various biotinylated Fc fusion proteins (or suitable controls) for 30 minutes on ice. Following incubation with Fc fusion proteins, the cell samples indicated in FIG. 11 were incubated with anti-CD3 (PharMingen) or anti-CD19 (Becton Dickinson) antibodies for 30 minutes on ice. Following incubation, cells were washed twice in wash buffer (PBS containing 0.5% BSA), and then were stained with FITC avidin (1:100 dilution) for 30 minutes on ice. The cells were resuspended in 1 ml wash buffer and were analyzed on a FACS Star.

Figure 11:
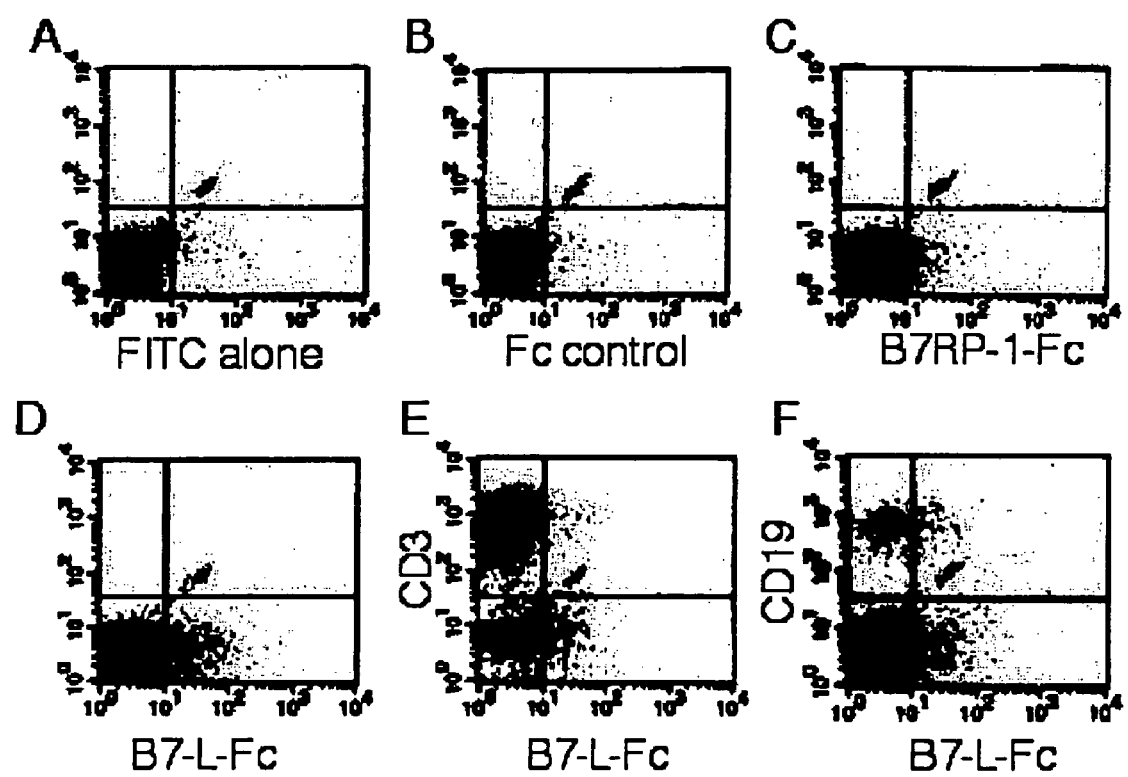
FIG. 11 shows the results of FACS analysis of human peripheral blood cells using FITC alone (A), Fc control (B), B7rp-1/Fc (C), B7-L polypeptide/Fc (D), B7-L polypeptide/Fc and anti-CD3 (E), or B7-L polypeptide/Fc and anti-CD19 (F).

As shown in FIG. 11, the B7-L polypeptide/Fc protein bound to significant populations of peripheral blood mononuclear cells (PBMC). Double-staining with B7-L polypeptide/Fc fusion protein and T-cell (CD3) or B-cell (CD19) markers indicated that a portion of the cells to which B7-L polypeptide/Fc fusion protein bound were T-cells and B-cells. Significant numbers of the B7-L polypeptide receptor-expressing cells, however, were also shown not to be T-cells or B-cells. Therefore, non-lymphocytes, as well as, lymphocytes in PMBC may be regulated by B7-L polypeptide. This pattern of binding is consistent with that with the pattern of PD-1 expression (Ishida et al., 1992, *EMBO J.* 11:3887-95).

EXAMPLE 7

Production of Anti-B7-L Polypeptide Antibodies

Antibodies to B7-L polypeptides may be obtained by immunization with purified protein or with B7-L peptides produced by biological or chemical synthesis. Suitable procedures for generating antibodies include those described in Hudson and Bay, *Practical Immunology* (2nd ed., Blackwell Scientific Publications).

In one procedure for the production of antibodies, animals (typically mice or rabbits) are injected with a B7-L antigen (such as a B7-L polypeptide), and those with sufficient serum titer levels as determined by ELISA are selected for hybridoma production. Spleens of immunized animals are collected and prepared as single cell suspensions from which splenocytes are recovered. The splenocytes are fused to mouse myeloma cells (such as Sp2/0-Ag14 cells), are first incubated in DMEM with 200 U/mL penicillin, 200 µg/mL streptomycin sulfate, and 4 mM glutamine, and are then incubated in HAT selection medium (hypoxanthine, aminopterin, and thymidine). After selection, the tissue culture supernatants are taken from each fusion well and tested for anti-B7-L antibody production by ELISA.

Alternative procedures for obtaining anti-B7-L antibodies may also be employed, such as the immunization of transgenic mice harboring human Ig loci for production of human antibodies, and the screening of synthetic antibody libraries, such as those generated by mutagenesis of an antibody variable domain.

EXAMPLE 8

Expression of B7-L Polypeptide in Transgenic Mice

To assess the biological activity of B7-L polypeptide, a construct encoding a B7-L polypeptide/Fc fusion protein under the control of a liver specific ApoE promoter is prepared. The delivery of this construct is expected to cause pathological changes that are informative as to the function of B7-L polypeptide. Similarly, a construct containing the full-length B7-L polypeptide under the control of the beta actin promoter is prepared. The delivery of this construct is expected to result in ubiquitous expression.

To generate these constructs, PCR is used to amplify template DNA sequences encoding a B7-L polypeptide using primers that correspond to the 5' and 3' ends of the desired sequence and which incorporate restriction enzyme sites to permit insertion of the amplified product into an expression vector. Following amplification, PCR products are gel purified, digested with the appropriate restriction enzymes, and ligated into an expression vector using standard recombinant DNA techniques. For example, amplified B7-L polypeptide sequences can be cloned into an expression vector under the control of the human β-actin promoter as described by Graham et al., 1997, *Nature Genetics*, 17:272-74 and Ray et al., 1991, *Genes Dev.* 5:2265-73.

Following ligation, reaction mixtures are used to transform an *E. coli* host strain by electroporation and transformants are selected for drug resistance. Plasmid DNA from selected colonies is isolated and subjected to DNA sequencing to confirm the presence of an appropriate insert and absence of mutation. The B7-L polypeptide expression vector is purified through two rounds of CsCl density gradient centrifugation, cleaved with a suitable restriction enzyme, and the linearized fragment containing the B7-L polypeptide transgene is purified by gel electrophoresis. The purified fragment is resuspended in 5 mM Tris, pH 7.4, and 0.2 mM EDTA at a concentration of 2 mg/mL.

Single-cell embryos from BDF1×BDF1 bred mice are injected as described (International Pub. No. WO 97/23614). Embryos are cultured overnight in a $CO_2$ incubator and 15-20 two-cell embryos are transferred to the oviducts of a pseudopregnant CD1 female mice. Offspring obtained from the implantation of microinjected embryos are screened by PCR amplification of the integrated transgene in genomic DNA samples as follows. Ear pieces are digested in 20 mL ear buffer (20 mM Tris, pH 8.0, 10 mM EDTA, 0.5% SDS, and 500 mg/mL proteinase K) at 55° C. overnight. The sample is then diluted with 200 mL of TE, and 2 mL of the ear sample is used in a PCR reaction using appropriate primers.

At 8 weeks of age, transgenic founder animals and control animals are sacrificed for necropsy and pathological analysis. Portions of spleen are removed and total cellular RNA isolated from the spleens using the Total RNA Extraction Kit (Qiagen) and transgene expression determined by RT-PCR. RNA recovered from spleens is converted to cDNA using the SuperScript™ Preamplification System (Gibco-BRL) as follows. A suitable primer, located in the expression vector sequence and 3' to the B7-L polypeptide transgene, is used to prime cDNA synthesis from the transgene transcripts. Ten mg of total spleen RNA from transgenic founders and controls is incubated with 1 mM of primer for 10 minutes at 70° C. and placed on ice. The reaction is then supplemented with 10 mM Tris-HCl, pH 8.3, 50 mM KCl, 2.5 mM $MgCl_2$, 10 mM of each DNTP, 0.1 mM DTT, and 200 U of SuperScript II reverse transcriptase. Following incubation for 50 minutes at 42° C., the reaction is stopped by heating for 15 minutes at 72° C. and digested with 2 U of RNase H for 20 minutes at 37° C. Samples are then amplified by PCR using primers specific for B7-L polypeptide.

EXAMPLE 9

Biological Activity of B7-L Polypeptide in Transgenic Mice

Prior to euthanasia, transgenic animals are weighed, anesthetized by isofluorane and blood drawn by cardiac puncture. The samples are subjected to hematology and serum chemistry analysis. Radiography is performed after terminal exsanguination. Upon gross dissection, major visceral organs are subject to weight analysis.

Following gross dissection, tissues (i.e., liver, spleen, pancreas, stomach, the entire gastrointestinal tract, kidney, reproductive organs, skin and mammary glands, bone, brain, heart, lung, thymus, trachea, esophagus, thyroid, adrenals, urinary bladder, lymph nodes and skeletal muscle) are removed and fixed in 10% buffered Zn-Formalin for histological examination. After fixation, the tissues are processed into paraffin blocks, and 3 mm sections are obtained. All sections are stained with hematoxylin and exosin, and are then subjected to histological analysis.

The spleen, lymph node, and Peyer's patches of both the transgenic and the control mice are subjected to immunohistology analysis with B cell and T cell specific antibodies as follows. The formalin fixed paraffin embedded sections are deparaffinized and hydrated in deionized water. The sections are quenched with 3% hydrogen peroxide, blocked with Protein Block (Lipshaw, Pittsburgh, Pa.), and incubated in rat monoclonal anti-mouse B220 and CD3 (Harlan, Indianapolis, Ind.). Antibody binding is detected by biotinylated rabbit anti-rat immunoglobulins and peroxidase conjugated streptavidin (BioGenex, San Ramon, Calif.) with DAB as a chromagen (BioTek, Santa Barbara, Calif.). Sections are counterstained with hematoxylin.

After necropsy, MLN and sections of spleen and thymus from transgenic animals and control littermates are removed. Single cell suspensions are prepared by gently grinding the tissues with the flat end of a syringe against the bottom of a 100 mm nylon cell strainer (Becton Dickinson, Franklin Lakes, N.J.). Cells are washed twice, counted, and approximately $1 \times 10^6$ cells from each tissue are then incubated for 10 minutes with 0.5 μg CD16/32(FcγIII/II) Fc block in a 20 μL volume. Samples are then stained for 30 minutes at 2-8° C. in a 100 μL volume of PBS (lacking $Ca^+$ and $Mg^+$), 0.1% bovine serum albumin, and 0.01% sodium azide with 0.5 μg antibody of FITC or PE-conjugated monoclonal antibodies against CD90.2 (Thy-1.2), CD45R (B220), CD11b (Mac-1), Gr-1, CD4, or CD8 (PharMingen, San Diego, Calif.). Following antibody binding, the cells are washed and then analyzed by flow cytometry on a FACScan (Becton Dickinson).

While the present invention has been described in terms of the preferred embodiments, it is understood that variations and modifications will occur to those skilled in the art. Therefore, it is intended that the appended claims cover all such equivalent variations that come within the scope of the invention as claimed.

What claimed is:

1. An isolated nucleic acid molecule comprising the nucleotide sequence as set forth in SEQ ID NO: 1.

2. A vector comprising the nucleic acid molecule of claim 1.

3. An isolated host cell comprising the vector of claim 2.

4. The host cell of claim 3 that is a eukaryotic cell.

5. The host cell of claim 3 that is a prokaryotic cell.

6. A process of producing a B7-L polypeptide comprising culturing the host cell of claim 3 under suitable conditions to express the polypeptide, and optionally isolating the polypeptide from the culture.

7. The process of claim 6, wherein the nucleic acid molecule comprises promoter DNA other than the promoter DNA for the native B7-L polypeptide operatively linked to the DNA encoding the B7-L polypeptide.

8. A composition comprising a nucleic acid molecule of claim 1 and a pharmaceutically acceptable formulation agent.

9. The composition of claim 8, wherein said nucleic acid molecule is contained in a viral vector.

10. A viral vector comprising a nucleic acid molecule of any of claim 1.

11. A nucleic acid molecule of claim 1, attached to a solid support.

12. An array of nucleic acid molecules comprising at least one nucleic acid molecule of claim 1.

* * * * *

SEQUENCE LISTING

<160> NUMBER OF SEQ ID NOS: 30

<210> SEQ ID NO 1
<211> LENGTH: 1209
<212> TYPE: DNA
<213> ORGANISM: Homo sapiens
<220> FEATURE:
<221> NAME/KEY: CDS
<222> LOCATION: (33)..(854)
<220> FEATURE:
<221> NAME/KEY: sig_peptide
<222> LOCATION: (33)..(89)
<220> FEATURE:
<221> NAME/KEY: misc_feature
<222> LOCATION: (693)..(755)
<223> OTHER INFORMATION: predicted transmembrane domain

<400> SEQUENCE: 1

```
cagaaagaga cctatatgat caaatacaga ac atg atc ttc ctc ctg cta atg       53
                                   Met Ile Phe Leu Leu Leu Met
                                     1               5 ttg agc ctg gaa ttg cag ctt cac cag ata gca gct tta ttc aca gtg      101
Leu Ser Leu Glu Leu Gln Leu His Gln Ile Ala Ala Leu Phe Thr Val
         10                  15                  20 aca gtc cct aag gaa ctg tac ata ata gag cat ggc agc aat gtg acc      149
Thr Val Pro Lys Glu Leu Tyr Ile Ile Glu His Gly Ser Asn Val Thr
 25                  30                  35 ctg gaa tgc aac ttt gac act gga agt cat gtg aac ctt gga gca ata      197
Leu Glu Cys Asn Phe Asp Thr Gly Ser His Val Asn Leu Gly Ala Ile
 40                  45                  50                  55 aca gcc agt ttg caa aag gtg gaa aat gat aca tcc cca cac cgt gaa      245
Thr Ala Ser Leu Gln Lys Val Glu Asn Asp Thr Ser Pro His Arg Glu
                 60                  65                  70 aga gcc act ttg ctg gag gag cag ctg ccc cta ggg aag gcc tcg ttc      293
Arg Ala Thr Leu Leu Glu Glu Gln Leu Pro Leu Gly Lys Ala Ser Phe
             75                  80                  85 cac ata cct caa gtc caa gtg agg gac gaa gga cag tac caa tgc ata      341
His Ile Pro Gln Val Gln Val Arg Asp Glu Gly Gln Tyr Gln Cys Ile
         90                  95                 100 atc atc tat ggg gtc gcc tgg gac tac aag tac ctg act ctg aaa gtc      389
Ile Ile Tyr Gly Val Ala Trp Asp Tyr Lys Tyr Leu Thr Leu Lys Val
     105                 110                 115 aaa gct tcc tac agg aaa ata aac act cac atc cta aag gtt cca gaa      437
Lys Ala Ser Tyr Arg Lys Ile Asn Thr His Ile Leu Lys Val Pro Glu
120                 125                 130                 135 aca gat gag gta gag ctc acc tgc cag gct aca ggt tat cct ctg gca      485
Thr Asp Glu Val Glu Leu Thr Cys Gln Ala Thr Gly Tyr Pro Leu Ala
                 140                 145                 150 gaa gta tcc tgg cca aac gtc agc gtt cct gcc aac acc agc cac tcc      533
Glu Val Ser Trp Pro Asn Val Ser Val Pro Ala Asn Thr Ser His Ser
             155                 160                 165 agg acc cct gaa ggc ctc tac cag gtc acc agt gtt ctg cgc cta aag      581
Arg Thr Pro Glu Gly Leu Tyr Gln Val Thr Ser Val Leu Arg Leu Lys
         170                 175                 180 cca ccc cct ggc aga aac ttc agc tgt gtg ttc tgg aat act cac gtg      629
Pro Pro Pro Gly Arg Asn Phe Ser Cys Val Phe Trp Asn Thr His Val
     185                 190                 195 agg gaa ctt act ttg gcc agc att gac ctt caa agt cag atg gaa ccc      677
Arg Glu Leu Thr Leu Ala Ser Ile Asp Leu Gln Ser Gln Met Glu Pro
200                 205                 210                 215 agg acc cat cca act tgg ctg ctt cac att ttc atc ccc tcc tgc atc      725
```

```
Arg Thr His Pro Thr Trp Leu Leu His Ile Phe Ile Pro Ser Cys Ile
            220                 225                 230 att gct ttc att ttc ata gcc aca gtg ata gcc cta aga aaa caa ctc      773
Ile Ala Phe Ile Phe Ile Ala Thr Val Ile Ala Leu Arg Lys Gln Leu
            235                 240                 245 tgt caa aag ctg tat tct tca aaa gac aca aca aaa aga cct gtc acc      821
Cys Gln Lys Leu Tyr Ser Ser Lys Asp Thr Thr Lys Arg Pro Val Thr
            250                 255                 260 aca aca aag agg gaa gtg aac agt gct atc tga acctgtggtc ttgggagcca    874
Thr Thr Lys Arg Glu Val Asn Ser Ala Ile
            265                 270 gggtgacctg atatgacatc taaagaagct tctggactct gaacaagaat tcggtggcct    934
gcagagcttg ccatttgcac ttttcaaatg cctttggatg acccagcact ttaatctgaa    994
acctgcaaca agactagcca acacctggcc atgaaacttg ccccttcact gatctggact    1054
cacctctgga gcctatggct ttaagcaagc actactgcac tttacagaat taccccactg    1114
gatcctggac ccacagaatt ccttcaggat ccttcttgct gccagactga aagcaaaagg    1174
aattatttcc cctcaagttt tctaagtgat ttcca                               1209

<210> SEQ ID NO 2
<211> LENGTH: 273
<212> TYPE: PRT
<213> ORGANISM: Homo sapiens

<400> SEQUENCE: 2

Met Ile Phe Leu Leu Leu Met Leu Ser Leu Glu Leu Gln Leu His Gln
 1               5                  10                  15

Ile Ala Ala Leu Phe Thr Val Thr Val Pro Lys Glu Leu Tyr Ile Ile
                20                  25                  30

Glu His Gly Ser Asn Val Thr Leu Glu Cys Asn Phe Asp Thr Gly Ser
            35                  40                  45

His Val Asn Leu Gly Ala Ile Thr Ala Ser Leu Gln Lys Val Glu Asn
        50                  55                  60

Asp Thr Ser Pro His Arg Glu Arg Ala Thr Leu Leu Glu Glu Gln Leu
 65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Ser Cys Ile Ile Ala Phe Ile Phe Ile Ala Thr Val
225                 230                 235                 240
```

```
Ile Ala Leu Arg Lys Gln Leu Cys Gln Lys Leu Tyr Ser Ser Lys Asp
                245                 250                 255

Thr Thr Lys Arg Pro Val Thr Thr Lys Arg Glu Val Asn Ser Ala
            260                 265                 270

Ile

<210> SEQ ID NO 3
<211> LENGTH: 254
<212> TYPE: PRT
<213> ORGANISM: Homo sapiens
<220> FEATURE:
<221> NAME/KEY: TRANSMEM
<222> LOCATION: (202)..(222)

<400> SEQUENCE: 3

Leu Phe Thr Val Thr Val Pro Lys Glu Leu Tyr Ile Ile Glu His Gly
  1               5                  10                  15

Ser Asn Val Thr Leu Glu Cys Asn Phe Asp Thr Gly Ser His Val Asn
                 20                  25                  30

Leu Gly Ala Ile Thr Ala Ser Leu Gln Lys Val Glu Asn Asp Thr Ser
             35                  40                  45

Pro His Arg Glu Arg Ala Thr Leu Leu Glu Glu Gln Leu Pro Leu Gly
         50                  55                  60

Lys Ala Ser Phe His Ile Pro Gln Val Gln Val Arg Asp Glu Gly Gln
 65                  70                  75                  80

Tyr Gln Cys Ile Ile Ile Tyr Gly Val Ala Trp Asp Tyr Lys Tyr Leu
                 85                  90                  95

Thr Leu Lys Val Lys Ala Ser Tyr Arg Lys Ile Asn Thr His Ile Leu
                100                 105                 110

Lys Val Pro Glu Thr Asp Glu Val Glu Leu Thr Cys Gln Ala Thr Gly
            115                 120                 125

Tyr Pro Leu Ala Glu Val Ser Trp Pro Asn Val Ser Val Pro Ala Asn
130                 135                 140

Thr Ser His Ser Arg Thr Pro Glu Gly Leu Tyr Gln Val Thr Ser Val
145                 150                 155                 160

Leu Arg Leu Lys Pro Pro Pro Gly Arg Asn Phe Ser Cys Val Phe Trp
                165                 170                 175

Asn Thr His Val Arg Glu Leu Thr Leu Ala Ser Ile Asp Leu Gln Ser
                180                 185                 190

Gln Met Glu Pro Arg Thr His Pro Thr Trp Leu Leu His Ile Phe Ile
            195                 200                 205

Pro Ser Cys Ile Ile Ala Phe Ile Phe Ile Ala Thr Val Ile Ala Leu
210                 215                 220

Arg Lys Gln Leu Cys Gln Lys Leu Tyr Ser Ser Lys Asp Thr Thr Lys
225                 230                 235                 240

Arg Pro Val Thr Thr Thr Lys Arg Glu Val Asn Ser Ala Ile
                245                 250

<210> SEQ ID NO 4
<211> LENGTH: 224
<212> TYPE: PRT
<213> ORGANISM: Homo sapiens

<400> SEQUENCE: 4

Met Gly His Thr Arg Arg Gln Gly Thr Ser Pro Ser Lys Cys Pro Tyr
  1               5                  10                  15
```

```
Leu Asn Phe Phe Gln Leu Leu Val Leu Ala Gly Leu Ser His Phe Cys
             20                  25                  30

Ser Gly Val Ile His Val Thr Lys Glu Val Lys Val Ala Thr Leu
         35                  40                  45

Ser Cys Gly His Asn Val Ser Val Glu Glu Leu Ala Gln Thr Arg Ile
     50                  55                  60

Tyr Trp Gln Lys Glu Lys Lys Met Val Leu Thr Met Met Ser Gly Asp
 65                  70                  75                  80

Met Asn Ile Trp Pro Glu Tyr Lys Asn Arg Thr Ile Phe Asp Ile Thr
                 85                  90                  95

Asn Asn Leu Ser Ile Val Ile Leu Ala Leu Arg Pro Ser Asp Glu Gly
             100                 105                 110

Thr Tyr Glu Cys Val Val Leu Lys Tyr Glu Lys Asp Ala Phe Lys Arg
         115                 120                 125

Glu His Leu Ala Glu Val Thr Leu Ser Val Lys Ala Asp Phe Pro Thr
     130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                 165                 170                 175

Glu Asn Gly Glu Glu Leu Asn Ala Ile Asn Thr Thr Val Ser Gln Asp
             180                 185                 190

Pro Glu Thr Glu Leu Tyr Ala Val Ser Ser Lys Leu Asp Phe Asn Met
         195                 200                 205

Thr Thr Asn His Ser Phe Met Cys Leu Ile Lys Tyr Gly His Leu Arg
     210                 215                 220

<210> SEQ ID NO 5
<211> LENGTH: 323
<212> TYPE: PRT
<213> ORGANISM: Homo sapiens

<400> SEQUENCE: 5

Met Gly Leu Ser Asn Ile Leu Phe Val Met Ala Phe Leu Leu Ser Gly
 1               5                  10                  15

Ala Ala Pro Leu Lys Ile Gln Ala Tyr Phe Asn Glu Thr Ala Asp Leu
             20                  25                  30

Pro Cys Gln Phe Ala Asn Ser Gln Asn Gln Ser Leu Ser Glu Leu Val
         35                  40                  45

Val Phe Trp Gln Asp Gln Glu Asn Leu Val Leu Asn Glu Val Tyr Leu
     50                  55                  60

Gly Lys Glu Lys Phe Asp Ser Val His Ser Lys Tyr Met Gly Arg Thr
 65                  70                  75                  80

Ser Phe Asp Ser Asp Ser Trp Thr Leu Arg Leu His Asn Leu Gln Ile
                 85                  90                  95

Lys Asp Lys Gly Leu Tyr Gln Cys Ile Ile His His Lys Lys Pro Thr
             100                 105                 110

Gly Met Ile Arg Ile His Gln Met Asn Ser Glu Leu Ser Val Leu Ala
         115                 120                 125

Asn Phe Ser Gln Pro Glu Ile Val Pro Ile Ser Asn Ile Thr Glu Asn
     130                 135                 140

Val Tyr Ile Asn Leu Thr Cys Ser Ser Ile His Gly Tyr Pro Glu Pro
145                 150                 155                 160

Lys Lys Met Ser Val Leu Leu Arg Thr Lys Asn Ser Thr Ile Glu Tyr
                 165                 170                 175
```

```
Asp Gly Ile Met Gln Lys Ser Gln Asp Asn Val Thr Glu Leu Tyr Asp
            180                 185                 190

Val Ser Ile Ser Leu Ser Val Ser Phe Pro Asp Val Thr Ser Asn Met
            195                 200                 205

Thr Ile Phe Cys Ile Leu Glu Thr Asp Lys Thr Arg Leu Leu Ser Ser
            210                 215                 220

Pro Phe Ser Ile Glu Leu Glu Asp Pro Gln Pro Pro Asp His Ile
225                 230                 235                 240

Pro Trp Ile Thr Ala Val Leu Pro Thr Val Ile Cys Val Met Val
            245                 250                 255

Phe Cys Leu Ile Leu Trp Lys Trp Lys Lys Lys Arg Pro Arg Asn
            260                 265                 270

Ser Tyr Lys Cys Gly Thr Asn Thr Met Glu Arg Glu Ser Glu Gln
            275                 280                 285

Thr Lys Lys Arg Glu Lys Ile His Ile Pro Glu Arg Ser Asp Glu Ala
            290                 295                 300

Gln Arg Val Phe Lys Ser Ser Lys Thr Ser Ser Cys Asp Lys Ser Asp
305                 310                 315                 320

Thr Cys Phe

<210> SEQ ID NO 6
<211> LENGTH: 290
<212> TYPE: PRT
<213> ORGANISM: Homo sapiens

<400> SEQUENCE: 6

Met Arg Ile Phe Ala Val Phe Ile Phe Met Thr Tyr Trp His Leu Leu
  1               5                  10                  15

Asn Ala Phe Thr Val Thr Val Pro Asp Lys Leu Tyr Val Val Glu Tyr
                 20                  25                  30

Gly Ser Asn Met Thr Ile Glu Cys Lys Phe Pro Val Glu Lys Gln Leu
             35                  40                  45

Asp Leu Ala Ala Leu Ile Val Tyr Trp Glu Met Glu Asp Lys Asn Ile
         50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
            115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
            195                 200                 205

Cys Thr Phe Arg Arg Leu Asp Pro Glu Glu Asn His Thr Ala Glu Leu
            210                 215                 220
```

```
Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
            245                 250                 255

Phe Ile Phe Arg Leu Arg Lys Gly Arg Met Met Asp Val Lys Lys Cys
        260                 265                 270

Gly Ile Gln Asp Thr Asn Ser Lys Lys Gln Ser Asp Thr His Leu Glu
    275                 280                 285

Glu Thr
    290

<210> SEQ ID NO 7
<211> LENGTH: 302
<212> TYPE: PRT
<213> ORGANISM: Homo sapiens

<400> SEQUENCE: 7

Met Arg Leu Gly Ser Pro Gly Leu Leu Phe Leu Leu Phe Ser Ser Leu
1               5                   10                  15

Arg Ala Asp Thr Gln Glu Lys Glu Val Arg Ala Met Val Gly Ser Asp
            20                  25                  30

Val Glu Leu Ser Cys Ala Cys Pro Glu Gly Ser Arg Phe Asp Leu Asn
        35                  40                  45

Asp Val Tyr Val Tyr Trp Gln Thr Ser Glu Ser Lys Thr Val Val Thr
    50                  55                  60

Tyr His Ile Pro Gln Asn Ser Ser Leu Glu Asn Val Asp Ser Arg Tyr
65                  70                  75                  80

Arg Asn Arg Ala Leu Met Ser Pro Ala Gly Met Leu Arg Gly Asp Phe
                85                  90                  95

Ser Leu Arg Leu Phe Asn Val Thr Pro Gln Asp Glu Gln Lys Phe His
            100                 105                 110

Cys Leu Val Leu Ser Gln Ser Leu Gly Phe Gln Glu Val Leu Ser Val
        115                 120                 125

Glu Val Thr Leu His Val Ala Ala Asn Phe Ser Val Pro Val Val Ser
    130                 135                 140

Ala Pro His Ser Pro Ser Gln Asp Glu Leu Thr Phe Thr Cys Thr Ser
145                 150                 155                 160

Ile Asn Gly Tyr Pro Arg Pro Asn Val Tyr Trp Ile Asn Lys Thr Asp
                165                 170                 175

Asn Ser Leu Leu Asp Gln Ala Leu Gln Asn Asp Thr Val Phe Leu Asn
            180                 185                 190

Met Arg Gly Leu Tyr Asp Val Val Ser Val Leu Arg Ile Ala Arg Thr
        195                 200                 205

Pro Ser Val Asn Ile Gly Cys Cys Ile Glu Asn Val Leu Leu Gln Gln
    210                 215                 220

Asn Leu Thr Val Gly Ser Gln Thr Gly Asn Asp Ile Gly Glu Arg Asp
225                 230                 235                 240

Lys Ile Thr Glu Asn Pro Val Ser Thr Gly Glu Lys Asn Ala Ala Thr
                245                 250                 255

Trp Ser Ile Leu Ala Val Leu Cys Leu Leu Val Val Val Ala Val Ala
            260                 265                 270

Ile Gly Trp Val Cys Arg Asp Arg Cys Leu Gln His Ser Tyr Ala Gly
        275                 280                 285

Ala Trp Ala Val Ser Pro Glu Thr Glu Leu Thr Gly His Val
```

-continued

```
            290                 295                 300
```

<210> SEQ ID NO 8
<211> LENGTH: 316
<212> TYPE: PRT
<213> ORGANISM: Homo sapiens
<220> FEATURE:
<221> NAME/KEY: UNSURE
<222> LOCATION: (233)
<223> OTHER INFORMATION: "Xaa" can be any naturally-occurring amino acid

<400> SEQUENCE: 8

```
Met Leu Arg Arg Arg Gly Ser Pro Gly Met Gly Val His Val Gly Ala
  1               5                  10                  15

Ala Leu Gly Ala Leu Trp Phe Cys Leu Thr Gly Ala Leu Glu Val Gln
             20                  25                  30

Val Pro Glu Asp Pro Val Val Ala Leu Val Gly Thr Asp Ala Thr Leu
         35                  40                  45

Cys Cys Ser Phe Ser Pro Glu Pro Gly Phe Ser Leu Ala Gln Leu Asn
     50                  55                  60

Leu Ile Trp Gln Leu Thr Asp Thr Lys Gln Leu Val His Ser Phe Ala
 65                  70                  75                  80

Glu Gly Gln Asp Gln Gly Ser Ala Tyr Ala Asn Arg Thr Ala Leu Phe
                 85                  90                  95

Pro Asp Leu Leu Ala Gln Gly Asn Ala Ser Leu Arg Leu Gln Arg Val
            100                 105                 110

Arg Val Ala Asp Glu Gly Ser Phe Thr Cys Phe Val Ser Ile Arg Asp
        115                 120                 125

Phe Gly Ser Ala Ala Val Ser Leu Gln Val Ala Pro Tyr Ser Lys
    130                 135                 140

Pro Ser Met Thr Leu Glu Pro Asn Lys Asp Leu Arg Pro Gly Asp Thr
145                 150                 155                 160

Val Thr Ile Thr Cys Ser Ser Tyr Gln Gly Tyr Pro Glu Ala Glu Val
                165                 170                 175

Phe Trp Gln Asp Gly Gln Gly Val Pro Leu Thr Gly Asn Val Thr Thr
            180                 185                 190

Ser Gln Met Ala Asn Glu Gln Gly Leu Phe Asp Val His Ser Val Leu
        195                 200                 205

Arg Val Val Leu Gly Ala Asn Gly Thr Tyr Ser Cys Leu Val Arg Asn
    210                 215                 220

Pro Val Leu Gln Gln Asp Ala His Xaa Ser Val Thr Ile Thr Gly Gln
225                 230                 235                 240

Pro Met Thr Phe Pro Pro Glu Ala Leu Trp Val Thr Val Gly Leu Ser
                245                 250                 255

Val Cys Leu Ile Ala Leu Leu Val Ala Leu Ala Phe Val Cys Trp Arg
            260                 265                 270

Lys Ile Lys Gln Ser Cys Glu Glu Asn Ala Gly Ala Glu Asp Gln
        275                 280                 285

Asp Gly Glu Gly Glu Gly Ser Lys Thr Ala Leu Gln Pro Leu Lys His
    290                 295                 300

Ser Asp Ser Lys Glu Asp Asp Gly Gln Glu Ile Ala
305                 310                 315
```

<210> SEQ ID NO 9
<211> LENGTH: 276
<212> TYPE: PRT
<213> ORGANISM: Homo sapiens

<400> SEQUENCE: 9

```
Met Glu Ser Ala Ala Ala Leu His Phe Ser Arg Pro Ala Ser Leu Leu
 1               5                  10                  15

Leu Leu Leu Leu Ser Leu Cys Ala Leu Val Ser Ala Gln Phe Ile Val
                20                  25                  30

Val Gly Pro Thr Asp Pro Ile Leu Ala Thr Val Gly Glu Asn Thr Thr
            35                  40                  45

Leu Arg Cys His Leu Ser Pro Glu Lys Asn Ala Glu Asp Met Glu Val
        50                  55                  60

Arg Trp Phe Arg Ser Gln Phe Ser Pro Ala Val Phe Val Tyr Lys Gly
 65                  70                  75                  80

Gly Arg Glu Arg Thr Glu Glu Gln Met Glu Glu Tyr Arg Gly Arg Thr
                85                  90                  95

Thr Phe Val Ser Lys Asp Ile Ser Arg Gly Ser Val Ala Leu Val Ile
            100                 105                 110

His Asn Ile Thr Ala Gln Glu Asn Gly Thr Tyr Arg Cys Tyr Phe Gln
        115                 120                 125

Glu Gly Arg Ser Tyr Asp Glu Ala Ile Leu His Leu Val Val Ala Gly
    130                 135                 140

Leu Gly Ser Lys Pro Leu Ile Ser Met Arg Gly His Glu Asp Gly Gly
145                 150                 155                 160

Ile Arg Leu Glu Cys Ile Ser Arg Gly Trp Tyr Pro Lys Pro Leu Thr
                165                 170                 175

Val Trp Arg Asp Pro Tyr Gly Gly Val Ala Pro Ala Leu Lys Glu Val
            180                 185                 190

Ser Met Pro Asp Ala Asp Gly Leu Phe Met Val Thr Thr Ala Val Ile
        195                 200                 205

Ile Arg Asp Lys Ser Val Arg Asn Met Ser Cys Ser Ile Asn Asn Thr
    210                 215                 220

Leu Leu Gly Gln Lys Lys Glu Ser Val Ile Phe Ile Pro Glu Ser Phe
225                 230                 235                 240

Met Pro Ser Val Ser Pro Cys Ala Val Ala Leu Pro Ile Ile Val Val
                245                 250                 255

Ile Leu Met Ile Pro Ile Ala Val Cys Ile Tyr Trp Ile Asn Lys Leu
            260                 265                 270

Gln Lys Glu Lys
        275

<210> SEQ ID NO 10
<211> LENGTH: 523
<212> TYPE: PRT
<213> ORGANISM: Homo sapiens

<400> SEQUENCE: 10

Met Glu Pro Ala Ala Ala Leu His Phe Ser Leu Pro Ala Ser Leu Leu
 1               5                  10                  15

Leu Leu Leu Leu Leu Leu Leu Leu Ser Leu Cys Ala Leu Val Ser Ala
                20                  25                  30

Gln Phe Thr Val Val Gly Pro Ala Asn Pro Ile Leu Ala Met Val Gly
            35                  40                  45

Glu Asn Thr Thr Leu Arg Cys His Leu Ser Pro Glu Lys Asn Ala Glu
        50                  55                  60

Asp Met Glu Val Arg Trp Phe Arg Ser Gln Phe Ser Pro Ala Val Phe
 65                  70                  75                  80
```

```
Val Tyr Lys Gly Gly Arg Glu Arg Thr Glu Glu Gln Met Glu Glu Tyr
                85                  90                  95

Arg Gly Arg Ile Thr Phe Val Ser Lys Asp Ile Asn Arg Gly Ser Val
            100                 105                 110

Ala Leu Val Ile His Asn Val Thr Ala Gln Glu Asn Gly Ile Tyr Arg
            115                 120                 125

Cys Tyr Phe Gln Glu Gly Arg Ser Tyr Asp Glu Ala Ile Leu Arg Leu
130                 135                 140

Val Val Ala Gly Leu Gly Ser Lys Pro Leu Ile Glu Ile Lys Ala Gln
145                 150                 155                 160

Glu Asp Gly Ser Ile Trp Leu Glu Cys Ile Ser Gly Gly Trp Tyr Pro
                165                 170                 175

Glu Pro Leu Thr Val Trp Arg Asp Pro Tyr Gly Glu Val Val Pro Ala
            180                 185                 190

Leu Lys Glu Val Ser Ile Ala Asp Ala Asp Gly Leu Phe Met Val Thr
            195                 200                 205

Thr Ala Val Ile Ile Arg Asp Lys Tyr Val Arg Asn Val Ser Cys Ser
210                 215                 220

Val Asn Asn Thr Leu Leu Gly Gln Glu Lys Glu Thr Val Ile Phe Ile
225                 230                 235                 240

Pro Glu Ser Phe Met Pro Ser Ala Ser Pro Trp Met Val Ala Leu Ala
                245                 250                 255

Val Ile Leu Thr Ala Ser Pro Trp Met Val Ser Met Thr Val Ile Leu
            260                 265                 270

Ala Val Phe Ile Ile Phe Met Ala Val Ser Ile Cys Cys Ile Lys Lys
            275                 280                 285

Leu Gln Arg Glu Lys Lys Ile Leu Ser Gly Glu Lys Lys Val Glu Gln
            290                 295                 300

Glu Glu Lys Glu Ile Ala Gln Gln Leu Gln Glu Glu Leu Arg Trp Arg
305                 310                 315                 320

Arg Thr Phe Leu His Ala Ala Asp Val Val Leu Asp Pro Asp Thr Ala
                325                 330                 335

His Pro Glu Leu Phe Leu Ser Glu Asp Arg Arg Ser Val Arg Arg Gly
            340                 345                 350

Pro Tyr Arg Gln Arg Val Pro Asp Asn Pro Glu Arg Phe Asp Ser Gln
            355                 360                 365

Pro Cys Val Leu Gly Trp Glu Ser Phe Ala Ser Gly Lys His Tyr Trp
370                 375                 380

Glu Val Glu Val Glu Asn Val Met Val Trp Thr Val Gly Val Cys Arg
385                 390                 395                 400

His Ser Val Glu Arg Lys Gly Glu Val Leu Leu Ile Pro Gln Asn Gly
                405                 410                 415

Phe Trp Thr Leu Glu Met Phe Gly Asn Gln Tyr Arg Ala Leu Ser Ser
            420                 425                 430

Pro Glu Arg Ile Leu Pro Leu Lys Glu Ser Leu Cys Arg Val Gly Val
            435                 440                 445

Phe Leu Asp Tyr Glu Ala Gly Asp Val Ser Phe Tyr Asn Met Arg Asp
450                 455                 460

Arg Ser His Ile Tyr Thr Cys Pro Arg Ser Ala Phe Thr Val Pro Val
465                 470                 475                 480

Arg Pro Phe Phe Arg Leu Gly Ser Asp Asp Ser Pro Ile Phe Ile Cys
                485                 490                 495
```

```
Pro Ala Leu Thr Gly Ala Ser Gly Val Met Val Pro Glu Glu Gly Leu
            500                 505                 510

Lys Leu His Arg Val Gly Thr His Gln Ser Leu
        515                 520

<210> SEQ ID NO 11
<211> LENGTH: 263
<212> TYPE: PRT
<213> ORGANISM: Homo sapiens

<400> SEQUENCE: 11

Phe His Val Ser Leu Leu Val Gln Leu Leu Thr Pro Cys Ser Ala
  1               5                  10                  15

Gln Phe Ser Val Leu Gly Pro Ser Gly Pro Ile Leu Ala Met Val Gly
             20                  25                  30

Glu Asp Ala Asp Leu Pro Cys His Leu Phe Pro Thr Met Ser Ala Glu
         35                  40                  45

Thr Met Glu Leu Lys Trp Val Ser Ser Ser Leu Arg Gln Val Val Asn
     50                  55                  60

Val Tyr Ala Asp Gly Lys Glu Val Glu Asp Arg Gln Ser Ala Pro Tyr
 65                  70                  75                  80

Arg Gly Arg Thr Ser Ile Leu Arg Asp Gly Ile Thr Ala Gly Lys Ala
                 85                  90                  95

Ala Leu Arg Ile His Asn Val Thr Ala Ser Asp Ser Gly Lys Tyr Leu
            100                 105                 110

Cys Tyr Phe Gln Asp Gly Asp Phe Tyr Glu Lys Ala Leu Val Glu Leu
        115                 120                 125

Lys Val Ala Ala Leu Gly Ser Asn Leu His Val Glu Val Lys Gly Tyr
    130                 135                 140

Glu Asp Gly Gly Ile His Leu Glu Cys Arg Ser Thr Gly Trp Tyr Pro
145                 150                 155                 160

Gln Pro Gln Ile Gln Trp Ser Asn Ala Lys Gly Glu Asn Ile Pro Ala
                165                 170                 175

Val Glu Ala Pro Val Val Ala Asp Gly Val Gly Leu Tyr Glu Val Ala
            180                 185                 190

Ala Ser Val Ile Met Arg Gly Gly Ser Gly Glu Gly Val Ser Cys Ile
        195                 200                 205

Ile Arg Asn Ser Leu Leu Gly Leu Glu Lys Thr Ala Ser Ile Ser Ile
    210                 215                 220

Ala Asp Pro Phe Phe Arg Ser Ala Gln Pro Trp Ile Ala Ala Leu Ala
225                 230                 235                 240

Gly Thr Leu Pro Ile Leu Leu Leu Leu Ala Gly Ala Ser Tyr Phe
                245                 250                 255

Leu Trp Arg Gln Gln Lys Glu
            260

<210> SEQ ID NO 12
<211> LENGTH: 584
<212> TYPE: PRT
<213> ORGANISM: Homo sapiens

<400> SEQUENCE: 12

Met Lys Met Ala Ser Ser Leu Ala Phe Leu Leu Leu Asn Phe His Val
  1               5                  10                  15

Ser Leu Phe Leu Val Gln Leu Leu Thr Pro Cys Ser Ala Gln Phe Ser
             20                  25                  30
```

-continued

```
Val Leu Gly Pro Ser Gly Pro Ile Leu Ala Met Val Gly Glu Asp Ala
         35                  40                  45
Asp Leu Pro Cys His Leu Phe Pro Thr Met Ser Ala Glu Thr Met Glu
         50                  55                  60
Leu Arg Trp Val Ser Ser Leu Arg Gln Val Val Asn Val Tyr Ala
 65                  70                  75                  80
Asp Gly Lys Glu Val Glu Asp Arg Gln Ser Ala Pro Tyr Arg Gly Arg
                     85                  90                  95
Thr Ser Ile Leu Arg Asp Gly Ile Thr Ala Gly Lys Ala Ala Leu Arg
                100                 105                 110
Ile His Asn Val Thr Ala Ser Asp Ser Gly Lys Tyr Leu Cys Tyr Phe
             115                 120                 125
Gln Asp Gly Asp Phe Tyr Glu Lys Ala Leu Val Glu Leu Lys Val Ala
         130                 135                 140
Ala Leu Gly Ser Asp Leu His Ile Glu Val Lys Gly Tyr Glu Asp Gly
145                 150                 155                 160
Gly Ile His Leu Glu Cys Arg Ser Thr Gly Trp Tyr Pro Gln Pro Gln
                 165                 170                 175
Ile Lys Trp Ser Asp Thr Lys Gly Glu Asn Ile Pro Ala Val Glu Ala
             180                 185                 190
Pro Val Val Ala Asp Gly Val Gly Leu Tyr Ala Val Ala Ala Ser Val
         195                 200                 205
Ile Met Arg Gly Ser Ser Gly Gly Val Ser Cys Ile Ile Arg Asn
210                 215                 220
Ser Leu Leu Gly Leu Glu Lys Thr Ala Ser Ile Ser Ile Ala Asp Pro
225                 230                 235                 240
Phe Phe Arg Ser Ala Gln Pro Trp Ile Ala Ala Leu Ala Gly Thr Leu
                 245                 250                 255
Pro Ile Ser Leu Leu Leu Leu Ala Gly Ala Ser Tyr Phe Leu Trp Arg
             260                 265                 270
Gln Gln Lys Glu Lys Ile Ala Leu Ser Arg Glu Thr Glu Arg Glu Arg
         275                 280                 285
Glu Met Lys Glu Met Gly Tyr Ala Ala Thr Glu Gln Glu Ile Ser Leu
         290                 295                 300
Arg Glu Lys Leu Gln Glu Leu Lys Trp Arg Lys Ile Gln Tyr Met
305                 310                 315                 320
Ala Arg Gly Glu Lys Ser Leu Ala Tyr His Glu Trp Lys Met Ala Leu
                 325                 330                 335
Phe Lys Pro Ala Asp Val Ile Leu Asp Pro Asp Thr Ala Asn Ala Ile
             340                 345                 350
Leu Leu Val Ser Glu Asp Gln Arg Ser Val Gln Arg Ala Glu Glu Pro
         355                 360                 365
Arg Asp Leu Pro Asp Asn Pro Glu Arg Phe Glu Trp Arg Tyr Cys Val
         370                 375                 380
Leu Gly Cys Glu Asn Phe Thr Ser Gly Arg His Tyr Trp Glu Val Glu
385                 390                 395                 400
Val Gly Asp Arg Lys Glu Trp His Ile Gly Val Cys Ser Lys Asn Val
                 405                 410                 415
Glu Arg Lys Lys Gly Trp Val Lys Met Thr Pro Glu Asn Gly Tyr Trp
             420                 425                 430
Thr Met Gly Leu Thr Asp Gly Asn Lys Tyr Arg Ala Leu Thr Glu Pro
         435                 440                 445
Arg Thr Asn Leu Lys Leu Pro Glu Pro Pro Arg Lys Val Gly Ile Phe
```

```
                450             455             460
Leu Asp Tyr Glu Thr Gly Glu Ile Ser Phe Tyr Asn Ala Thr Asp Gly
465                 470                 475                 480

Ser His Ile Tyr Thr Phe Pro His Ala Ser Phe Ser Glu Pro Leu Tyr
                485                 490                 495

Pro Val Phe Arg Ile Leu Thr Leu Glu Pro Thr Ala Leu Thr Ile Cys
                500                 505                 510

Pro Ile Pro Lys Glu Val Glu Ser Pro Asp Pro Asp Leu Val Pro
                515                 520                 525

Asp His Ser Leu Glu Thr Pro Leu Thr Pro Gly Leu Ala Asn Glu Ser
530                 535                 540

Gly Glu Pro Gln Ala Glu Val Thr Ser Leu Leu Leu Pro Ala His Pro
545                 550                 555                 560

Gly Ala Glu Val Ser Pro Ser Ala Thr Thr Asn Gln Asn His Lys Leu
                565                 570                 575

Gln Ala Arg Thr Glu Ala Leu Tyr
                580

<210> SEQ ID NO 13
<211> LENGTH: 526
<212> TYPE: PRT
<213> ORGANISM: Homo sapiens

<400> SEQUENCE: 13

Met Ala Val Phe Pro Ser Ser Gly Leu Pro Arg Cys Leu Leu Thr Leu
1               5                   10                  15

Ile Leu Leu Gln Leu Pro Lys Leu Asp Ser Ala Pro Phe Asp Val Ile
                20                  25                  30

Gly Pro Pro Glu Pro Ile Leu Ala Val Val Gly Glu Asp Ala Glu Leu
            35                  40                  45

Pro Cys Arg Leu Ser Pro Asn Ala Ser Ala Glu His Leu Glu Leu Arg
        50                  55                  60

Trp Phe Arg Lys Lys Val Ser Pro Ala Val Leu Val His Arg Asp Gly
65                  70                  75                  80

Arg Glu Gln Glu Ala Glu Gln Met Pro Glu Tyr Arg Gly Arg Ala Thr
                85                  90                  95

Leu Val Gln Asp Gly Ile Ala Lys Gly Arg Val Ala Leu Arg Ile Arg
            100                 105                 110

Gly Val Arg Val Ser Asp Asp Gly Glu Tyr Thr Cys Phe Phe Arg Glu
        115                 120                 125

Asp Gly Ser Tyr Glu Glu Ala Leu Val His Leu Lys Val Ala Ala Leu
130                 135                 140

Gly Ser Asp Pro His Ile Ser Met Gln Val Gln Glu Asn Gly Glu Ile
145                 150                 155                 160

Cys Leu Glu Cys Thr Ser Val Gly Trp Tyr Pro Glu Pro Gln Val Gln
                165                 170                 175

Trp Arg Thr Ser Lys Gly Glu Lys Phe Pro Ser Thr Ser Glu Ser Arg
            180                 185                 190

Asn Pro Asp Glu Glu Gly Leu Phe Thr Val Ala Ala Ser Val Ile Ile
        195                 200                 205

Arg Asp Thr Ser Thr Lys Asn Val Ser Cys Tyr Ile Gln Asn Leu Leu
    210                 215                 220

Leu Gly Gln Glu Lys Lys Val Glu Ile Ser Ile Pro Ala Ser Ser Leu
225                 230                 235                 240
```

```
Pro Arg Leu Thr Pro Trp Ile Val Ala Val Ala Val Ile Leu Met Val
            245                 250                 255

Leu Gly Leu Leu Thr Ile Gly Ser Ile Phe Phe Thr Trp Arg Leu Tyr
            260                 265                 270

Asn Glu Arg Pro Arg Glu Arg Asn Glu Phe Ser Ser Lys Glu Arg
        275                 280                 285

Leu Leu Glu Glu Leu Lys Trp Lys Lys Ala Thr Leu His Ala Val Asp
    290                 295                 300

Val Thr Leu Asp Pro Asp Thr Ala His Pro His Leu Phe Leu Tyr Glu
305                 310                 315                 320

Asp Ser Lys Ser Val Arg Leu Glu Asp Ser Arg Gln Lys Leu Pro Glu
                325                 330                 335

Lys Thr Glu Arg Phe Asp Ser Trp Pro Cys Val Leu Gly Arg Glu Thr
            340                 345                 350

Phe Thr Ser Gly Arg His Tyr Trp Glu Val Glu Val Gly Asp Arg Thr
        355                 360                 365

Asp Trp Ala Ile Gly Val Cys Arg Glu Asn Val Met Lys Lys Gly Phe
    370                 375                 380

Asp Pro Met Thr Pro Glu Asn Gly Phe Trp Ala Val Glu Leu Tyr Gly
385                 390                 395                 400

Asn Gly Tyr Trp Ala Leu Thr Pro Leu Arg Thr Pro Leu Pro Leu Ala
                405                 410                 415

Gly Pro Pro Arg Arg Val Gly Ile Phe Leu Asp Tyr Glu Ser Gly Asp
            420                 425                 430

Ile Ser Phe Tyr Asn Met Asn Asp Gly Ser Asp Ile Tyr Thr Phe Ser
        435                 440                 445

Asn Val Thr Phe Ser Gly Pro Leu Arg Pro Phe Phe Cys Leu Trp Ser
    450                 455                 460

Ser Gly Lys Lys Pro Leu Thr Ile Cys Pro Ile Ala Asp Gly Pro Glu
465                 470                 475                 480

Arg Val Thr Val Ile Ala Asn Ala Gln Asp Leu Ser Lys Glu Ile Pro
                485                 490                 495

Leu Ser Pro Met Gly Glu Glu Ser Ala Pro Arg Asp Ala Asp Thr Leu
            500                 505                 510

His Ser Lys Leu Ile Pro Thr Gln Pro Ser Gln Gly Ala Pro
        515                 520                 525

<210> SEQ ID NO 14
<211> LENGTH: 7819
<212> TYPE: DNA
<213> ORGANISM: Homo sapiens
<220> FEATURE:
<221> NAME/KEY: exon
<222> LOCATION: (4599)..(4652)
<223> OTHER INFORMATION: coding portion of exon 1
<220> FEATURE:
<221> NAME/KEY: unsure
<222> LOCATION: (145)..(292)
<223> OTHER INFORMATION: "N" can be A, C, T, or G
<220> FEATURE:
<221> NAME/KEY: unsure
<222> LOCATION: (1977)..(2459)
<223> OTHER INFORMATION: "N" can be A, C, T, or G
<220> FEATURE:
<221> NAME/KEY: unsure
<222> LOCATION: (2465)..(2576)
<223> OTHER INFORMATION: "N" can be A, C, T, or G
<220> FEATURE:
<221> NAME/KEY: unsure
<222> LOCATION: (2593)..(3410)
<223> OTHER INFORMATION: "N" can be A, C, T, or G
```

```
<220> FEATURE:
<221> NAME/KEY: unsure
<222> LOCATION: (3490)..(3533)
<223> OTHER INFORMATION: "N" can be A, C, T, or G
<220> FEATURE:
<221> NAME/KEY: unsure
<222> LOCATION: (6111)..(6194)
<223> OTHER INFORMATION: "N" can be A, C, T, or G
<220> FEATURE:
<221> NAME/KEY: unsure
<222> LOCATION: (6836)..(6870)
<223> OTHER INFORMATION: "N" can be A, C, T, or G
<220> FEATURE:
<221> NAME/KEY: unsure
<222> LOCATION: (7091)..(7112)
<223> OTHER INFORMATION: "N" can be A, C, T, or G
<220> FEATURE:
<221> NAME/KEY: unsure
<222> LOCATION: (7118)..(7420)
<223> OTHER INFORMATION: "N" can be A, C, T, or G
<220> FEATURE:
<221> NAME/KEY: unsure
<222> LOCATION: (7554)..(7575)
<223> OTHER INFORMATION: "N" can be A, C, T, or G
<220> FEATURE:
<221> NAME/KEY: unsure
<222> LOCATION: (7694)..(7718)
<223> OTHER INFORMATION: "N" can be A, C, T, or G

<400> SEQUENCE: 14
```

| | | | | | |
|---|---|---|---|---|---|
| ataagaagct | gaattaaggt | gatggcagtg | gggtggaaga | aaggagagcc | accatgcaaa | 60 |
| aagtatccag | gagggagaat | taacaggact | aggggatggg | ccatatttgc | aagatgagaa | 120 |
| atgcagaggt | ctaagattct | agctnnnnnn | nnnnnnnnnn | nnnnnnnnnn | nnnnnnnnnn | 180 |
| nnnnnnnnnn | nnnnnnnnnn | nnnnnnnnnn | nnnnnnnnnn | nnnnnnnnnn | nnnnnnnnnn | 240 |
| nnnnnnnnnn | nnnnnnnnnn | nnnnnnnnnn | nnnnnnnnnn | nnnnnnnnnn | nngcataaac | 300 |
| catattttcc | ccagaggagg | attagtagga | aaggaagctg | ctggttggaa | agtatcttta | 360 |
| tagcagtgtc | tgttcctcgg | tttgctcaag | gggacagtgt | gccaggaaag | tccccgtgga | 420 |
| agggcaagga | agaaggggaa | gttaaagcca | gtggcaggtg | atccaagaat | cttttctgtt | 480 |
| gctagagcta | tgttacatgc | tgtcctttca | tgctctaaaa | ataagagtgc | tggcaagtgc | 540 |
| caggcctgtt | ggtgcagctt | aagatgatac | cttcttgga | tatatatgca | tctgaataag | 600 |
| gaaggctatc | ttctggtcaa | gctaaggtat | gccatgagca | tttccctgtg | aaagcactt | 660 |
| aattctgttc | ccagttgtta | cctgctgtaa | gatctcccct | tctaaaataa | aaacaagaat | 720 |
| acagctcact | gaggacctta | catttccctc | tagctactga | ctcatttctc | ttctcctttt | 780 |
| tatagcactc | ttcttgagag | agttgcctat | atttgttgcc | acatctttac | ccattctctt | 840 |
| ttgaacctat | tcaagctttc | atctgtacaa | aactcactga | tactgtgctt | gtcaggatca | 900 |
| tccatgacct | ccatactgct | aaatgcaact | ctcaagagta | tttggctcta | ctgatcactc | 960 |
| ctttgtagca | ctgtgttta | aaatataggt | tttattatta | tttaggtatg | gtgaggccaa | 1020 |
| tatatcagga | aatgactgtc | gttgaaaaaa | gtatgttgta | ctcacagatc | ccaagagaag | 1080 |
| gggggcacac | catgccacaa | agggccacat | ggggaagcac | cagggtcagc | caggaggtgg | 1140 |
| gtgggggtg | cgcaagatct | ttattgtggt | ttcaacagga | agaaatgggt | gaagcagggt | 1200 |
| gagtggattt | aggattagct | gatataaata | atttcagcag | gctctgggc | ataggggctg | 1260 |
| tccctagtct | tctggtactt | ggccctgggg | tgattaaggc | agttgcatag | tgttgggaat | 1320 |
| gtgaaagccc | ccaataaatg | aggcagttgt | gggtatgggc | tctgaaatgg | gttggtttgc | 1380 |
| atttgaaagg | tgtgctcatg | ggcaagtggt | ttactctctc | ttagaggtta | gaattggcta | 1440 |

```
accctgggag cggcagtccc ttcagggtca gcaaggcccc aggtgtcaaa gcatcagaat    1500
acagaaaata aaatgcatgg ataatacaca ctgccatttg cctttgtacc cttcctttca    1560
atcttctctg ctggtgaccg ctcttcacaa agatctataa atgttggaat accccatgtc    1620
tcagtccttg ggcactctct ttcctatctc tctgtaggtg atgtaatgca gatatccatg    1680
actttaaatc tttaacactt ctgcattgat gactcctaaa tttacatctc taccccaact    1740
gcctactaaa cacctccact tggctatcta ataggcattt caaaccaaat ctacaacaaa    1800
cgtaactctt tttcccctto cttaatttgc ttctccccca gccttctcca ttttaataaa    1860
cagcatctcc attgccttag tgactcaagc cccaaactta ggaattttcc cagatttccc    1920 tcttttctc aaactatata tctagcctgt cagcagttcc cttcaggtct tttttcnnnn    1980
nnnnnnnnnn nnnnnnnnnn nnnnnnnnnn nnnnnnnnnn nnnnnnnnnn nnnnnnnnnn    2040
nnnnnnnnnn nnnnnnnnnn nnnnnnnnnn nnnnnnnnnn nnnnnnnnnn nnnnnnnnnn    2100
nnnnnnnnnn nnnnnnnnnn nnnnnnnnnn nnnnnnnnnn nnnnnnnnnn nnnnnnnnnn    2160
nnnnnnnnnn nnnnnnnnnn nnnnnnnnnn nnnnnnnnnn nnnnnnnnnn nnnnnnnnnn    2220
nnnnnnnnnn nnnnnnnnnn nnnnnnnnnn nnnnnnnnnn nnnnnnnnnn nnnnnnnnnn    2280
nnnnnnnnnn nnnnnnnnnn nnnnnnnnnn nnnnnnnnnn nnnnnnnnnn nnnnnnnnnn    2340
nnnnnnnnnn nnnnnnnnnn nnnnnnnnnn nnnnnnnnnn nnnnnnnnnn nnnnnnnnnn    2400
nnnnnnnnnn nnnnnnnnnn nnnnnnnnnn nnnnnnnnnn nnnnnnnnnn nnnnnnnnna    2460
ctaannnnnn nnnnnnnnnn nnnnnnnnnn nnnnnnnnnn nnnnnnnnnn nnnnnnnnnn    2520
nnnnnnnnnn nnnnnnnnnn nnnnnnnnnn nnnnnnnnnn nnnnnnnnnn nnnnnngctc    2580
catttatatt tannnnnnnn nnnnnnnnnn nnnnnnnnnn nnnnnnnnnn nnnnnnnnnn    2640
nnnnnnnnnn nnnnnnnnnn nnnnnnnnnn nnnnnnnnnn nnnnnnnnnn nnnnnnnnnn    2700
nnnnnnnnnn nnnnnnnnnn nnnnnnnnnn nnnnnnnnnn nnnnnnnnnn nnnnnnnnnn    2760
nnnnnnnnnn nnnnnnnnnn nnnnnnnnnn nnnnnnnnnn nnnnnnnnnn nnnnnnnnnn    2820
nnnnnnnnnn nnnnnnnnnn nnnnnnnnnn nnnnnnnnnn nnnnnnnnnn nnnnnnnnnn    2880
nnnnnnnnnn nnnnnnnnnn nnnnnnnnnn nnnnnnnnnn nnnnnnnnnn nnnnnnnnnn    2940
nnnnnnnnnn nnnnnnnnnn nnnnnnnnnn nnnnnnnnnn nnnnnnnnnn nnnnnnnnnn    3000
nnnnnnnnnn nnnnnnnnnn nnnnnnnnnn nnnnnnnnnn nnnnnnnnnn nnnnnnnnnn    3060
nnnnnnnnnn nnnnnnnnnn nnnnnnnnnn nnnnnnnnnn nnnnnnnnnn nnnnnnnnnn    3120
nnnnnnnnnn nnnnnnnnnn nnnnnnnnnn nnnnnnnnnn nnnnnnnnnn nnnnnnnnnn    3180
nnnnnnnnnn nnnnnnnnnn nnnnnnnnnn nnnnnnnnnn nnnnnnnnnn nnnnnnnnnn    3240
nnnnnnnnnn nnnnnnnnnn nnnnnnnnnn nnnnnnnnnn nnnnnnnnnn nnnnnnnnnn    3300
nnnnnnnnnn nnnnnnnnnn nnnnnnnnnn nnnnnnnnnn nnnnnnnnnn nnnnnnnnnn    3360
nnnnnnnnnn nnnnnnnnnn nnnnnnnnnn nnnnnnnnnn nnnnnnnnnn ttgtgtttta    3420
aatatatata cacacttaga cacatataac cctctttcgt atatcaatta tactttaata    3480
aagctgttgn nnnnnnnnnn nnnnnnnnnn nnnnnnnnnn nnnnnnnnnn nnnctcgcca    3540
acagaccact tctcacccct actagcccct ctactctaag ctatcagcat ttctgcaaac    3600
acattcctaa ccgatctcac tgcttgtaat cttgccagca acctctccct tcagcaata    3660 gtctattgcc tacaccaaag cttagttgtc tcttaatgat gtaaatgagg ttctatcatt    3720
ctcctgaccc aaaccctcca ctgcttttca tcacactcag agcagctctg ctgttgcctg    3780
atttagatgt atggctccaa cagatttccc ctgaagaaat gattccatgg ctgataaaag    3840
```

```
ttggaaagcc tcctcagttt cagaccatta tcagattagc tgtgtgctct gtcccttttcc    3900 tcaaccataa gaagtccatg gataaagaaa gcttcagagt aaaggagaaa gcatgggagg    3960
tacagcagga ccaaggtggg gcattcgcag cccccaccct catcagagcc agttccctac    4020
tctccctgtc taaacctctt agtaagaggt agttcaagag aggggcaaac tcaattccag    4080
cactcaaaag cacttgacta ctttgctcag tcaactagca agtatttatt gagaatgtag    4140
ctctgttcta tggagtctta ttttcaagtg tcagactccc agacatccag tccaggtaaa    4200
gaagatggtg tccattattc atttgacaaa caaagttggg gttcaagggc cagctattga    4260
aaaaagctat ggaaagcttc atgagacgtg caggtaactg ccaatatgtg tggttcacaa    4320
ggactggttc atattcagaa acggccatta gaaaaggaag aagaacttct catttggatt    4380
tataaagagt gtcttgttta ctcttaattt atatcttctc ttctccagga aatcaaccta    4440
taacttctcc tcccagctcc actctaccat ggtctgtcac cttccccaaa tgatttgtta    4500
ttcccctgtt ttcaaaagtg aacaaagaac caaagaccca gcaaagtttc acaaggccct    4560
gagactttca attgtctatt tcagatcaaa tacagaac atg atc ttc ctc ctg cta    4616 atg ttg agc ctg gaa ttg cag ctt cac cag ata gca ggtaagaaag            4662 gacaagggga gaggcttaag aaagaagagc aggtggtggt tcctagccaa agccaaaaat    4722
gagaatgtgg ccctcaggct gagggctttc tttgagagga cgtatgattt ctgggctatt    4782
ccaagcacca caaaaaaaaa aagagtcccc atggtggctt atacatgcca atgtccctat    4842
ctgacagaaa cggtgactga gaatattgct ccatctattc ccactatcca gtgagggtaa    4902
tgacaagaag acaggatcac tcagaccatg taaatctaaa ctgatacaag agggcagggg    4962
ttgagttccc ttaaaggtga gatgccaagc agctgtcccc ttcctttctg gcagggagag    5022
taaggagaca atggccaggg aacaccgtta ctctaaagat aatgtcttga agacattctg    5082
catattatta gttgtttctg tgagtttctt ttttgaaaag caacaatagc agccgttggt    5142
cattcatacc ttaatgtggt ttactgagtc ttcctaaaac ccaaatgaac aatgaacctt    5202
aaggctatcc ctttggactt gaagaaagga cttctattgg aggatgaggg tgagcagaaa    5262
gaaaagcagt tcacagttg gttgttctcc tggggaaggt agttcagacc attcgagggt    5322
gtagttagaa ccatgagtgc actattttgg atgaacacca ggagctaaga gagtaacata    5382
gaggtgtgga cagaggatta agtcctcaag acaatagccc cagccccatg ggaaatcatc    5442
tttctgctca tgattgagaa ataatggctc ccttggcact tgataacctt tcgaagagct    5502
ttctcctccc tactagctgg ttccagatca ctcttcaccc agtcacattc ctctcactca    5562
cttgagctgc ccagcctggt ctggcactag agacatgcac ttggggcccct cctcaaagga    5622 agaccctgag atattctgct tacttctact ctgctcctgc ctgcagggcc agctaaagga    5682
acttttcatg ttttctttgc aaggaaccct gcctggctgg cattttagag acaagcaaaa    5742
ggggcaataa cttccttgct acaaaacagc ttcaagtttc catagagtga aagggaaat    5802 gagggccaaa agacactgtt ccccatcctg tggcaggact gggggcttca ggagaaaact    5862
tggggaatgt gtaacctctg tgggtttgta gcttaaaaac actgagatcc tgggttttct    5922
gtctttgttt tttgcctttt ctcttaggaa aggagtgagc tagggtgaca aggggcaaca    5982
ttttttatcc ctcattggct ctttctacag aggaaggatc ttttcttcta agataatcag    6042
cacaagacaa tgaagatagg cactagctcc cagttaggta tactaatggg gcaaaaggaa    6102
gagcatttnn nnnnnnnnnn nnnnnnnnnn nnnnnnnnnn nnnnnnnnnn nnnnnnnnnn    6162
```

```
nnnnnnnnnn nnnnnnnnn nnnnnnnnnn nnattttgca ggtgagggaa ctagaactca    6222
gaaaaggtac ttaatttccc caagattaca tagttattag gtgacaccgg caagatttca    6282
acaaagctaa tgtcctttct actttactgt gctaccatga tgatggtaat caaaaatggc    6342
agacaaccca taaatcttcc aactttggaa taggttttg cactgaagtc tgaatatgga     6402
tacgtattga atgtttattc tggatattca cagaatcaaa aaatatgtgt aatgaattat    6462
gttgctgaat taactgaaag gaaagtaaaa atgtagcgct ttctcatttt cttcacgaat    6522
ttggaattct tttctgcttt ccactatgca gataacatca gttcagacaa atattaaata    6582
cctacctaaa ttagaatgcc ttctcctcat gggattttt taaaatcttg tcatttcatg     6642
tctctttaat taaagagttt tgatttcaga ggagggtacc tgcaaaagaa aacaacaaaa    6702
aaactaaagg atctgagaaa taattagtgt ttacttctgg ggaggggagg aggtctggga    6762
tgggggtaaa aaggatagtc ttatctatta tgtatattca ggttttgtt ttttacaaga     6822
agcatgtatt aggnnnnnnn nnnnnnnnnn nnnnnnnnnn nnnnnnnca agaaatttct     6882
catataaaaa tatgaaagta atcagactgc aacactcagt gcctgagaca gagctacagc    6942
tatcagggtg tccagacaga cagaagatta cattttcttc cttgctcctt gtacagcccc    7002
agacctgcat gcttcattga aaagaaaaga agatacctga attaaatcaa tgtgatgctt    7062
agtaccctat cagtgcacat ttcttttcnn nnnnnnnnnn nnnnnnnnnn cacttnnnnn    7122
nnnnnnnnnn nnnnnnnnnn nnnnnnnnnn nnnnnnnnnn nnnnnnnnnn nnnnnnnnnn    7182
nnnnnnnnnn nnnnnnnnnn nnnnnnnnnn nnnnnnnnnn nnnnnnnnnn nnnnnnnnnn    7242
nnnnnnnnnn nnnnnnnnnn nnnnnnnnnn nnnnnnnnnn nnnnnnnnnn nnnnnnnnnn    7302
nnnnnnnnnn nnnnnnnnnn nnnnnnnnnn nnnnnnnnnn nnnnnnnnnn nnnnnnnnnn    7362
nnnnnnnnnn nnnnnnnnnn nnnnnnnnnn nnnnnnnnnn nnnnnnnnnn nnnnnnnca    7422
cttatggcgg tattctcagt cattacaaat aaataaaaac aatccatatg ccctggagaa    7482
tttgattcca ggagtaggtc tagaagaact tcaactggag aatggataga gaaatcatgg    7542
tatatttgca gnnnnnnnnn nnnnnnnnnn nnngatagca tgtgaataaa ttaattacaa    7602
aaacatatga ctacatctat tattatatag catgtagata aattacaaaa acatgtaact    7662
acatctatga atcttagagc ataatattga gnnnnnnnnn nnnnnnnnnn nnnnnnggcc    7722
agaagataac acatagcaca atgtcctttt cataaataaa tatattgctt aagcatacct    7782
tatatataga agataaagct taaaaagtaa agaagag                             7819
```

<210> SEQ ID NO 15
<211> LENGTH: 650
<212> TYPE: DNA
<213> ORGANISM: Homo sapiens
<220> FEATURE:
<221> NAME/KEY: unsure
<222> LOCATION: (20)..(175)
<223> OTHER INFORMATION: "N" can be A, C, T, or G

<400> SEQUENCE: 15

```
attatcactt atgagggtgn nnnnnnnnnn nnnnnnnnnn nnnnnnnnnn nnnnnnnnnn      60
nnnnnnnnnn nnnnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnctgcc     180
ctttattttt tcatgaaaga aattgctgaa gaggactaaa agaagtttta gtaagcattc      240
aataaatgta tgttctttat agtttccaaa tcagcaaata tagacatcct gcattttaa      300
ggagatttat atatttttatt ggacatgctg taatttattt aaccacttcc ctgttggtag    360
```

```
acattatttc cattttcttc tgctagatta atgcttgaaa aaaatgtgtg cctcctaaag      420
actgtgatga aagttgcctc tgaataaaac tcaaacaaat cattaatcat taactctttc      480
cttacttgta tgctctttgg atgctctact gtgttatcta taaataaag tttgaagtga       540 aaaattaggg taaaacattt tatatcattt ttaaaggata tacatgga tgtacttaca        600 tatgcatgtt taaatttata taccataaca tttatttctt tttttaaaaa                 650

<210> SEQ ID NO 16
<211> LENGTH: 9179
<212> TYPE: DNA
<213> ORGANISM: Homo sapiens
<220> FEATURE:
<221> NAME/KEY: exon
<222> LOCATION: (5211)..(5516)
<223> OTHER INFORMATION: exon 2
<220> FEATURE:
<221> NAME/KEY: unsure
<222> LOCATION: (1054)..(1198)
<223> OTHER INFORMATION: "N" can be A, C, T, or G
<220> FEATURE:
<221> NAME/KEY: unsure
<222> LOCATION: (1297)..(1430)
<223> OTHER INFORMATION: "N" can be A, C, T, or G
<220> FEATURE:
<221> NAME/KEY: unsure
<222> LOCATION: (1482)..(1658)
<223> OTHER INFORMATION: "N" can be A, C, T, or G
<220> FEATURE:
<221> NAME/KEY: unsure
<222> LOCATION: (3286)..(3529)
<223> OTHER INFORMATION: "N" can be A, C, T, or G
<220> FEATURE:
<221> NAME/KEY: unsure
<222> LOCATION: (3580)..(3620)
<223> OTHER INFORMATION: "N" can be A, C, T, or G
<220> FEATURE:
<221> NAME/KEY: unsure
<222> LOCATION: (4193)..(4416)
<223> OTHER INFORMATION: "N" can be A, C, T, or G
<220> FEATURE:
<221> NAME/KEY: unsure
<222> LOCATION: (4506)..(4682)
<223> OTHER INFORMATION: "N" can be A, C, T, or G
<220> FEATURE:
<221> NAME/KEY: unsure
<222> LOCATION: (6166)..(6223)
<223> OTHER INFORMATION: "N" can be A, C, T, or G
<220> FEATURE:
<221> NAME/KEY: unsure
<222> LOCATION: (6635)..(6803)
<223> OTHER INFORMATION: "N" can be A, C, T, or G
<220> FEATURE:
<221> NAME/KEY: unsure
<222> LOCATION: (7946)..(8351)
<223> OTHER INFORMATION: "N" can be A, C, T, or G
<220> FEATURE:
<221> NAME/KEY: unsure
<222> LOCATION: (8578)..(8609)
<223> OTHER INFORMATION: "N" can be A, C, T, or G
<220> FEATURE:
<221> NAME/KEY: unsure
<222> LOCATION: (8870)..(9178)
<223> OTHER INFORMATION: "N" can be A, C, T, or G

<400> SEQUENCE: 16
tatatttgtt ttttttctta cattttatt tcaaaatcta aggacatctt ataacccaga       60 aatattttt taccttgtc atgtcttaga ggaaagagcc accccagtct tttttcattg        120 atgttttct tctctcttcg tactccagag gtagatgaaa accagagggc cacaatgacc       180
atggtgatgc ctgaggtcat tctggggcac agacctcagc ctaggttact ccacttcgcc     240
```

-continued

```
tatctttaga tccaaaacta ccctgctgac tgctgagata aacaaaggag aataatcagg    300
ttggggaaag gatttctatg cgaagacatg tctccatgca gtcctcctac actgagcaga    360
gcatgagtca ggtgcttaga gcaggatttt gtcctaaacc aggaacttca gagttttctg    420
aagaatgtgg ctatgtaaag cacccccca ccccacccctt acttctcaag tacattacgt    480
ggcaagtctg aaaaaactta cacttctgtt gttaaatgtg ggggataaaa tataaactta    540
gtttcaagag gaagctatct tgggaggtaa tgcaaataat tcgttgtgtg tttcctgaat    600
aagtgacagg tgctgactac cattgatgct tcattgcaat aaaatgcaaa gctcccccaa    660 gaattttga aatgcatcaa gctaggtgtt ctaatctagc aaaaggacct gcatacatga    720 attttcatg cttttgccaa gtcttttgcc ctttagttta gttaagggcc ccacatgaat    780
ggaaagcctg tgttgtcagc ttaattttgt agttgtggaa accttccagt tttctccttt    840
gtctaatacc ttcaggagtt caatcctagg ttgaagctta atttaataac catgtggcat    900
gtaaagtaga aaacaaaaca tcttttcctt agcatacagc aaaaaaaaaa aaaaaactca    960
ctcatggatg tagtgtacac atgccagtgg atatatagtc ataactgcag tcattggtag   1020
cacagaaata aatgtgcatt gaagacacag agannnnnnn nnnnnnnnnn nnnnnnnnnn   1080
nnnnnnnnnn nnnnnnnnnn nnnnnnnnnn nnnnnnnnnn nnnnnnnnnn nnnnnnnnnn   1140
nnnnnnnnnn nnnnnnnnnn nnnnnnnnnn nnnnnnnnnn nnnnnnnnnn nnnnnnnngg   1200
gctagcccag tgtctgactt actgtgttta agaaatatca actattacgc tacttcccag   1260
tgacagtcca aatgcagacc agtgttataa ctctacnnnn nnnnnnnnnn nnnnnnnnnn   1320
nnnnnnnnnn nnnnnnnnnn nnnnnnnnnn nnnnnnnnnn nnnnnnnnnn nnnnnnnnnn   1380
nnnnnnnnnn nnnnnnnnnn nnnnnnnnnn nnnnnnnnnn nnnnnnnnnn aggcaaggtg   1440
gtaaaagacg cttgcacgtg caaatgttac tttgtgtaac tnnnnnnnnn nnnnnnnnnn   1500
nnnnnnnnnn nnnnnnnnnn nnnnnnnnnn nnnnnnnnnn nnnnnnnnnn nnnnnnnnnn   1560
nnnnnnnnnn nnnnnnnnnn nnnnnnnnnn nnnnnnnnnn nnnnnnnnnn nnnnnnnnnn   1620
nnnnnnnnnn nnnnnnnnnn nnnnnnnnnn nnnnnnnnct tagtgaatct aatttgcagc   1680
tgggcttgag aaaaaacctc ttcatagaat tgtttgcatc agtgtcttga ttgcctctgt   1740
aacttacaat aagcaagaat gtttcaggat ttcaaaaatc tattgcattg cctaaacctc   1800 ttatttgta tggagtaatc aagctcaaag tttgcatgtc ttagaaactt tacttggggc   1860
aaaattagac caagtaacaa ttaatcttct aggtattctg agctattcag acatatgatt   1920 catgttttgct aattgctctt ttctcttgta aatattagct gaaaaatgtc acctgtctga   1980
caagtagcat attttatgcc tatcactcct ggcacgcatt cttacaaggc agacaggaaa   2040
aataggaaga aaatggactt ttatcaaagg cccaggcagt aaagagggga gttctgctgt   2100
aagctaaggg gagttccaga ggaagttata ggcgttccct ttcttatgac aagaaagcat   2160
agtgcagtaa ataaatttgc taaatagatt caacagtctc tacccaaagt catctattta   2220
attcttgttg ttatgcagac tcagcaacta accttccttg taagcccat tttcttccct   2280 gtttcctgtt tatcaaatgt aattaaacaa gagaagtatt atagaagagt aaagtagta    2340 ggtaattctt gaacttggca tatgattact acatatttga tgaatagttg aatattattc   2400
ttcaaggaca gattggattt ggtatcaggt ggctctgcat taagttataa gggacttaat   2460
aactcaagta tttaaggacg gcttccatca taagggatc tgcccttaag agggtcccat    2520
tatggagatt ctgaggtgag agctattcca agtgtgcagt ggattaaaat aaaagaatca   2580
tacaggaaat ctcttttttac atgccttatt ccagggtctt tgcaacctgg cacagcaagt   2640
```

```
gcagatatga ttagcattgt tttacacatg tacactcacc ttatagccct gcccctgtgc   2700
ccctcctgca caaagaatg ctgggcacac gtgaactcct ctctgtagaa aggcacatta   2760
atgttctagc catggttaaa acagggatag aggcaagcca aaaatgtcgg tcatttgaaa   2820
taaatctcaa gtttgtgcat atcactatca agtgtgctgt gtggcaatta agaatgccaa   2880
tttgtgtgat cacaggcaag ttgcagtttg atgaaaggaa agcagaggtg aatatataac   2940
cagggtcatc ctttctttct ccctctctct ctttctgtca tttatttgcc aagctcttaa   3000
ctagaacttg ctatgtgcta ggtactggat atatcaaagc aaactcagcc tggtcttttgc  3060 cttcaaagat ttgcaggata gtgggaagaa aaacttgaat cagaggacat ctgcagtggg   3120
aatcattcaa gcagcagaaa acccaaaagt tacttatact gtgaaatctg atcagagaat   3180
ggactgtcct ggttagtaaa atatcctgga ggataaagat tggccatgca ttccacatat   3240
gaattaccac tttcccaaga attaaaacat ggtacgaaag aaaggnnnnn nnnnnnnnnn   3300
nnnnnnnnnn nnnnnnnnnn nnnnnnnnnn nnnnnnnnnn nnnnnnnnnn nnnnnnnnnn   3360
nnnnnnnnnn nnnnnnnnnn nnnnnnnnnn nnnnnnnnnn nnnnnnnnnn nnnnnnnnnn   3420
nnnnnnnnnn nnnnnnnnnn nnnnnnnnnn nnnnnnnnnn nnnnnnnnnn nnnnnnnnnn   3480
nnnnnnnnnn nnnnnnnnnn nnnnnnnnnn nnnnnnnnnn nnnnnnnnna aacaacttct   3540
ggaatagcta atgcttagaa gcagctccca atatttgtn nnnnnnnnnn nnnnnnnnnn   3600
nnnnnnnnnn nnnnnnnnnn gcaagctcta ctgaacataa tttgatctaa tcttctgtga   3660
ttattcagaa actacttcaa gattttccta tacctccatc ataatgaata cccattcatt   3720
aatgatggaa gcagcctaat tttgtcattt ttcacactt attgatgtaa cactaccttt    3780
actagtttgg ccactcctta tgcttttttt atagaactat ttagatcaat tcaacttta    3840 aaaaataaag ccacataccc ctgtggtaga tgaaaaacaa gtatcatttg cactggtaaa   3900
tagagaatag gaagaaaaat aaatgcagtg aaaataaagc agtgttatca aatcctaccc   3960
agatactgtt atctacccgg aagcttcctg tttgattaaa aggaaaaata gccagtgtta   4020
gaggtgtgga agtctagttg aaattatatg caattgaagg attaaaatag aattgaaaag   4080
ggaataaatt cctctctgaa taatttaact cccttaggc tttgattctg cctcatctaa    4140
aatcatctta catacttcta gtggcgtgtc cctcacattt tggtaaactc tgnnnnnnnn   4200
nnnnnnnnnn nnnnnnnnnn nnnnnnnnnn nnnnnnnnnn nnnnnnnnnn nnnnnnnnnn   4260
nnnnnnnnnn nnnnnnnnnn nnnnnnnnnn nnnnnnnnnn nnnnnnnnnn nnnnnnnnnn   4320
nnnnnnnnnn nnnnnnnnnn nnnnnnnnnn nnnnnnnnnn nnnnnnnnnn nnnnnnnnnn   4380
nnnnnnnnnn nnnnnnnnnn nnnnnnnnnn nnnnnccat ttttccttc ctttattgt     4440 cagaaaatag aaagcatcta cagtgggctt gtatgatgtg gtggttagaa atacctgatc   4500
tgattnnnnn nnnnnnnnnn nnnnnnnnnn nnnnnnnnnn nnnnnnnnnn nnnnnnnnnn   4560
nnnnnnnnnn nnnnnnnnnn nnnnnnnnnn nnnnnnnnnn nnnnnnnnnn nnnnnnnnnn   4620
nnnnnnnnnn nnnnnnnnnn nnnnnnnnnn nnnnnnnnnn nnnnnnnnnn nnnnnnnnnn   4680
nnaccatcac tggtgagagg aagtgatacc tggcacaaaa atatatggat taatcaatat   4740
ggattgaggg aaacaaacct ggagaatagg atgtgaaggt attaagtaa catgagctca    4800 gaccttgatg gtagggaagt cgaaaggaag cattttgttc ttatatgaca gatgacctgg   4860
aatgactgca gggcttgggg ggtcagggac tggaggtggg agaggcctct gagagcaagc   4920
agtgctgtcc accagaagct cttgctgggg tgcccagaga ggagcaaagg gcagtcagct   4980
```

```
gcacaggagg gaatgtttgg aggagagagc cacctcagat cagcgggtca agaatcccac      5040
tcttgcccag atggatgggg caaaggagaa aaaggattcg ccacgggaat gtccagataa      5100
gacaggtgcc ttttggaaaa tgggggtgag atgggtctca ggttacactt cgtaagaact      5160
ggaatgtaaa gtaaaggcag acaatgacaa atatcttgt tttctttca gct tta          5216 ttc aca gtg aca gtc cct aag gaa ctg tac ata ata gag cat ggc agc        5264 aat gtg acc ctg gaa tgc aac ttt gac act gga agt cat gtg aac ctt        5312 gga gca ata aca gcc agt ttg caa aag gtg gaa aat gat aca tcc cca        5360 cac cgt gaa aga gcc act ttg ctg gag gag cag ctg ccc cta ggg aag        5408 gcc tcg ttc cac ata cct caa gtc caa gtg agg gac gaa gga cag tac        5456 caa tgc ata atc atc tat ggg gtc gcc tgg gac tac aag tac ctg act        5504 ctg aaa gtc aaa ggtgagtggt gtcaaggact agaatccatg gaagctctct            5556
ccaacagagg atctgcaagt cacagaaacc cattaaaggt agctcaagca aaaacaagca      5616
ggctgctttt aaggagacag ctatttcaga gaaaatgaaa gcatctgctc ggaaataatt      5676
tttgacatct gagtacaaag cagccgaagt acaagtgaaa gggggtagga cctataggaa      5736
taaaatggga ctggaggaag ccaggaaaat tagtccctga aatgtgggag ggtatgaaaa      5796
ataagctttg cctaattcac aattctccca tggaacatcc ctgacttgat tattaagata      5856 ctcttttca atagtttata ccctgaatcc agagttttta aaaccatggt tgccgccca        5916 ttcatggatt aaaatatcaa tttagtgagt agcaaccaga tgcacgtttc ccgcccttta     5976
aaaaataatg tatagaagag aatagacaga gtagatcaga cgatatcaca gagtaggact     6036
gagtactgta aaactaattt ctgagggacg tgtgtgtgtg tgtgcgtgtt gggtcatggt     6096
ataaattttt ttttcttac tttggatcat aaaaagttac aagtttggaa aacactgctc      6156
aaatgcaagn nnnnnnnnn nnnnnnnnnn nnnnnnnnnn nnnnnnnnnn nnnnnnnnnn      6216
nnnnnnnaga gtcccatgaa gtctatagct gtccctattc ctctggattc agggatctct     6276
ccactccagc acaattgaaa atctaaatat aaagagaatc ttcacactct tgtttgttct     6336
agaaaaggtg atttgaggaa agacatataa caactataaa aaatagattt tgcttgttca     6396
ttggcttatg gtctccaggc ttgaatgctc tgagataaat gatgccaata tttctctggc     6456
ctcttcccat cccacgcatt ggacctcaga tggtctgtac tgtcttctag agggtttgtg     6516
ggttttggcc ccaaaaaacc attaaccttg gcagaaagtg tgtgacttta tgatctggta     6576
caaagaagga caaactagag ggactggaca tgaggatgaa tattgtgttc gcccttatnn     6636 nnnnnnnnn nnnnnnnnnn nnnnnnnnnn nnnnnnnnnn nnnnnnnnnn nnnnnnnnnn      6696
nnnnnnnnnn nnnnnnnnnn nnnnnnnnnn nnnnnnnnnn nnnnnnnnnn nnnnnnnnnn     6756
nnnnnnnnnn nnnnnnnnnn nnnnnnnnnn nnnnnnnnnn nnnnnnnaaa gaccctcagt     6816
tgttacaggg gcagtgacct cctcacacct caaccatcaa tgagtcacca ggaaagccat     6876
tagcctagat gtaactgttt tctatcttta ttgcatttcc tacatccagg cagcagctgg     6936
gaggaactct agaacactga gtttgtctg agttccctta atgtaaggct gtacattctc      6996
aggatgcctt gatgtactcg aatatctgca accctaaatc accacctctg tttttattga     7056
tctctatctg aatgctgtat taatgggcca ggccttctgc ccattctctc aaactgagaa     7116
ctgtctctca ttcctgggga ggcaccctgc ctactcctta cctagatcag ggatttctca    7176
gttgtggaga gatttgttcc ttatagtgtt ggtcatcaaa ctgggatatt tggggattac    7236
aaagactttt caagggatgt atgggcacag gcagttttag gaagtgagtt cctagatcct   7296
```

```
catcttcccc aaatactcgt tcccaaaatt gacgagcctg acaatgtgca tgccaggcaa      7356
ggctcttggg gttcccctaa aacacttcct cttttaagcc taccactcac tcatcatgaa      7416
tatagtccat tgtcccaggg tgtaaaaccc tctatagtgt taaataaaag aatgattggg      7476
aacattgaca cctgatggaa ctgttatgac taaaaaccct tttgcaaata atgtggtatc      7536
taattttctg ctttcaacaa aattgaagga ggcccttata aagttaataa ctgataatca      7596
aaaatgagta attttttgcca tgtaaatcag gtcaaagaat gaaatggcat tgctgtaacg      7656
aaactgcttc cattcccatt gatttactca tacgaacaag attccttagc ctttataagc      7716
tacaaaaaaa tgaaaaatag aaatagaatt gaggctgaat tctattatat aaaatcattc      7776
caaccatgtc atatggttct tcggattcat gaataatttg gaaagagag ccatatccat       7836 cttattaagg gacacattcc caataaattt tcatctttca tgtttaataa ttatcaatat      7896
tcataacatt ttcatttttg atcaaatatg tgttaataat aatagaaatn nnnnnnnnnn     7956
nnnnnnnnnn nnnnnnnnnn nnnnnnnnnn nnnnnnnnnn nnnnnnnnnn nnnnnnnnnn     8016
nnnnnnnnnn nnnnnnnnnn nnnnnnnnnn nnnnnnnnnn nnnnnnnnnn nnnnnnnnnn     8076
nnnnnnnnnn nnnnnnnnnn nnnnnnnnnn nnnnnnnnnn nnnnnnnnnn nnnnnnnnnn     8136
nnnnnnnnnn nnnnnnnnnn nnnnnnnnnn nnnnnnnnnn nnnnnnnnnn nnnnnnnnnn     8196
nnnnnnnnnn nnnnnnnnnn nnnnnnnnnn nnnnnnnnnn nnnnnnnnnn nnnnnnnnnn     8256
nnnnnnnnnn nnnnnnnnnn nnnnnnnnnn nnnnnnnnnn nnnnnnnnnn nnnnnnnnnn     8316
nnnnnnnnnn nnnnnnnnnn nnnnnnnnnn nnnnnattag atcttaatgc agaacaccct     8376
gaacatttaa agcttcatag tcacaagaga aaagttttca tttcaatagc tataaatatt     8436
ttgttgttgt aaagacatat aacgataatc aatacaaaat ctgtcaaaca aaatatgtt      8496 acattaagat aaaattctgt agggaaggtg aaattggaag tgagtttcaa tgaatgaaaa     8556
gaaacaattt agacagagaa gnnnnnnnnn nnnnnnnnnn nnnnnnnnnn nnncttagaa     8616
ggaattgaat agattaggtt ccttacccaa aaagcctctg ttatttgtct tatttattta     8676
ttctcttttt tccacattct ccagtctcat tcccctttt taacacagga aattattcca     8736
gcatgtttca tacatattct tttgtttgta agagcttatt taaaatatgt aatattgttt      8796
tagatgcata tattttttt cttgtggaaa ctatattgta ctatatatat atattttaga     8856
aatggacaca ttannnnnnn nnnnnnnnnn nnnnnnnnnn nnnnnnnnnn nnnnnnnnnn     8916
nnnnnnnnnn nnnnnnnnnn nnnnnnnnnn nnnnnnnnnn nnnnnnnnnn nnnnnnnnnn     8976
nnnnnnnnnn nnnnnnnnnn nnnnnnnnnn nnnnnnnnnn nnnnnnnnnn nnnnnnnnnn     9036
nnnnnnnnnn nnnnnnnnnn nnnnnnnnnn nnnnnnnnnn nnnnnnnnnn nnnnnnnnnn     9096
nnnnnnnnnn nnnnnnnnnn nnnnnnnnnn nnnnnnnnnn nnnnnnnnnn nnnnnnnnnn     9156
nnnnnnnnnn nnnnnnnnnn nnt                                            9179
```

<210> SEQ ID NO 17
<211> LENGTH: 1814
<212> TYPE: DNA
<213> ORGANISM: Homo sapiens
<220> FEATURE:
<221> NAME/KEY: exon
<222> LOCATION: (738)..(1010)
<223> OTHER INFORMATION: exon 3
<220> FEATURE:
<221> NAME/KEY: unsure
<222> LOCATION: (72)..(118)
<223> OTHER INFORMATION: "N" can be A, C, T, or G
<220> FEATURE:

<221> NAME/KEY: unsure
<222> LOCATION: (405)..(630)
<223> OTHER INFORMATION: "N" can be A, C, T, or G

<400> SEQUENCE: 17

```
tagatctcag ctttcttgag gcagggagcc atatctgttt aattcactca gcatatactg    60
caaagaagca gnnnnnnnnn nnnnnnnnnn nnnnnnnnnn nnnnnnnnnn nnnnnnnnta   120
gggagaagtg cagaataaat atcccaact ctttactatg tatagacatt atctaggtct    180
ttattttttt tctcttctta atctcaaaga aaacagagga aggaggaag taaaaagtaa    240 attttgcct gaagatgttt ggaaaaaata ccaaataaag tgagatagtg ggtaatctag    300 tgattttat ttttccgtcc tctttctggc ctccaattgt gaaataattt atagcactgt    360
aagaaagaag ccacaaattg tggtagcttg gaccactgtt gaggnnnnnn nnnnnnnnnn    420
nnnnnnnnnn nnnnnnnnnn nnnnnnnnnn nnnnnnnnnn nnnnnnnnnn nnnnnnnnnn    480
nnnnnnnnnn nnnnnnnnnn nnnnnnnnnn nnnnnnnnnn nnnnnnnnnn nnnnnnnnnn    540
nnnnnnnnnn nnnnnnnnnn nnnnnnnnnn nnnnnnnnnn nnnnnnnnnn nnnnnnnnnn    600
nnnnnnnnnn nnnnnnnnnn nnnnnnnnnn acttaatatt gatagtgata attttattca    660
tttcacatgg catgaagtac caagctctat aggaatcaga aaataaagtc ttatttcttt    720
ttcttctcta ttgtcca gct tcc tac agg aaa ata aac act cac atc cta     770 aag gtt cca gaa aca gat gag gta gag ctc acc tgc cag gct aca ggt    818 tat cct ctg gca gaa gta tcc tgg cca aac gtc agc gtt cct gcc aac    866 acc agc cac tcc agg acc cct gaa ggc ctc tac cag gtc acc agt gtt    914 ctg cgc cta aag cca ccc cct ggc aga aac ttc agc tgt gtg ttc tgg    962 aat act cac gtg agg gaa ctt act ttg gcc agc att gac ctt caa agt   1010 aagagctgcc cccacttcct aggtctatca gttagggttc agacaagaaa cagatggcat   1070
actcgagtga tttgaggaga gtgtaataaa gggactgttt acaaaggtgt gatcaccatt   1130
tggagaaact acaaggata gtgcagaaca ctgggcttc aatgttggga gggcaattac   1190
cactgttgga gaagttactg gaatcagaag ggagctgtag ggaaagcccc acttcccagg   1250
agctgtagcc acagaatagg gaagctgcca catgcagcga ctccaaaggg tggaaactgg   1310
atgaatgaat accccaactc attctcctcc caccctccaa tctcctgcta gcacctccca   1370
ttggctgaac ccagctagaa gtcagagaat acaagggtcc actgttgtat tccataaaag   1430
tcaacttctc agggctcaga gcaatattga catgtacaga atagatctgg agaggaaaca   1490
gaaaatatct agtacaatag ctaatcactg tgattcatgc acagtgtcat gagccagcag   1550
gatgaatatt cctttgctgt acttgctgcc agtcagctgg ttatgggttt ttccaagaaa   1610
tttggtctct aacaaaattc ttcagagcct ttactgacta tgctggatat ttttggaagg   1670
gatcccatac ttttgaactt catacagcag aatttcaaac aatcttggga aaataacaac   1730
ttttatctgc ccagtaagga caactaacac ctagtatcat aatcatttcg taagagacag   1790
gtaatttcat caccgagtgc atat                                         1814
```

<210> SEQ ID NO 18
<211> LENGTH: 19217
<212> TYPE: DNA
<213> ORGANISM: Homo sapiens
<220> FEATURE:
<221> NAME/KEY: exon
<222> LOCATION: (6412)..(6543)
<223> OTHER INFORMATION: exon 4

-continued

```
<220> FEATURE:
<221> NAME/KEY: exon
<222> LOCATION: (11953)..(12003)
<223> OTHER INFORMATION: exon 5
<220> FEATURE:
<221> NAME/KEY: exon
<222> LOCATION: (18746)..(18751)
<223> OTHER INFORMATION: coding portion of exon 6
<220> FEATURE:
<221> NAME/KEY: unsure
<222> LOCATION: (722)..(1277)
<223> OTHER INFORMATION: "N" can be A, C, T, or G
<220> FEATURE:
<221> NAME/KEY: unsure
<222> LOCATION: (1740)..(1924)
<223> OTHER INFORMATION: "N" can be A, C, T, or G
<220> FEATURE:
<221> NAME/KEY: unsure
<222> LOCATION: (3585)..(3783)
<223> OTHER INFORMATION: "N" can be A, C, T, or G
<220> FEATURE:
<221> NAME/KEY: unsure
<222> LOCATION: (3929)..(4224)
<223> OTHER INFORMATION: "N" can be A, C, T, or G
<220> FEATURE:
<221> NAME/KEY: unsure
<222> LOCATION: (5233)..(5352)
<223> OTHER INFORMATION: "N" can be A, C, T, or G
<220> FEATURE:
<221> NAME/KEY: unsure
<222> LOCATION: (5974)..(6030)
<223> OTHER INFORMATION: "N" can be A, C, T, or G
<220> FEATURE:
<221> NAME/KEY: unsure
<222> LOCATION: (6048)..(6073)
<223> OTHER INFORMATION: "N" can be A, C, T, or G
<220> FEATURE:
<221> NAME/KEY: unsure
<222> LOCATION: (6091)..(6306)
<223> OTHER INFORMATION: "N" can be A, C, T, or G
<220> FEATURE:
<221> NAME/KEY: unsure
<222> LOCATION: (7576)..(7688)
<223> OTHER INFORMATION: "N" can be A, C, T, or G
<220> FEATURE:
<221> NAME/KEY: unsure
<222> LOCATION: (8259)..(8368)
<223> OTHER INFORMATION: "N" can be A, C, T, or G
<220> FEATURE:
<221> NAME/KEY: unsure
<222> LOCATION: (9787)..(9885)
<223> OTHER INFORMATION: "N" can be A, C, T, or G
<220> FEATURE:
<221> NAME/KEY: unsure
<222> LOCATION: (9926)..(10110)
<223> OTHER INFORMATION: "N" can be A, C, T, or G
<220> FEATURE:
<221> NAME/KEY: unsure
<222> LOCATION: (10113)..(10241)
<223> OTHER INFORMATION: "N" can be A, C, T, or G
<220> FEATURE:
<221> NAME/KEY: unsure
<222> LOCATION: (11000)..(11438)
<223> OTHER INFORMATION: "N" can be A, C, T, or G
<220> FEATURE:
<221> NAME/KEY: unsure
<222> LOCATION: (12528)..(12844)
<223> OTHER INFORMATION: "N" can be A, C, T, or G
<220> FEATURE:
<221> NAME/KEY: unsure
<222> LOCATION: (13720)..(13963)
<223> OTHER INFORMATION: "N" can be A, C, T, or G
<220> FEATURE:
<221> NAME/KEY: unsure
<222> LOCATION: (13983)..(14275)
<223> OTHER INFORMATION: "N" can be A, C, T, or G
<220> FEATURE:
<221> NAME/KEY: unsure
<222> LOCATION: (14529)..(14551)
```

```
<223> OTHER INFORMATION: "N" can be A, C, T, or G
<220> FEATURE:
<221> NAME/KEY: unsure
<222> LOCATION: (14585)..(14621)
<223> OTHER INFORMATION: "N" can be A, C, T, or G
<220> FEATURE:
<221> NAME/KEY: unsure
<222> LOCATION: (14703)..(14749)
<223> OTHER INFORMATION: "N" can be A, C, T, or G
<220> FEATURE:
<221> NAME/KEY: unsure
<222> LOCATION: (16380)..(16436)
<223> OTHER INFORMATION: "N" can be A, C, T, or G
<220> FEATURE:
<221> NAME/KEY: unsure
<222> LOCATION: (16484)..(16517)
<223> OTHER INFORMATION: "N" can be A, C, T, or G
<220> FEATURE:
<221> NAME/KEY: unsure
<222> LOCATION: (17022)..(17366)
<223> OTHER INFORMATION: "N" can be A, C, T, or G

<400> SEQUENCE: 18
ctactgagaa gggatatact ctcagactaa aggacagtcc ctagtactga ttcaatctgg      60
ctttatagaa aattcactat attgtcattg tatttcacag tttgcccttt gtcttagctg     120
gtaagacaga gcctatgata aggacttgtg tggcatgcag gtatttaatt ggcaaccccca    180
gagggcagaa gcaagagatt taggagttta agagagggta atataagagt atattatcaa    240
agttgtagtg tggacaacag aaactcaaat attcaaggac cagcatgtag acagcctcct    300
aagatgtcta ctcagacaaa gaatttcagg tggaaggact tgttcatctg cttcacgccc    360
attggttgac aggaatatga actccattct gctgctgggc tagacatgca tgtgggctga    420
gtgagctttc cccagtatcc gtagcatcag aaaagtcgca gggcagaaag aaaagtatcc    480
aatttgaggt gaattactga ccttgaagtg agtgtaagcc taactagaat tctaccccag    540
ctggctgaag tgaaaggtga ggctgagagg aaataaggca ggactgcaca gtccccaatt    600
gtactgttca aatccactca tgcccttcat taagtcagct ctgccactga gccttccagc    660
tgggaggcag ccacaatctc tgcagaagat ttaatataca ccagtttgtg aacaagctg     720
tnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnnnnnnnn    840
nnnnnnnnnn nnnnnnnnnn nnnnnnnnnn nnnnnnnnnn nnnnnnnnnn nnnnnnnnnn    900
nnnnnnnnnn nnnnnnnnnn nnnnnnnnnn nnnnnnnnnn nnnnnnnnnn nnnnnnnnnn    960
nnnnnnnnnn nnnnnnnnnn nnnnnnnnnn nnnnnnnnnn nnnnnnnnnn nnnnnnnnnn   1020
nnnnnnnnnn nnnnnnnnnn nnnnnnnnnn nnnnnnnnnn nnnnnnnnnn nnnnnnnnnn   1080
nnnnnnnnnn nnnnnnnnnn nnnnnnnnnn nnnnnnnnnn nnnnnnnnnn nnnnnnnnnn   1140
nnnnnnnnnn nnnnnnnnnn nnnnnnnnnn nnnnnnnnnn nnnnnnnnnn nnnnnnnnnn   1200
nnnnnnnnnn nnnnnnnnnn nnnnnnnnnn nnnnnnnnnn nnnnnnnnnn nnnnnnnnnn   1260
nnnnnnnnnn nnnnnnnacc tgcagcactg ggatagccct ggtacagacg tagaacatgc   1320
ttgaggaggt tgtcaggagg aaatgagtta gaccttgcac agaactacca ccatcaagta   1380
cagttggggt gaggcagaca tggtatgagt tgaggcatca gagatatctg atgctttatg   1440
ccaaattaaa attaatttt tcatggagtg acactgatcc acagaccaga ctccaagaac    1500
tttgcagtga ctaaataccc atctcatcat aactttcctg gtattttctt ctggaaaaaa    1560
ttcttccctg atacagtttt cagaggcagc tagatgcact gtcatctctc ccctttccc    1620
acttccctac ctatccacaa tttactaccc aatgccaaca ctaaagttag cccaacttcc    1680
```

```
ttctaactaa attattagtt tagaaggaaa gagaggagtc atgctaagga tcttaactgn    1740
nnnnnnnnnn nnnnnnnnnn nnnnnnnnnn nnnnnnnnnn nnnnnnnnnn nnnnnnnnnn    1800
nnnnnnnnnn nnnnnnnnnn nnnnnnnnnn nnnnnnnnnn nnnnnnnnnn nnnnnnnnnn    1860
nnnnnnnnnn nnnnnnnnnn nnnnnnnnnn nnnnnnnnnn nnnnnnnnnn nnnnnnnnnn    1920
nnnngggag aggagggag aggaggtagg gagggaaag aaagaaacta gaaatccatc       1980
aattttagga ccaacttcag gtaaaaaaat gaattaggca agttggtctt tcaacattct    2040
ctacctctct ttatatcatg gttgagacca cagacttctc acctcatgaa agatgaactc    2100
taactaattc atactaaagc taaagcctct aaagaggatt aaatatgagc aatcccacga    2160
gaactttttt cccctggaat tgtttattca actgtcgttc gttatatgga atttcctgcc    2220
tggttaagtg taggccagta ctttggatga attgtagttt tctagaaaga cgcttcttat    2280
ataagaacct ctccagggaa acaggggcct gtatgagatg aattgagaaa taactttaca    2340
ccactgatta tgtcagtgtt ctattctgca tggtagagat gtgaagggc agactgacca     2400
ttgctctgga agccttttacg ctgtgagaag ttaacagtgg agtaaaatgg ccactccact   2460
ctcttcatgg aagccaacat ggcttactaa atagtcaaca accatgggag agacctgtgg    2520
ggtcttcatc agagctcagg atctcctagg gtatcactca taaatacagc catcagggag    2580
atggagaaat ctttgtgcag ccagaaattc tcaacctggt tttacccatc cttcccaact    2640
ttgtattcgt cctactgttt actgacatgg atcctctgct tcattaacca tcccttcctc    2700
accacatgct ctctgaactt ggctgcacct tttctacctc catgccttct ttgctcaggt    2760
ttttccacat aaatatcatt atttccctct ctactagctc caagcccacc ctctctctgg    2820
ggcagctcag tcactccagg gcacaagggg gtctttccct catcccacat tttgagacct    2880
actacctgga ccatttgttt gccttgtaac tatgcttgcc ttttaattg ctatttatt     2940
ttccatgtat tttcattgtt cacacaagtc ttctttattc cacactaagg caaaagcaga    3000
gtcctgtgtt cataataagt gctcaacaaa tgttgggttg attgggttgg agattccatc    3060
ttagataatc gcagtcccat catgccagct accagactgt gtggacagcc aggtcagagc    3120
agccaaatga tattctagct tgtggcacaa ataccagcaa caaaataacc aaagtcacac    3180
atctgcctct gagttcctgg cttctatttc tcaagggcat ttttaagttg tcttatgact    3240
gttccctttc tactcattct cataaattga gctgtggact gctgtgaccc acaagcttct    3300
ccggaagtca atgtataaaa caaacacgga aacgaagagt atggtgggtg gagggtactc    3360
cactgactct agaatggatg actgaacatt ccaaatttca agcacaagtt agggagcaac    3420
agatcatttt ccttttgaaa tagggtttct tctgctcagc cagttgttgt attttcatta    3480
ggaaatggaa tgggactaca gcacaaaaaa taaatataaa aggacccttg tagggctggc    3540
agaaaagaga atccttccta ggagacctgg aggtgattcc aggcnnnnnn nnnnnnnnnn    3600
nnnnnnnnnn nnnnnnnnnn nnnnnnnnnn nnnnnnnnnn nnnnnnnnnn nnnnnnnnnn    3660
nnnnnnnnnn nnnnnnnnnn nnnnnnnnnn nnnnnnnnnn nnnnnnnnnn nnnnnnnnnn    3720
nnnnnnnnnn nnnnnnnnnn nnnnnnnnnn nnnnnnnnnn nnnnnnnnnn nnnnnnnnnn    3780
nnntcagaaa gtgtgcaaac agtaaaaaaa aatggtatat ctagcaagtt gcatgcctta    3840
cttgtgagtt catgaagttg tggcaaggat aagacaaata ttttttgcca ttgcatcatt    3900
atatcattgc taagagtatg ccattattnn nnnnnnnnnn nnnnnnnnnn nnnnnnnnnn    3960
nnnnnnnnnn nnnnnnnnnn nnnnnnnnnn nnnnnnnnnn nnnnnnnnnn nnnnnnnnnn    4020
```

```
nnnnnnnnnn nnnnnnnnnn nnnnnnnnnn nnnnnnnnnn nnnnnnnnnn nnnnnnnnnn   4080
nnnnnnnnnn nnnnnnnnnn nnnnnnnnnn nnnnnnnnnn nnnnnnnnnn nnnnnnnnnn   4140
nnnnnnnnnn nnnnnnnnnn nnnnnnnnnn nnnnnnnnnn nnnnnnnnnn nnnnnnnnnn   4200
nnnnnnnnnn nnnnnnnnnn nnnnttaatt aattaaatta aagaaacgac aaaagagtat   4260
gcaagaattt taaaacaact tagaggaata tgtatgagga tacaggctaa gctaccataa   4320
tgaagagacc tcgaaataca gtgagaagcg agacagaagt atctttcgtt ccatgtaaca   4380
ctcaggtggt tcagagcagc taagcagcta tgttccatag agtcattcag tgatccagat   4440
tattttcatc tgttgctctg ccattctcca ggatgttgtc cctataaaat tgtcaaagct   4500
cagtcagtgc caaacccatg tttcaacctt cagaaagtaa acgagtggtg aaaacacat    4560 tcaatgtttt aaggccaaga ccttgaaaac tcactctctt agcctgaact tagattacat   4620
ggctgggccc acttaactat aggggaggct tggaaacata gtctctgaga agccatgtgt   4680
ccagctaatt ccctaatact aaagttgaaa gaaagaatgg attaaccagc agtataccac   4740
aaggtaacaa atgactagga ggatcaggct aggtggacta gaaaagagac agtcaattca   4800
gtgcaacaat tccatattga cacttttcat gtagctgttg cttggctcta tctagagagg   4860
actcagaggt agtttagata aggcctttgc cctccaaata cagtctaagc agactgattt   4920
cctactggat gttcaacttt ggagtcttca gggatgagta gggcttctgt acgtggaaga   4980
gactatgagg gaacctgcac aggacaaggg tttgcataaa gacactgagg tagggacctc   5040
tcctgttgtg gggacagtga gaggcccagg tctccttgac tcacaaagtg cttactaagc   5100
acttactaga aattaagaag cagattataa tcaatatggg ttatccaatg tttggatgag   5160
caaggctcct tatcttttct tcgttaatgt taatcacact cttttggatg gagacaaata   5220
tctgtggggg ctnnnnnnnn nnnnnnnnnn nnnnnnnnnn nnnnnnnnnn nnnnnnnnnn   5280
nnnnnnnnnn nnnnnnnnnn nnnnnnnnnn nnnnnnnnnn nnnnnnnnnn nnnnnnnnnn   5340
nnnnnnnnnn nnggctcaga ctaaataatg tctaatctct tctccagtaa aacaatccgt   5400
ggttctcaga tagcactgtg ctggaggtag tggggtttga gggctgggaa gttgggagga   5460
ctgagcccct cccgctgagc agtttcgtcc agtttttcct gtaccagcct gtcatgttta   5520
ttccatgtga atgactccag aggcaaaatt caagcttttg aatagggcac aaattaactt   5580
gagtacccct tcatttccct gtaggtgaac actcctctag ccctgccttt tgtcagtctg   5640
gagcccttgt tctaatctgt acacaccaga ggactttaca aggctttccc cagcctccag   5700
aattattctt ctgatccacc ctctactaaa ctcacccttt cctcagtgct aggacgttga   5760
aaaaccgaaa caaggcaaag ggccaattgt aataattcac actaaggcat gagtgactag   5820
gtttagtata ttaacactac ctaggatatt ctatttcttc caaaaggatc ctgttaatcc   5880
ttgaaattta acaactaatg gtatagattc taagcactgt gagtacttgt cagtggggga   5940
aagacatttt tgggctgaga gactttgcca ctgnnnnnnn nnnnnnnnnn nnnnnnnnnn   6000
nnnnnnnnnn nnnnnnnnnn nnnnnnnnnn aagaaagatg attagatnnn nnnnnnnnn    6060 nnnnnnnnnn nnnaaaaaat aacatgagag nnnnnnnnnn nnnnnnnnnn nnnnnnnnnn   6120
nnnnnnnnnn nnnnnnnnnn nnnnnnnnnn nnnnnnnnnn nnnnnnnnnn nnnnnnnnnn   6180
nnnnnnnnnn nnnnnnnnnn nnnnnnnnnn nnnnnnnnnn nnnnnnnnnn nnnnnnnnnn   6240
nnnnnnnnnn nnnnnnnnnn nnnnnnnnnn nnnnnnnnnn nnnnnnnnnn nnnnnnnnnn   6300
nnnnnncaca gagctagccg tgttggctgt cacccactca tgtggccagc ctgttggtct   6360
acctcttagt tgccatgtaa caggattctg gtgcttttcc tttgcccagg t cag atg    6417
```

```
gaa ccc agg acc cat cca act tgg ctg ctt cac att ttc atc ccc tcc     6465 tgc atc att gct ttc att ttc ata gcc aca gtg ata gcc cta aga aaa     6513 caa ctc tgt caa aag ctg tat tct tca aaa ggtaagtgag ttttattcat       6563
ggtaacccaa tgcactgggt gtctgcagca tgagccactg ctttgcactg caggcctatg   6623
gcttgctgct ttcatgctaa acccactcag agcttatgaa ccactttgag cttgtcttga   6683
tgattatttt tccccagaag aaaatggctc tcatcgtcag tgagctgaac ttcttacact   6743
gagtttttta aagggaatgt tttgttctta tgtctgaaag agtttgtctt attctttgag   6803
ccaagagctt tcatcagcct catgagagtg atgttatttt ggcaatgcag agagctacgt   6863
gctccgattt tgctggtggg aggttgccag gatcctttct gaggattcct tccattttca   6923
cccctctttt ccccagtctg gatatgacct gggttaaacc caccccctct cccaggaatc   6983
tcaacctcac ggttgggtaa ggaaaggaga aaggtttgtg aggccatttg gggataagga   7043
aacagctggt tggtggtgca ttaacgtctt tcagcagctc ccttcgagtt tctccttagc   7103
ctgttgtatt cttaccaaca cactcctgtt ctgttgtacc agctgggaca gagcatgctg   7163
aagcctttca gccctgattt cattgcttca ttgttcatgt gtctgtcttt ggtttcctgg   7223
gtggagcctg cccacaaaac ccccagaatg tatgcaggcc tagctggtgc tttcctaaac   7283
ggctcccttg tctgcactca atgaacttct ccaaagatct atacatggcc tcatctatag   7343
aaagagaaat gacatgtgga ataattcag taggagtttg cagcagcact atctgaggac    7403 tagggaatt ttaagtggtt gttatcttac atttatactc ataacttcta tattttcatc    7463
tgccataaaa tattgtcatg ttctatttgt ccattgccct atgtgtgtat gtattcactt   7523
gggtgctgac cacaatattt ctaactgtag aatgcaagga attgttgcca aannnnnnnn   7583
nnnnnnnnnn nnnnnnnnnn nnnnnnnnnn nnnnnnnnnn nnnnnnnnnn nnnnnnnnnn   7643
nnnnnnnnnn nnnnnnnnnn nnnnnnnnnn nnnnnnnnnn nnnncttca tggtaaagga    7703 ggaggtatgt ccaacagaac ttcgactttt aaatagaacc acttcagaga gttgtgtcag   7763
gtgcacctca gttgtcttat cttctgccat tcttctttta cctctcacac ccatacctca   7823
gggttcaagg cctggggcct gaggactcct taataacttc agaaatgagc agctgagtgt   7883
tccgttccag ctgtctttgg gagaatggaa tggagtcaca ctcaaagata gagtggaaat   7943
aaatcctctc ctcatccttc accccaatct taagagtgag tgaggatatc agtagctccg   8003
agctgggagg taaagctcaa gttctaactg tgattaggag acctttctta caaataagaa   8063
ttaagtgaat aaatgtgcaa acaatttctt ttatattttt aatgaaccag agagaaatca   8123
tggttgccta tataaccctt gtctccaact cacttgcatt cagatctgct ttcttacatg   8183
tgtctgccat gcacacaaac ttgtgtgcca tggaaaaggg ttgagaactg ctggtgatgc   8243
agacagagct ttaaannnnn nnnnnnnnnn nnnnnnnnnn nnnnnnnnnn nnnnnnnnnn   8303
nnnnnnnnnn nnnnnnnnnn nnnnnnnnnn nnnnnnnnnn nnnnnnnnnn nnnnnnnnnn   8363
nnnnngcagc aagagaagga acattttaca gcttattggc cgaacttcac tgccgctagt   8423
gtggttcaac ttggactaca gagaaatctt cctaactggt ttccctgtat tcactcctgc   8483
tacctccaac ttggtctgtt ctcacttttt gctataatag ctttttaaaa atcataaatc   8543
taccatgtgt cctctgtcca gaccttctcc atggcttctt attgctcact ggatgaagtt   8603
ccaacgagcc caggatggtt tgactcatgt ctccagcttt aactgcatca ccatcacctt   8663
cattgtctaa agctctaacc acacaggatt ttctagtcct cagaggcatg gcagtctttc   8723
```

```
aattccgagt tttctcatac aatattgtct cttcttaaaa tatttttct tgttgtccac      8783 ctgagttgga gtcatctttt aaatctcagc taagcttata cttcatcaag tctttcctaa      8843
ttctacctcc acgcaccaca cccattacat taaatcccct tattatatgt ttccatagca      8903
cctactttct tcttttcagt atactcagca cacaatcaca tgtctaggat ctgttttaat      8963
agcttggact accaattaaa ttgcatccct tttaattgtc cattgattcc tcaagtaccc      9023
acatgcccat cttagcaaga agttcagtgt ctccctctta tagcatgtac ttctccacct      9083
cccacaaact gccagaaagc ttacttagcc cacagggcca gtgctaggca gctaggttag      9143
tcctccagag ggccctggtt ttgagcagtt gctgtctact ccggccatgc agaatctctg      9203
gtccttccag atgtctccat ccactgtgca aaggtaacct tgctggttcc gatccccaca      9263
cagaccacag tgctacaaga ttacagttct tatggttccc caacacatgc tctgtcattg      9323
gtcccaaagc aggaccccta tgggttgatg aggtaggagg aggtccctgc cttagccaca      9383
gctgcacaca gccagcctct tcccttctag gccctcatgt tgagcctggg acgccagtcc      9443
taacttcctt ctcttcagtt cctcttaggg ccattggtat cctgaatttc ttagtccatt      9503
gcaaagttaa gtaagaagc agcaggcttg gtccctttcc ttccagatgg cttcttagct      9563
cctgaacaga tttacccacc tatacctcag tgactagctc tgtgtactaa agtgtattgg      9623
gagggcagcc attattggtc cataaaaggt cctgcttacc atttccccct aagaggaacc      9683
attcaacagt ttggggctcg agggtgacct gctgggctct agagaagaag ctggcaactt      9743
ctgttgcaaa ataatgttaa attctgcttc atctgcttgt cttnnnnnnn nnnnnnnnnn      9803
nnnnnnnnnn nnnnnnnnnn nnnnnnnnnn nnnnnnnnnn nnnnnnnnnn nnnnnnnnnn      9863
nnnnnnnnnn nnnnnnnnnn nntaaacatt gaacctacta tatgcaggtg agtatgctag      9923
atnnnnnnnn nnnnnnnnnn nnnnnnnnnn nnnnnnnnnn nnnnnnnnnn nnnnnnnnnn      9983
nnnnnnnnnn nnnnnnnnnn nnnnnnnnnn nnnnnnnnnn nnnnnnnnnn nnnnnnnnnn     10043
nnnnnnnnnn nnnnnnnnnn nnnnnnnnnn nnnnnnnnnn nnnnnnnnnn nnnnnnnnnn     10103
nnnnnnntgn nnnnnnnnnn nnnnnnnnnn nnnnnnnnnn nnnnnnnnnn nnnnnnnnnn     10163
nnnnnnnnnn nnnnnnnnnn nnnnnnnnnn nnnnnnnnnn nnnnnnnnnn nnnnnnnnnn     10223
nnnnnnnnnn nnnnnnnnga tttgaataca ggtctgtttg actccaaaac ttgtggccta     10283
tttgttgcaa aagtgcttaa tacaaattgg ttcagtcaat attattatct ttgaacaatg     10343
gaaggagaaa gtaagtttca atccaaaata attgagtgac ttatacattg acttgctgag     10403
ccaatggcaa agtcaagtta gaatccagca gaagtcacca gctacagaat ctagatcttt     10463
agaacatgtc ttcagatctt cagaacagtg tttcttaaac tctcttgtga aggaacagtt     10523
atcatcatag gctggtaaca gttcacctac cagcaccagc ccatgaacca gactctaagt     10583
ggcacagccc tagaagattg agccagaatt ttacagaggt ttaaagacca aatatgctgg     10643
tttatggtta cctgtggccc acagagaatg gcagcactaa cctcaggcat aaatgaggta     10703
cccactgaag ccaacattca agagcaattc ctatgggtta accattgggc tcctttcaaa     10763
tgcaaaccct catgaaagag actacagtgc tgaatagaa cctccaaatt ccaggccaag     10823
ctcaggatag tcatgaggga attactaaaa acctggtata tagggcaaaa gcagaattag     10883
gaatggactg atttcaggaa cccaggcaat ggcaggagtt gggcattaaa tcctaaaaga     10943
gaatcagagt gggagggaat atgtgaaatc agaggttaag aaaaaagtga aaacctnnnn     11003
nnnnnnnnnn nnnnnnnnnn nnnnnnnnnn nnnnnnnnnn nnnnnnnnnn nnnnnnnnnn     11063
nnnnnnnnnn nnnnnnnnnn nnnnnnnnnn nnnnnnnnnn nnnnnnnnnn nnnnnnnnnn     11123
```

```
nnnnnnnnnn nnnnnnnnnn nnnnnnnnnn nnnnnnnnnn nnnnnnnnnn nnnnnnnnnn    11183
nnnnnnnnnn nnnnnnnnnn nnnnnnnnnn nnnnnnnnnn nnnnnnnnnn nnnnnnnnnn    11243
nnnnnnnnnn nnnnnnnnnn nnnnnnnnnn nnnnnnnnnn nnnnnnnnnn nnnnnnnnnn    11303
nnnnnnnnnn nnnnnnnnnn nnnnnnnnnn nnnnnnnnnn nnnnnnnnnn nnnnnnnnnn    11363
nnnnnnnnnn nnnnnnnnnn nnnnnnnnnn nnnnnnnnnn nnnnnnnnnn nnnnnnnnnn    11423
nnnnnnnnnn nnnnnaaaaa attaaaagaa agatgtgaaa tcaaggaaac ttactggtga    11483
gcagcatccc attatgtgaa cttgtgcttc tgaaccagta acttgagtta ctttgagcca    11543
gtatcagtca cttataccct agtgcaaaat taattgatca gacattctga cctggaccag    11603
ggaaggcagg cagaagtagc agtcaagact aaagcagaaa agggagagct aattctgcag    11663
ccagacattt cctggattga atacccaaat tagtccctca gcctttaagt gcctgagggc    11723
caggagtaga cagaggaatg gaaagtgtga gacttctttg ttcacactct ttgcctaggg    11783
gccagatttt gctttatgca ttaccatccg aagtcccagg ccacagtgaa catttgggct    11843
tcgctatgtg gatttattta gatttacttt ttgtcctgcc atattttaat ctataagcca    11903
aacagttttc tcattaatct tattccattt ctggaatttt tccttttca gac aca aca   11961
aaa aga cct gtc acc aca aca aag agg gaa gtg aac agt gct             12003
gtgagtaagc atgatttta cttttctttc ttactttctt ttctctctca gcttgaattt    12063
taaagtaacc actgttctat taattcatgg aaggcaactg aatagttcca gcttatagaa    12123
tcttcctgtt tggtagcatt tcagcgaagc ctcgttctta gccccagaac aatcatgcca    12183
tcttttgctc ggtctatatt cctaagcact cctagatgat actgcactgg acctctggtc    12243
tcacatagtt agaaacagag ttaaaatcga acagcaaaga gaagatattc aactgcgatg    12303
caattgacaa tggatgtttt tgcaacaaac aatgattaag aagtacattg ttgtgggctc    12363
tgagtcaaga gtaatatggg aaaaacacaa gtctcttcat gaggttgaca ggtttggagc    12423
tggaatctgt ggaggaggaa ggatatgatc tagggggtcag aagaagtggg ttactaaaat   12483
cattaagcct ggttggatga aaagcttaga ctcaggggaa gcagnnnnnn nnnnnnnnnn    12543
nnnnnnnnnn nnnnnnnnnn nnnnnnnnnn nnnnnnnnnn nnnnnnnnnn nnnnnnnnnn    12603
nnnnnnnnnn nnnnnnnnnn nnnnnnnnnn nnnnnnnnnn nnnnnnnnnn nnnnnnnnnn    12663
nnnnnnnnnn nnnnnnnnnn nnnnnnnnnn nnnnnnnnnn nnnnnnnnnn nnnnnnnnnn    12723
nnnnnnnnnn nnnnnnnnnn nnnnnnnnnn nnnnnnnnnn nnnnnnnnnn nnnnnnnnnn    12783
nnnnnnnnnn nnnnnnnnnn nnnnnnnnnn nnnnnnnnnn nnnnnnnnnn nnnnnnnnnn    12843
nggcaccaag agatgagggg ggcagtcttg gccatatatt tggctgaagt aagtcaattt    12903
gtcattcctg catgagcctt tataaacaga agtaagtaac caactactat ttggtcattg    12963
gagttgtcca agaggccagg gttctgtcta atacctgttc atgcatgaac atgccaacct    13023
agattgcatg cagactacca gttttgggtt tttgtttagt tcagcaggat ttttctcagc    13083
tcactgcctc tcaaactttc agcaacaaaa ggacatctgt gatatcagaa tctaccactc    13143
taagtatttg gatgcaatag caatgaatat ctgagtaaat ctaggtgggg agtgggggca    13203
ccctgtagcc aaaatgattt aacaaaatca aaccaaaatt ttggaaatga tgccttggta    13263
caatgaagag actacttgag gtaggtttga cttatctaat atcttatttt ctttaccaat    13323
acctaatgag gaatttaaat atttctagat agctttggaa aggtccctta aagaggcacc    13383
agcataccac tgccagatct aatcccccca aacactgttt tcatcatcat catgtcatct    13443
```

```
cttgtctcta tagatcatat caaatccttc ccagagtttt tcaggccttt tgacaactag    13503
ccacatttca ctaagccaac tcatctacca ctcttcaaca aaacttttcc tcaagttgag    13563
ctgctccacc aacaccactg ccatgagctc attcccactt ctgtggcttt gctcatgttg    13623 gttattttt  tggagtgtcc tccctattcc ttcttacttg tcccaatccc aacttttggc    13683
atggtctact ttaagataca gtaatgagta actttannnn nnnnnnnnnn nnnnnnnnnn    13743
nnnnnnnnnn nnnnnnnnnn nnnnnnnnnn nnnnnnnnnn nnnnnnnnnn nnnnnnnnnn    13803
nnnnnnnnnn nnnnnnnnnn nnnnnnnnnn nnnnnnnnnn nnnnnnnnnn nnnnnnnnnn    13863
nnnnnnnnnn nnnnnnnnnn nnnnnnnnnn nnnnnnnnnn nnnnnnnnnn nnnnnnnnnn    13923
nnnnnnnnnn nnnnnnnnnn nnnnnnnnnn nnnnnnnnnn tttttaaaat ttaattcaan    13983
nnnnnnnnnn nnnnnnnnnn nnnnnnnnnn nnnnnnnnnn nnnnnnnnnn nnnnnnnnnn    14043
nnnnnnnnnn nnnnnnnnnn nnnnnnnnnn nnnnnnnnnn nnnnnnnnnn nnnnnnnnnn    14103
nnnnnnnnnn nnnnnnnnnn nnnnnnnnnn nnnnnnnnnn nnnnnnnnnn nnnnnnnnnn    14163
nnnnnnnnnn nnnnnnnnnn nnnnnnnnnn nnnnnnnnnn nnnnnnnnnn nnnnnnnnnn    14223
nnnnnnnnnn nnnnnnnnnn nnnnnnnnnn nnnnnnnnnn nnnnnnnnnn nntacataca    14283
caacactctc ttgcttaatc tgtaagactc tctcccccac tcatacctt  ttatttttcc    14343 tctgcattgt acacacaatc tataccactc ttaagcacat gattacagcg ttattttctg    14403
gctgcttcta tgtgtctata ttttaggtcc acctggtcaa tataataaag tgggatatta    14463
gtgttaatgc aactatatgg tatttgatat ttgtctttct gtccgtttat caatgtttct    14523
tatagnnnnn nnnnnnnnnn nnnnnnnngg tgtctgattt tgaccaaatt tgactaaata    14583
cnnnnnnnnn nnnnnnnnnn nnnnnnnnnn nnnnnnnngt tgagtctatc aactcaaaaa    14643
agaataacct acaacaataa caagtttcag aacatttttt aaattactga ttttatgagn    14703
nnnnnnnnnn nnnnnnnnnn nnnnnnnnnn nnnnnnnnnn nnnnnngaat ccattgccta    14763
gaaattgcca tggttaagat tttaatattg ctcaggccca gacagctcag ggctttgaca    14823
ttcccacacc cattctctgc catcccagtt ctatctcatc ccaaaaccat ccattatgag    14883
gagagtgtac agctctaggc tgcccgggag ccatcccgca ctctcatttt gtgactcggc    14943
atcttgggag atggagtctt gggacttagc ctggacatgt cccttgcatg tacttcttac    15003 aagacttta  ttcagatgaa tattttccct tccaacttaa gaagcacagg gcttgctggt    15063
tttgcttcac taaccagcaa ctgaagcaag acctgacttg tgaaaatgcc taatagagtt    15123
cagtattagc gctgtttcac catttcctgg atctcttgcc tttgtgcaca tgatagaatt    15183
gcacttctct gtgattaatt tgtagttaag tgtggtcatg taactcgctt tggtcaatta    15243
aatgtaagca taagtgatgc gtgttatttc tgggtagaag atgtaagagt tggcatatgc    15303
tttgccatat tttctttatc catctggcat ggtaaccagt aacattctag gtagtaattg    15363
ctccatcagt ctcagtctct gagtgactaa aattgacaga gtcccctgct gaccctcaat    15423
gtacatggaa catgaacaag aataagcttt tgttttttat attgagattt tggagttgtt    15483
tgttcctaca gcattaccta gtttactcta atacaacatg gaaaaaactg gaacctataa    15543
taaatagacc ctacgttgcc atttaaactt ctagttctga ggaataataa tgtggggaaa    15603
tactttctat ataataaaaa aatagaaaat tgcaaaataa aaatatactt atgtatcatt    15663
catgtcctat taaaaatgtt atttatagac tcaccatatt cccttcctcc agaaaaatag    15723
aagtaaaaat atgaaaatgc ctgtaatcat gttttggat  tatggaatca agtattgctt    15783
tttactttta tgttttctga attttttgttg tacttcacta cattttttgag tgccctgatg    15843
```

```
tattactttc aaaaagaaga agaatacttt ctgaagccat ttcaaccatc cccactcacc   15903
tctctagatc ccagtaacca aatacattat ataggactct tcatcagtcc ttatcaagtt   15963
taggaagggc gatgctatac cttctttaaa ggacacctac caatgtctta gttgcctttc   16023
aaagactcct agcacagcta aatgtgatgg atatgctcta aggatataag agctgaagtg   16083
acttgcataa ggtcatatca taacttactg ttagaaatgg agctagaact cagacccact   16143
gagtccttgt ctgtgacaca ctgccctttc catttgtgga agttgttctt gtatctaact   16203
ttatctgtgc tactatttgg gcctagccat tctccctctt atgcagacaa gcagataaac   16263
agtaaaactt taggagtgga ttatgatacc atagatatat atcatctatc ctttacaaaa   16323
tagttattac agtcatcaag ccttggttag agtttacaga ccatgtatcc tagctannnn   16383
nnnnnnnnnn nnnnnnnnnn nnnnnnnnnn nnnnnnnnnn nnnnnnnnnn nnntgaaaca   16443
gtagcagacc aaaagaagtc atgattccca gcatagtgct nnnnnnnnnn nnnnnnnnnn   16503
nnnnnnnnnn nnnnaaacct gtattaagtt tctgttattt gcaagaccct gtcagttagg   16563
ccatgtggga actagaagga tgaatttatc agtcatccaa gattcttaca attaagtatt   16623
accgataagg tactcaagaa acagttctca ttcacataat ttgggttaaa acaaaaagaa   16683
gccagctttc tatatacttt tggtccagtc tttacgtttt ttgttttgtt ttgtttgttt   16743
tcatgagtat cccgacttcc ttctaagaac ttccacctga gaactgacca cagcgtcagc   16803
attccacatg ggtgtgtttc cttccccctt tcccatttca gtggtttcca atttcttttt   16863
cttttggcac tataaacctt tcgcaaagga aatattagac agaactccta catgtcaagc   16923
aaattaaaat agtggtgaaa ttagagtgga ggacataatc accctatcat ataggctatt   16983
tgtccatatc atatttgtcc ctacaaaggc ctctaaggnn nnnnnnnnnn nnnnnnnnnn   17043
nnnnnnnnnn nnnnnnnnnn nnnnnnnnnn nnnnnnnnnn nnnnnnnnnn nnnnnnnnnn   17103
nnnnnnnnnn nnnnnnnnnn nnnnnnnnnn nnnnnnnnnn nnnnnnnnnn nnnnnnnnnn   17163
nnnnnnnnnn nnnnnnnnnn nnnnnnnnnn nnnnnnnnnn nnnnnnnnnn nnnnnnnnnn   17223
nnnnnnnnnn nnnnnnnnnn nnnnnnnnnn nnnnnnnnnn nnnnnnnnnn nnnnnnnnnn   17283
nnnnnnnnnn nnnnnnnnnn nnnnnnnnnn nnnnnnnnnn nnnnnnnnnn nnnnnnnnnn   17343
nnnnnnnnnn nnnnnnnnnn nnnctctaag ataccttgtg cttcttggaa catatttgga   17403
aaatcatgta gctctcaaat tatccctatg tcctgaagcc caccttacca tcaatcctca   17463
gaaataccca acccatgtca ggcaacttca cactttcttt cttcaggcag cacagttgtc   17523
tcagggaggg aggagagtgc tattagcaag aggagtcact aacagcttca ctcacctgtg   17583
cccatgaatt tttaatggtg tgaaaagtct gtgtattttt tatggttctc tatggctcat   17643
ataagaggga caaacaatac atgaaagttc agagatgggg acaaatatca ctttaagctg   17703
gggataatca gggaagaaga aagttttcat ggagaaggtg acttttgaat caggaagaaa   17763
tggaaacagc aaactcttct agatagagga gacactaaca ggaaaggcag agaggcagga   17823
aggtgtggga aagtgcacgt gaccccgttc agagagaaag ccaggtgtga gataagggg    17883
aaagactgtt agggcatgta ttgtaaacca ctaattccag gcaaaagtta gatttttactt  17943
actaagcaag agtgcttcag ttagatccta gcaggaaatg gagggtatgc ttagaagagg  18003
taactgaggc aagtttaatt tataaaggtg tgtgcagcat taagggaaac cagcaaggga  18063
tactgagcat gccaggatgc aagagcaggc agggaaggtg actattccta ggtctgaagg  18123
agaaagggga gggagcagtt cccagaaccc tagtaaaaat ggcaatgaga aaggtccatc  18183
```

```
tggcaggacc tatggtctttt aacagaggga caaagtcaac ccacaacttg tctgggaggt  18243
tgctgaggaa tagataccccc aacctctctc tcaacccact gcaacactct ttttccccta  18303
gactgagccc agtcaaagac agagggagga gcccagtgat gcagtctgca atgtcatcat  18363
cctggagcat gaatagagtg cagcagggtg aataatgagt ctgcaggaat taatagaaat  18423
atctgacaca atagggaact ataagaggtt ttgaatagga gaggcccctg aaatgtgctc  18483
caatattact gaactatgtg tggcccaaag aatggaagag aacagctct tgcaataggt   18543
ctgaggagag aagctgaaga cttggactag ggcaatggta aaaactgtgg aagaagttt   18603
taaatgaaaa gttttaaacc atgcggcttc cagctagatg aacttttta aaaaattag    18663
ttcctcactc aaattttggg gaggttatat attttctaat cataaaaaat gattttctt   18723
atttgtgggc ttttctcccc ag atc tga acctgtggtc ttgggagcca gggtgacctg  18781
atatgacatc taaagaagct tctggactct gaacaagaat tcggtggcct gcagagcttg  18841
ccatttgcac ttttcaaatg cctttggatg acccagcact ttaatctgaa acctgcaaca  18901
agactagcca acacctggcc atgaaacttg ccccttcact gatctggact cacctctgga  18961
gcctatggct ttaagcaagc actactgcac tttacagaat taccccactg gatcctggac  19021
ccacagaatt ccttcaggat ccttcttgct gccagactga aagcaaaagg aattatttcc  19081
cctcaagttt tctaagtgat ttccaaaagc agaggtgtgt ggaaatttcc agtaacagaa  19141
acagatgggt tgccaataga gttattttt atctatagct tcctctgggt actagaagag   19201
gctattgaga ctatga                                                   19217
```

<210> SEQ ID NO 19
<211> LENGTH: 18
<212> TYPE: PRT
<213> ORGANISM: Homo sapiens

<400> SEQUENCE: 19

Met Ile Phe Leu Leu Leu Met Leu Ser Leu Glu Leu Gln Leu His Gln
1               5                   10                  15

Ile Ala

<210> SEQ ID NO 20
<211> LENGTH: 102
<212> TYPE: PRT
<213> ORGANISM: Homo sapiens

<400> SEQUENCE: 20

Ala Leu Phe Thr Val Thr Val Pro Lys Glu Leu Tyr Ile Ile Glu His
1               5                   10                  15

Gly Ser Asn Val Thr Leu Glu Cys Asn Phe Asp Thr Gly Ser His Val
                20                  25                  30

Asn Leu Gly Ala Ile Thr Ala Ser Leu Gln Lys Val Glu Asn Asp Thr
            35                  40                  45

Ser Pro His Arg Glu Arg Ala Thr Leu Leu Glu Glu Gln Leu Pro Leu
        50                  55                  60

Gly Lys Ala Ser Phe His Ile Pro Gln Val Gln Val Arg Asp Glu Gly
65                  70                  75                  80

Gln Tyr Gln Cys Ile Ile Ile Tyr Gly Val Ala Trp Asp Tyr Lys Tyr
                85                  90                  95

Leu Thr Leu Lys Val Lys
            100

<210> SEQ ID NO 21
<211> LENGTH: 91
<212> TYPE: PRT
<213> ORGANISM: Homo sapiens

<400> SEQUENCE: 21

```
Ala Ser Tyr Arg Lys Ile Asn Thr His Ile Leu Lys Val Pro Glu Thr
  1               5                  10                  15

Asp Glu Val Glu Leu Thr Cys Gln Ala Thr Gly Tyr Pro Leu Ala Glu
             20                  25                  30

Val Ser Trp Pro Asn Val Ser Val Pro Ala Asn Thr Ser His Ser Arg
         35                  40                  45

Thr Pro Glu Gly Leu Tyr Gln Val Thr Ser Val Leu Arg Leu Lys Pro
     50                  55                  60

Pro Pro Gly Arg Asn Phe Ser Cys Val Phe Trp Asn Thr His Val Arg
 65                  70                  75                  80

Glu Leu Thr Leu Ala Ser Ile Asp Leu Gln Ser
                 85                  90
```

<210> SEQ ID NO 22
<211> LENGTH: 44
<212> TYPE: PRT
<213> ORGANISM: Homo sapiens

<400> SEQUENCE: 22

```
Gln Met Glu Pro Arg Thr His Pro Thr Trp Leu Leu His Ile Phe Ile
  1               5                  10                  15

Pro Ser Cys Ile Ile Ala Phe Ile Phe Ile Ala Thr Val Ile Ala Leu
             20                  25                  30

Arg Lys Gln Leu Cys Gln Lys Leu Tyr Ser Ser Lys
         35                  40
```

<210> SEQ ID NO 23
<211> LENGTH: 17
<212> TYPE: PRT
<213> ORGANISM: Homo sapiens

<400> SEQUENCE: 23

```
Asp Thr Thr Lys Arg Pro Val Thr Thr Thr Lys Arg Glu Val Asn Ser
  1               5                  10                  15

Ala
```

<210> SEQ ID NO 24
<211> LENGTH: 11
<212> TYPE: PRT
<213> ORGANISM: Human immunodeficiency virus type 1

<400> SEQUENCE: 24

```
Tyr Gly Arg Lys Lys Arg Arg Gln Arg Arg Arg
  1               5                  10
```

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence:
      Internalizing domain derived from HIV tat protein

<400> SEQUENCE: 25

```
Gly Gly Gly Gly Tyr Gly Arg Lys Lys Arg Arg Gln Arg Arg Arg
  1               5                  10                  15
```

```
<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide Primer 2515-27

<400> SEQUENCE: 26
cataatagag catggcagca atgtgac                                            27

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide Primer 2524-63

<400> SEQUENCE: 27
gggtcctgga gtggctggtg ttg                                                23

<210> SEQ ID NO 28
<211> LENGTH: 14
<212> TYPE: PRT
<213> ORGANISM: Homo sapiens

<400> SEQUENCE: 28

Leu Phe Thr Val Thr Val Pro Lys Glu Leu Tyr Ile Ile Glu
 1               5                  10

<210> SEQ ID NO 29
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide Primer 2515-24

<400> SEQUENCE: 29
gtggctcttt cacggtgtgg ggatg                                              25

<210> SEQ ID NO 30
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide Primer 2538-68

<400> SEQUENCE: 30
ccagtgtcaa agttgcattc cagggt                                             26
```